(12) United States Patent
Botta et al.

(10) Patent No.: US 11,098,094 B2
(45) Date of Patent: Aug. 24, 2021

(54) ARTIFICIAL DNA-BINDING PROTEINS AND USES THEREOF

(71) Applicant: FONDAZIONE TELETHON, Rome (IT)

(72) Inventors: Salvatore Botta, Naples (IT); Enrico Maria Surace, Naples (IT); Elena Marrocco, Naples (IT)

(73) Assignee: FONDAZIONE TELETHON, Rome (IT)

( * ) Notice: Subject to any disclaimer, the term of this patent is extended or adjusted under 35 U.S.C. 154(b) by 338 days.

(21) Appl. No.: 15/037,864

(22) PCT Filed: Nov. 20, 2014

(86) PCT No.: PCT/EP2014/075212
§ 371 (c)(1),
(2) Date: May 19, 2016

(87) PCT Pub. No.: WO2015/075154
PCT Pub. Date: May 28, 2015

(65) Prior Publication Data
US 2016/0289284 A1 Oct. 6, 2016

(30) Foreign Application Priority Data

Nov. 20, 2013 (EP) .................................... 13193739

(51) Int. Cl.
| | | |
|---|---|---|
| *C07K 14/47* | (2006.01) | |
| *C12N 15/86* | (2006.01) | |
| *A61K 48/00* | (2006.01) | |
| *C12N 7/00* | (2006.01) | |
| *A61K 38/00* | (2006.01) | |

(52) U.S. Cl.
CPC ........ *C07K 14/4703* (2013.01); *A61K 48/005* (2013.01); *C12N 7/00* (2013.01); *C12N 15/86* (2013.01); *A61K 38/00* (2013.01); *A61K 48/00* (2013.01); *C12N 2750/14143* (2013.01); *C12N 2750/14171* (2013.01); *C12N 2830/008* (2013.01)

(58) Field of Classification Search
CPC .......... A61K 48/00–48/0066; C07K 14/4703; C12N 15/85–15/86; C12N 2830/008; C12N 7/00; C12N 2750/14143
See application file for complete search history.

(56) References Cited

U.S. PATENT DOCUMENTS

2012/0178647 A1* 7/2012 Joung ................ C12N 15/1093
506/9

FOREIGN PATENT DOCUMENTS

WO 201206725 A2 8/2012

OTHER PUBLICATIONS

Chang et al. (1998, Molecular and Cellular Biology, vol. 18(9), pp. 4986-4993). (Year: 1998).*
Kim et al. Zinc-finger-based transcriptional repression of rhodopsin in a model of dominant retinitis pigmentosa. Proceedings of the National Academy of Sciences, USA, vol. 95, No. 6, pp. 2812-2817, Mar. 1998. (Year: 1998).*
Lee et al. Quantitative fine-tuning of photoreceptor cis-regulatory elements through affinity modulation of transcription factor binding sites. Gene Therapy, vol. 17, pp. 1390-1399, 2010. (Year: 2010).*
Boulikas, T. Nuclar Localization Signals (NLS). Critical Reviews in Eukaryotic Gene Expression, vol. 3, No. 3, pp. 193-227, 1993. (Year: 1993).*
Klug et al. Zinc finger peptides for the regulation of gene expression. Journal of Molecular Biology, vol. 293, pp. 215-218, 1999. (Year: 1999).*
Wiemann et al. From ORFeome to Biology: A functional genomics pipeline. Genome Research, vol. 14, pp. 2136-2144, 2004. (Year: 2004).*
Friedberg et al. Automated protein function prediction—the genomic challenge. Briefings in Bioinformatics, vol. 7, No. 3, pp. 225-242, 2006. (Year: 2006).*
Kost et al. Baculovirus as versatile vectors for protein expression in insect and mammalian cells. Nature Biotechnology, V9ol. 23, pp. 567-575, 2005. (Year: 2005).*
Schembri et al. The HA tag is cleaved and loses immunoreactivity during apoptosis. Nature Methods, vol. 4, No. 2, pp. 107-108, 2007. (Year: 2007).*
Pouton et al. Nuclear import of polypeptides, polynucleotides and supramolecular complexes. Advanced Drug Delivery Reviews, vol. 34, pp. 51-64, 1998. (Year: 1998).*
Yoneda, Y. How proteins are transported from cytoplasm to the nucleus. Journal of Biochemistry, vol. 121, pp. 811-817, 1997. (Year: 1997).*
Stinski et al. Activation of the major immediate early gene of human cytomegalovirus by cis-acting elements in the promoter-regulatory sequence and by virus-specific trans-acting components. Journal of Virology, vol. 55, No. 2, pp. 431-441, 1985. (Year: 1985).*

(Continued)

*Primary Examiner* — Jennifer Dunston
(74) *Attorney, Agent, or Firm* — Lucas & Mercanti, LLP

(57) ABSTRACT

The present invention relates to proteins consisting of an artificial DNA-binding domain (DBD) and related molecules and uses thereof. In particular, the proteins are ZF-DBD or TALE-DBD and are used for the treatment of eye disorders caused by gain of function mutation. The disorder may be ADRP, in particular ADRP caused by mutation in the rhodopsin gene. The present invention also relates to a method to identify cis-regulatory elements and to modulate them via DBDs.

17 Claims, 33 Drawing Sheets
Specification includes a Sequence Listing.

(56) References Cited

OTHER PUBLICATIONS

Mussolino et al., "Zinc-finger-based transcriptional repression of rhodopsin in a model of dominant retinitis pigmentosa", EMBO Molecular Medicine, 2011, vol. 3, No. 3, pp. 118-128.
Botta et al., "Somatic Rhodopsin Transcriptional Repression by Artificial DNA-Binding Proteins Targeted to Cis-Regulatory Elements", Molecular Therapy, 2014, vol. 22, Suppl. 1, pp. S147-S148.
International Search Report and Written Opinion for International Application No. PCT/EP2014/075212 (dated May 26, 2015) (24 Pages).

* cited by examiner

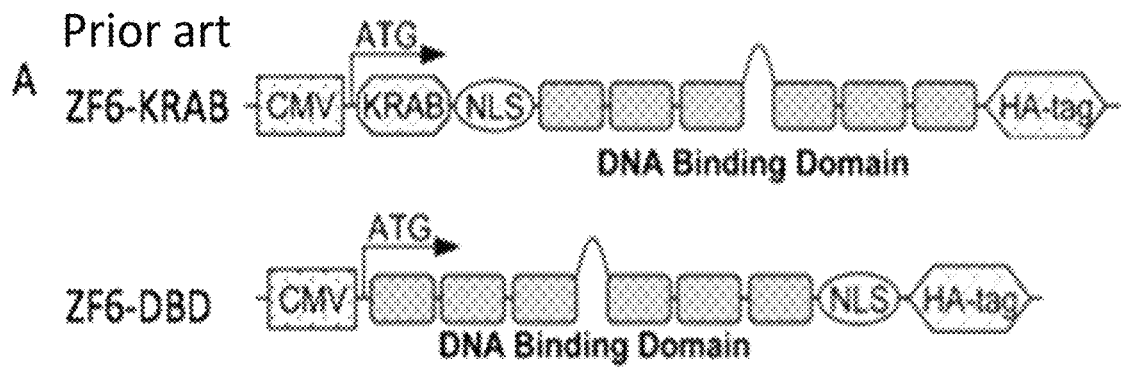
B   - cttgtGGGGGTTAGagGGTCTACGActaa   SEQ ID NO: 85
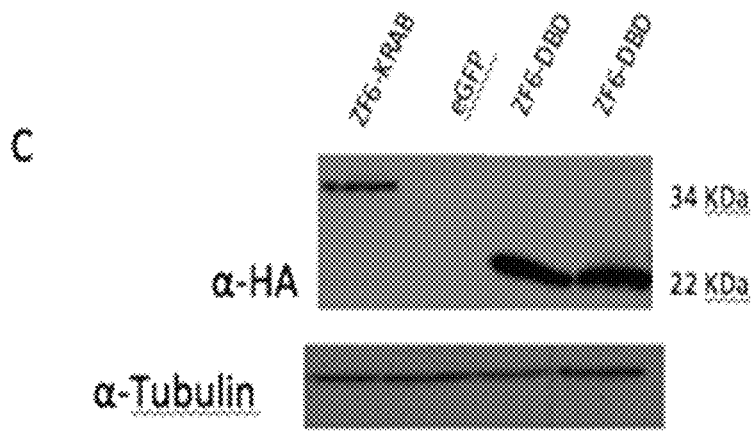
Fig. 1

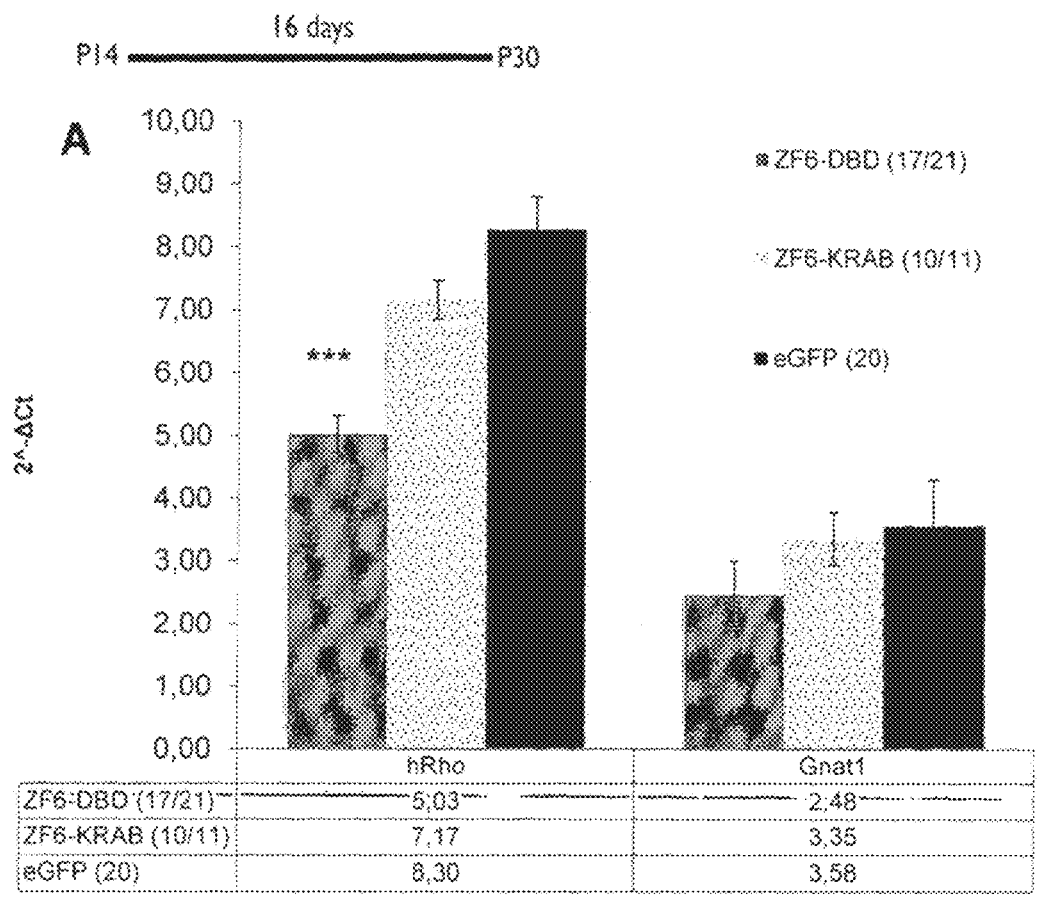
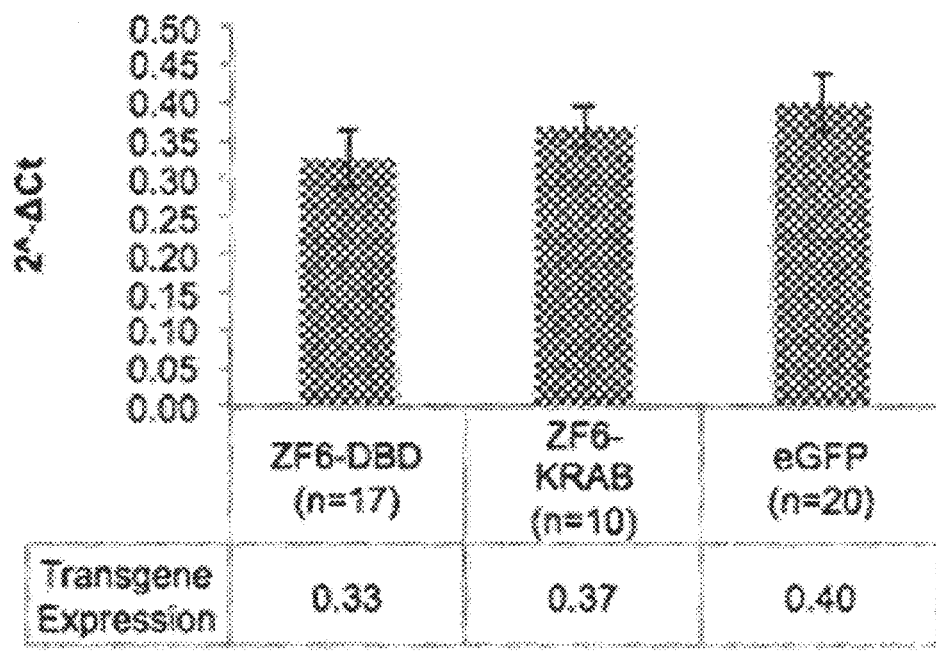
Fig.4 (1/2)

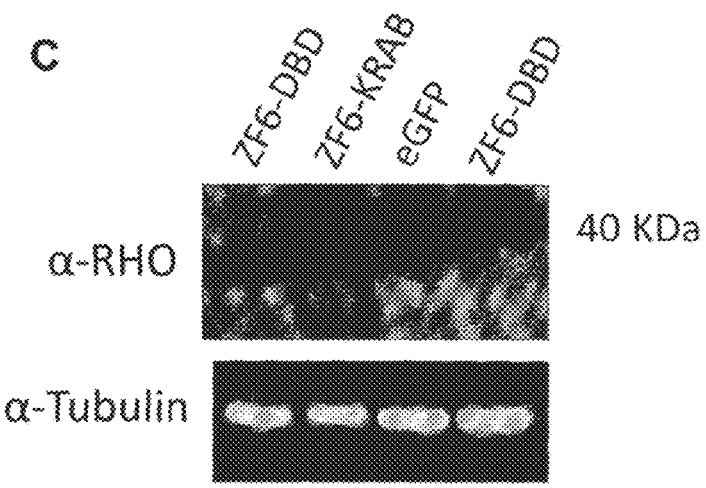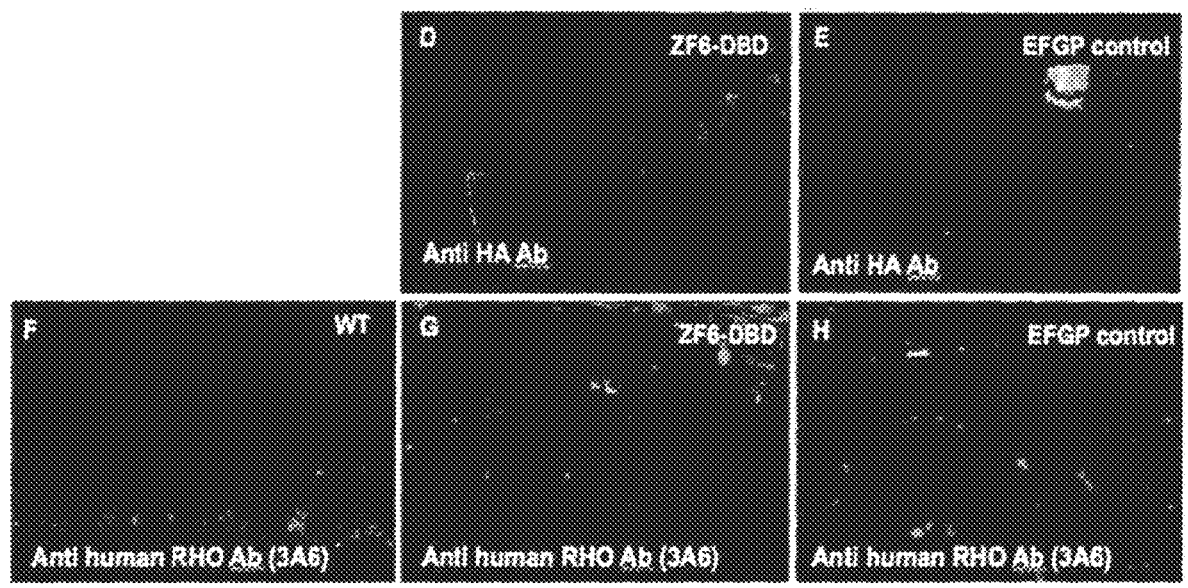
Fig. 4 (2/2)

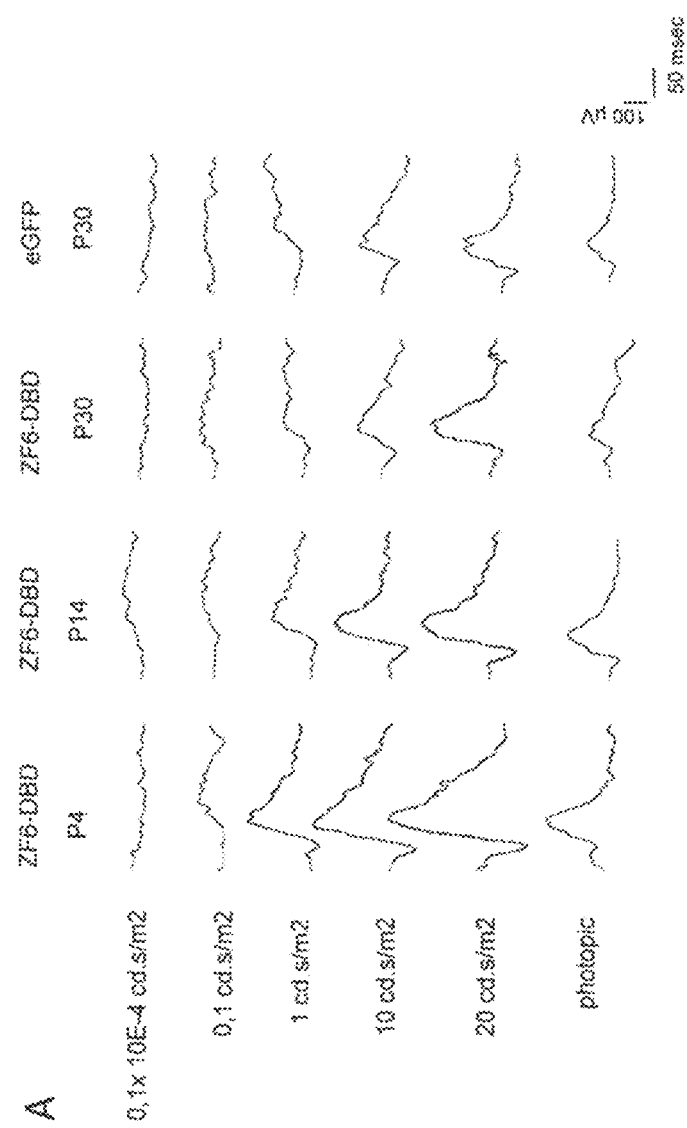
Fig. 6 (1/2)

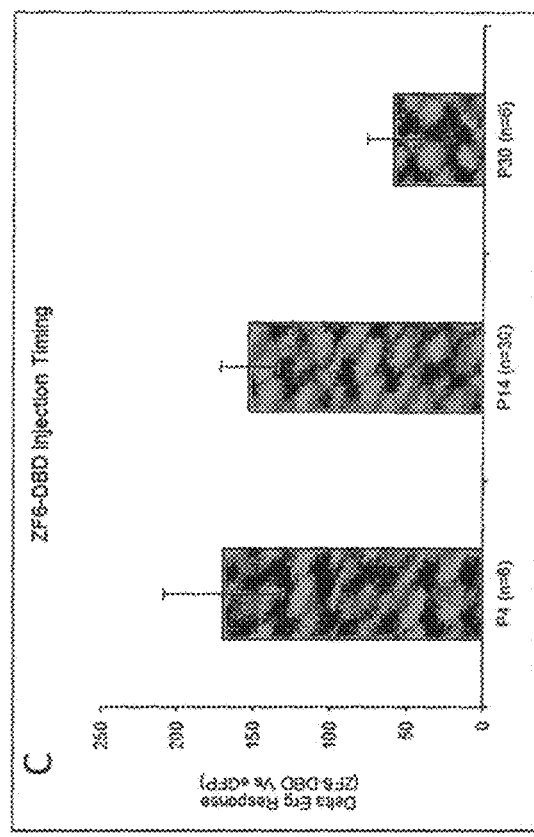
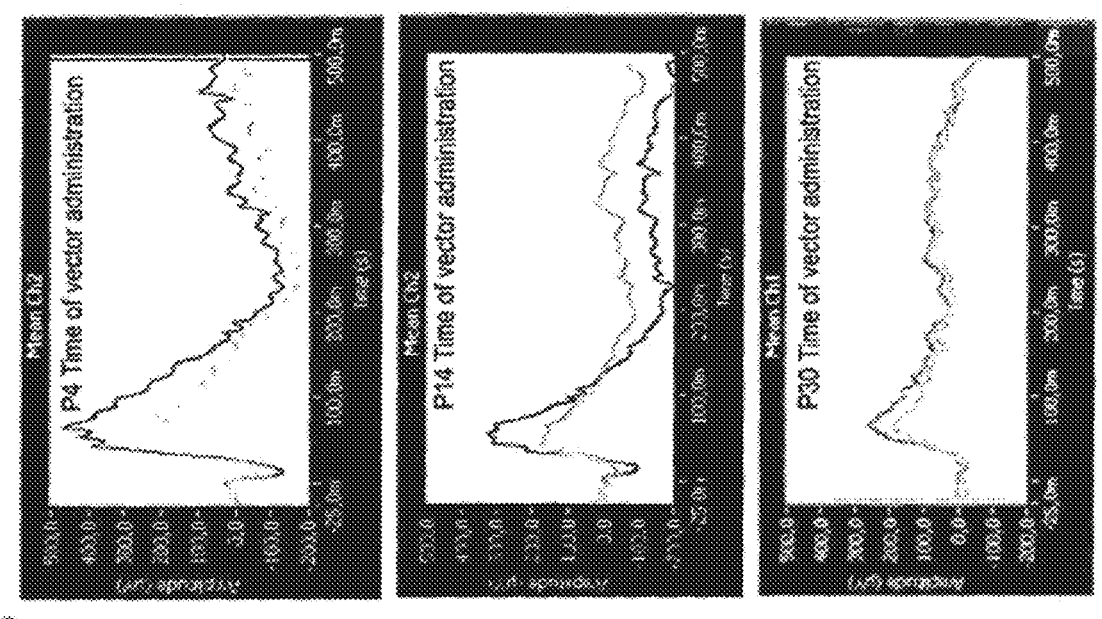
Fig 6 (2/2)

Fig. 9
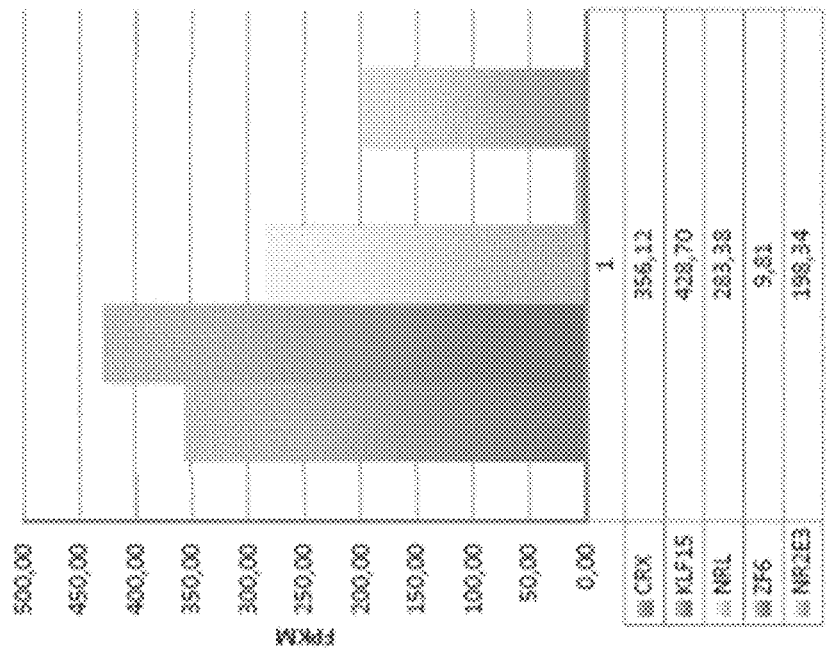
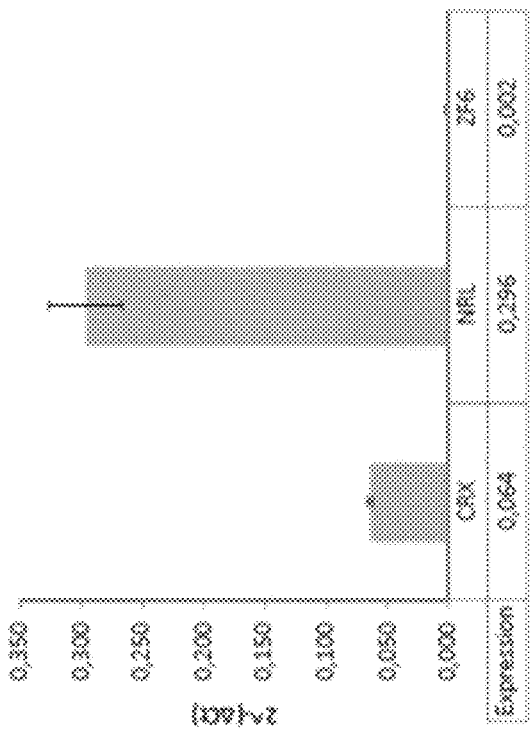

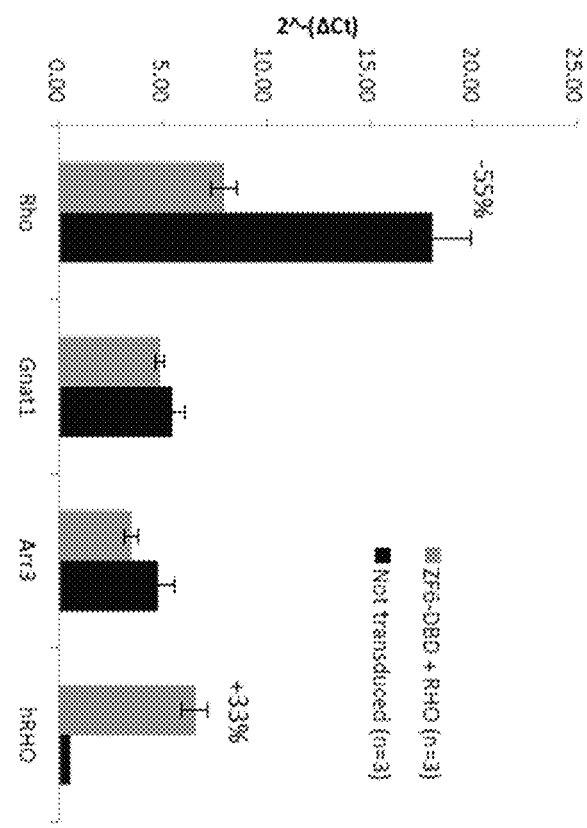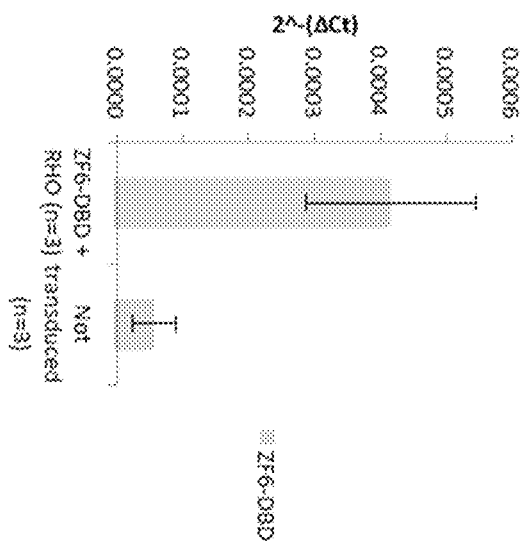
Fig. 16

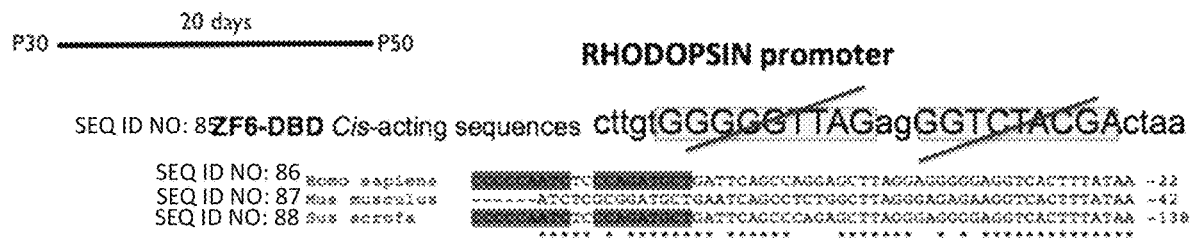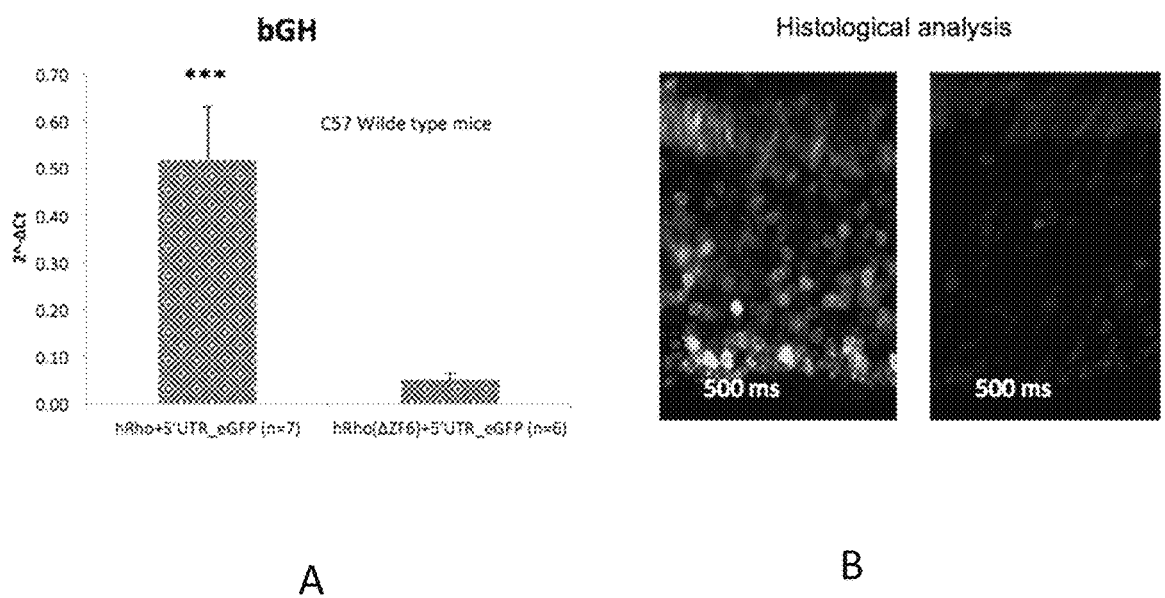
Fig. 19

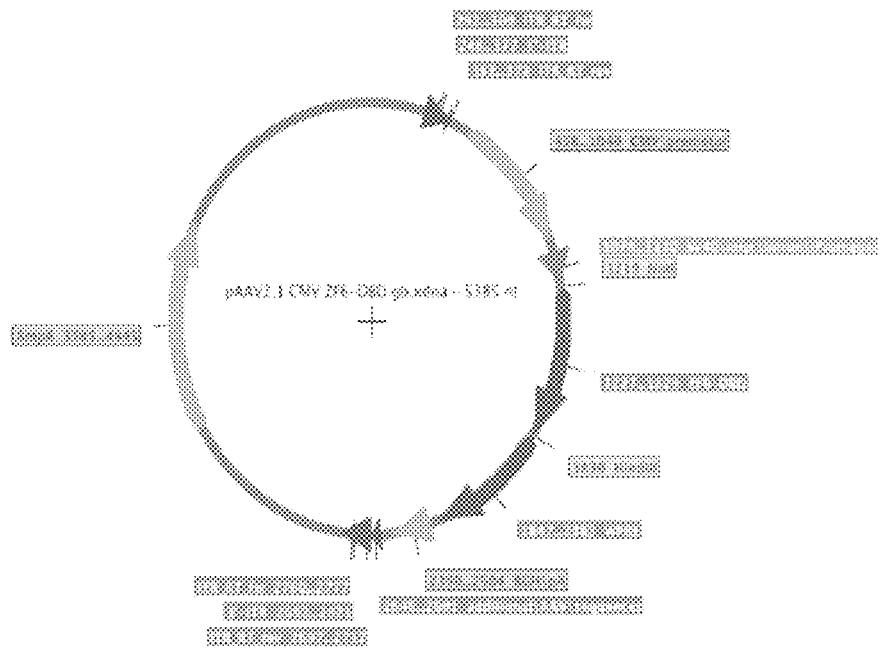

Features :

| | | |
|---|---|---|
| 5'-ITR | : | [248 : 377 - CW] |
| 3'-ITR | : | [2692 : 2821 - CW] |
| additional\AAV\sequences | : | [2646 : 2691 - CW] |
| CMV\promotor | : | [458 : 1040 - CW] |
| SV40\misc\intron\(Promega) | : | [1078 : 1210 - CW] |
| WPRE | : | [1847 : 2383 - CW] |
| BGH\pA | : | [2390 : 2604 - CW] |
| ITR_RT_fw | : | [292 : 309 - CW] |
| ITR_RT_rev | : | [352 : 372 - CW] |
| ITR_RT_rev | : | [2697 : 2717 - CW] |
| ITR_RT_fw | : | [2760 : 2777 - CW] |
| AmpR | : | [3585 : 4445 - CW] |
| ZF6\DBD | : | [1227 : 1829 - CW] |

ITR  Inverted Terminal Repeat
CMV  Cytomegalovirus
BGH  bovine growth hormone polyA
AmpR Ampicillin Resistance
WPRE woodchuck hepatitis posttranscriptional regulatory element

Fig. 24

```
Features :
5'-ITR                        : [248 ; 377 - CW]
3'-ITR                        : [3029 ; 3158 - CW]
additional\AAV\sequences      : [2983 ; 3028 - CW]
WPRE                          : [2179 ; 2720 - CW]
BGH\pA                        : [2727 ; 2941 - CW]
Rev\Ori\NheI                  : [5572 ; 5597 - CW]
Fw\NheI\Ori                   : [4779 ; 4802 - CW]
M13-fwd                       : [3194 ; 3177 - CCW]
M13-rev                       : [205 ; 225 - CW]
ColE1 origin                  : [4931 ; 5559 - CW]
LacZ alpha                    : [3265 ; 3333 - CW]
LacO                          : [177 ; 199 - CW]
Amp prom                      : [3852 ; 3880 - CW]
lac                           : [143 ; 172 - CW]
hGnat1 prom                   : [458 ; 1119 - CW]
hRho CDS                      : [1120 ; 2167 - CW]
```

```
Features :
5' ITR                           : [248 : 377 - CW]
CMV promoter                     : [458 : 1040 - CW]
SV40 misc intron (promega)       : [1078 : 1210 - CW]
BGH pA                           : [2309 : 2523 - CW]
Additional AVV sequence          : [2565 : 2610 - CW]
3' ITR                           : [2611 : 2740 - CW]
WPRE                             : [1761 : 2302 - CW]
M13-fwd                          : [2776 : 2759 - CCW]
M13-rev                          : [205 : 225 - CW]
ColE1 origin                     : [4513 : 5141 - CW]
LacZ alpha                       : [2847 : 2915 - CW]
LacO                             : [177 : 199 - CW]
Amp prom                         : [3434 : 3462 - CW]
lac                              : [143 : 172 - CW]
HA tag                           : [1713 : 1739 - CW]
FactorXa site                    : [2243 : 2232 - CCW]
ZF6-5F (also called ZF6-5)       : [1227 : 1748 - CW]
```

Features :
5' ITR                          : [248 : 377 - CW]
CMV promoter                    : [458 : 1040 - CW]
SV40 misc intron (promega)      : [1078 : 1210 - CW]
NLS                             : [1227 : 1256 - CW]
TAL7-DBD                        : [1257 : 3305 - CW]
bGH                             : [3312 : 3526 - CW]
3' ITR                          : [3568 : 3743 - CW]

Features:
5' ITR                         : [248 : 377 - CW]
CMV promoter                   : [458 : 1040 - CW]
SV40 misc intron (promega)     : [1078 : 1210 - CW]
NLS (*)                        : [1227 : 1251 - CW]
TALRHO(02)DBD                  : [1252 : 3566 - CW]
HA                             : [3567 : 3602 - CW]
3' ITR                         : [3917 : 4046 - CW]
bGH PolyA                      : [3615 : 3829 - CW]

Fig. 30

SEQUENCE LISTING

```
<160> NUMBER OF SEQ ID NOS: 101

<210> SEQ ID NO 1
<211> LENGTH: 891
<212> TYPE: DNA
<213> ORGANISM: Artificial Sequence
<220> FEATURE:
<223> OTHER INFORMATION: synthetic

<400> SEQUENCE: 1
cagatcttcc ccacctagcc acctggcaaa ctgctccttc tctcaaaggc ccaaacatgg      60
cctcccagac tgcaaccccc aggcagtcag gccctgtctc cacaacctca cagccaccct     120
ggacggaatc tgcttcttcc cacatttgag tcctcctcag cccctgagct cctctgggca     180
gggctgtttc tttccatctt tgtattccca ggggcctgca aataaatgtt taatgaacga     240
acaagagagt gaattccaat tccatgcaac aaggattggg ctcctgggcc ctaggctatg     300
tgtctggcac cagaaacgga agctgcaggt tgcagcccct gccctcatgg agctcctcct     360
gtcagaggag tgtggggact ggatgactcc agaggtaact tgtgggggaa cgaacaggta     420
aggggctgtg tgacgagatg agagactggg agaataaacc agaaagtctc tagctgtcca     480
gaggacatag cacagaggcc catggtccct atttcaaacc caggccacca gactgagctg     540
ggaccttggg acagacaagt catgcagaag ttaggggacc ttctcctccc ttttcctgga     600
tcctgagtac ctctcctccc tgacctcagg cttcctccta gtgtcacctt ggcccctctt     660
agaagccaat taggccctca gtttctgcag cggggattaa tatgattatg aacacccccca    720 atctcccaga tgctgattca gccaggagct taggaggggg aggtcacttt ataagggtct     780
gggggggtca gaacccagag tcatccagct ggagccctga gtggctgagc tcaggccttc     840
gcagcattct tgggtgggag cagccacggg tcagccacaa gggccacagc c              891

<210> SEQ ID NO 2
<211> LENGTH: 603
<212> TYPE: DNA
<213> ORGANISM: Artificial Sequence
<220> FEATURE:
<223> OTHER INFORMATION: synthetic

<400> SEQUENCE: 2
atgatcgatc tggaacctgg cgaaaaaccg tataagtgcc cagaatgcgg caagtctttt      60
tcccagtctg gccacctgac ggaacatcag cgcactcaca ccggcgagaa accatataaa     120
tgtccggagt gcggcaagag ctttagccag aatagcaccc tgaccgaaca tcagcgtacg     180
cacacgggtg aaaagccata taatgccct gagtgcggca aatcctttag cacctctggc     240
catctggtcc gtcaccagcg cacccaccag aataagaagg gcggttctgg tgacggtaaa     300
aagaaacagc acgcctgtcc agagtgtggc aaatctttt cccgtgaaga caacctgcac     360
actcaccagc gcactcatac tggcgagaaa ccttacaagt gtccggaatg tggtaagagc     420
ttctccactt ccggccatct ggttcgtcac cagcgcacgc acaccggcga aaaaccatac     480
```

```
aagtgcccgg aatgcggcaa atcattctcc cgtagcgaca aactggttcg tcaccaacgt      540
acgcataccg gtaaaaagac ttcctctaga tacccgtacg acgttccaga ctatgcatct      600
tga                                                                    603
```

<210> SEQ ID NO 3
<211> LENGTH: 200
<212> TYPE: PRT
<213> ORGANISM: Artificial Sequence
<220> FEATURE:
<223> OTHER INFORMATION: synthetic

<400> SEQUENCE: 3

```
Met Ile Asp Leu Glu Pro Gly Glu Lys Pro Tyr Lys Cys Pro Glu Cys
1               5                   10                  15

Gly Lys Ser Phe Ser Gln Ser Gly His Leu Thr Glu His Gln Arg Thr
            20                  25                  30

His Thr Gly Glu Lys Pro Tyr Lys Cys Pro Glu Cys Gly Lys Ser Phe
        35                  40                  45

Ser Gln Asn Ser Thr Leu Thr Glu His Gln Arg Thr His Thr Gly Glu
    50                  55                  60

Lys Pro Tyr Lys Cys Pro Glu Cys Gly Lys Ser Phe Ser Thr Ser Gly
65                  70                  75                  80

His Leu Val Arg His Gln Arg Thr His Gln Asn Lys Lys Gly Gly Ser
                85                  90                  95

Gly Asp Gly Lys Lys Lys Gln His Ala Cys Pro Glu Cys Gly Lys Ser
            100                 105                 110

Phe Ser Arg Glu Asp Asn Leu His Thr His Gln Arg Thr His Thr Gly
        115                 120                 125

Glu Lys Pro Tyr Lys Cys Pro Glu Cys Gly Lys Ser Phe Ser Thr Ser
    130                 135                 140

Gly His Leu Val Arg His Gln Arg Thr His Thr Gly Glu Lys Pro Tyr
145                 150                 155                 160

Lys Cys Pro Glu Cys Gly Lys Ser Phe Ser Arg Ser Asp Lys Leu Val
                165                 170                 175

Arg His Gln Arg Thr His Thr Gly Lys Lys Thr Ser Ser Arg Tyr Pro
            180                 185                 190

Tyr Asp Val Pro Asp Tyr Ala Ser
        195                 200
```

<210> SEQ ID NO 4
<211> LENGTH: 681
<212> TYPE: DNA
<213> ORGANISM: Artificial Sequence
<220> FEATURE:
<223> OTHER INFORMATION: synthetic

<400> SEQUENCE: 4

```
atgatcgatc tggaacctgg cgaaaaaccg tataagtgcc cagaatgcgg caagtctttt      60
tccacctctg gcaatctggt cgccatcag cgcactcaca ccggcgagaa accatataaa     120
tgtccggagt gcggcaagag ctttagcact agcggcgagc tggtccgtca tcagcgtacg     180
cacacgggtg aaaagccata taatgccct gagtgcggca atcctttag cacctctggt      240 aacctggtac gtcaccagcg cacccacacg ggccgttctt ctgtagagtc tgcgtgcgtc     300
acctctgtat tggttgccct cctgccggct acctctgcac cgactcaggt gagcggtgaa     360
aagccataca atgtccaga gtgtggcaaa tctttttccc agtctggcaa cctgactgaa     420
```

```
caccagcgca ctcatactgg cgagaaacct tacaagtgtc cggaatgtgg taagagcttc    480
tcctccaaaa agcatctggc tgagcaccag cgcacgcaca ccggcgaaaa accatacaag    540
tgcccggaat gcggcaaatc attcagctcc aaaaaggctc tgactgagca ccaacgtacg    600
cataccggta aaaagacttc ctctagaccg aaaaagaaac gcaaagttta cccatacgac    660
gtacctgatt atgcaagctg a                                              681
```

<210> SEQ ID NO 5
<211> LENGTH: 226
<212> TYPE: PRT
<213> ORGANISM: Artificial Sequence
<220> FEATURE:
<223> OTHER INFORMATION: synthetic

<400> SEQUENCE: 5

```
Met Ile Asp Leu Glu Pro Gly Glu Lys Pro Tyr Lys Cys Pro Glu Cys
1               5                   10                  15

Gly Lys Ser Phe Ser Thr Ser Gly Asn Leu Val Arg His Gln Arg Thr
            20                  25                  30

His Thr Gly Glu Lys Pro Tyr Lys Cys Pro Glu Cys Gly Lys Ser Phe
        35                  40                  45

Ser Thr Ser Gly Glu Leu Val Arg His Gln Arg Thr His Thr Gly Glu
    50                  55                  60

Lys Pro Tyr Lys Cys Pro Glu Cys Gly Lys Ser Phe Ser Thr Ser Gly
65                  70                  75                  80

Asn Leu Val Arg His Gln Arg Thr His Thr Gly Arg Ser Ser Val Glu
                85                  90                  95

Ser Ala Cys Val Thr Ser Val Leu Val Ala Leu Leu Pro Ala Thr Ser
            100                 105                 110

Ala Pro Thr Gln Val Ser Gly Glu Lys Pro Tyr Lys Cys Pro Glu Cys
        115                 120                 125

Gly Lys Ser Phe Ser Gln Ser Gly Asn Leu Thr Glu His Gln Arg Thr
    130                 135                 140

His Thr Gly Glu Lys Pro Tyr Lys Cys Pro Glu Cys Gly Lys Ser Phe
145                 150                 155                 160

Ser Ser Lys Lys His Leu Ala Glu His Gln Arg Thr His Thr Gly Glu
                165                 170                 175

Lys Pro Tyr Lys Cys Pro Glu Cys Gly Lys Ser Phe Ser Ser Lys Lys
            180                 185                 190

Ala Leu Thr Glu His Gln Arg Thr His Thr Gly Lys Lys Thr Ser Ser
        195                 200                 205

Arg Pro Lys Lys Lys Arg Lys Val Tyr Pro Tyr Asp Val Pro Asp Tyr
    210                 215                 220

Ala Ser
225
```

<210> SEQ ID NO 6
<211> LENGTH: 3021
<212> TYPE: DNA
<213> ORGANISM: Artificial Sequence
<220> FEATURE:
<223> OTHER INFORMATION: synthetic

<400> SEQUENCE: 6

```
atgtacccat acgatgtccc agactacgcg aatttaatgt cgcggaccccg gctcccttcc    60 ccacccgcac ccagcccagc gttttcggcc gactcgttct cagacctgct taggcagttc   120
```

```
gacccctcac tgtttaacac atcgttgttc gactcccttc ctccgtttgg ggcgcaccat    180
acggaggcgg ccaccgggga gtgggatgag gtgcagtcgg gattgagagc tgcggatgca    240
ccacccccaa ccatgcgggt ggccgtcacc gctgcccgac cgccgagggc gaagcccgca    300
ccaaggcgga gggcagcgca accgtccgac gcaagcccg cagcgcaagt agatttgaga    360
actttgggat attcacagca gcagcaggaa aagatcaagc ccaaagtgag gtcgacagtc    420
gcgcagcatc acgaagcgct ggtgggtcat gggtttacac atgcccacat cgtagccttg    480
tcgcagcacc ctgcagccct tggcacggtc gccgtcaagt accaggacat gattgcggcg    540
ttgccggaag ccacacatga ggcgatcgtc ggtgtgggga acagtggag cggagcccga    600 gcgcttgagg ccctgttgac ggtcgcggga gagctgagag ggcctcccct tcagctggac    660
acgggccagt tgctgaagat cgcgaagcgg ggaggagtca cggcggtcga ggcggtgcac    720
gcgtggcgca atgcgctcac gggagcaccc ctcaacctga ccccagagca ggtcgtggca    780
attgcgagcc atgacggggg aaagcaggca ctcgaaaccg tccagaggtt gctgcctgtg    840
ctgtgccaag cgcacggact tacgccagag caggtcgtgg caattgcgag caacatcggg    900
ggaaagcagg cactcgaaac cgtccagagg ttgctgcctg tgctgtgcca agcgcacgga    960
ctaaccccag agcaggtcgt ggcaattgcg agcaacaacg ggggaaagca ggcactcgaa   1020
accgtccaga ggttgctgcc tgtgctgtgc caagcgcacg gttgacccc agagcaggtc   1080 gtggcaattg cgagccatga cggggggaaag caggcactcg aaaccgtcca gaggttgctg   1140
cctgtgctgt gccaagcgca cggcctgacc ccagagcagg tcgtggcaat tgcgagcaac   1200
atcgggggaa agcaggcact cgaaaccgtc cagaggttgc tgcctgtgct gtgccaagcg   1260
cacggactga caccagagca ggtcgtggca attgcgagca acggaggggg aaagcaggca   1320
ctcgaaaccg tccagaggtt gctgcctgtg ctgtgccaag cgcacggact tacacccgaa   1380
caagtcgtgg caattgcgag ccatgacggg ggaaagcagg cactcgaaac cgtccagagg   1440
ttgctgcctg tgctgtgcca agcgcacgga cttacgccag agcaggtcgt ggcaattgcg   1500
agcaacggag ggggaaagca ggcactcgaa accgtccaga ggttgctgcc tgtgctgtgc   1560
caagcgcacg gactaacccc agagcaggtc gtggcaattg cgagcaacaa cggggggaaag   1620 caggcactcg aaaccgtcca gaggttgctg cctgtgctgt gccaagcgca cgggttgacc   1680
ccagagcagg tcgtggcaat tgcgagcaac aacggggggaa agcaggcact cgaaaccgtc   1740
cagaggttgc tgcctgtgct gtgccaagcg cacggcctga ccccagagca ggtcgtggca   1800
attgcgagca caacgggggg aaagcaggca ctcgaaaccg tccagaggtt gctgcctgtg   1860
ctgtgccaag cgcacggact gacaccagag caggtcgtgg caattgcgag caacatcggg   1920
ggaaagcagg cactcgaaac cgtccagagg ttgctgcctg tgctgtgcca agcgcacggc   1980
ctcaccccag agcaggtcgt ggcaattgcg agcaacaacg ggggaaagca ggcactcgaa   2040
accgtccaga ggttgctgcc tgtgctgtgc caagcgcacg gacttacgcc agagcaggtc   2100
gtggcaattg cgagcaacat cgggggaaag caggcactcg aaaccgtcca gaggttgctg   2160
cctgtgctgt gccaagcgca cggactaacc ccagagcagg tcgtggcaat tgcgagcaac   2220
ggagggggaa agcaggcact cgaaaccgtc cagaggttgc tgcctgtgct gtgccaagcg   2280
cacgggttga ccccagagca ggtcgtggca attgcgagca acggaggggg aaagcaggca   2340
ctcgaaaccg tccagaggtt gctgcctgtg ctgtgccaag cgcacggact cacgcctgag   2400
caggtagtgg ctattgcatc caataacggg ggcagacccg cactggagtc aatcgtggcc   2460
```

```
cagctttcga ggccggaccc cgcgctggcc gcactcacta atgatcatct tgtagcgctg    2520
gcctgcctcg gcggacgacc cgccttggat gcggtgaaga aggggctccc gcacgcgcct    2580
gcattgatta agcggaccaa cagaaggatt cccgagagga catcacatcg agtggcagat    2640
cacgcgcaag tggtccgcgt gctcggattc ttccagtgtc actccacccc cgcacaagcg    2700
ttcgatgacg ccatgactca atttggtatg tcgagacacg gactgctgca gctctttcgt    2760
agagtcggtg tcacagaact cgaggcccgc tcgggcacac tgcctcccgc ctcccagcgg    2820
tgggacagga ttctccaagc gagcggtatg aaacgcgcga agccttcacc tacgtcaact    2880
cagacacctg accaggcgag ccttcatgcg ttcgcagact cgctggagag ggatttggac    2940
gcgccctcgc ccatgcatga aggggaccaa actcgcgcgt cagctagccc caagaagaag    3000
agaaaggtgg aggccagctg a                                              3021
```

<210> SEQ ID NO 7
<211> LENGTH: 1006
<212> TYPE: PRT
<213> ORGANISM: Artificial Sequence
<220> FEATURE:
<223> OTHER INFORMATION: synthetic

<400> SEQUENCE: 7

```
Met Tyr Pro Tyr Asp Val Pro Asp Tyr Ala Asn Leu Met Ser Arg Thr
1               5                   10                  15

Arg Leu Pro Ser Pro Pro Ala Pro Ser Pro Ala Phe Ser Ala Asp Ser
            20                  25                  30

Phe Ser Asp Leu Leu Arg Gln Phe Asp Pro Ser Leu Phe Asn Thr Ser
        35                  40                  45

Leu Phe Asp Ser Leu Pro Pro Phe Gly Ala His His Thr Glu Ala Ala
    50                  55                  60

Thr Gly Glu Trp Asp Glu Val Gln Ser Gly Leu Arg Ala Ala Asp Ala
65                  70                  75                  80

Pro Pro Pro Thr Met Arg Val Ala Val Thr Ala Ala Arg Pro Pro Arg
                85                  90                  95

Ala Lys Pro Ala Pro Arg Arg Arg Ala Ala Gln Pro Ser Asp Ala Ser
            100                 105                 110

Pro Ala Ala Gln Val Asp Leu Arg Thr Leu Gly Tyr Ser Gln Gln Gln
        115                 120                 125

Gln Glu Lys Ile Lys Pro Lys Val Arg Ser Thr Val Ala Gln His His
    130                 135                 140

Glu Ala Leu Val Gly His Gly Phe Thr His Ala His Ile Val Ala Leu
145                 150                 155                 160

Ser Gln His Pro Ala Ala Leu Gly Thr Val Ala Val Lys Tyr Gln Asp
                165                 170                 175

Met Ile Ala Ala Leu Pro Glu Ala Thr His Glu Ala Ile Val Gly Val
            180                 185                 190

Gly Lys Gln Trp Ser Gly Ala Arg Ala Leu Glu Ala Leu Leu Thr Val
        195                 200                 205

Ala Gly Glu Leu Arg Gly Pro Pro Leu Gln Leu Asp Thr Gly Gln Leu
    210                 215                 220

Leu Lys Ile Ala Lys Arg Gly Gly Val Thr Ala Val Glu Ala Val His
225                 230                 235                 240

Ala Trp Arg Asn Ala Leu Thr Gly Ala Pro Leu Asn Leu Thr Pro Glu
                245                 250                 255

Gln Val Val Ala Ile Ala Ser His Asp Gly Gly Lys Gln Ala Leu Glu
```

-continued

```
                260             265             270
Thr Val Gln Arg Leu Leu Pro Val Leu Cys Gln Ala His Gly Leu Thr
            275             280             285
Pro Glu Gln Val Val Ala Ile Ala Ser Asn Ile Gly Gly Lys Gln Ala
        290             295             300
Leu Glu Thr Val Gln Arg Leu Leu Pro Val Leu Cys Gln Ala His Gly
305             310             315             320
Leu Thr Pro Glu Gln Val Val Ala Ile Ala Ser Asn Asn Gly Gly Lys
            325             330             335
Gln Ala Leu Glu Thr Val Gln Arg Leu Leu Pro Val Leu Cys Gln Ala
        340             345             350
His Gly Leu Thr Pro Glu Gln Val Val Ala Ile Ala Ser His Asp Gly
    355             360             365
Gly Lys Gln Ala Leu Glu Thr Val Gln Arg Leu Leu Pro Val Leu Cys
370             375             380
Gln Ala His Gly Leu Thr Pro Glu Gln Val Val Ala Ile Ala Ser Asn
385             390             395             400
Ile Gly Gly Lys Gln Ala Leu Glu Thr Val Gln Arg Leu Leu Pro Val
            405             410             415
Leu Cys Gln Ala His Gly Leu Thr Pro Glu Gln Val Val Ala Ile Ala
        420             425             430
Ser Asn Gly Gly Lys Gln Ala Leu Glu Thr Val Gln Arg Leu Leu
435             440             445
Pro Val Leu Cys Gln Ala His Gly Leu Thr Pro Glu Gln Val Val Ala
    450             455             460
Ile Ala Ser His Asp Gly Gly Lys Gln Ala Leu Glu Thr Val Gln Arg
465             470             475             480
Leu Leu Pro Val Leu Cys Gln Ala His Gly Leu Thr Pro Glu Gln Val
            485             490             495
Val Ala Ile Ala Ser Asn Gly Gly Gly Lys Gln Ala Leu Glu Thr Val
        500             505             510
Gln Arg Leu Leu Pro Val Leu Cys Gln Ala His Gly Leu Thr Pro Glu
    515             520             525
Gln Val Val Ala Ile Ala Ser Asn Asn Gly Gly Lys Gln Ala Leu Glu
    530             535             540
Thr Val Gln Arg Leu Leu Pro Val Leu Cys Gln Ala His Gly Leu Thr
545             550             555             560
Pro Glu Gln Val Val Ala Ile Ala Ser Asn Asn Gly Gly Lys Gln Ala
            565             570             575
Leu Glu Thr Val Gln Arg Leu Leu Pro Val Leu Cys Gln Ala His Gly
        580             585             590
Leu Thr Pro Glu Gln Val Val Ala Ile Ala Ser Asn Asn Gly Gly Lys
    595             600             605
Gln Ala Leu Glu Thr Val Gln Arg Leu Leu Pro Val Leu Cys Gln Ala
    610             615             620
His Gly Leu Thr Pro Glu Gln Val Val Ala Ile Ala Ser Asn Ile Gly
625             630             635             640
Gly Lys Gln Ala Leu Glu Thr Val Gln Arg Leu Leu Pro Val Leu Cys
            645             650             655
Gln Ala His Gly Leu Thr Pro Glu Gln Val Val Ala Ile Ala Ser Asn
        660             665             670
Asn Gly Gly Lys Gln Ala Leu Glu Thr Val Gln Arg Leu Leu Pro Val
    675             680             685
```

| Leu | Cys | Gln | Ala | His | Gly | Leu | Thr | Pro | Glu | Gln | Val | Ala | Ile | Ala |
|---|---|---|---|---|---|---|---|---|---|---|---|---|---|---|
| | 690 | | | | 695 | | | | 700 | | | | | |

Ser Asn Ile Gly Gly Lys Gln Ala Leu Glu Thr Val Gln Arg Leu Leu
705              710                  715                  720

Pro Val Leu Cys Gln Ala His Gly Leu Thr Pro Glu Gln Val Ala
         725                  730                  735

Ile Ala Ser Asn Gly Gly Lys Gln Ala Leu Glu Thr Val Gln Arg
             740                  745                  750

Leu Leu Pro Val Leu Cys Gln Ala His Gly Leu Thr Pro Glu Gln Val
         755                  760                  765

Val Ala Ile Ala Ser Asn Gly Gly Lys Gln Ala Leu Glu Thr Val
770                  775                  780

Gln Arg Leu Leu Pro Val Leu Cys Gln Ala His Gly Leu Thr Pro Glu
785                  790                  795                  800

Gln Val Val Ala Ile Ala Ser Asn Asn Gly Gly Arg Pro Ala Leu Glu
                 805                  810                  815

Ser Ile Val Ala Gln Leu Ser Arg Pro Asp Pro Ala Leu Ala Ala Leu
             820                  825                  830

Thr Asn Asp His Leu Val Ala Leu Ala Cys Leu Gly Gly Arg Pro Ala
         835                  840                  845

Leu Asp Ala Val Lys Lys Gly Leu Pro His Ala Pro Ala Leu Ile Lys
    850                  855                  860

Arg Thr Asn Arg Arg Ile Pro Glu Arg Thr Ser His Arg Val Ala Asp
865                  870                  875                  880

His Ala Gln Val Val Arg Val Leu Gly Phe Phe Gln Cys His Ser His
                 885                  890                  895

Pro Ala Gln Ala Phe Asp Asp Ala Met Thr Gln Phe Gly Met Ser Arg
             900                  905                  910

His Gly Leu Leu Gln Leu Phe Arg Arg Val Gly Val Thr Glu Leu Glu
         915                  920                  925

Ala Arg Ser Gly Thr Leu Pro Pro Ala Ser Gln Arg Trp Asp Arg Ile
    930                  935                  940

Leu Gln Ala Ser Gly Met Lys Arg Ala Lys Pro Ser Pro Thr Ser Thr
945                  950                  955                  960

Gln Thr Pro Asp Gln Ala Ser Leu His Ala Phe Ala Asp Ser Leu Glu
                 965                  970                  975

Arg Asp Leu Asp Ala Pro Ser Pro Met His Glu Gly Asp Gln Thr Arg
             980                  985                  990

Ala Ser Ala Ser Pro Lys Lys Lys Arg Lys Val Glu Ala Ser
         995                  1000                 1005

<210> SEQ ID NO 8
<211> LENGTH: 2085
<212> TYPE: DNA
<213> ORGANISM: Artificial Sequence
<220> FEATURE:
<223> OTHER INFORMATION: synthetic

<400> SEQUENCE: 8

| atgtacccat acgatgtccc agactacgcg aatttaaaacc ccaagaagaa gcggaaggtg | 60 |
|---|---|
| cacgggaatt ctgcgagcgc gccgcgccgc cgcgcggcgc agccgagcga tgcgagcccg | 120 |
| gcggcgcagg tggatctgcg caccctgggc tatagccagc agcagcagga aaaaattaaa | 180 |
| ccgaaagtgc gcagcaccgt ggcgcagcat catgaagcgc tggtgggcca tggctttacc | 240 |

| | |
|---|---|
| catgcgcata ttgtggcgct gagccagcat ccggcggcgc tgggcaccgt ggcggtgaaa | 300 |
| tatcaggata tgattgcggc gctgccggaa gcgacccatg aagcgattgt gggcgtgggc | 360 |
| aaacagtgga gcggcgcgcg cgcgctggaa gcgctgctga ccgtggcggg cgaactgcgc | 420 |
| ggcccgccgc tgcagctgga taccggccag ctgctgaaaa ttgcgaaacg cggcggcgtg | 480 |
| accgcggtgg aagcggtgca tgcgtggcgc aacgcgctga ccggcgcgcc gctgaacctg | 540 |
| accccgcagc aggtggtggc gattgcgagc catgatggcg gcaaacaggc gctggaaacc | 600 |
| gtgcagcgcc tgctgccggt gctgtgccag gcgcatggcc tgaccccgga acaggtggtg | 660 |
| gcgattgcga gcaacggcgg cggcaaacag cgcgctgaaa ccgtgcagcg cctgctgccg | 720 |
| gtgctgtgcc aggcgcatgg cctgaccccg aacaggtgg tggcgattgc gagcaacaac | 780 |
| ggcggcaaac aggcgctgga accgtgcag cgcctgctgc cggtgctgtg ccaggcgcat | 840 |
| ggcctgaccc cggaacaggt ggtggcgatt gcgagcaaca acgcggcaa acaggcgctg | 900 |
| gaaaccgtgc agcgcctgct gccggtgctg tgccaggcgc atggcctgac cccggaacag | 960 |
| gtggtggcga ttgcgagcaa caacggcggc aaacaggcgc tggaaaccgt gcagcgcctg | 1020 |
| ctgccggtgc tgtgccaggc gcatggcctg accccggaac aggtggtggc gattgcgagc | 1080 |
| aacattggcg gcaaacaggc gctggaaacc gtgcagcgcc tgctgccggt gctgtgccag | 1140 |
| gcgcatggcc tgaccccgca gcaggtggtg gcgattgcga gcaacaacgg cggcaaacag | 1200 |
| gcgctggaaa ccgtgcaggc gctgctgccg gtgctgtgcc aggcgcatgg cctgaccccg | 1260 |
| gaacaggtgg tggcgattgc gagcaacatt ggcggcaaac aggcgctgga accgtgcag | 1320 |
| gcgctgctgc cggtgctgtg ccaggcgcat ggcctgaccc cggaacaggt ggtggcgatt | 1380 |
| gcgagcaacg gcggcggcaa acaggcgctg gaaaccgtgc agcgcctgct gccggtgctg | 1440 |
| tgccaggcgc atggcctgac cccgcagcag gtggtgcga ttgcgagcaa cggcggcggc | 1500 |
| aaacaggcgc tggaaaccgt gcagcgcctg ctgccggtgc tgtgccaggc gcatggcctg | 1560 |
| accccgcagc aggtggtggc gattgcgagc aacaacggcg gcaaacaggc gctggaaacc | 1620 |
| gtgcagcgcc tgctgccggt gctgtgccag gcgcatggcc tgaccccgga acaggtggtg | 1680 |
| gcgattgcga gcaacaacgg cggcaaacag gcgctggaaa ccgtgcagcg cctgctgccg | 1740 |
| gtgctgtgcc aggcgcatgg cctgaccccg aacaggtgg tggcgattgc gagcaacaac | 1800 |
| ggcggcaaac aggcgctgga accgtgcag cgcctgctgc cggtgctgtg ccaggcgcat | 1860 |
| ggcctgaccc cggaacaggt ggtggcgatt gcgagcaaca acgcggcaa acaggcgctg | 1920 |
| gaaaccgtgc agcgcctgct gccggtgctg tgccaggcgc atggcctgac cccgcagcag | 1980 |
| gtggtggcga ttgcgagcaa caacggcggc cgcccggcgc tggaaagcat tgtggcgcag | 2040 |
| ctgagccgcc cggatccggc gctggcggcg ctgaccggca gctga | 2085 |

<210> SEQ ID NO 9
<211> LENGTH: 694
<212> TYPE: PRT
<213> ORGANISM: Artificial Sequence
<220> FEATURE:
<223> OTHER INFORMATION: synthetic

<400> SEQUENCE: 9

Met Tyr Pro Tyr Asp Val Pro Asp Tyr Ala Asn Leu Asn Pro Lys Lys
1               5                   10                  15

Lys Arg Lys Val His Gly Asn Ser Ala Ser Ala Pro Arg Arg Arg Ala
            20                  25                  30

Ala Gln Pro Ser Asp Ala Ser Pro Ala Ala Gln Val Asp Leu Arg Thr

```
                 35                  40                  45
Leu Gly Tyr Ser Gln Gln Gln Glu Lys Ile Lys Pro Lys Val Arg
 50                  55                  60

Ser Thr Val Ala Gln His His Glu Ala Leu Val Gly His Gly Phe Thr
 65                  70                  75                  80

His Ala His Ile Val Ala Leu Ser Gln His Pro Ala Ala Leu Gly Thr
                 85                  90                  95

Val Ala Val Lys Tyr Gln Asp Met Ile Ala Ala Leu Pro Glu Ala Thr
                100                 105                 110

His Glu Ala Ile Val Gly Val Gly Lys Gln Trp Ser Gly Ala Arg Ala
                115                 120                 125

Leu Glu Ala Leu Leu Thr Val Ala Gly Glu Leu Arg Gly Pro Pro Leu
130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Gln Gln Val Val Ala Ile Ala Ser His Asp
                180                 185                 190

Gly Gly Lys Gln Ala Leu Glu Thr Val Gln Arg Leu Leu Pro Val Leu
                195                 200                 205

Cys Gln Ala His Gly Leu Thr Pro Glu Gln Val Val Ala Ile Ala Ser
210                 215                 220

Asn Gly Gly Lys Gln Ala Leu Glu Thr Val Gln Arg Leu Leu Pro
225                 230                 235                 240

Val Leu Cys Gln Ala His Gly Leu Thr Pro Glu Gln Val Val Ala Ile
                245                 250                 255

Ala Ser Asn Asn Gly Gly Lys Gln Ala Leu Glu Thr Val Gln Arg Leu
                260                 265                 270

Leu Pro Val Leu Cys Gln Ala His Gly Leu Thr Pro Glu Gln Val Val
                275                 280                 285

Ala Ile Ala Ser Asn Asn Gly Gly Lys Gln Ala Leu Glu Thr Val Gln
290                 295                 300

Arg Leu Leu Pro Val Leu Cys Gln Ala His Gly Leu Thr Pro Glu Gln
305                 310                 315                 320

Val Val Ala Ile Ala Ser Asn Asn Gly Gly Lys Gln Ala Leu Glu Thr
                325                 330                 335

Val Gln Arg Leu Leu Pro Val Leu Cys Gln Ala His Gly Leu Thr Pro
                340                 345                 350

Glu Gln Val Val Ala Ile Ala Ser Asn Ile Gly Gly Lys Gln Ala Leu
                355                 360                 365

Glu Thr Val Gln Arg Leu Leu Pro Val Leu Cys Gln Ala His Gly Leu
                370                 375                 380

Thr Pro Gln Gln Val Val Ala Ile Ala Ser Asn Gly Gly Lys Gln
385                 390                 395                 400

Ala Leu Glu Thr Val Gln Ala Leu Leu Pro Val Leu Cys Gln Ala His
                405                 410                 415

Gly Leu Thr Pro Glu Gln Val Val Ala Ile Ala Ser Asn Ile Gly Gly
                420                 425                 430

Lys Gln Ala Leu Glu Thr Val Gln Ala Leu Leu Pro Val Leu Cys Gln
                435                 440                 445

Ala His Gly Leu Thr Pro Glu Gln Val Val Ala Ile Ala Ser Asn Gly
                450                 455                 460
```

Gly Gly Lys Gln Ala Leu Glu Thr Val Gln Arg Leu Leu Pro Val Leu
465                 470                 475                 480

Cys Gln Ala His Gly Leu Thr Pro Gln Gln Val Val Ala Ile Ala Ser
                485                 490                 495

Asn Gly Gly Lys Gln Ala Leu Glu Thr Val Gln Arg Leu Leu Pro
            500                 505                 510

Val Leu Cys Gln Ala His Gly Leu Thr Pro Gln Gln Val Val Ala Ile
        515                 520                 525

Ala Ser Asn Asn Gly Gly Lys Gln Ala Leu Glu Thr Val Gln Arg Leu
    530                 535                 540

Leu Pro Val Leu Cys Gln Ala His Gly Leu Thr Pro Glu Gln Val Val
545                 550                 555                 560

Ala Ile Ala Ser Asn Asn Gly Gly Lys Gln Ala Leu Glu Thr Val Gln
                565                 570                 575

Arg Leu Leu Pro Val Leu Cys Gln Ala His Gly Leu Thr Pro Glu Gln
            580                 585                 590

Val Val Ala Ile Ala Ser Asn Asn Gly Gly Lys Gln Ala Leu Glu Thr
        595                 600                 605

Val Gln Arg Leu Leu Pro Val Leu Cys Gln Ala His Gly Leu Thr Pro
610                 615                 620

Glu Gln Val Val Ala Ile Ala Ser Asn Asn Gly Gly Lys Gln Ala Leu
625                 630                 635                 640

Glu Thr Val Gln Arg Leu Leu Pro Val Leu Cys Gln Ala His Gly Leu
                645                 650                 655

Thr Pro Gln Gln Val Val Ala Ile Ala Ser Asn Asn Gly Gly Arg Pro
            660                 665                 670

Ala Leu Glu Ser Ile Val Ala Gln Leu Ser Arg Pro Asp Pro Ala Leu
        675                 680                 685

Ala Ala Leu Thr Gly Ser
    690

<210> SEQ ID NO 10
<211> LENGTH: 5385
<212> TYPE: DNA
<213> ORGANISM: Artificial Sequence
<220> FEATURE:
<223> OTHER INFORMATION: synthetic

<400> SEQUENCE: 10
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccagattta   240
attaaggctg cgcgctcgct cgctcactga ggccgcccgg gcaaagcccg ggcgtcgggc   300
gacctttggt cgcccggcct cagtgagcga gcgagcgcgc agagagggag tggccaactc   360
catcactagg ggttccttgt agttaatgat taacccgcca tgctacttat ctacgtagcc   420
atgctctagg aagatcggaa ttcgccctta agctagctag ttattaatag taatcaatta   480
cggggtcatt agttcatagc ccatatatgg agttccgcgt tacataactt acggtaaatg   540
gcccgcctgg ctgaccgccc aacgaccccc gcccattgac gtcaataatg acgtatgttc   600
ccatagtaac gccaataggg actttccatt gacgtcaatg ggtggagtat ttacggtaaa   660
ctgcccactt ggcagtacat caagtgtatc atatgccaag tacgccccct attgacgtca   720

```
atgacggtaa atggcccgcc tggcattatg cccagtacat gaccttatgg gactttccta    780
cttggcagta catctacgta ttagtcatcg ctattaccat ggtgatgcgg ttttggcagt    840
acatcaatgg gcgtggatag cggtttgact cacggggatt ccaagtctc caccccattg     900
acgtcaatgg gagtttgttt tggcaccaaa atcaacggga cttccaaaa tgtcgtaaca     960
actccgcccc attgacgcaa atgggcggta ggcgtgtacg gtgggaggtc tatataagca   1020
gagctggttt agtgaaccgt cagatcctgc agaagttggt cgtgaggcac tgggcaggta   1080
agtatcaagg ttacaagaca ggtttaagga gaccaataga aactgggctt gtcgagacag   1140
agaagactct tgcgtttctg ataggcacct attggtctta ctgacatcca ctttgccttt   1200
ctctccacag gtgtccaggc ggccgcatga tcgatctgga acctggcgaa aaaccgtata   1260
agtgcccaga atgcggcaag tcttttcccc agtctggcca cctgacgaa catcagcgca    1320
ctcacaccgg cgagaaacca tataaatgtc cggagtgcgg caagagcttt agccagaata   1380
gcaccctgac cgaacatcag cgtacgcaca cgggtgaaaa gccatataaa tgccctgagt   1440
gcggcaaatc ctttagcacc tctggccatc tggtccgtca ccagcgcacc caccagaata   1500
agaagggcgg ttctggtgac ggtaaaaaga aacagcacgc ctgtccagag tgtggcaaat   1560
ctttttcccg tgaagacaac ctgcacactc accagcgcac tcatactggc gagaaacctt   1620
acaagtgtcc ggaatgtggt aagagcttct ccacttccgg ccatctggtt cgtcaccagc   1680
gcacgcacac cggcgaaaaa ccatacaagt gcccggaatg cggcaaatca ttctcccgta   1740
gcgacaaact ggttcgtcac caacgtacgc ataccggtaa aaagacttcc tctagatacc   1800
cgtacgacgt tccagactat gcatcttgaa agcttggatc caatcaacct ctggattaca   1860
aaatttgtga agattgact ggtattctta actatgttgc tccttttacg ctatgtggat    1920
acgctgcttt aatgcctttg tatcatgcta ttgcttcccg tatggctttc attttctcct   1980
ccttgtataa atcctggttg ctgtctcttt atgaggagtt gtggcccgtt gtcaggcaac   2040
gtggcgtggt gtgcactgtg tttgctgacg caaccccac tggttgggc attgccacca    2100
cctgtcagct cctttccggg actttcgctt tccccctccc tattgccacg gcggaactca   2160
tcgccgcctg ccttgcccgc tgctggacag gggctcggct gttgggcact gacaattccg   2220
tggtgttgtc ggggaagctg acgtcctttc catggctgct cgcctgtgtt gccacctgga   2280
ttctgcgcgg gacgtccttc tgctacgtcc cttcggccct caatccagcg gaccttcctt   2340
cccgcggcct gctgccggct ctgcggcctc ttccgcgtct tcgagatctg cctcgactgt   2400
gccttctagt tgccagccat ctgttgtttg cccctccccc gtgccttcct tgaccctgga   2460
aggtgccact cccactgtcc tttcctaata aaatgaggaa attgcatcgc attgtctgag   2520
taggtgtcat tctattctgg ggggtgggt ggggcaggac agcaagggg aggattggga    2580
agacaatagc aggcatgctg gggactcgag ttaagggcga attcccgatt aggatcttcc   2640
tagagcatgg ctacgtagat aagtagcatg gcgggttaat cattaactac aaggaacccc   2700
tagtgatgga gttggccact ccctctctgc gcgctcgctc gctcactgag gccgggcgac   2760
caaaggtcgc ccgacgcccg ggctttgccc gggcggcctc agtgagcgag cgagcgcgca   2820
gccttaatta acctaattca ctggccgtcg ttttacaacg tcgtgactgg gaaaaccctg   2880
gcgttaccca acttaatcgc cttgcagcac atcccccttt cgccagctgg cgtaatagcg   2940
aagaggcccg caccgatcgc ccttcccaac agttgcgcag cctgaatggc gaatgggacg   3000
cgccctgtag cggcgcatta agcgcggcgg gtgtggtggt tacgcgcagc gtgaccgcta   3060
```

```
cacttgccag cgccctagcg cccgctcctt tcgctttctt cccttccttt ctcgccacgt    3120
tcgccggctt tccccgtcaa gctctaaatc ggggctccc  tttagggttc cgatttagtg    3180
ctttacggca cctcgacccc aaaaaacttg attagggtga tggttcacgt agtgggccat    3240
cgccccgata gacggttttt cgcccttga  cgctggagtt cacgttcctc aatagtggac    3300
tcttgttcca aactggaaca acactcaacc ctatctcggt ctattctttt gatttataag    3360
ggatttttcc gatttcggcc tattggttaa aaatgagct  gatttaacaa aaatttaacg    3420
cgaattttaa caaaatatta acgtttataa tttcaggtgg catctttcgg ggaaatgtgc    3480
gcggaaccc  tatttgttta ttttctaaa  tacattcaaa tatgtatccg ctcatgagac    3540
aataaccctg ataaatgctt caataatatt gaaaaggaa  gagtatgagt attcaacatt    3600
tccgtgtcgc ccttattccc ttttttgcgg cattttgcct tcctgttttt gctcacccag    3660
aaacgctggt gaaagtaaaa gatgctgaag atcagttggg tgcacgagtg ggttacatcg    3720
aactggatct caatagtggt aagatccttg agagttttcg ccccgaagaa cgttttccaa    3780
tgatgagcac ttttaaagtt ctgctatgtg gcgcggtatt atcccgtatt gacgccgggc    3840
aagagcaact cggtcgccgc atacactatt ctcagaatga cttggttgag tactcaccag    3900
tcacagaaaa gcatcttacg gatggcatga cagtaagaga attatgcagt gctgccataa    3960
ccatgagtga taacactgcg gccaacttac ttctgacaac gatcggagga ccgaaggagc    4020
taaccgcttt tttgcacaac atgggggatc atgtaactcg ccttgatcgt tgggaaccgg    4080
agctgaatga agccatacca aacgacgagc gtgacaccac gatgcctgta gtaatggtaa    4140
caacgttgcg caaactatta actggcgaac tacttactct agcttcccgg caacaattaa    4200
tagactggat ggaggcggat aaagttgcag gaccacttct gcgctcggcc cttccggctg    4260
gctggtttat tgctgataaa tctggagccg gtgagcgtgg gtctcgcggt atcattgcag    4320
cactggggcc agatggtaag ccctcccgta tcgtagttat ctacacgacg gggagtcagg    4380
caactatgga tgaacgaaat agacagatcg ctgagatagg tgcctcactg attaagcatt    4440
ggtaactgtc agaccaagtt tactcatata ctttagat   tgatttaaaa cttcattttt    4500
aatttaaaag gatctaggtg aagatccttt ttgataatct catgaccaaa atcccttaac    4560
gtgagttttc gttccactga gcgtcagacc ccgtagaaaa gatcaaagga tcttcttgag    4620
atcctttttt tctgcgcgta atctgctgct tgcaaacaaa aaaaccaccg ctaccagcgg    4680
tggtttgttt gccggatcaa gagctaccaa ctcttttcc  gaaggtaact ggcttcagca    4740
gagcgcagat accaaatact gtccttctag tgtagccgta gttaggccac cacttcaaga    4800
actctgtagc accgcctaca tacctcgctc tgctaatcct gttaccagtg gctgctgcca    4860
gtggcgataa gtcgtgtctt accgggttgg actcaagacg atagttaccg gataaggcgc    4920
agcggtcggg ctgaacgggg ggttcgtgca cacagcccag cttggagcga acgacctaca    4980
ccgaactgag atacctacag cgtgagctat gagaaagcgc cacgcttccc gaagggagaa    5040
aggcggacag gtatccggta agcggcaggg tcggaacagg agagcgcacg agggagcttc    5100
caggggaaa  cgcctggtat ctttatagtc ctgtcgggtt tcgccacctc tgacttgagc    5160
gtcgatttt  gtgatgctcg tcaggggggc ggagcctatg gaaaaacgcc agcaacgcgg    5220
cctttttacg gttcctggcc ttttgctgcg gttttgctca catgttcttt cctgcgttat    5280
cccctgattc tgtggataac cgtattaccg cctttgagtg agctgatacc gctcgccgca    5340
gccgaacgac cgagcgcagc gagtcagtga gcgaggaagc ggaag                    5385
```

<210> SEQ ID NO 11
<211> LENGTH: 662
<212> TYPE: DNA
<213> ORGANISM: Artificial Sequence
<220> FEATURE:
<223> OTHER INFORMATION: synthetic

<400> SEQUENCE: 11

```
tccctgcagg tcataaaatc ccagtccaga gtcaccagcc cttcttaacc acttcctact    60
gtgtgaccct ttcagccttt acttcctcat cagtaaaatg aggctgatga tatgggcatc   120
catactccag ggccagtgtg agcttacaac aagataagga gtggtgctga gcctggtgcc   180
gggcaggcag caggcatgtt tctcccaatt atgccctctc actgccagcc ccacctccat   240
tgtcctcacc cccagggctc aaggttctgc cttccccttt ctcagccctg accctactga   300
acatgtctcc ccactcccag gcagtgccag ggcctctcct ggagggttgc ggggacagaa   360
ggacagccgg agtgcagagt cagcggttga gggattgggg ctatgccagc taatccgaag   420
ggttggggggg gctgagctgg attcacctgt ccttgtctct gattggctct tggacacccc   480
tagcccccaa atcccactaa gcagccccac cagggattgc acaggtccgt agagagccag   540
ttgattgcag gtcctcctgg ggccagaagg gtgcctggga ggccaggttc tggggatccc   600
ctccatccag aagaaccacc tgctcactct gtcccttcgc ctgctgctgg accgcggcc   660
gc                                                                 662
```

<210> SEQ ID NO 12
<211> LENGTH: 522
<212> TYPE: DNA
<213> ORGANISM: Artificial Sequence
<220> FEATURE:
<223> OTHER INFORMATION: synthetic

<400> SEQUENCE: 12

```
atgatcgatc tggagccagg tgaaaagcct tataagtgcc ctgaatgcgg gaaatcattc    60
agccagaact ccacacttac cgagcaccag agaacccata ctggggagaa accctataag   120
tgcccagaat gtgggaagtc tttctctacc agcggacact tggtcaggca ccagagaacg   180
caccagaaca agaaaggagg ttctggtgat ggcaagaaga agcagcatgc ttgtcccgaa   240
tgcggcaagt cctttagcag ggaggacaat ctgcacactc accaacgcac acatactggc   300
gagaagccgt acaagtgtcc cgaatgtggc aaaagtttct ccacaagtgg acatctcgtt   360
cgtcaccagc gaacccacac cggagagaaa ccctacaaat gcccagagtg tgggaaatcc   420
ttttcacgga gcgacaaact ggtgagacat caacgcactc atacaggcaa gaaaacgagc   480
tcacggtacc cttacgatgt gcctgactat gccagttaat aa                     522
```

<210> SEQ ID NO 13
<211> LENGTH: 172
<212> TYPE: PRT
<213> ORGANISM: Artificial Sequence
<220> FEATURE:
<223> OTHER INFORMATION: synthetic

<400> SEQUENCE: 13

```
Met Ile Asp Leu Glu Pro Gly Glu Lys Pro Tyr Lys Cys Pro Glu Cys
1               5                   10                  15

Gly Lys Ser Phe Ser Gln Asn Ser Thr Leu Thr Glu His Gln Arg Thr
            20                  25                  30

His Thr Gly Glu Lys Pro Tyr Lys Cys Pro Glu Cys Gly Lys Ser Phe
        35                  40                  45
```

```
Ser Thr Ser Gly His Leu Val Arg His Gln Arg Thr His Gln Asn Lys
 50                  55                  60

Lys Gly Gly Ser Gly Asp Gly Lys Lys Lys Gln His Ala Cys Pro Glu
 65                  70                  75                  80

Cys Gly Lys Ser Phe Ser Arg Glu Asp Asn Leu His Thr His Gln Arg
                 85                  90                  95

Thr His Thr Gly Glu Lys Pro Tyr Lys Cys Pro Glu Cys Gly Lys Ser
            100                 105                 110

Phe Ser Thr Ser Gly His Leu Val Arg His Gln Arg Thr His Thr Gly
        115                 120                 125

Glu Lys Pro Tyr Lys Cys Pro Glu Cys Gly Lys Ser Phe Ser Arg Ser
    130                 135                 140

Asp Lys Leu Val Arg His Gln Arg Thr His Thr Gly Lys Lys Thr Ser
145                 150                 155                 160

Ser Arg Tyr Pro Tyr Asp Val Pro Asp Tyr Ala Ser
                165                 170
```

<210> SEQ ID NO 14
<211> LENGTH: 2049
<212> TYPE: DNA
<213> ORGANISM: Artificial Sequence
<220> FEATURE:
<223> OTHER INFORMATION: synthetic

<400> SEQUENCE: 14

```
gcaagtgccc caagaaggcg ggccgcccag ccttctgacg ctagccccgc tgcccaggtg      60
gatctgcgaa cgctgggtta ttctcagcag cagcaagaga agattaagcc taaggtccgg     120
agtactgtgg cacagcacca tgaggctctg gtcgggcacg gcttcacgca cgcacacatc     180
gttgcactct cccagcaccc tgccgcgctg ggcacagtgg cagtgaagta ccaagatatg     240
attgcggcac ttcccgaagc tactcacgag gccatcgtcg gcgttgggaa gcagtggtca     300
ggcgctaggg cactggaggc actgctgact gtggccgggg agcttcgcgg accccccctg     360
cagttggaca caggccagct gctgaagata gcaaaacgag gaggcgtcac agctgtagag     420
gccgtgcatg cgtggcgcaa tgcccttacc ggggcccctc tgaatctgac cccgcagcaa     480
gtggtagcca ttgcgtctaa caacggaggg aaacaggcac tcgagacagt tcaacggctg     540
ctccccgtgc tttgccaggc gcacggactg accccagaac aagtggtggc gatcgcctca     600
ataacggcg gcaaacaggc tcttgaaacc gtgcagagac tgctgccagt actgtgccag     660
gctcatggcc tgaccccaga gcaggttgtg gccatcgctt caaacaatgg cggtaaacag     720
gcgctcgaga ctgtccagag gctgttgcct gtgctctgcc aagctcatgg cctgacgccc     780
gaacaggtgg ttgccatcgc tagcaacatc ggcggcaagc aagctctcga cagtgcaa     840
cggctgctgc ccgtactctg ccaggcacat gggctgactc ccgagcaagt ggttgctatt     900
gcatctaaca acgcggaaa gcaggcgctg gagactgtcc agcgtttgct tcctgttttg     960
tgtcaggctc acggcttgac gcccgaacag gtagtggcca tagcctccaa catcggagga    1020
aaacaggcac ttgaaacagt ccagaggctt ctccccgtcc tgtgccaagc ccatggcctc    1080
actccacagc aagtagtggc tattgcatcc aatgaggcg ggaaacaagc cttggaaacc    1140
gtccaggccc tgctgcctgt cctgtgccag gcacacgggc tgacacctga acaggtggtc    1200
gcaattgcca gtaatggtgg cgggaagcaa gccctggaga ctgttcaggc tttgctgccc    1260
gttctgtgtc aagcacacgg tctgactcca gaacaggttg tggctatcgc ctccaataat    1320
```

```
ggtggcaaac aggctctcga acagtgcag aggctgctgc ccgtgctgtg tcaagcccat   1380
ggcctgaccc cacagcaggt cgtggccatt gcctctaata atggaggtaa acaggccctg   1440
gagacagtcc agagattgct tccagttctg tgtcaggccc acgggctgac ccctcaacag   1500
gtcgtcgcca tcgcctcaaa caacggtggc aagcaggcac tcgagactgt gcagcggctc   1560
ttgcctgtgc tgtgtcaagc ccatggactg accccggaac aggtggttgc cattgccagc   1620
aacaacggtg ggaaacaggc tttggaaacc gtgcaacgcc tgctgccggt tctgtgccag   1680
gctcacgggc ttaccccgga acaggtggta gctatcgcta gcaataatgg agggaagcag   1740
gccctggaaa cagtgcagag actgctcccc gtcctctgcc aggcacacgg actcaccccg   1800
gagcaagtgg tcgccatagc ctccaacggt ggagggaagc aggcactgga gacagtgcag   1860
agacttctcc cagtgctctg tcaggctcat gggctcaccc ctcaacaggt agtagccata   1920
gctagtaaca atggaggtcg tccagcattg gagagcatcg tggcgcagct gagccgccca   1980
gacccagcgc ttgccgcctt gaccggaagc tatccctacg acgtgcctga ttacgcttaa   2040
taaaagctt                                                          2049
```

<210> SEQ ID NO 15
<211> LENGTH: 689
<212> TYPE: PRT
<213> ORGANISM: Artificial Sequence
<220> FEATURE:
<223> OTHER INFORMATION: synthetic

<400> SEQUENCE: 15

```
Met Pro Lys Lys Arg Lys Val Thr Ser Ala Ser Ala Pro Arg Arg
1               5                   10                  15

Arg Ala Ala Gln Pro Ser Asp Ala Ser Pro Ala Ala Gln Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Gln Gln Val Val Ala Ile Ala Ser
                165                 170                 175

Asn Asn Gly Gly Lys Gln Ala Leu Glu Thr Val Gln Arg Leu Leu Pro
            180                 185                 190

Val Leu Cys Gln Ala His Gly Leu Thr Pro Glu Gln Val Val Ala Ile
        195                 200                 205

Ala Ser Asn Asn Gly Gly Lys Gln Ala Leu Glu Thr Val Gln Arg Leu
    210                 215                 220

Leu Pro Val Leu Cys Gln Ala His Gly Leu Thr Pro Glu Gln Val Val
```

```
            225                 230                 235                 240
Ala Ile Ala Ser Asn Asn Gly Gly Lys Gln Ala Leu Glu Thr Val Gln
                245                 250                 255

Arg Leu Leu Pro Val Leu Cys Gln Ala His Gly Leu Thr Pro Glu Gln
                260                 265                 270

Val Val Ala Ile Ala Ser Asn Ile Gly Gly Lys Gln Ala Leu Glu Thr
                275                 280                 285

Val Gln Arg Leu Leu Pro Val Leu Cys Gln Ala His Gly Leu Thr Pro
        290                 295                 300

Glu Gln Val Val Ala Ile Ala Ser Asn Gly Gly Lys Gln Ala Leu
305                 310                 315                 320

Glu Thr Val Gln Arg Leu Leu Pro Val Leu Cys Gln Ala His Gly Leu
                    325                 330                 335

Thr Pro Glu Gln Val Val Ala Ile Ala Ser Asn Ile Gly Gly Lys Gln
                340                 345                 350

Ala Leu Glu Thr Val Gln Arg Leu Leu Pro Val Leu Cys Gln Ala His
            355                 360                 365

Gly Leu Thr Pro Gln Gln Val Val Ala Ile Ala Ser Asn Gly Gly Gly
        370                 375                 380

Lys Gln Ala Leu Glu Thr Val Gln Ala Leu Leu Pro Val Leu Cys Gln
385                 390                 395                 400

Ala His Gly Leu Thr Pro Glu Gln Val Val Ala Ile Ala Ser Asn Gly
                405                 410                 415

Gly Gly Lys Gln Ala Leu Glu Thr Val Gln Ala Leu Leu Pro Val Leu
                420                 425                 430

Cys Gln Ala His Gly Leu Thr Pro Glu Gln Val Val Ala Ile Ala Ser
            435                 440                 445

Asn Asn Gly Gly Lys Gln Ala Leu Glu Thr Val Gln Arg Leu Leu Pro
        450                 455                 460

Val Leu Cys Gln Ala His Gly Leu Thr Pro Gln Gln Val Val Ala Ile
465                 470                 475                 480

Ala Ser Asn Asn Gly Gly Lys Gln Ala Leu Glu Thr Val Gln Arg Leu
                485                 490                 495

Leu Pro Val Leu Cys Gln Ala His Gly Leu Thr Pro Gln Gln Val Val
                500                 505                 510

Ala Ile Ala Ser Asn Asn Gly Gly Lys Gln Ala Leu Glu Thr Val Gln
            515                 520                 525

Arg Leu Leu Pro Val Leu Cys Gln Ala His Gly Leu Thr Pro Glu Gln
        530                 535                 540

Val Val Ala Ile Ala Ser Asn Asn Gly Gly Lys Gln Ala Leu Glu Thr
545                 550                 555                 560

Val Gln Arg Leu Leu Pro Val Leu Cys Gln Ala His Gly Leu Thr Pro
                565                 570                 575

Glu Gln Val Val Ala Ile Ala Ser Asn Asn Gly Gly Lys Gln Ala Leu
                580                 585                 590

Glu Thr Val Gln Arg Leu Leu Pro Val Leu Cys Gln Ala His Gly Leu
            595                 600                 605

Thr Pro Glu Gln Val Val Ala Ile Ala Ser Asn Gly Gly Gly Lys Gln
        610                 615                 620

Ala Leu Glu Thr Val Gln Arg Leu Leu Pro Val Leu Cys Gln Ala His
625                 630                 635                 640

Gly Leu Thr Pro Gln Gln Val Val Ala Ile Ala Ser Asn Asn Gly Gly
                645                 650                 655
```

Arg Pro Ala Leu Glu Ser Ile Val Ala Gln Leu Ser Arg Pro Asp Pro
                660                 665                 670

Ala Leu Ala Ala Leu Thr Gly Ser Tyr Pro Tyr Asp Val Pro Asp Tyr
            675                 680                 685

Ala

<210> SEQ ID NO 16
<211> LENGTH: 2315
<212> TYPE: DNA
<213> ORGANISM: Artificial Sequence
<220> FEATURE:
<223> OTHER INFORMATION: synthetic

<400> SEQUENCE: 16

| | | | | | |
|---|---|---|---|---|---|
| ctagcgcccc | cagaagaagg | gccgctcagc | cttccgatgc | ctctcctgcc | gcccaggtgg | 60 |
| acctgagaac | cctgggctac | agccagcagc | agcaggaaaa | gatcaagccc | aaagtgcgga | 120 |
| gcaccgtggc | ccagcaccac | gaagccctcg | tgggccacgg | ctttacccac | gctcacatcg | 180 |
| tggccctgag | ccagcatcct | gccgctctgg | gaaccgtggc | cgtgaagtac | caggacatga | 240 |
| tcgccgccct | gcccgaggcc | acacacgagg | ctatcgtggg | cgtgggcaag | cagtggtccg | 300 |
| gcgctagagc | actcgaggcc | ttgctgacag | tggccggcga | gctgagaggc | cctccactgc | 360 |
| agctggacac | cggccagctg | ctgaagatcg | ccaagcgggg | aggcgtgaca | gccgtggaag | 420 |
| ccgtgcacgc | ttggcggaat | gccctgacag | gcgctcccct | gaaccttacg | ccgcagcagg | 480 |
| tggtggccat | cgccagccac | gatggcggca | gcaggcgct | ggagacggtg | cagcggctgc | 540 |
| ttccggtgct | gtgccaggcc | catggcctga | ccccggagca | ggtggtggcc | atcgccagca | 600 |
| atattggtgg | caagcaggcg | ctggagacgt | gcagcgatt | gttgccggtg | ctgtgccagg | 660 |
| cccatggcct | gaccccggag | caggtggtgg | ccatcgccag | ccacgacggt | ggcaagcagg | 720 |
| cgctggagac | tgtccagcgg | ctgttgccgg | tgctgtgcca | ggcccatggc | ctgaccccgg | 780 |
| agcaggtggt | ggccatcgcc | agcaatggcg | gtggcaagca | ggcgcttgag | acggtgcagc | 840 |
| ggctgttgcc | ggtgctgtgc | caggcccatg | gcctgacccc | ggagcaggtg | gtggccatcg | 900 |
| ccagcaatgg | cggtggcaag | caggctctgg | agacggtgca | gcggctgttg | ccggtgctgt | 960 |
| gccaggccca | tggcctgacc | ccggagcagg | tggtggccat | cgccagcaat | ggcggggca | 1020 |
| agcaggcgct | ggagacggtg | cagcggctgt | tgccggtgct | gtgccaggcc | catggcctga | 1080 |
| ccccgcagca | ggtggtggcc | atcgccagca | atattggcgg | caagcaggcg | ctggagacgg | 1140 |
| tgcaggcgct | gttgccggtg | ctgtgccagg | cccatggcct | gaccccggag | caggtggtgg | 1200 |
| ccatcgcaag | caatggcggt | ggcaagcagg | cgctggagac | ggtgcaggcg | ctgttgccgg | 1260 |
| tgctgtgcca | ggcccatggc | ctgaccccgg | agcaggtggt | ggcaatcgcc | agcaatattg | 1320 |
| gtggcaagca | ggcgctggag | acggtgcagc | ggctgttgcc | ggtgctgtgc | caggcccatg | 1380 |
| gcctgacccc | gcaacaggtg | gtagccatcg | ccagcaatat | tggtggcaag | caggcgctgg | 1440 |
| agacggtgca | gcggctgttg | ccggtgctgt | gccaggccca | tggcctgaca | ccccagcagg | 1500 |
| tggtagcgat | cgccagcaat | aagggtggca | agcaggcgct | ggagacggtg | cagcggctgc | 1560 |
| ttccggtgct | gtgccaggcc | catggcctga | ccccggagca | ggtggtggcc | atcgccagca | 1620 |
| ataagggtgg | caagcaggcg | ctggagacgg | tgcagcgatt | gttgccggtg | ctgtgccagg | 1680 |
| cccatggcct | gaccccggag | caggtggtgg | ccatcgccag | caataagggt | ggcaagcagg | 1740 |
| cgctggagac | tgtccagcgg | ctgttgccgg | tgctgtgcca | ggcccatggc | ctgaccccgg | 1800 |

```
agcaggtggt ggccatcgcc agcaatggcg gtggcaagca ggcgcttgag acggtgcagc    1860
ggctgttgcc ggtgctgtgc caggcccatg gcctgacccc gcagcaggtg gtggccatcg    1920
ccagccacga cggtggcaag caggctctgg agacggtgca gcggctgttg ccggtgctgt    1980
gccaggccca tggcctgacc ccggagcagg tggtggccat cgccagcaat ggcgggggca    2040
agcaggcgct ggagacggtg cagcggctgt tgccggtgct gtgccaggcc catggcctga    2100
ccccgcagca ggtggtggcc atcgccagca taagggcgg caagcaggcg ctggagacgg    2160
tgcaggcgct gttgccggtg ctgtgccagg cccatggcct gacacccag caggtcgtgg    2220 ccattgccag caacaaggga ggcagacccg ccctggaatc tattgtggcc cagctgagca    2280
gacccgaccc agctctggcc gccctgacag gatcc                              2315
```

<210> SEQ ID NO 17
<211> LENGTH: 790
<212> TYPE: PRT
<213> ORGANISM: Artificial Sequence
<220> FEATURE:
<223> OTHER INFORMATION: synthetic

<400> SEQUENCE: 17

```
Met Pro Lys Lys Lys Arg Lys Val Thr Ser Ala Pro Arg Arg Arg Ala
1               5                   10                  15

Ala Gln Pro Ser Asp Ala Ser Pro Ala Ala Gln Val Asp Leu Arg Thr
            20                  25                  30

Leu Gly Tyr Ser Gln Gln Gln Glu Lys Ile Lys Pro Lys Val Arg
        35                  40                  45

Ser Thr Val Ala Gln His His Glu Ala Leu Val Gly His Gly Phe Thr
    50                  55                  60

His Ala His Ile Val Ala Leu Ser Gln His Pro Ala Ala Leu Gly Thr
65                  70                  75                  80

Val Ala Val Lys Tyr Gln Asp Met Ile Ala Ala Leu Pro Glu Ala Thr
                85                  90                  95

His Glu Ala Ile Val Gly Val Gly Lys Gln Trp Ser Gly Ala Arg Ala
            100                 105                 110

Leu Glu Ala Leu Leu Thr Val Ala Gly Glu Leu Arg Gly Pro Pro Leu
        115                 120                 125

Gln Leu Asp Thr Gly Gln Leu Leu Lys Ile Ala Lys Arg Gly Gly Val
    130                 135                 140

Thr Ala Val Glu Ala Val His Ala Trp Arg Asn Ala Leu Thr Gly Ala
145                 150                 155                 160

Pro Leu Asn Leu Thr Pro Gln Gln Val Val Ala Ile Ala Ser His Asp
                165                 170                 175

Gly Gly Lys Gln Ala Leu Glu Thr Val Gln Arg Leu Leu Pro Val Leu
            180                 185                 190

Cys Gln Ala His Gly Leu Thr Pro Glu Gln Val Val Ala Ile Ala Ser
        195                 200                 205

Asn Ile Gly Gly Lys Gln Ala Leu Glu Thr Val Gln Arg Leu Leu Pro
    210                 215                 220

Val Leu Cys Gln Ala His Gly Leu Thr Pro Glu Gln Val Val Ala Ile
225                 230                 235                 240

Ala Ser His Asp Gly Gly Lys Gln Ala Leu Glu Thr Val Gln Arg Leu
                245                 250                 255

Leu Pro Val Leu Cys Gln Ala His Gly Leu Thr Pro Glu Gln Val Val
            260                 265                 270
```

```
Ala Ile Ala Ser Asn Gly Gly Gly Lys Gln Ala Leu Glu Thr Val Gln
            275                 280                 285

Arg Leu Leu Pro Val Leu Cys Gln Ala His Gly Leu Thr Pro Glu Gln
    290                 295                 300

Val Val Ala Ile Ala Ser Asn Gly Gly Gly Lys Gln Ala Leu Glu Thr
305                 310                 315                 320

Val Gln Arg Leu Leu Pro Val Leu Cys Gln Ala His Gly Leu Thr Pro
                325                 330                 335

Glu Gln Val Val Ala Ile Ala Ser Asn Gly Gly Gly Lys Gln Ala Leu
                340                 345                 350

Glu Thr Val Gln Arg Leu Leu Pro Val Leu Cys Gln Ala His Gly Leu
            355                 360                 365

Thr Pro Gln Gln Val Val Ala Ile Ala Ser Asn Ile Gly Gly Lys Gln
        370                 375                 380

Ala Leu Glu Thr Val Gln Ala Leu Leu Pro Val Leu Cys Gln Ala His
385                 390                 395                 400

Gly Leu Thr Pro Glu Gln Val Val Ala Ile Ala Ser Asn Gly Gly Gly
                405                 410                 415

Lys Gln Ala Leu Glu Thr Val Gln Ala Leu Leu Pro Val Leu Cys Gln
            420                 425                 430

Ala His Gly Leu Thr Pro Glu Gln Val Val Ala Ile Ala Ser Asn Ile
        435                 440                 445

Gly Gly Lys Gln Ala Leu Glu Thr Val Gln Arg Leu Leu Pro Val Leu
    450                 455                 460

Cys Gln Ala His Gly Leu Thr Pro Gln Gln Val Val Ala Ile Ala Ser
465                 470                 475                 480

Asn Ile Gly Gly Lys Gln Ala Leu Glu Thr Val Gln Arg Leu Leu Pro
                485                 490                 495

Val Leu Cys Gln Ala His Gly Leu Thr Pro Gln Gln Val Val Ala Ile
            500                 505                 510

Ala Ser Asn Lys Gly Gly Lys Gln Ala Leu Glu Thr Val Gln Arg Leu
        515                 520                 525

Leu Pro Val Leu Cys Gln Ala His Gly Leu Thr Pro Glu Gln Val Val
    530                 535                 540

Ala Ile Ala Ser Asn Lys Gly Gly Lys Gln Ala Leu Glu Thr Val Gln
545                 550                 555                 560

Arg Leu Leu Pro Val Leu Cys Gln Ala His Gly Leu Thr Pro Glu Gln
                565                 570                 575

Val Val Ala Ile Ala Ser Asn Lys Gly Gly Lys Gln Ala Leu Glu Thr
            580                 585                 590

Val Gln Arg Leu Leu Pro Val Leu Cys Gln Ala His Gly Leu Thr Pro
        595                 600                 605

Glu Gln Val Val Ala Ile Ala Ser Asn Gly Gly Gly Lys Gln Ala Leu
    610                 615                 620

Glu Thr Val Gln Arg Leu Leu Pro Val Leu Cys Gln Ala His Gly Leu
625                 630                 635                 640

Thr Pro Gln Gln Val Val Ala Ile Ala Ser His Asp Gly Gly Lys Gln
                645                 650                 655

Ala Leu Glu Thr Val Gln Arg Leu Leu Pro Val Leu Cys Gln Ala His
            660                 665                 670

Gly Leu Thr Pro Glu Gln Val Val Ala Ile Ala Ser Asn Gly Gly Gly
        675                 680                 685

Lys Gln Ala Leu Glu Thr Val Gln Arg Leu Leu Pro Val Leu Cys Gln
```

Ala His Gly Leu Thr Pro Gln Gln Val Val Ala Ile Ala Ser Asn Lys
705                 710                 715                 720

Gly Gly Lys Gln Ala Leu Glu Thr Val Gln Ala Leu Leu Pro Val Leu
                725                 730                 735

Cys Gln Ala His Gly Leu Thr Pro Gln Gln Val Val Ala Ile Ala Ser
                740                 745                 750

Asn Lys Gly Gly Arg Pro Ala Leu Glu Ser Ile Val Ala Gln Leu Ser
        755                 760                 765

Arg Pro Asp Pro Ala Leu Ala Ala Leu Thr Gly Ser Tyr Pro Tyr Asp
    770                 775                 780

Val Pro Asp Tyr Ala Ser
785                 790

<210> SEQ ID NO 18
<211> LENGTH: 5722
<212> TYPE: DNA
<213> ORGANISM: Artificial Sequence
<220> FEATURE:
<223> OTHER INFORMATION: synthetic

<400> SEQUENCE: 18
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccagattta   240
attaaggctg cgcgctcgct cgctcactga ggccgcccgg gcaaagcccg ggcgtcgggc   300
gacctttggt cgcccggcct cagtgagcga gcgagcgcgc agagagggag tggccaactc   360
catcactagg ggttccttgt agttaatgat taacccgcca tgctacttat ctacgtagcc   420
atgctctagg aagatcggaa ttcgccctta agctagctcc ctgcaggtca taaatcccag   480
tccagagtc accagcccct cttaaccact tcctactgtg tgaccctttc agcctttact   540
tcctcatcag taaaatgagg ctgatgatat gggcatccat actccagggc cagtgtgagc   600
ttacaacaag ataaggagtg tgctgagcc tggtgccggg caggcagcag gcatgtttct   660
cccaattatg ccctctcact gccagcccca cctccattgt cctcaccccc agggctcaag   720
gttctgcctt cccctttctc agccctgacc ctactgaaca tgtctcccca ctcccaggca   780
gtgccagggc ctctcctgga gggttgcggg gacagaagga cagccggagt gcagagtcag   840
cggttgaggg attggggcta tgccagctaa tccgaagggt tggggggggct gagctggatt   900
cacctgtcct tgtctctgat tggctcttgg acacccctag cccccaaatc ccactaagca   960
gccccaccag ggattgcaca ggtccgtaga gagccagttg attgcaggtc ctcctgggc   1020
cagaagggtg cctgggaggc caggttctgg ggatccctc catccagaag aaccacctgc   1080
tcactctgtc ccttcgcctg ctgctgggac gcgggccgca tgaatggcac agaaggccct   1140
aacttctacg tgcccttctc caatgcgacg ggtgtggtac gcagccccct cgagtaccca   1200
cagtactacc tggctgagcc atggcagttc ccatgctgg ccgcctacat gtttctgctg   1260
atcgtgctgg gcttccccat caacttcctc acgctctacg tcaccgtcca gcacaagaag   1320
ctgcgcacgc ctctcaacta catcctgctc aacctagccg tggctgacct cttcatggtc   1380
ctaggtggct tcaccagcac cctctacacc tctctgcatg gatacttcgt cttcgggccc   1440
acaggatgca atttggaggg cttctttgcc accctgggcg gtgaaattgc cctgtggtcc   1500

```
ttggtggtcc tggccatcga gcggtacgtg gtggtgtgta agcccatgag caacttccgc    1560
ttcggggaga accatgccat catgggcgtt gccttcacct gggtcatggc gctggcctgc    1620
gccgcacccc cactcgccgg ctggtccagg tacatccccg agggcctgca gtgctcgtgt    1680
ggaatcgact actacacgct caagccggag gtcaacaacg agtctttttgt catctacatg    1740 ttcgtggtcc acttcaccat ccccatgatt atcatctttt tctgctatgg gcagctcgtc    1800
ttcaccgtca aggaggccgc tgcccagcag caggagtcag ccaccacaca gaaggcagag    1860
aaggaggtca cccgcatggt catcatcatg gtcatcgctt tcctgatctg ctgggtgccc    1920
tacgccagcg tggcattcta catcttcacc caccagggct ccaacttcgg tcccatcttc    1980
atgaccatcc cagcgttctt tgccaagagc gccgccatct acaaccctgt catctatatc    2040
atgatgaaca gcagttccg gaactgcatg ctcaccacca tctgctgcgg caagaaccca    2100
ctgggtgacg atgaggcctc tgctaccgtg tccaagacgg agacgagcca ggtggccccg    2160
gcctaaaagc ttggatccaa tcaacctctg gattacaaaa tttgtgaaag attgactggt    2220
attcttaact atgttgctcc ttttacgcta tgtggatacg ctgctttaat gcctttgtat    2280
catgctattg cttcccgtat ggctttcatt ttctcctcct tgtataaatc ctggttgctg    2340
tctctttatg aggagttgtg gcccgttgtc aggcaacgtg gcgtggtgtg cactgtgttt    2400
gctgacgcaa ccccccactgg ttggggcatt gccaccacct gtcagctcct ttccgggact    2460
ttcgctttcc cctccctat tgccacggcg gaactcatcg ccgcctgcct tgcccgctgc    2520
tggacagggg ctcggctgtt gggcactgac aattccgtgg tgttgtcggg gaagctgacg    2580
tcctttccat ggctgctcgc ctgtgttgcc acctggattc tgcgcgggac gtccttctgc    2640
tacgtccctt cggccctcaa tccagcggac cttccttccc gcggcctgct gccggctctg    2700
cggcctcttc cgcgtcttcg agatctgcct cgactgtgcc ttctagttgc cagccatctg    2760
ttgtttgccc ctccccgtg ccttccttga ccctggaagg tgccactccc actgtccttt    2820
cctaataaaa tgaggaaatt gcatcgcatt gtctgagtag gtgtcattct attctggggg    2880
gtggggtggg gcaggacagc aagggggagg attgggaaga caatagcagg catgctgggg    2940
actcgagtta agggcgaatt cccgattagg atcttcctag agcatggcta cgtagataag    3000
tagcatggcg ggttaatcat taactacaag gaacccctag tgatggagtt ggccactccc    3060
tctctgcgcg ctcgctcgct cactgaggcc gggcgaccaa aggtcgcccg acgcccgggc    3120
tttgcccggg cggcctcagt gagcgagcga gcgcgcagcc ttaattaacc taattcactg    3180
gccgtcgttt tacaacgtcg tgactgggaa accctggcg ttacccaact taatcgcctt    3240
gcagcacatc ccccttttcgc cagctggcgt aatagcgaag aggcccgcac cgatcgccct    3300
tcccaacagt tgcgcagcct gaatggcgaa tgggacgcgc cctgtagcgg cgcattaagc    3360
gcggcgggtg tggtggttac gcgcagcgtg accgctacac ttgccagcgc cctagcgccc    3420
gctcctttcg ctttcttccc ttcctttctc gccacgttcg ccggctttcc ccgtcaagct    3480
ctaaatcggg ggctcccttt agggttccga tttagtgctt tacggcacct cgaccccaaa    3540
aaacttgatt agggtgatgg ttcacgtagt gggccatcgc cccgatagac ggttttttcgc    3600 cctttgacgc tggagttcac gttcctcaat agtggactct tgttccaaac tggaacaaca    3660
ctcaacccta tctcggtcta ttcttttgat ttataaggga ttttccgat ttcggcctat    3720 tggttaaaaa atgagctgat ttaacaaaaa tttaacgcga attttaacaa aatattaacg    3780
tttataattt caggtggcat ctttcgggga aatgtgcgcg gaacccctat ttgtttattt    3840
```

| | |
|---|---|
| ttctaaatac attcaaatat gtatccgctc atgagacaat aaccctgata aatgcttcaa | 3900 |
| taatattgaa aaaggaagag tatgagtatt caacatttcc gtgtcgccct tattcccttt | 3960 |
| tttgcggcat tttgccttcc tgttttttgct cacccagaaa cgctggtgaa agtaaaagat | 4020 |
| gctgaagatc agttgggtgc acgagtgggt tacatcgaac tggatctcaa tagtggtaag | 4080 |
| atccttgaga gttttcgccc cgaagaacgt tttccaatga tgagcacttt taaagttctg | 4140 |
| ctatgtggcg cggtattatc ccgtattgac gccgggcaag agcaactcgg tcgccgcata | 4200 |
| cactattctc agaatgactt ggttgagtac tcaccagtca cagaaaagca tcttacggat | 4260 |
| ggcatgacag taagagaatt atgcagtgct gccataacca tgagtgataa cactgcggcc | 4320 |
| aacttacttc tgacaacgat cggaggaccg aaggagctaa ccgcttttttt gcacaacatg | 4380 |
| gggatcatg taactcgcct tgatcgttgg gaaccggagc tgaatgaagc cataccaaac | 4440 |
| gacgagcgtg acaccacgat gcctgtagta atggtaacaa cgttgcgcaa actattaact | 4500 |
| ggcgaactac ttactctagc ttcccggcaa caattaatag actggatgga ggcggataaa | 4560 |
| gttgcaggac cacttctgcg ctcggccctt ccggctggct ggtttattgc tgataaatct | 4620 |
| ggagccggtg agcgtgggtc tcgcggtatc attgcagcac tggggccaga tggtaagccc | 4680 |
| tcccgtatcg tagttatcta cacgacgggg agtcaggcaa ctatggatga acgaaataga | 4740 |
| cagatcgctg agataggtgc ctcactgatt aagcattggt aactgtcaga ccaagtttac | 4800 |
| tcatatatac tttagattga tttaaaactt cattttttaat ttaaaaggat ctaggtgaag | 4860 |
| atcctttttg ataatctcat gaccaaaatc ccttaacgtg agttttcgtt ccactgagcg | 4920 |
| tcagaccccg tagaaaagat caaaggatct tcttgagatc cttttttttct gcgcgtaatc | 4980 |
| tgctgcttgc aaacaaaaaa accaccgcta ccagcggtgg tttgtttgcc ggatcaagag | 5040 |
| ctaccaactc ttttccgaa ggtaactggc ttcagcagag cgcagatacc aaatactgtc | 5100 |
| cttctagtgt agccgtagtt aggccaccac ttcaagaact ctgtagcacc gcctacatac | 5160 |
| ctcgctctgc taatcctgtt accagtggct gctgccagtg gcgataagtc gtgtcttacc | 5220 |
| gggttggact caagacgata gttaccggat aaggcgcagc ggtcgggctg aacggggggt | 5280 |
| tcgtgcacac agcccagctt ggagcgaacg acctacaccg aactgagata cctacagcgt | 5340 |
| gagctatgag aaagcgccac gcttcccgaa gggagaaagg cggacaggta tccggtaagc | 5400 |
| ggcagggtcg aacaggaga gcgcacgagg gagcttccag ggggaaacgc ctggtatctt | 5460 |
| tatagtcctg tcgggtttcg ccacctctga cttgagcgtc gatttttgtg atgctcgtca | 5520 |
| ggggggcgga gcctatggaa aaacgccagc aacgcggcct ttttacggtt cctggccttt | 5580 |
| tgctgcggtt ttgctcacat gttctttcct gcgttatccc ctgattctgt ggataaccgt | 5640 |
| attaccgcct ttgagtgagc tgataccgct cgccgcagcc gaacgaccga gcgcagcgag | 5700 |
| tcagtgagcg aggaagcgga ag | 5722 |

```
<210> SEQ ID NO 19
<211> LENGTH: 5304
<212> TYPE: DNA
<213> ORGANISM: Artificial Sequence
<220> FEATURE:
<223> OTHER INFORMATION: synthetic

<400> SEQUENCE: 19
```

| | |
|---|---|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |

```
ttgtgagcgg ataacaattt cacacaggaa acagctatga ccatgattac gccagattta      240
attaaggctg cgcgctcgct cgctcactga ggccgcccgg gcaaagcccg ggcgtcgggc      300
gacctttggt cgcccggcct cagtgagcga gcgagcgcgc agagagggag tggccaactc      360
catcactagg ggttccttgt agttaatgat taacccgcca tgctacttat ctacgtagcc      420
atgctctagg aagatcggaa ttcgccctta agctagctag ttattaatag taatcaatta      480
cggggtcatt agttcatagc ccatatatgg agttccgcgt tacataactt acggtaaatg      540
gcccgcctgg ctgaccgccc aacgacccc gcccattgac gtcaataatg acgtatgttc       600
ccatagtaac gccaataggg actttccatt gacgtcaatg ggtggagtat ttacggtaaa      660
ctgcccactt ggcagtacat caagtgtatc atatgccaag tacgccccct attgacgtca      720
atgacggtaa atggcccgcc tggcattatg cccagtacat gaccttatgg gactttccta      780
cttggcagta catctacgta ttagtcatcg ctattaccat ggtgatgcgg ttttggcagt      840
acatcaatgg gcgtggatag cggtttgact cacggggatt tccaagtctc cacccccattg     900 acgtcaatgg gagtttgttt tggcaccaaa atcaacggga ctttccaaaa tgtcgtaaca      960
actccgcccc attgacgcaa atgggcggta ggcgtgtacg gtgggaggtc tatataagca     1020
gagctggttt agtgaaccgt cagatcctgc agaagttggt cgtgaggcac tgggcaggta     1080
agtatcaagt ttacaagaca ggtttaagga gaccaataga aactgggctt gtcgagacag     1140
agaagactct tgcgtttctg ataggcacct attggtctta ctgacatcca ctttgccttt     1200
ctctccacag gtgtccaggc ggccgcatga tcgatctgga gccaggtgaa aagccttata     1260
agtgccctga atgcgggaaa tcattcagcc agaactccac acttaccgag caccagagaa     1320
cccatactgg ggagaaaccc tataagtgcc cagaatgtgg gaagtctttc tctaccagcg     1380
gacacttggt caggcaccag agaacgcacc agaacaagaa aggaggttct ggtgatggca     1440
agaagaagca gcatgcttgt cccgaatgcg gcaagtcctt tagcagggag acaatctgc      1500 acactcacca acgcacacat actggcgaga agccgtacaa gtgtcccgaa tgtggcaaaa     1560
gtttctccac aagtggacat ctcgttcgtc accagcgaac ccacaccgga gagaaaccct     1620
acaaatgccc agagtgtggg aaatcctttt cacggagcga caaactggtg agacatcaac     1680
gcactcatac aggcaagaaa acgagctcac ggtaccctta cgatgtgcct gactatgcca     1740
gttaataaaa gcttggatcc aatcaacctc tggattacaa aatttgtgaa agattgactg     1800
gtattcttaa ctatgttgct ccttttacgc tatgtggata cgctgcttta atgcctttgt     1860
atcatgctat tgcttcccgt atggctttca ttttctcctc cttgtataaa tcctggttgc     1920
tgtctcttta tgaggagttg tggcccgttg tcaggcaacg tggcgtggtg tgcactgtgt     1980
ttgctgacgc aaccccact ggttgggca ttgccaccac ctgtcagctc ctttccggga      2040
ctttcgcttt ccccctccct attgccacgg cggaactcat cgccgcctgc cttgcccgct     2100
gctggacagg ggctcggctg ttgggcactg acaattccgt ggtgttgtcg gggaagctga     2160
cgtcctttcc atggctgctc gcctgtgttg ccacctggat tctgcgcggg acgtccttct     2220
gctacgtccc ttcggccctc aatccagcgg accttccttc ccgcggcctg ctgccggctc     2280
tgcggcctct tccgcgtctt cgagatctgc ctcgactgtg ccttctagtt gccagccatc     2340
tgttgtttgc ccctccccg tgccttcctt gaccctggaa ggtgccactc ccactgtcct     2400
ttcctaataa aatgaggaaa ttgcatcgca ttgtctgagt aggtgtcatt ctattctggg     2460
gggtggggtg gggcaggaca gcaagggga ggattgggaa gacaatagca ggcatgctgg      2520
```

-continued

```
ggactcgagt taagggcgaa ttcccgatta ggatcttcct agagcatggc tacgtagata    2580
agtagcatgg cggttaatc attaactaca aggaacccct agtgatgag ttggccactc      2640 cctctctgcg cgctcgctcg ctcactgagg ccgggcgacc aaaggtcgcc cgacgcccgg    2700
gctttgcccg gcggcctca gtgagcgagc gagcgcgcag ccttaattaa cctaattcac     2760
tggccgtcgt tttacaacgt cgtgactggg aaaaccctgg cgttacccaa cttaatcgcc    2820
ttgcagcaca tccccctttc gccagctggc gtaatagcga gaggcccgc accgatcgcc     2880 cttcccaaca gttgcgcagc ctgaatggcg aatgggacgc gccctgtagc ggcgcattaa    2940
gcgcggcggg tgtggtggtt acgcgcagcg tgaccgctac acttgccagc gccctagcgc    3000
ccgctccttt cgctttcttc ccttcctttc tcgccacgtt cgccggcttt ccccgtcaag    3060
ctctaaatcg gggctccct ttaggggttcc gatttagtgc tttacggcac ctcgacccca    3120
aaaaacttga ttagggtgat ggttcacgta gtgggccatc gccccgatag acggttttc     3180 gcccttgac gctggagttc acgttcctca atagtggact cttgttccaa actggaacaa    3240
cactcaaccc tatctcggtc tattcttttg attttataagg gattttccg atttcggcct    3300 attggttaaa aaatgagctg atttaacaaa aattttaacgc gaattttaac aaaatattaa   3360
cgtttataat ttcaggtggc atctttcggg gaaatgtgcg cggaacccct atttgtttat    3420 tttctaaat acattcaat atgtatccgc tcatgagaca ataaccctga taaatgcttc      3480
aataatattg aaaaaggaag agtatgagta ttcaacattt ccgtgtcgcc cttattccct    3540 ttttttgcggc attttgcctt cctgtttttg ctcacccaga aacgctggtg aaagtaaaag    3600
atgctgaaga tcagttgggt gcacgagtgg gttacatcga actggatctc aatagtggta    3660
agatccttga gagttttcgc cccgaagaac gttttccaat gatgagcact tttaaagttc    3720
tgctatgtgg cgcggtatta ccccgtattg acgccgggca agagcaactc ggtcgccgca    3780
tacactattc tcagaatgac ttggttgagt actcaccagt cacagaaaag catcttacgg    3840
atggcatgac agtaagagaa ttatgcagtg ctgccataac catgagtgat aacactgcgg    3900
ccaacttact tctgacaacg atcggaggac cgaaggagct aaccgctttt ttgcacaaca    3960
tgggggatca tgtaactcgc cttgatcgtt gggaaccgga gctgaatgaa gccataccaa    4020
acgacgagcg tgacaccacg atgcctgtag taatggtaac aacgttgcgc aaactattaa    4080
ctggcgaact acttactcta gcttcccggc aacaattaat agactggatg gaggcggata    4140
aagttgcagg accacttctg cgctcggccc ttccggctgg ctggtttatt gctgataaat    4200
ctggagccgg tgagcgtggg tctcgcggta tcattgcagc actggggcca gatggtaagc    4260
cctcccgtat cgtagttatc tacacgacgg ggagtcaggc aactatggat gaacgaaata    4320
gacagatcgc tgagataggt gcctcactga ttaagcattg gtaactgtca gaccaagttt    4380
actcatatat actttagatt gatttaaaac ttcattttta atttaaaagg atctaggtga    4440 agatccttt tgataatctc atgaccaaaa tcccttaacg tgagttttcg ttccactgag    4500
cgtcagaccc cgtagaaaag atcaaaggat cttcttgaga tccttttttt ctgcgcgtaa    4560
tctgctgctt gcaaacaaaa aaaccaccgc taccagcggt ggtttgtttg ccggatcaag    4620
agctaccaac tctttttccg aaggtaactg gcttcagcag agcgcagata ccaaatactg    4680
tccttctagt gtagccgtag ttaggccacc acttcaagaa ctctgtagca ccgcctacat    4740
acctcgctct gctaatcctg ttaccagtgg ctgctgccag tggcgataag tcgtgtctta    4800
ccgggttgga ctcaagacga tagttaccgg ataaggcgca gcggtcgggc tgaacggggg    4860
gttcgtgcac acagcccagc ttggagcgaa cgacctacac cgaactgaga tacctacagc    4920
```

```
gtgagctatg agaaagcgcc acgcttcccg aagggagaaa ggcggacagg tatccggtaa    4980
gcggcagggt cggaacagga gagcgcacga gggagcttcc aggggaaaac gcctggtatc    5040
tttatagtcc tgtcgggttt cgccacctct gacttgagcg tcgattttg tgatgctcgt     5100 caggggggcg gagcctatgg aaaaacgcca gcaacgcggc cttttacgg ttcctggcct     5160 tttgctgcgg ttttgctcac atgttctttc ctgcgttatc ccctgattct gtggataacc    5220
gtattaccgc ctttgagtga gctgataccg ctcgccgcag ccgaacgacc gagcgcagcg    5280
agtcagtgag cgaggaagcg gaag                                           5304

<210> SEQ ID NO 20
<211> LENGTH: 6610
<212> TYPE: DNA
<213> ORGANISM: Artificial Sequence
<220> FEATURE:
<223> OTHER INFORMATION: synthetic

<400> SEQUENCE: 20
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccagattta     240
attaaggctg cgcgctcgct cgctcactga ggccgcccgg gcaaagcccg ggcgtcgggc     300
gacctttggt cgcccggcct cagtgagcga gcgagcgcgc agagagggag tggccaactc     360
catcactagg ggttccttgt agttaatgat taacccgcca tgctacttat ctacgtagcc     420
atgctctagg aagatcggaa ttcgccctta agctagctag ttattaatag taatcaatta     480
cggggtcatt agttcatagc ccatatatgg agttccgcgt tacataactt acggtaaatg     540
gcccgcctgg ctgaccgccc aacgaccccc gcccattgac gtcaataatg acgtatgttc     600
ccatagtaac gccaataggg actttccatt gacgtcaatg ggtggagtat ttacggtaaa     660
ctgcccactt ggcagtacat caagtgtatc atatgccaag tacgccccct attgacgtca     720
atgacggtaa atggcccgcc tggcattatg cccagtacat gaccttatgg actttcta      780 cttggcagta catctacgta ttagtcatcg ctattaccat ggtgatgcgg ttttggcagt     840
acatcaatgg gcgtggatag cggtttgact cacggggatt tccaagtctc caccccattg     900
acgtcaatgg gagtttgttt tggcaccaaa atcaacggga ctttccaaaa tgtcgtaaca     960
actccgcccc attgacgcaa atgggcggta ggcgtgtacg gtgggaggtc tatataagca    1020
gagctggttt agtgaaccgt cagatcctgc agaagttggt cgtgaggcac tgggcaggta    1080
agtatcaagg ttacaagaca ggtttaagga gaccaataga aactgggctt gtcgagacag    1140
agaagactct tgcgtttctg ataggcacct attggtctta ctgacatcca ctttgccttt    1200
ctctccacag gtgtccaggc ggccgcatgc cgaagaagaa gcgtaaagtc actagcgccc    1260
ccagaagaag ggccgctcag ccttccgatg cctctcctgc cgcccaggtg gacctgagaa    1320
ccctgggcta cagccagcag cagcaggaaa agatcaagcc caaagtgcgg agcaccgtgg    1380
cccagcacca cgaagccctc gtgggccacg gctttaccca cgctcacatc gtggccctga    1440
gccagcatcc tgccgctctg ggaaccgtgg ccgtgaagta ccaggacatg atcgccgccc    1500
tgcccgaggc cacacacgag gctatcgtgg gcgtgggcaa gcagtggtcc ggcgctagag    1560
cactcgaggc cttgctgaca gtggccggcg agctgagagg ccctccactg cagctggaca    1620
```

-continued

```
ccggccagct gctgaagatc gccaagcggg gaggcgtgac agccgtggaa gccgtgcacg    1680
cttggcggaa tgccctgaca ggcgctcccc tgaaccttac gccgcagcag gtggtggcca    1740
tcgccagcca cgatggcggc aagcaggcgc tggagacggt gcagcggctg cttccggtgc    1800
tgtgccaggc ccatggcctg accccggagc aggtggtggc catcgccagc aatattggtg    1860
gcaagcaggc gctggagacg gtgcagcgat gttgccggt gctgtgccag gcccatggcc    1920
tgaccccgga gcaggtggtg gccatcgcca gccacgacgg tggcaagcag gcgctggaga    1980
ctgtccagcg gctgttgccg gtgctgtgcc aggcccatgg cctgaccccg gagcaggtgg    2040
tggccatcgc cagcaatggc ggtggcaagc aggcgcttga gacggtgcag cggctgttgc    2100
cggtgctgtg ccaggcccat ggcctgaccc ggagcaggt ggtggccatc gccagcaatg    2160
gcggtggcaa gcaggctctg gagacggtgc agcggctgtt gccggtgctg tgccaggccc    2220
atggcctgac cccggagcag gtggtggcca tcgccagcaa tggcgggggc aagcaggcgc    2280
tggagacggt gcagcggctg ttgccggtgc tgtgccaggc ccatggcctg accccgcagc    2340
aggtggtggc catcgccagc aatattggcg gcaagcaggc gctggagacg gtgcaggcgc    2400
tgttgccggt gctgtgccag gcccatggcc tgaccccgga gcaggtggtg gccatcgcaa    2460
gcaatggcgg tggcaagcag gcgctggaga cggtgcaggc gctgttgccg gtgctgtgcc    2520
aggcccatgg cctgaccccg gagcaggtgg tggcaatcgc cagcaatatt ggtggcaagc    2580
aggcgctgga gacggtgcag cggctgttgc ggtgctgtg ccaggcccat ggcctgaccc    2640
cgcaacaggt ggtagccatc gccagcaata ttggtggcaa gcaggcgctg gagacggtgc    2700
agcggctgtt gccggtgctg tgccaggccc atggcctgac ccccagcag gtggtagcga    2760
tcgccagcaa taagggtggc aagcaggcgc tggagacggt gcagcggctg cttccggtgc    2820
tgtgccaggc ccatggcctg accccggagc aggtggtggc catcgccagc aataagggtg    2880
gcaagcaggc gctggagacg gtgcagcgat gttgccggt gctgtgccag gcccatggcc    2940
tgaccccgga gcaggtggtg gccatcgcca gcaataaggg tggcaagcag gcgctggaga    3000
ctgtccagcg gctgttgccg gtgctgtgcc aggcccatgg cctgaccccg gagcaggtgg    3060
tggccatcgc cagcaatggc ggtggcaagc aggcgcttga gacggtgcag cggctgttgc    3120
cggtgctgtg ccaggcccat ggcctgaccc cgcagcaggt ggtggccatc gccagccacg    3180
acggtggcaa gcaggctctg gagacggtgc agcggctgtt gccggtgctg tgccaggccc    3240
atggcctgac cccggagcag gtggtggcca tcgccagcaa tggcgggggc aagcaggcgc    3300
tggagacggt gcagcggctg ttgccggtgc tgtgccaggc ccatggcctg accccgcagc    3360
aggtggtggc catcgccagc aataagggcg gcaagcaggc gctggagacg gtgcaggcgc    3420
tgttgccggt gctgtgccag gcccatggcc tgacacccca gcaggtcgtg gccattgcca    3480
gcaacaaggg aggcagaccc gccctggaat ctattgtggc ccagctgagc agacccgacc    3540
cagctctggc cgccctgaca ggatcctacc cgtacgacgt tccagactat gcatcttaat    3600
aaaagcttag atctgcctcg actgtgcctt ctagttgcca gccatctgtt gtttgcccct    3660
cccccgtgcc ttccttgacc ctggaaggtg ccactcccac tgtcctttcc taataaaatg    3720
aggaaattgc atcgcattgt ctgagtaggt gtcattctat tctggggggt ggggtggggc    3780
aggacagcaa gggggaggat tgggaagaca atagcaggca tgctggggac tcgagttaag    3840
ggcgaattcc cgattaggat cttcctagag catggctacg tagataagta gcatggcggg    3900
ttaatcatta actacaagga accccctagtg atggagttgg ccactccctc tctgcgcgct    3960
cgctcgctca ctgaggccgg gcgaccaaag gtcgcccgac gcccgggctt tgcccgggcg    4020
```

```
gcctcagtga gcgagcgagc gcgcagcctt aattaaccta attcactggc cgtcgtttta   4080
caacgtcgtg actgggaaaa ccctggcgtt acccaactta atcgccttgc agcacatccc   4140
cctttcgcca gctggcgtaa tagcgaagag gcccgcaccg atcgcccttc ccaacagttg   4200
cgcagcctga atggcgaatg ggacgcgccc tgtagcggcg cattaagcgc ggcgggtgtg   4260
gtggttacgc gcagcgtgac cgctacactt gccagcgccc tagcgcccgc tcctttcgct   4320
ttcttccctt cctttctcgc cacgttcgcc ggctttcccc gtcaagctct aaatcggggg   4380
ctccctttag ggttccgatt tagtgcttta cggcacctcg accccaaaaa acttgattag   4440
ggtgatggtt cacgtagtgg gccatcgccc tgatagacgg ttttttcgccc tttgacgctg   4500
gagttcacgt tcctcaatag tggactcttg ttccaaactg gaacaacact caaccctatc   4560
tcggtctatt cttttgattt ataagggatt tttccgattt cggcctattg gttaaaaaat   4620
gagctgattt aacaaaaatt taacgcgaat tttaacaaaa tattaacgtt tataatttca   4680
ggtggcatct ttcggggaaa tgtgcgcgga acccctattt gtttattttt ctaaatacat   4740
tcaaatatgt atccgctcat gagacaataa ccctgataaa tgcttcaata atattgaaaa   4800
aggaagagta tgagtattca acatttccgt gtcgccctta ttcccttttt tgcggcattt   4860
tgccttcctg tttttgctca cccagaaacg ctggtgaaag taaaagatgc tgaagatcag   4920
ttgggtgcac gagtgggtta catcgaactg gatctcaata gtggtaagat ccttgagagt   4980
tttcgccccg aagaacgttt tccaatgatg agcacttttta aagttctgct atgtggcgcg   5040
gtattatccc gtattgacgc cgggcaagag caactcggtc gccgcataca ctattctcag   5100
aatgacttgg ttgagtactc accagtcaca gaaaagcatc ttacggatgg catgacagta   5160
agagaattat gcagtgctgc cataaccatg agtgataaca ctgcggccaa cttacttctg   5220
acaacgatcg gaggaccgaa ggagctaacc gcttttttgc acaacatggg ggatcatgta   5280
actcgccttg atcgttggga accggagctg aatgaagcca taccaaacga cgagcgtgac   5340
accacgatgc ctgtagtaat ggtaacaacg ttgcgcaaac tattaactgg cgaactactt   5400
actctagctt cccggcaaca attaatagac tggatggagg cggataaagt tgcaggacca   5460
cttctgcgct cggcccttcc ggctggctgg tttattgctg ataaatctgg agccggtgag   5520
cgtgggtctc gcggtatcat tgcagcactg gggccagatg gtaagccctc ccgtatcgta   5580
gttatctaca cgacggggag tcaggcaact atggatgaac gaaatagaca gatcgctgag   5640
ataggtgcct cactgattaa gcattggtaa ctgtcagacc aagtttactc atatatactt   5700
tagattgatt taaaacttca ttttttaattt aaaaggatct aggtgaagat cctttttgat   5760
aatctcatga ccaaaatccc ttaacgtgag ttttcgttcc actgagcgtc agaccccgta   5820
gaaaagatca aaggatcttc ttgagatcct ttttttctgc gcgtaatctg ctgcttgcaa   5880
acaaaaaaac caccgctacc agcggtggtt tgtttgccgg atcaagagct accaactctt   5940
tttccgaagg taactggctt cagcagagcg cagataccaa atactgtcct tctagtgtag   6000
ccgtagttag gccaccactt caagaactct gtagcaccgc ctacatacct cgctctgcta   6060
atcctgttac cagtggctgc tgccagtggc gataagtcgt gtcttaccgg gttggactca   6120
agacgatagt taccggataa ggcgcagcgg tcgggctgaa cggggggttc gtgcacacag   6180
cccagcttgg agcgaacgac ctacaccgaa ctgagatacc tacagcgtga gctatgagaa   6240
agcgccacgc ttcccgaagg gagaaaggcg gacaggtatc cggtaagcgg cagggtcgga   6300
acaggagagc gcacgaggga gcttccaggg ggaaacgcct ggtatcttta tagtcctgtc   6360
```

```
gggtttcgcc acctctgact tgagcgtcga ttttttgtgat gctcgtcagg ggggcggagc    6420
ctatggaaaa acgccagcaa cgcggccttt ttacggttcc tggccttttg ctgcggtttt    6480
gctcacatgt tctttcctgc gttatcccct gattctgtgg ataaccgtat taccgccttt    6540
gagtgagctg ataccgctcg ccgcagccga acgaccgagc gcagcgagtc agtgagcgag    6600
gaagcggaag                                                          6610

<210> SEQ ID NO 21
<211> LENGTH: 6307
<212> TYPE: DNA
<213> ORGANISM: Artificial Sequence
<220> FEATURE:
<223> OTHER INFORMATION: synthetic

<400> SEQUENCE: 21
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccagattta     240
attaaggctg cgcgctcgct cgctcactga ggccgcccgg gcaaagcccg ggcgtcgggc     300
gacctttggt cgcccggcct cagtgagcga gcgagcgcgc agagagggag tggccaactc     360
catcactagg ggttccttgt agttaatgat taacccgcca tgctacttat ctacgtagcc     420
atgctctagg aagatcggaa ttcgccctta agctagctag ttattaatag taatcaatta     480
cggggtcatt agttcatagc ccatatatgg agttccgcgt tacataactt acggtaaatg     540
gcccgcctgg ctgaccgccc aacgaccccc gcccattgac gtcaataatg acgtatgttc     600
ccatagtaac gccaataggg actttccatt gacgtcaatg ggtggagtat ttacggtaaa     660
ctgcccactt ggcagtacat caagtgtatc atatgccaag tacgccccct attgacgtca     720
atgacggtaa atggcccgcc tggcattatg cccagtacat gaccttatgg gactttccta     780
cttggcagta catctacgta ttagtcatcg ctattaccat ggtgatgcgg ttttggcagt     840
acatcaatgg gcgtggatag cggtttgact cacggggatt tccaagtctc cacccattg     900 acgtcaatgg gagtttgttt tggcaccaaa atcaacggga ctttccaaaa tgtcgtaaca     960
actccgcccc attgacgcaa atgggcggta ggcgtgtacg gtgggaggtc tatataagca    1020
gagctggttt agtgaaccgt cagatcctgc agaagttggt cgtgaggcac tgggcaggta    1080
agtatcaagg ttacaagaca ggtttaagga gaccaataga aactgggctt gtcgagacag    1140
agaagactct tgcgtttctg ataggcacct attggtctta ctgacatcca ctttgccttt    1200
ctctccacag tgtccaggc ggccgcatgc cgaagaagaa gcgtaaagtc actagtgcaa    1260 gtgcccaag aaggcgggcc gcccagcctt ctgacgctag ccccgctgcc caggtggatc    1320
tgcgaacgct gggttattct cagcagcagc aagagaagat taagcctaag gtccggagta    1380
ctgtggcaca gcaccatgag gctctggtcg ggcacggctt cacgcacgca cacatcgttg    1440
cactctccca gcaccctgcc gcgctgggca cagtggcagt gaagtaccaa gatatgattg    1500
cggcacttcc cgaagctact cacgaggcca tcgtcggcgt tgggaagcag tggtcaggcg    1560
ctagggcact ggaggcactg ctgactgtgg ccggggagct tcgcggaccc ccctgcagt    1620 tggacacagg ccagctgctg aagatagcaa aacgaggagg cgtcacagct gtagaggccg    1680
tgcatgcgtg gcgcaatgcc cttaccgggg cccctctgaa tctgacccg cagcaagtgg    1740 tagccattgc gtctaacaac ggagggaaac aggcactcga cacagttcaa cggctgctcc    1800
```

```
ccgtgctttg ccaggcgcac ggactgaccc cagaacaagt ggtggcgatc gcctcaaata      1860
acggcggcaa acaggctctt gaaaccgtgc agagactgct gccagtactg tgccaggctc      1920
atggcctgac cccagagcag gttgtggcca tcgcttcaaa caatggcggt aaacaggcgc      1980
tcgagactgt ccagaggctg ttgcctgtgc tctgccaagc tcatggcctg acgcccgaac      2040
aggtggttgc catcgctagc aacatcggcg gcaagcaagc tctcgagaca gtgcaacggc      2100
tgctgcccgt actctgccag gcacatgggc tgactcccga gcaagtggtt gctattgcat      2160
ctaacaacgg cggaaagcag gcgctggaga ctgtccagcg tttgcttcct gttttgtgtc      2220
aggctcacgg cttgacgccc gaacaggtag tggccatagc ctccaacatc ggaggaaaac      2280
aggcacttga acagtccag aggcttctcc ccgtcctgtg ccagcccat ggcctcactc        2340 cacagcaagt agtggctatt gcatccaatg gaggcgggaa acaagccttg aaaccgtcc       2400 aggccctgct gcctgtcctg tgccaggcac acgggctgac acctgaacag gtggtcgcaa      2460
ttgccagtaa tggtggcggg aagcaagccc tggagactgt tcaggctttg ctgcccgttc      2520
tgtgtcaagc acacggtctg actccagaac aggttgtggc tatcgcctcc aataatggtg      2580
gcaaacaggc tctcgaaaca gtgcagaggc tgctgcccgt gctgtgtcaa gcccatggcc      2640 tgacccccaca gcaggtcgtg gccattgcct ctaataatgg aggtaaacag gccctggaga     2700
cagtccagag attgcttcca gttctgtgtc aggcccacgg gctgacccct caacaggtcg      2760
tcgccatcgc ctcaaacaac ggtggcaagc aggcactcga gactgtgcag cggctcttgc      2820
ctgtgctgtg tcaagcccat ggactgaccc cggaacaggg ggttgccatt gccagcaaca     2880
acggtgggaa acaggctttg gaaaccgtgc aacgcctgct gccggttctg tgccaggctc      2940
acgggcttac cccggaacag gtggtagcta tcgctagcaa taatggaggg aagcaggccc      3000
tggaaacagt gcagagactg ctccccgtcc tctgccaggc acacggactc acccggagc       3060 aagtggtcgc catagcctcc aacggtggag ggaagcaggc actggagaca gtgcagagac      3120
ttctcccagt gctctgtcag gctcatgggc tcaccectca acaggtagta gccatagcta      3180
gtaacaatgg aggtcgtcca gcattggaga gcatcgtggc gcagctgagc cgcccagacc      3240
cagcgcttgc cgccttgacc ggaagctatc cctacgacgt gcctgattac gcttaataaa      3300
agcttagatc tgcctcgact gtgccttcta gttgccagcc atctgttgtt tgcccctccc      3360
ccgtgccttc cttgaccctg gaaggtgcca ctcccactgt cctttcctaa taaaatgagg      3420
aaattgcatc gcattgtctg agtaggtgtc attctattct ggggggtggg gtggggcagg      3480
acagcaaggg ggaggattgg gaagacaata gcaggcatgc tggggactcg agttaagggc      3540
gaattcccga ttaggatctt cctagagcat ggctacgtag ataagtagca tggcgggtta      3600
atcattaact acaaggaacc cctagtgatg gagttggcca ctccctctct gcgcgctcgc      3660
tcgctcactg aggccgggcg accaaaggtc gcccgacgcc cgggctttgc ccgggcggcc      3720
tcagtgagcg agcgagcgcg cagccttaat taacctaatt cactggccgt cgttttacaa      3780
cgtcgtgact gggaaaaccc tggcgttacc caacttaatc gccttgcagc acatccccct      3840
ttcgccagct ggcgtaatag cgaagaggcc cgcaccgatc gcccttccca acagttgcgc      3900
agcctgaatg gcgaatggga cgcgccctgt agcggcgcat taagcgcggc gggtgtggtg      3960
gttacgcgca gcgtgaccgc tacacttgcc agcgccctag cgcccgctcc tttcgctttc      4020
ttcccttcct ttctcgccac gttcgccggc tttccccgtc aagctctaaa tcggggctc      4080 ccttagggt tccgatttag tgctttacgg cacctcgacc ccaaaaaact tgattagggt      4140
```

```
gatggttcac gtagtgggcc atcgccccga tagacggttt ttcgcccttt gacgctggag    4200
ttcacgttcc tcaatagtgg actcttgttc caaactggaa caacactcaa ccctatctcg    4260
gtctattctt ttgatttata agggattttt ccgatttcgg cctattggtt aaaaaatgag    4320
ctgatttaac aaaaatttaa cgcgaatttt aacaaaatat taacgtttat aatttcaggt    4380
ggcatctttc ggggaaatgt gcgcggaacc cctatttgtt tattttttcta aatacattca    4440 aatatgtatc cgctcatgag acaataaccc tgataaatgc ttcaataata ttgaaaaagg    4500
aagagtatga gtattcaaca tttccgtgtc gcccttattc cctttttgc ggcattttgc     4560 cttcctgttt ttgctcaccc agaaacgctg gtgaaagtaa aagatgctga agatcagttg    4620
ggtgcacgag tgggttacat cgaactggat ctcaatagtg gtaagatcct tgagagtttt    4680
cgccccgaag aacgttttcc aatgatgagc acttttaaag ttctgctatg tggcgcggta    4740
ttatcccgta ttgacgccgg gcaagagcaa ctcggtcgcc gcatacacta ttctcagaat    4800
gacttggttg agtactcacc agtcacagaa aagcatctta cggatggcat gacagtaaga    4860
gaattatgca gtgctgccat aaccatgagt gataacactg cggccaactt acttctgaca    4920
acgatcggag gaccgaagga gctaaccgct tttttgcaca acatggggga tcatgtaact    4980
cgccttgatc gttgggaacc ggagctgaat gaagccatac caaacgacga gcgtgacacc    5040
acgatgcctg tagtaatggt aacaacgttg cgcaaactat taactggcga actacttact    5100
ctagcttccc ggcaacaatt aatagactgg atggaggcgg ataaagttgc aggaccactt    5160
ctgcgctcgg cccttccggc tggctggttt attgctgata aatctggagc cggtgagcgt    5220
gggtctcgcg gtatcattgc agcactgggg ccagatggta agccctcccg tatcgtagtt    5280
atctacacga cggggagtca ggcaactatg gatgaacgaa atagacagat cgctgagata    5340
ggtgcctcac tgattaagca ttggtaactg tcagaccaag tttactcata tactttag     5400 attgatttaa aacttcattt ttaatttaaa aggatctagg tgaagatcct ttttgataat    5460
ctcatgacca aaatccctta acgtgagttt tcgttccact gagcgtcaga ccccgtagaa    5520
aagatcaaag gatcttcttg agatcctttt tttctgcgcg taatctgctg cttgcaaaca    5580
aaaaaaccac cgctaccagc ggtggtttgt ttgccggatc aagagctacc aactcttttt    5640
ccgaaggtaa ctggcttcag cagagcgcag ataccaaata ctgtccttct agtgtagccg    5700
tagttaggcc accacttcaa gaactctgta gcaccgccta catacctcgc tctgctaatc    5760
ctgttaccag tggctgctgc cagtggcgat aagtcgtgtc ttaccgggtt ggactcaaga    5820
cgatagttac cggataaggc gcagcggtcg ggctgaacgg ggggttcgtg cacacagccc    5880
agcttggagc gaacgaccta caccgaactg agatacctac agcgtgagct atgagaaagc    5940
gccacgcttc ccgaagggag aaaggcggac aggtatccgg taagcggcag ggtcggaaca    6000
ggagagcgca cgagggagct tccaggggga aacgcctggt atctttatag tcctgtcggg    6060
tttcgccacc tctgacttga gcgtcgattt ttgtgatgct cgtcaggggg gcggagccta    6120
tggaaaaacg ccagcaacgc ggccttttta cggttcctgg ccttttgctg cggttttgct    6180
cacatgttct ttcctgcgtt atcccctgat tctgtggata accgtattac cgcctttgag    6240
tgagctgata ccgctcgccg cagccgaacg accgagcgca gcgagtcagt gagcgaggaa    6300
gcggaag                                                              6307
```

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22 ggggggttaga gggtctacga                    20

<210> SEQ ID NO 23
<211> LENGTH: 25
<212> TYPE: DNA
<213> ORGANISM: Artificial Sequence
<220> FEATURE:
<223> OTHER INFORMATION: synthetic

<400> SEQUENCE: 23 caccccccaat ctcccagatg ctgat              25

<210> SEQ ID NO 24
<211> LENGTH: 18
<212> TYPE: DNA
<213> ORGANISM: Artificial Sequence
<220> FEATURE:
<223> OTHER INFORMATION: synthetic

<400> SEQUENCE: 24
tcagcatctg ggagattg                       18

<210> SEQ ID NO 25
<211> LENGTH: 16
<212> TYPE: DNA
<213> ORGANISM: Artificial Sequence
<220> FEATURE:
<223> OTHER INFORMATION: synthetic

<400> SEQUENCE: 25 ggggggttaga gggtct                        16

<210> SEQ ID NO 26
<211> LENGTH: 17
<212> TYPE: DNA
<213> ORGANISM: Artificial Sequence
<220> FEATURE:
<223> OTHER INFORMATION: synthetic

<400> SEQUENCE: 26 ggggggttaga gggtcta                       17

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
tgaacacccc caatctcc                       18

<210> SEQ ID NO 28
<211> LENGTH: 16
<212> TYPE: DNA
<213> ORGANISM: Artificial Sequence
<220> FEATURE:
<223> OTHER INFORMATION: synthetic

<400> SEQUENCE: 28
gtgggggtta gagggt                         16

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
ttactgtaat cttaaccgga                                              20

<210> SEQ ID NO 30
<211> LENGTH: 6
<212> TYPE: DNA
<213> ORGANISM: Artificial Sequence
<220> FEATURE:
<223> OTHER INFORMATION: synthetic

<400> SEQUENCE: 30 cccccа                                                              6

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
ccatcccagc gttctttgcc                                              20

<210> SEQ ID NO 32
<211> LENGTH: 22
<212> TYPE: DNA
<213> ORGANISM: Artificial Sequence
<220> FEATURE:
<223> OTHER INFORMATION: synthetic

<400> SEQUENCE: 32
ggcctcatcg tcacccagtg gg                                           22

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
ctctgccagc tttctttgct                                              20

<210> SEQ ID NO 34
<211> LENGTH: 22
<212> TYPE: DNA
<213> ORGANISM: Artificial Sequence
<220> FEATURE:
<223> OTHER INFORMATION: synthetic

<400> SEQUENCE: 34
ggcgtcgtca tctcccagtg ga                                           22

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
gaccgagcct cagaatacca                                          20

<210> SEQ ID NO 36
<211> LENGTH: 24
<212> TYPE: DNA
<213> ORGANISM: Artificial Sequence
<220> FEATURE:
<223> OTHER INFORMATION: synthetic

<400> SEQUENCE: 36
ggagaattga gtctcgataa tacc                                     24

<210> SEQ ID NO 37
<211> LENGTH: 23
<212> TYPE: DNA
<213> ORGANISM: Artificial Sequence
<220> FEATURE:
<223> OTHER INFORMATION: synthetic

<400> SEQUENCE: 37
tctagttgcc agccatctgt tgt                                      23

<210> SEQ ID NO 38
<211> LENGTH: 16
<212> TYPE: DNA
<213> ORGANISM: Artificial Sequence
<220> FEATURE:
<223> OTHER INFORMATION: synthetic

<400> SEQUENCE: 38
gggagtggca ccttcc                                              16

<210> SEQ ID NO 39
<211> LENGTH: 19
<212> TYPE: DNA
<213> ORGANISM: Artificial Sequence
<220> FEATURE:
<223> OTHER INFORMATION: synthetic

<400> SEQUENCE: 39
gtcggtgtga acggatttg                                           19

<210> SEQ ID NO 40
<211> LENGTH: 20
<212> TYPE: DNA
<213> ORGANISM: Artificial Sequence
<220> FEATURE:
<223> OTHER INFORMATION: synthetic

<400> SEQUENCE: 40
caatgaaggg gtcgttgatg                                          20

<210> SEQ ID NO 41
<211> LENGTH: 21
<212> TYPE: DNA
<213> ORGANISM: Artificial Sequence
<220> FEATURE:
<223> OTHER INFORMATION: synthetic

<400> SEQUENCE: 41
caagatcatt gctcctcctg a                                        21

<210> SEQ ID NO 42

```
<211> LENGTH: 21
<212> TYPE: DNA
<213> ORGANISM: Artificial Sequence
<220> FEATURE:
<223> OTHER INFORMATION: synthetic

<400> SEQUENCE: 42
catcgtactc ctgcttgctg a                                              21

<210> SEQ ID NO 43
<211> LENGTH: 37
<212> TYPE: DNA
<213> ORGANISM: Artificial Sequence
<220> FEATURE:
<223> OTHER INFORMATION: synthetic

<400> SEQUENCE: 43
attaatatga ttatgaacag attcagccag gagctta                             37

<210> SEQ ID NO 44
<211> LENGTH: 37
<212> TYPE: DNA
<213> ORGANISM: Artificial Sequence
<220> FEATURE:
<223> OTHER INFORMATION: synthetic

<400> SEQUENCE: 44
taagctcctg gctgaatctg ttcataatca tattaat                             37

<210> SEQ ID NO 45
<211> LENGTH: 57
<212> TYPE: DNA
<213> ORGANISM: Artificial Sequence
<220> FEATURE:
<223> OTHER INFORMATION: synthetic

<400> SEQUENCE: 45
attaatatga ttatgaacat tactgtaatc ttaaccggag attcagccag gagctta       57

<210> SEQ ID NO 46
<211> LENGTH: 57
<212> TYPE: DNA
<213> ORGANISM: Artificial Sequence
<220> FEATURE:
<223> OTHER INFORMATION: synthetic

<400> SEQUENCE: 46
taagctcctg gctgaatctc cggttaagat tacagtaatg ttcataatca tattaat       57

<210> SEQ ID NO 47
<211> LENGTH: 30
<212> TYPE: DNA
<213> ORGANISM: Artificial Sequence
<220> FEATURE:
<223> OTHER INFORMATION: synthetic

<400> SEQUENCE: 47
ggaattccat atggaattcc ccatggatgc                                     30

<210> SEQ ID NO 48
<211> LENGTH: 35
<212> TYPE: DNA
<213> ORGANISM: Artificial Sequence
<220> FEATURE:
<223> OTHER INFORMATION: synthetic

<400> SEQUENCE: 48
```
cgggatccct atctagaagt ctttttaccg gtatg                                35

<210> SEQ ID NO 49
<211> LENGTH: 34
<212> TYPE: DNA
<213> ORGANISM: Artificial Sequence
<220> FEATURE:
<223> OTHER INFORMATION: synthetic

<400> SEQUENCE: 49
ggaattccat atgctggaac ctggcgaaaa accg                                 34

<210> SEQ ID NO 50
<211> LENGTH: 35
<212> TYPE: DNA
<213> ORGANISM: Artificial Sequence
<220> FEATURE:
<223> OTHER INFORMATION: synthetic

<400> SEQUENCE: 50
cgggatccct atctagaagt ctttttaccg gtatg                                35

<210> SEQ ID NO 51
<211> LENGTH: 32
<212> TYPE: DNA
<213> ORGANISM: Artificial Sequence
<220> FEATURE:
<223> OTHER INFORMATION: synthetic

<400> SEQUENCE: 51
ggaattccat atggagacca gaccaacagc tc                                   32

<210> SEQ ID NO 52
<211> LENGTH: 28
<212> TYPE: DNA
<213> ORGANISM: Artificial Sequence
<220> FEATURE:
<223> OTHER INFORMATION: synthetic

<400> SEQUENCE: 52
cggaattcct agttttgaa catatcac                                         28

<210> SEQ ID NO 53
<211> LENGTH: 32
<212> TYPE: DNA
<213> ORGANISM: Artificial Sequence
<220> FEATURE:
<223> OTHER INFORMATION: synthetic

<400> SEQUENCE: 53
ggaattccat atggtggacc acttacttcc ag                                   32

<210> SEQ ID NO 54
<211> LENGTH: 30
<212> TYPE: DNA
<213> ORGANISM: Artificial Sequence
<220> FEATURE:
<223> OTHER INFORMATION: synthetic

<400> SEQUENCE: 54
cgggatcctc agttcacgga gcgcacggag                                      30

<210> SEQ ID NO 55
<211> LENGTH: 8
<212> TYPE: DNA

```
<213> ORGANISM: Artificial Sequence
<220> FEATURE:
<223> OTHER INFORMATION: synthetic

<400> SEQUENCE: 55 caccccca                                                                   8

<210> SEQ ID NO 56
<211> LENGTH: 5
<212> TYPE: DNA
<213> ORGANISM: Artificial Sequence
<220> FEATURE:
<223> OTHER INFORMATION: synthetic

<400> SEQUENCE: 56 ccccc                                                                      5

<210> SEQ ID NO 57
<211> LENGTH: 5
<212> TYPE: DNA
<213> ORGANISM: Artificial Sequence
<220> FEATURE:
<223> OTHER INFORMATION: synthetic

<400> SEQUENCE: 57 ggggg                                                                      5

<210> SEQ ID NO 58
<211> LENGTH: 5
<212> TYPE: DNA
<213> ORGANISM: Artificial Sequence
<220> FEATURE:
<223> OTHER INFORMATION: synthetic

<400> SEQUENCE: 58 ccacc                                                                      5

<210> SEQ ID NO 59
<211> LENGTH: 20
<212> TYPE: DNA
<213> ORGANISM: Artificial Sequence
<220> FEATURE:
<223> OTHER INFORMATION: synthetic

<400> SEQUENCE: 59
tatgatatct cgcggatgct                                                     20

<210> SEQ ID NO 60
<211> LENGTH: 16
<212> TYPE: DNA
<213> ORGANISM: Artificial Sequence
<220> FEATURE:
<223> OTHER INFORMATION: synthetic

<400> SEQUENCE: 60
tctgggagat tggggg                                                         16

<210> SEQ ID NO 61
<211> LENGTH: 29
<212> TYPE: DNA
<213> ORGANISM: Artificial Sequence
<220> FEATURE:
<223> OTHER INFORMATION: synthetic

<400> SEQUENCE: 61 cttgtgggggg ttagagggtc tacgactaa                                          29
```

<210> SEQ ID NO 62
<211> LENGTH: 114
<212> TYPE: DNA
<213> ORGANISM: Artificial Sequence
<220> FEATURE:
<223> OTHER INFORMATION: synthetic

<400> SEQUENCE: 62
gggattaata tgattatgaa caccccccaat ctcccagatg ctgattcagc caggagctta      60 ggaggggggag gtcactttat aagggtctgg gggggtcaga acccagagtc atcg           114

<210> SEQ ID NO 63
<211> LENGTH: 75
<212> TYPE: DNA
<213> ORGANISM: Artificial Sequence
<220> FEATURE:
<223> OTHER INFORMATION: synthetic

<400> SEQUENCE: 63
agtttctgca gcggggatta atatgattat gaacaccccc aatctcccag atgctgattc      60
agccaggagc ttagg                                                       75

<210> SEQ ID NO 64
<211> LENGTH: 75
<212> TYPE: DNA
<213> ORGANISM: Artificial Sequence
<220> FEATURE:
<223> OTHER INFORMATION: synthetic

<400> SEQUENCE: 64
agttgcagcc gtggggatta atatgattaa taacgccccc aatctcccag gtgctgattc      60
agcccagagc ttagg                                                       75

<210> SEQ ID NO 65
<211> LENGTH: 20
<212> TYPE: DNA
<213> ORGANISM: Artificial Sequence
<220> FEATURE:
<223> OTHER INFORMATION: synthetic

<400> SEQUENCE: 65
cccccaatct cccagatgct                                                  20

<210> SEQ ID NO 66
<211> LENGTH: 20
<212> TYPE: DNA
<213> ORGANISM: Artificial Sequence
<220> FEATURE:
<223> OTHER INFORMATION: synthetic

<400> SEQUENCE: 66
agcatctggg agattggggg                                                  20

<210> SEQ ID NO 67
<211> LENGTH: 20
<212> TYPE: DNA
<213> ORGANISM: Artificial Sequence
<220> FEATURE:
<223> OTHER INFORMATION: synthetic

<400> SEQUENCE: 67
cccccaatct cccaggtgct                                                  20

```
<210> SEQ ID NO 68
<211> LENGTH: 20
<212> TYPE: DNA
<213> ORGANISM: Artificial Sequence
<220> FEATURE:
<223> OTHER INFORMATION: synthetic

<400> SEQUENCE: 68
agcacctggg agattggggg                                               20

<210> SEQ ID NO 69
<211> LENGTH: 66
<212> TYPE: DNA
<213> ORGANISM: Artificial Sequence
<220> FEATURE:
<223> OTHER INFORMATION: synthetic

<400> SEQUENCE: 69
aggggtgcca agtcagcagt tgaaggattg gggccttgcc agccagatta taatgctagg   60
agactg                                                              66

<210> SEQ ID NO 70
<211> LENGTH: 66
<212> TYPE: DNA
<213> ORGANISM: Artificial Sequence
<220> FEATURE:
<223> OTHER INFORMATION: synthetic

<400> SEQUENCE: 70
aggggtgcca agtcagcagt tgatggattg gggccttgcc agactgatta aaaggctagg   60
agactg                                                              66

<210> SEQ ID NO 71
<211> LENGTH: 66
<212> TYPE: DNA
<213> ORGANISM: Artificial Sequence
<220> FEATURE:
<223> OTHER INFORMATION: synthetic

<400> SEQUENCE: 71
aggagtgcag agtcagcggt tgagggattg gggctatgcc agcccgatta gaagggtggg   60
gggctg                                                              66

<210> SEQ ID NO 72
<211> LENGTH: 66
<212> TYPE: DNA
<213> ORGANISM: Artificial Sequence
<220> FEATURE:
<223> OTHER INFORMATION: synthetic

<400> SEQUENCE: 72
aggggtgcag agtcagcagt tgagggattg gggccatgcc agcctgatta gaagggtgg    60 gggctg                                                              66

<210> SEQ ID NO 73
<211> LENGTH: 61
<212> TYPE: DNA
<213> ORGANISM: Artificial Sequence
<220> FEATURE:
<223> OTHER INFORMATION: synthetic

<400> SEQUENCE: 73
cacagagtca gcttggaagg gattggggac agggccgcct gattagaagg gggggggact   60
``` g                                                              61

<210> SEQ ID NO 74
<211> LENGTH: 8
<212> TYPE: DNA
<213> ORGANISM: Artificial Sequence
<220> FEATURE:
<223> OTHER INFORMATION: synthetic

<400> SEQUENCE: 74 cagattaa                                                        8

<210> SEQ ID NO 75
<211> LENGTH: 8
<212> TYPE: DNA
<213> ORGANISM: Artificial Sequence
<220> FEATURE:
<223> OTHER INFORMATION: synthetic

<400> SEQUENCE: 75 gtctaatt                                                        8

<210> SEQ ID NO 76
<211> LENGTH: 43
<212> TYPE: DNA
<213> ORGANISM: Artificial Sequence
<220> FEATURE:
<223> OTHER INFORMATION: synthetic

<400> SEQUENCE: 76
atgaacaccc ccaatctccc agatgctgat tcagccagga gct                 43

<210> SEQ ID NO 77
<211> LENGTH: 43
<212> TYPE: DNA
<213> ORGANISM: Artificial Sequence
<220> FEATURE:
<223> OTHER INFORMATION: synthetic

<400> SEQUENCE: 77
agctcctggc tgaatcagca tctgggagat tgggggtgtt cat                 43

<210> SEQ ID NO 78
<211> LENGTH: 43
<212> TYPE: DNA
<213> ORGANISM: Artificial Sequence
<220> FEATURE:
<223> OTHER INFORMATION: synthetic

<400> SEQUENCE: 78
cgtccacccc ccaatctccc agatgcttcg gactaacttc tag                 43

<210> SEQ ID NO 79
<211> LENGTH: 43
<212> TYPE: DNA
<213> ORGANISM: Artificial Sequence
<220> FEATURE:
<223> OTHER INFORMATION: synthetic

<400> SEQUENCE: 79
ctagaagtta gtccgaagca tctgggagat tgggggtgg acg                  43

<210> SEQ ID NO 80
<211> LENGTH: 43
<212> TYPE: DNA

<210> SEQ ID NO 80
<211> LENGTH: 43
<212> TYPE: DNA
<213> ORGANISM: Artificial Sequence
<220> FEATURE:
<223> OTHER INFORMATION: synthetic

<400> SEQUENCE: 80
atgaacaccc ccaatcgacc agatgctgat tcagccagga gct    43

<210> SEQ ID NO 81
<211> LENGTH: 43
<212> TYPE: DNA
<213> ORGANISM: Artificial Sequence
<220> FEATURE:
<223> OTHER INFORMATION: synthetic

<400> SEQUENCE: 81
agctcctggc tgaatcagca tctggtcgat tgggggtgtt cat    43

<210> SEQ ID NO 82
<211> LENGTH: 62
<212> TYPE: DNA
<213> ORGANISM: Artificial Sequence
<220> FEATURE:
<223> OTHER INFORMATION: synthetic

<400> SEQUENCE: 82
gggattaata tgattatgaa cacccccaat ctcccagatg ctgattcagc caggagctta    60
gg    62

<210> SEQ ID NO 83
<211> LENGTH: 62
<212> TYPE: DNA
<213> ORGANISM: Artificial Sequence
<220> FEATURE:
<223> OTHER INFORMATION: synthetic

<400> SEQUENCE: 83
gggattaata tgattatgaa cattactgta atcttaaccg agattcagc caggagctta    60 gg    62

<210> SEQ ID NO 84
<211> LENGTH: 42
<212> TYPE: DNA
<213> ORGANISM: Artificial Sequence
<220> FEATURE:
<223> OTHER INFORMATION: synthetic

<400> SEQUENCE: 84
gggattaata tgattatgaa cagattcagc caggagctta gg    42

<210> SEQ ID NO 85
<211> LENGTH: 29
<212> TYPE: DNA
<213> ORGANISM: Artificial Sequence
<220> FEATURE:
<223> OTHER INFORMATION: synthetic

<400> SEQUENCE: 85
cttgtggggg ttagagggtc tacgactaa    29

<210> SEQ ID NO 86
<211> LENGTH: 60
<212> TYPE: DNA
<213> ORGANISM: Artificial Sequence
<220> FEATURE:
<223> OTHER INFORMATION: synthetic

<400> SEQUENCE: 86
cccccaatct cccagatgct gattcagcca ggagcttagg aggggaggt cactttataa    60

<210> SEQ ID NO 87
<211> LENGTH: 54
<212> TYPE: DNA
<213> ORGANISM: Artificial Sequence
<220> FEATURE:
<223> OTHER INFORMATION: synthetic

<400> SEQUENCE: 87
atctcgcgga tgctgaatca gcctctggct tagggagaga aggtcacttt ataa    54

<210> SEQ ID NO 88
<211> LENGTH: 60
<212> TYPE: DNA
<213> ORGANISM: Artificial Sequence
<220> FEATURE:
<223> OTHER INFORMATION: synthetic

<400> SEQUENCE: 88
cccccaatct cccagatgct gattcagccc agagcttagg gaggggaggt cactttataa    60

<210> SEQ ID NO 89
<211> LENGTH: 29
<212> TYPE: DNA
<213> ORGANISM: Artificial Sequence
<220> FEATURE:
<223> OTHER INFORMATION: synthetic

<400> SEQUENCE: 89
cttgtttact gtaatcttaa ccggactaa    29

<210> SEQ ID NO 90
<211> LENGTH: 62
<212> TYPE: DNA
<213> ORGANISM: Artificial Sequence
<220> FEATURE:
<223> OTHER INFORMATION: synthetic

<400> SEQUENCE: 90
gggattaata tgattatgaa caccccaat ctcccagatg ctgattcagc caggagctta    60
gg    62

<210> SEQ ID NO 91
<211> LENGTH: 53
<212> TYPE: DNA
<213> ORGANISM: Artificial Sequence
<220> FEATURE:
<223> OTHER INFORMATION: synthetic

<400> SEQUENCE: 91
ggattagcgt tagtatgata tctcgcggat gctgaatcag cctctggctt agg    53

<210> SEQ ID NO 92
<211> LENGTH: 54
<212> TYPE: DNA
<213> ORGANISM: Artificial Sequence
<220> FEATURE:
<223> OTHER INFORMATION: synthetic

<400> SEQUENCE: 92
gggattagcg ttagtatgat atctcgcgga tgctgaatca gccaggagct tagg    54

```
<210> SEQ ID NO 93
<211> LENGTH: 62
<212> TYPE: DNA
<213> ORGANISM: Artificial Sequence
<220> FEATURE:
<223> OTHER INFORMATION: synthetic

<400> SEQUENCE: 93
gggattaata tgattatgaa caccccccaat ctcccagatg ctcattcagc ctctggctta      60
gg                                                                     62

<210> SEQ ID NO 94
<211> LENGTH: 54
<212> TYPE: DNA
<213> ORGANISM: Artificial Sequence
<220> FEATURE:
<223> OTHER INFORMATION: synthetic

<400> SEQUENCE: 94
gggattaata tgattatgaa atctcccaga tgctgattca gccaggagct tagg            54

<210> SEQ ID NO 95
<211> LENGTH: 62
<212> TYPE: DNA
<213> ORGANISM: Artificial Sequence
<220> FEATURE:
<223> OTHER INFORMATION: synthetic

<400> SEQUENCE: 95
gggattaata tgattatgaa acaaaaacat ctcccagatg ctgattcagc caggagctta      60
gg                                                                     62

<210> SEQ ID NO 96
<211> LENGTH: 62
<212> TYPE: DNA
<213> ORGANISM: Artificial Sequence
<220> FEATURE:
<223> OTHER INFORMATION: synthetic

<400> SEQUENCE: 96
gggattaata tgattatgaa caggggggaat ctcccagatg ctgattcagc caggagctta     60
gg                                                                     62

<210> SEQ ID NO 97
<211> LENGTH: 62
<212> TYPE: DNA
<213> ORGANISM: Artificial Sequence
<220> FEATURE:
<223> OTHER INFORMATION: synthetic

<400> SEQUENCE: 97
gggattaata tgattatgaa caccaccaat ctcccagatg ctgattcagc caggagctta      60
gg                                                                     62

<210> SEQ ID NO 98
<211> LENGTH: 20
<212> TYPE: DNA
<213> ORGANISM: Artificial Sequence
<220> FEATURE:
<223> OTHER INFORMATION: synthetic

<400> SEQUENCE: 98
cccccaatct cccagatgct                                                  20
```

```
<210> SEQ ID NO 99
<211> LENGTH: 20
<212> TYPE: DNA
<213> ORGANISM: Artificial Sequence
<220> FEATURE:
<223> OTHER INFORMATION: synthetic

<400> SEQUENCE: 99
tatgatatct cgcggatgct                                              20

<210> SEQ ID NO 100
<211> LENGTH: 54
<212> TYPE: DNA
<213> ORGANISM: Artificial Sequence
<220> FEATURE:
<223> OTHER INFORMATION: synthetic

<400> SEQUENCE: 100
gggattaata tgattatgaa caccccaat ctcccagatg ctgattcagc cagg         54

<210> SEQ ID NO 101
<211> LENGTH: 54
<212> TYPE: DNA
<213> ORGANISM: Artificial Sequence
<220> FEATURE:
<223> OTHER INFORMATION: synthetic

<400> SEQUENCE: 101
cctggctgaa tcagcatctg ggagattggg ggtgttcata atcatattaa tccc        54
```

ARTIFICIAL DNA-BINDING PROTEINS AND USES THEREOF

CROSS-REFERENCE TO RELATED APPLICATIONS

This application is a 371 of PCT/EP2014/075212, filed Nov. 20, 2014, which claims the benefit of European Patent Application No. EP13193739.3 filed Nov. 20, 2013.

FIELD OF INVENTION

The present invention relates to proteins consisting of an artificial DNA-binding domain (DBD) and related molecules and uses thereof. In particular, the proteins are ZF-DBD or TALE-DBD and are used for the treatment of eye disorders caused by gain of function mutation. The disorder may be ADRP, in particular ADRP caused by mutation in the rhodopsin gene. The present invention also relates to a method to identify cis-regulatory elements.

BACKGROUND OF THE INVENTION

Extraction of Biological Information content from genomic sequence remains challenging. Besides conserved DNA-sequence motif along evolution, prediction of cis-regulatory modules/elements (CRMs/CREs, i.e. a stretch of DNA where a number of effector/transcription factors can bind and regulate expression of nearby genes.) embodied in a specific DNA sequence and understanding their function remains a challenging task. Furthermore, the existing models of DNA sequence function generally are not capable to extract the special properties of CRM sequences. The special properties of CRM sequences are partly uncovered by the ENCODE project which is providing key insight into CRMs and gene regulation. The emerging scenario is showing that the architecture of physical connectivity among CRMs and the spatial distribution along the chromosomes play a critical role in gene regulation. Indeed, gene regulation is fundamentally a dynamic process involving the combinatorial interactions between genomic DNA and nuclear protein machinery. What is apparent is that the wiring of specific CREs determine cell type-selective DNA regulatory transcriptional network. Therefore, what is emerging is that gene regulation, rather than function, had to evolve to associate regulatory alternatives to particular genes, and this in turn generate diversity intra and inter individuals and among species. Therefore, cell-specific diversity is generated by regulatory combinatorial properties contained in genomic regulatory regions, CREs, eventually modulating genes sets.

The Encyclopedia of DNA Elements (ENCODE) Consortium is an international collaboration of research groups funded by the National Human Genome Research Institute (NHGRI). The goal of ENCODE is to build a comprehensive parts list of functional elements in the human genome, including elements that act at the protein and RNA levels, and regulatory elements that control cells and circumstances in which a gene is active. However, it is widely acknowledged that the same DNA element may be recognized by different (generally related) transcription factors in different cellular environments, with alternative functional consequences. Additionally, the authors now know that the biochemical signatures of many ENCODE-defined elements exhibit complex trans-cellular patterns of activity (The ENCODE Project Consortium. 2012. An integrated encyclopedia of DNA elements in the human genome Nature. 2012 Sep. 6; 489(7414):57-74. doi: 10.1038/nature11247; Thurman et al. 2012. The accessible chromatin landscape of the human genome. Nature. 2012 Sep. 6; 489(7414):75-82. doi: 10.1038/nature11232), which may be accompanied by functional behaviors such as an enhancer interacting with different target genes (Santos-Rosa et al. 2002 Active genes are tri-methylated at K4 of histone H3. Nature 419: 407-411; Sanyal et al. 2012. The long-range interaction landscape of gene promoters. Nature. 2012 Sep. 6; 489(7414):109-13. doi: 10.1038/nature11279; Thurman et al. 2012 The accessible chromatin landscape of the human genome. Nature. 2012 Sep. 6; 489(7414):75-82. doi: 10.1038/nature11232). Together, these observations suggest that the genome may, in fact, be extensively multiply encoded—i.e., that the same DNA element gives rise to different activities in different cell types. Cross-cell-type regulatory patterning evident in distal regulatory DNA uncovered by ENCODE (Song et al. 2011 Open chromatin defined by DNase I and FAIRE identifies regulatory elements that shape cell-type identity. Genome Res 21: 1757-1767; Thurman et al. 2012 The accessible chromatin landscape of the human genome. Nature. 2012 Sep. 6; 489(7414):75-82. doi: 10.1038/nature11232) suggests tremendous heterogeneity and functional diversity.

The above mentioned consideration suggests that the protein composition of a DNA-binding protein is not bound uniquely to the same DNA element in the same cell type. On the contrary, the same DNA element gives rise to different activities in different cell types.

Thus, the interface and interaction between cis regulatory elements and trans elements strongly depend on the cis regulatory elements in exquisite unique cellular subtype milieu and trans-binding elements properties (biochemical properties) that change accordingly to a specific cellular subtype (Stamatoyannopoulos J A. Genome Res. 2012 September; 22(9):1602-11).

Gene therapy for dominantly inherited genetic disease is more difficult than gene-based therapy for recessive disorders, which can be treated with gene supplementation. Treatment of dominant disease requires gene supplementation partnered with suppression of the expression of the mutant gene either at the DNA level, by gene repair, or at the RNA level by RNA interference or transcriptional repression.

The main target of genetic silencing strategies is the messenger RNA (mRNA) transcript, the function of which can be inhibited by antisense-RNA-based, ribozyme-based and more recently by small interfering (si)RNA-based and micro (mi)RNA-based approaches. In particular, RNA interference (RNAi) has great promise for treating dominant diseases in both mutation dependent and -independent manners, through its efficiency of mRNA transcript cleavage (La Vail et al. 2000 PNAS USA 97:11488-11493; Lewin et al. 1998 Nat Med 4:967-971; O'Reilly et al. 2007 Am 0.1 Hum Genet 81:127-135; Xia et al. 2004 Nat Med 10:816-820). Nevertheless, studies have shown that high levels of siRNAs can cause cellular toxicity through various mechanisms (Boudreau et al, 2009; Grimm et al, 2006).

A possible alternative to such RNA-targeting approaches is the modulation of gene expression at the transcriptional level, by using zinc-finger (ZF)-based artificial transcription factors (ZF-ATFs) that can be tailored to a desired DNA target sequence. Such artificial ZF proteins (also designated as ZFPs) are becoming a novel and powerful technological platform for both gene manipulation and development of therapeutics (Jamieson et al. 2003 Nat Rev Drug Discov 2:361-368; Pearson 2008 Nature 455:160-164; Segal & Barbas 2001 Curr Opin Biotechnol 12:632-637). Artificial ZFPs are composed of a DNA-binding domain (DBD, i.e. an independently folded protein domain that contains at least one motif that recognizes double- or single-stranded DNA. A DBD can recognize a specific DNA sequence (a recognition sequence) or have a general affinity to DNA.) that is based on the Cys2His2 ZF scaffold fused with a transcriptional regulation domain (such as an activator or repressor). Their modular structure enables both the sequential assembling of multiple ZFs to generate DBDs with different target specificities and the use of various effector domains to engineer ATFs or nucleases.

To date, several functional ZF-ATFs have been generated to modulate target gene expression in vitro and in vivo (Mattei et al. 2007 PLOS One 2:e774; Rebar et al. 2002 Nat Med 8:1427-1432). Mussolino et al. were able to demonstrate in vivo silencing of the human disease gene rhodopsin (hRHO) in a ADRP mouse model via vector-mediated somatic-gene transfer thanks to a ZF comprising a repressor domain (Mussolino et al. 2011 EMBO Mol Med 3:118-128). WO2012106725 relates to a fusion protein comprising an engineered DNA binding domain and a functional domain, wherein the protein binds to a target site in, and modulates expression of, at least one endogenous rhodopsin allele. This document discloses rhodopsin-targeted zinc finger proteins comprising nucleases as effector domain. Such proteins recognize specific target sequences of the rhodopsin gene. Such sequences correspond to the location of the cleavage site of the specific nuclease and are located in the vicinity of specific RHO mutations. Therefore, each described zinc finger proteins acts only on a specific mutation of rhodopsin that can be modified by ZFN-driven DNA repair.

Similarly, artificial TAL (transcription activator-like) effectors protein (often referred to as TALEs) may be used. They are composed of a DBD that can recognize DNA sequences through a central repeat domain consisting of a variable number of around 34 amino acid repeats fused with a transcriptional regulation domain (such as an activator or repressor). There appears to be a one-to-one correspondence between the identity of two critical amino acids in each repeat and each DNA base in the target sequence. Numerous groups have designed artificial TAL effectors capable of recognizing new DNA sequences in a variety of experimental systems. Such engineered TAL effectors have been used to create artificial transcription factors that can be used to target and activate or repress endogenous genes also in human cells (Miller et al. (2010). "A TALE nuclease architecture for efficient genome editing". Nature Biotechnology 29 (2): 143-148; Cong et al. "Comprehensive interrogation of natural TALE DNA-binding modules and transcriptional repressor domains". Nature Communications. 968 3; Zhang et al. (2011). "Efficient construction of sequence-specific TAL effectors for modulating mammalian transcription". Nature Biotechnology 29 (2): 149).

Autosomal dominant retinitis pigmentosa (ADRP) is the most genetically heterogeneous inherited disease in humans: more than 30 genes and many different mutations, over 100 mutations in rhodopsin alone, have been associated with retinitis pigmentosa. Dominant forms of retinitis pigmentosa include those that molecularly are owed to gain of function mutation but either those due to aplo-insufficiency or dominant negative effect. This genetic heterogeneity is associated with differences in rate and the extent of the degeneration. Accounting for 30%-40% of all cases of retinitis pigmentosa, autosomal dominant retinitis pigmentosa (ADRP) is the consequence of mutations in 24 known genes (Table 1) (Rossmiller et al. Molecular Vision 2012; 18:2479-2496). Despite the range of genes responsible for ADRP, approximately 30% of ADRP arises from mutations in the rhodopsin gene and therefore the authors focused the authors' attention on treatment of mutations affecting the rhodopsin gene.

TABLE 1

Known gene causing ADRP and associated proteins names.
References are at RetNet: https://sph.uth.edu/retnet/.

| Protein | Disease Gene |
|---|---|
| Bestrophin-1 | BEST1 |
| Carbonic anhydrase IV | CA4, RP17 |
| Cone-Rod Homeobox | CRX |
| Fascin homolog 2 | FSCN2, RP30 |
| Guanylate cyclase activator 1B | GUCA1B, RP48 |
| Inosine monophosphate dehydrogenase 1 | IMPDH1, RP10 |
| kelch-like protein 7 | KLHL7, RP42 |
| Nuclear receptor subfamily 2 group E member 3 | NR2E3 |
| Neural retina leucine zipper | NRL, RP27 |
| OSBP-related protein 1 | ORP1, DCDC4A, RP1 |
| pre-mRNA processing factor 3 | PRPF3, RP18 |
| pre-mRNA processing factor 31 homolog | PRPF31 |
| pre-mRNA processing factor 6 | PRPF6, rp60 |
| pre-mRNA processing factor 8 | PRPF8 |
| Peripherin 2 | PRPH2, RDS, RP7 |
| Rhodopsin | RHO |
| Retinal outer segment membrane protein 1 | ROM1 |
| Retinitis pigmentosa 1 protein | RP1, L1 |
| Unknown | RP63 |
| Retinitis pigmentosa 9 protein | RP9 |
| Retinal pigment epithelium-specific protein | RPE65, RP20 |
| Semiphorin | SEMA4A, RP35 |
| Proto-oncogene tyrosine-protein kinase MER | MERTK, RP33 |
| Topoisomerase I-binding arginine/serine-rich protein | TOPORS |
| hexokinase 1 | HK1 |
| pre-mRNA processing factor 4 | PRPF4 |
| retinol dehydrogenase 12 | RDH12, LCA13, RP53 |
| small nuclear ribonucleoprotein 200 kDa (U5) | SNRNP200, ASCC3L1, BRR2, HECIC2, RP33 |

Currently, there are no effective treatments for ADRP. Nutritional therapy featuring vitamin A or vitamin A plus docosahexaenoic acid reduces the rate of degeneration in some patients. Retinal analogs and pharmaceuticals functioning as chaperones show some progress in protecting the retina in animal models, and several antioxidant studies have shown lipophilic antioxidant taurousodeoxycholic acid (TUDCA), metallocomplex zinc desferrioxamine, N-acetylcysteine, and a mixture of antioxidants slow retinal degeneration in rodent rd1, rd10, and Q344ter models. A clinical trial is under way to test the efficacy of the protein deacetylase inhibitor valproic acid as a treatment for retinitis pigmentosa. Valproic acid blocks T-type calcium channels and voltage-gated sodium channels, and is associated with significant side effects such as hearing loss and diarrhea. Therefore, the use of valproic acid as a treatment for retinitis pigmentosa has been questioned (Rossmiller et al. Molecular Vision 2012; 18:2479-2496).

SUMMARY OF THE INVENTION

In the present invention, the authors generated a novel functional DNA binding domain and surprisingly determined novel properties of this isolated domain by comparing it to a previously described system comprising also repressor domains and by functionally assessing the transcriptional output and the physiological and pathophysiological consequences on a healthy and diseased retina photoreceptor cellular specific subtypes in two animal species. In addition, the authors also studied the consequences of altering the cis-acting elements on a DNA target site in photoreceptor cellular specific subtypes.

In particular, in the present study authors demonstrate that an artificial DNA-binding domain (ZF6-DBD) targeted to 20 base-pair (bp) long sequence of human RHODOPSIN (RHO) proximal promoter when expressed via somatic gene transfer to retinal-rod photoreceptors blocks per se Rhodopsin expression. Differentially from a natural transcription factor (TF) this artificial DNA-binding domain lacks the effector domain, thus, this ZF6-DBD surprisingly generates transcriptional silencing per se owed to its DNA-binding properties.

Here the authors demonstrate that the sole ZF-DBD, without other functional domain such as the repressor domain, is surprisingly able to repress the human disease gene rhodopsin in two different animal settings (mouse and pig). The present finding is an example and is also applicable to other DNA binding domains, e.g. other zinc finger and TAL derived DNA binding domains and RNA-guided DNA-binding domain (Crispr/cas 9).

These surprising results have dramatic beneficial effects for dominantly inherited genetic eye diseases, in particular, Autosomal Dominant Retinitis Pigmentosa. Specifically the ablation of the effector domain from an artificial DNA-binding protein generates a protein with different properties (compared to an intact protein composed of a DNA-binding domain and a effector domain, i.e KRAB), which are mirrored in different functional outcomes, these include:

1—higher recovery of retinal function when delivered to photoreceptors of a mouse model of autosomal dominant retinitis pigmentosa (adRP) through an Adeno-associated virus (AAV) vector (FIG. 3),
2—higher recovery of retinal function when delivered to photoreceptors of a mouse model of adRP through an AAV vector at different time points (FIG. 6),
3—higher rhodopsin transcriptional down-regulation when delivered to photoreceptors of two species (mouse and pig) through an Adeno-associated virus (AAV) vector (FIGS. 4 and 8),
4—higher rhodopsin transcriptional down-regulation when delivered to photoreceptors of two species (mouse and pig) through an Adeno-associated virus (AAV) vector at different time points (FIGS. 4, 8, 12).
5—absence of potential side effects (no off-targets; no reduction in Arr3, FIG. 8);
6—good vector yield (improved production of protein), In particular in an adeno-associated viral vector, mare particularly in a AAV8-CMV system (FIG. 14).

Natural transcription factors (TFs) have both a DBD and effectors domains, which attracts by protein-protein interactions a number of other proteins which can ultimately result in either transcriptional repression or transcriptional activation. Transcriptional repression and transcriptional activation generate cell-specific signaling, including whole cell-specific transcriptome map. On the contrary, artificial DBDs are external and independent to the topology of the regulatory network (they are driven as in the example thereof by a CMV promoter and they are not connected by protein-protein regulatory maps) and are transcriptionally independent from the endogenous cell-specific regulatory code (whole cell-specific transcriptome map). Indeed, natural TFs them self belong to a cell-specific transcriptome map, i.e. regulators of regulators, therefore they are finely tuned by other cell-specific TFs sets which control through binding to TFs binding sites either transcriptional activation or repression eventually resulting in cell-specific function.

Data of the present Invention suggest the identification of a novel short (20 bp) cis-acting DNA sequence (cis-regulatory element, CRE) not fully conserved in evolution that is not an enhancer but can significantly control RHO levels. These results support that per se the DNA target cis-acting element (besides the activity of the binding protein) contains critical information content for RHO expression.

Regarding the cis-acting DNA target sequence, it was observed that:
1—site-specific ablation of the DNA target result in a significant drop of transgene expression when expressed with AAV vectors in the proper specific cellular subtype milieu (FIG. 19),
2—site-specific mutagenesis of the DNA target result in a significant drop of transgene expression when expressed with AAV vectors in the proper specific cellular subtype milieu (FIG. 20).

The authors then propose a two-step repression-replacement strategy: (i) mutational-independent silencing of the human rhodopsin gene (transcriptional silencing targeted to both wild-type and mutated RHO alleles) through ZF-DBDs; and optionally (ii) gene replacement of the endogenous RHO copies by vector-mediated photoreceptor exogenous gene transfer.

The feasibility of this proposed approach is based on the following considerations:
(i) the authors have demonstrated the superior ability of ZF-DBD delivery to down-regulate the levels of RHO gene transcription, which represents the major limiting step in the strategy;
(ii) the therapeutic levels of transcriptional silencing result in phenotype amelioration;
(iii) the authors have demonstrated the superior safety of ZF-DBD delivery compared to a protein comprising DNA binding domain and functional domain (in particular due to fewer off-target effects);
(iv) there is the possibility to incorporate both the silencing and the replacement constructs into the same vector.

Indeed, a vector that incorporates both the ZF-DBD and the replacement gene will ensure their simultaneous action in the same transduced photoreceptors e.g. with bidirectional promoters allowing the coordinated expression of the two transgenes.

The present invention provides a protein consisting of a DNA binding domain targeting a DNA regulatory sequence of a gene selected from the group consisting of: RHO, BEST1, CA4, RP17, CRX, FSCN2, RP30, GUCA1B, RP48, IMPDH1, RP10, KLHL7, RP42, NR2E3, NRL, RP27, ORP1, DCDCl$_4$A, RP1, PRPF3, RP18, PRPF31, PRPF6, rp60, PRPF8, PRPH2, RDS, RP7, ROM1, RP1, L1, RP63, RP9, RPE65, RP20, SEMA4A, RP35, MERTK, RP33, TOPORS, HK1, PRPF4, RDH12, LCA13, RP53, SNRNP200, ASCC3L1, BRR2, HECIC2, RP33.

Preferably the targeting of the DNA regulatory sequence induces the repression of the expression of said gene.

Preferably said gene is in a mutated form or a wild-type form. The mutated form of said genes is responsible for an inherited eye disease, preferably an autosomal dominant inherited eye disease, preferably an autosomal recessive inherited eye disease. It can be any mutation in the genes reported in Table 1.

In a preferred embodiment the gene is in a mutated form.

In a preferred embodiment the DNA binding domain is selected from the group consisting of: a zinc finger domain, a transcription activator-like (TAL) DNA binding domain or a RNA-guided DNA-binding domain or a functional fragment thereof or a derivative thereof.

Preferably, the DNA regulatory sequence is comprised in a promoter region sequence of said gene.

Still preferably the DNA regulatory sequence is comprised in the promoter region sequence of RHO.

Yet preferably the DNA regulatory sequence comprises a sequence selected from the group of: GGGGGT-TAGAGGGTCTACGA (SEQ ID No. 22), CACCCC-CAATCTCCCAGATGCTGAT (SEQ ID No. 23), TCAG-CATCTGGGAGATTG (SEQ ID No. 24), GGGGGTTAGAGGGTCT (SEQ ID No. 25), GGGGGT-TAGAGGGTCTA (SEQ ID No. 26), TGAACACCCC-CAATCTCC (SEQ ID No. 27) or GTGGGGGT-TAGAGGGT (SEQ ID No. 28).

More preferably the DNA regulatory sequence has essentially a sequence selected from the group of: GGGGGT-TAGAGGGTCTACGA (SEQ ID No. 22), CACCCC-CAATCTCCCAGATGCTGAT (SEQ ID No. 23), TCAGCATCTGGGAGATTG (SEQ ID No. 24), GGGGGT-TAGAGGGTCT (SEQ ID No. 25), GGGGGT-TAGAGGGTCTA (SEQ ID No. 26), TGAACACCCC-CAATCTCC (SEQ ID No. 27) or GTGGGGGTTAGAGGGT (SEQ ID No. 28).

In a preferred embodiment the protein consists essentially of a sequence selected from the group consisting of: SEQ ID No. 3, SEQ ID No. 5, SEQ ID No. 7, SEQ ID No. 9, SEQ ID No. 13, SEQ ID No. 15, SEQ ID No. 17, or a fragment or derivative thereof.

The present invention provides a nucleic acid molecule encoding the protein as defined above The present invention provides a vector comprising the nucleic acid molecule of the invention. Preferably said vector is a viral vector. Preferably the vector is selected from the group consisting of: adenoviral vectors, lentiviral vectors, retroviral vectors, adeno associated vectors (AAV) or naked plasmid DNA vectors.

In a preferred embodiment said vector further comprises a nucleotide sequence of a gene selected from the group consisting of: RHO, BEST1, CA4, RP17, CRX, FSCN2, RP30, GUCA1B, RP48, IMPDH1, RP10, KLHL7, RP42, NR2E3, NRL, RP27, ORP1, DCDCl$_4$A, RP1, PRPF3, RP18, PRPF31, PRPF6, rp60, PRPF8, PRPH2, RDS, RP7, ROM1, RP1, L1, RP63, RP9, RPE65, RP20, SEMA4A, RP35, MERTK, RP33, TOPORS, HK1, PRPF4, RDH12, LCA13, RP53, SNRNP200, ASCC3L1, BRR2, HECIC2 and RP33.

In a preferred embodiment the vector further comprises a retina specific promoter and, optionally, regulatory sequences.

Preferably the retina specific promoter is the rhodopsin kinase (RHOK) promoter or the transducin 1 (GNAT1) promoter, preferably the human transducin 1 (GNAT1) promoter. The present invention provides a host cell transformed by the vector of the invention. The present invention provides a viral particle containing the vector of the invention.

The present invention provides a pharmaceutical composition comprising the protein as defined above or the nucleic acid or the host cell or the viral particle containing the vector as defined above and a pharmaceutically acceptable excipient.

The present invention provides a pharmaceutical composition comprising the vector as defined above and a pharmaceutically acceptable excipient.

In the present invention any combination of the protein, nucleic acid, host cell or vector as defined above may be used in the pharmaceutical composition.

Preferably the composition further comprises a vector comprising a nucleotide sequence of a gene selected from the group consisting of: RHO, BEST1, CA4, RP17, CRX, FSCN2, RP30, GUCA1B, RP48, IMPDH1, RP10, KLHL7, RP42, NR2E3, NRL, RP27, ORP1, DCDCl$_4$A, RP1, PRPF3, RP18, PRPF31, PRPF6, rp60, PRPF8, PRPH2, RDS, RP7, ROM1, RP1, L1, RP63, RP9, RPE65, RP20, SEMA4A, RP35, MERTK, RP33, TOPORS, HK1, PRPF4, RDH12, LCA13, RP53, SNRNP200, ASCC3L1, BRR2, HECIC2 and RP33.

Preferably he protein or the nucleic acid or the vector or the host cell or the viral particle or the pharmaceutical composition of the invention as defined above is for use in the treatment of an autosomal dominant inherited eye disease and/or of an autosomal recessive inherited eye disease.

In particular BEST1, NR2E3, NRL, RHO, RP1, RPE65 are genes that cause both autosomal dominant and recessive inherited eye disease, such as Autosomal Dominant Retinitis Pigmentosa and Autosomal Recessive Retinitis Pigmentosa.

Preferably the treatment is a gene therapy. Still preferably the autosomal dominant inherited eye disease is autosomal dominant retinitis pigmentosa (ADRP) or Congenital Stationary Night Blindness. Yet preferably the autosomal dominant inherited eye disease is autosomal dominant retinitis pigmentosa (ADRP).

Preferably the autosomal recessive inherited eye disease is autosomal recessive retinitis pigmentosa.

The present invention provides a method for the treatment of an autosomal dominant inherited eye disease or of an autosomal recessive inherited eye disease of a subject in need thereof, said method comprising administering a suitable amount of the protein or the nucleic acid or the vector or the host cell or the viral or the pharmaceutical composition as defined above.

The present invention provides a method to identify a DNA binding domain targeting a potential DNA regulatory sequence comprising:
 a) generating two independent constructs:
  a first construct comprising a sequence of a reporter gene under the control of the potential DNA regulatory sequence;
  a second construct comprising a sequence of a reporter gene under the control of the potential DNA regulatory sequence that has been mutated;
 b) expressing each construct of step a) in vivo in the retina;
 c) comparing the expression of the reporter gene under the control of the potential DNA regulatory sequence with the expression of the reporter gene under the control of the mutated potential DNA regulatory sequence;
 wherein if a reduction in the expression of the reporter gene under the control of the mutated potential DNA regulatory sequence is observed when compared to the expression of the reporter gene under the control of the potential DNA regulatory sequence, the potential DNA regulatory sequence is a DNA regulatory sequence and a DNA binding domain is identified;
 d) Optionally, designing a DNA binding protein targeting the DNA regulatory sequence.

The present invention provides a DNA binding domain targeting a potential DNA regulatory sequence identified by the method as defined above. Preferably the DNA binding domain targeting a potential DNA regulatory sequence identified by the above method is as defined above.

In the present invention, the targeting of the DNA regulatory sequence by means of the sole DNA-binding domain induces the repression of the expression of the gene of interest. The term repression means inhibition, lowering, decreasing gene expression.

In the present invention, the gene therapy may be achieved by the administration of a single vector comprising:
- a nucleic acid molecule encoding a DNA binding domain targeting a DNA regulatory sequence controlling the expression of a gene selected from the group consisting of: RHO, BEST1, CA4, RP17, CRX, FSCN2, RP30, GUCA1B, RP48, IMPDH1, RP10, KLHL7, RP42, NR2E3, NRL, RP27, ORP1, DCDCl$_4$A, RP1, PRPF3, RP18, PRPF31, PRPF6, rp60, PRPF8, PRPH2, RDS, RP7, ROM1, RP1, L1, RP63, RP9, RPE65, RP20, SEMA4A, RP35, MERTK, RP33, TOPORS, HK1, PRPF4, RDH12, LCA13, RP53, SNRNP200, ASCC3L1, BRR2, HECIC2 and RP33,
- a nucleic acid molecule of a wild type gene selected from the group consisting of: RHO, BEST1, CA4, RP17, CRX, FSCN2, RP30, GUCA1B, RP48, IMPDH1, RP10, KLHL7, RP42, NR2E3, NRL, RP27, ORP1, DCDCl$_4$A, RP1, PRPF3, RP18, PRPF31, PRPF6, rp60, PRPF8, PRPH2, RDS, RP7, ROM1, RP1, L1, RP63, RP9, RPE65, RP20, SEMA4A, RP35, MERTK, RP33, TOPORS, HK1, PRPF4, RDH12, LCA13, RP53, SNRNP200, ASCC3L1, BRR2, HECIC2 and RP33.

Alternatively, two vectors may be used, each comprising i) or ii), respectively. In the present invention the doses to be administered may be determined easily based on the desired effect and known methods. Preferably the molecule or the composition of the invention is administered in the retina.

The delivery vehicles of the present invention may be administered to a patient. A skilled worker would be able to determine appropriate dosage rates. The term "administered" includes delivery by viral or non-viral techniques. The vectors may, for example, be plasmid vectors, mRNA vectors (e.g. in vitro transcribed mRNA vectors) or viral vectors. Viral delivery mechanisms include but are not limited to adenoviral vectors, adeno-associated viral (AAV) vectors, herpes viral vectors, retroviral vectors, lentiviral vectors, and baculoviral vectors vaccinia viruses, foamy viruses, cytomegaloviruses, Semliki forest virus, poxviruses, RNA virus vector and DNA virus vector. etc as described above. Such viral vectors are well known in the art. Non-viral delivery mechanisms include lipid mediated transfection, liposomes, immunoliposomes, lipofectin, cationic facial amphiphiles (CFAs) and combinations thereof. As an alternative to the delivery of polynucleotides to cells, the DBD of the present invention may be delivered to cells by protein transduction. The protein transduction may, for example, be via vector delivery or by direct protein delivery.

The present invention also provides a pharmaceutical composition for treating an individual, wherein the composition comprises a therapeutically effective amount of the protein/nucleic acid/vector or host cell of the present invention or a viral particle produced by or obtained from same. The pharmaceutical composition may be for human or animal usage. Typically, a physician will determine the actual dosage which will be most suitable for an individual subject and it will vary with the age, weight and response of the particular individual. The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder; by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. In one aspect, the parenteral administration route may be intraocular administration. Intraocular administration of the present composition can be accomplished by injection or direct (e.g., topical) administration to the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art.

For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The man skilled in the art is well aware of the standard methods for incorporation of a polynucleotide or vector into a host cell, for example transfection, lipofection, electroporation, microinjection, viral infection, thermal shock, transformation after chemical permeabilisation of the membrane or cell fusion.

As used herein, the term "host cell or host cell genetically engineered" relates to host cells which have been transduced, transformed or transfected with the construct or with the vector here described.

As representative examples of appropriate host cells, one can cites bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein. Preferably, said host cell is an animal cell, and most preferably a human cell. The host cell can be a cultured cell or a primary cell, i.e., isolated directly from an organism, e.g., a human. The host cell can be an adherent cell or a suspended cell, i.e., a cell that grows in suspension. Administration of a therapeutically active amount of the pharmaceutical compositions of the present invention, or an "effective amount", is defined as an amount effective at dosages and for periods of time, necessary to achieve the desired result of increasing/decreasing the production of proteins. A therapeutically effective amount of a substance may vary according to factors such as the disease state/health, age, sex, and weight of the recipient, and the inherent ability of the particular polypeptide, nucleic acid coding therefore, or recombinant virus to elicit the desired response. Dosage regimen may be adjusted to provide the optimum therapeutic response. For example, several divided doses may be administered daily or at periodic intervals, and/or the dose may be proportionally reduced as indicated by the exigencies of the therapeutic situation. For instance, in general for viral vectors administration, suitable dosages will vary from 10$^8$ to 10$^{13}$ vg (vector genomes)/eye.

The transcriptional, mutational-independent strategy used in the present study is aimed at improving the use of ZFs to overcome the hurdles in the development of an effective therapeutic strategy for gain-of function mutations in autosomal dominant inherited eye diseases.

A "protein domain" is a conserved part of a given protein sequence and structure that can evolve, function, and exist independently of the rest of the protein chain. Each domain forms a compact three-dimensional structure and often can be independently stable and folded. Many proteins consist of several structural domains. Molecular evolution uses domains as building blocks and these may be recombined in different arrangements to create proteins with different functions. Domains vary in length from between about 25 amino acids up to 500 amino acids in length. Because they are independently stable, domains can be "swapped" by genetic engineering between one protein and another to make chimeric proteins.

A "DNA-binding domain" (DBD) is an independently folded protein domain that contains at least one motif that recognizes double- or single-stranded DNA. A DBD can recognize a specific DNA sequence (a recognition or regulatory sequence) or have a general affinity to DNA. One or more DNA-binding domains are usually part of a so-called DNA binding protein, i.e. a larger protein consisting of additional domains with differing function. The additional domains often regulate the activity of the DNA-binding domain. The function of DNA binding is either structural or involving transcription regulation, with the two roles sometimes overlapping.

In the present invention the DNA binding domain may be a zinc finger domain (ZF domain) or a transcription activator-like DNA binding domain (TAL domain) or a RNA-guided DNA-binding domain (Crispr/cas 9). In particular synthetic or artificial ZF or TAL domains or RNA-guided DNA-binding domain (Crispr/cas 9). The DNA binding domain may be a functional fragment or a functional derivative of the above domain. A functional fragment is a domain that lacks one or more modules and that nevertheless maintains the ability to recognize the specific regulatory sequence. A functional derivative is a domain that contains mutation, substitutions and that nevertheless maintains the ability to recognize the specific regulatory sequence. A man skilled in the art is well aware of the methods for designing ZF or TAL or Crispr/cas domains and functional fragments and functional derivative thereof and testing specificity.

A single ZF motif (also called module) consists of approximately 30 amino acids with a simple beta-beta-alpha fold that is stabilized by hydrophobic interactions and the chelation of a single zinc ion. Each ZF module primarily recognizes an overlapping 3-4-bp DNA sequence, where the last base pair is the first of the following target (the fourth base of each target is on the opposite strand). The binding takes place through key amino-acid residues, which can be exchanged to generate ZF modules with different sequence specificities. To obtain a DBD that is tailored to a unique target sequence (also called regulatory sequence) in mammalian genomic DNA (genome size in humans, 3.0_109 bp), theoretically a sequence longer than 18 bp is needed, and this can be achieved by consecutive linking of one or more ZF modules, in particular at least two ZF modules, at least three ZF modules, at least four ZF modules, at least five ZF modules or six ZF modules. However this theoretical sequence length is a general speculation that does not take into account cell-specific genomic features of human photoreceptors. Therefore, a specific sequence shorter than 18 bp could be equally uniquely recognized in specific tissue and cell types.

The general structural of DNA-binding domains derived from transcription activator-like effectors (TALEs), which are derived from the plant pathogenic *Xanthomonas* spp. bacterium or TALE-like proteins from *Ralstonia* spp. can also be engineered to bind to predetermined DNA sequences (Li, L. et al. Characterization and DNA-binding specificities of *Ralstonia* TAL-like effectors. Mol. Plant 6, 1318-1330; 2013). TAL-DBD are composed of tandem arrays of 33-35 amino acid repeats, each of which recognizes a single base-pair in the major groove. The nucleotide specificity of each repeat module is determined by the two amino acids at positions 12 and 13 (Moscou, M. J. & Bogdanove, A. J. A simple cipher governs DNA recognition by TAL effectors. Science 326, 1501; 2009), which are called repeat variable diresidues (RVDs). Four different RVD modules—namely Asn-Asn, Asn-Ile, His-Asp and Asn-Gly—are most widely used to recognize guanine, adenine, cytosine and thymine, respectively.

The CRISPR (clustered regularly interspaced short palindromic repeats) system provides a potential platform for targeted gene regulation (Barrangou et al., 2007). CRISPR systems have been found in different organisms; one of the simplest is the type II CRISPR system from *Streptococcus pyogenes*. In this system a single gene encoding the Cas9 protein and two RNAs, a mature CRISPR RNA (crRNA) and a partially complementary trans-acting RNA (tracrRNA), are necessary and sufficient for RNA-guided silencing of foreign DNAs. The mutant protein Cas9, which is defective in DNA cleavage, can actually act as a simple RNA-guided DNA-binding domain.

Therefore, the CRISPR/Cas system of *Streptococcus pyogenes* can be programmed to design DNA binding domain to specific eukaryotic regulatory sequences through the simple engineering of guide RNAs with base-pairing complementarity to such regulatory DNA sites. Cas9 can be used as a customizable RNA-guided DNA-binding platform.

DNA-binding domains (i.e. DNA-binding proteins lacking an effector domain) are potent by their nature because they are acting at the source of signaling (genomic DNA), mimicking the intrinsic robustness of the nature of transcriptional signaling and outperforming it considering the specificity and thus, in therapeutic perspective safety and efficacy.

Transcription factors (TFs) are DNA-binding proteins composed of two main functional domains, the effector domain and the DNA binding domain. The effector domains are responsible of transcription activation and repression. The activator-domain and repressor-domain work mainly by recruitment of large transcriptional coactivators and corepressors complexes via protein-protein interactions These cofactors then act both directly and indirectly to regulate the activity of the RNA polymerase II transcriptional machinery at the core promoter. The DNA binding domains have the function of determining DNA recognition properties (DNA-binding specificities). Members of a particular class (i.e., paralogous TFs) often have similar DNA binding preferences (Badis et al., 2009). However, despite apparently shared protein structure of DNA binding domains, TFs might exhibit non-conserved binding properties. In these cases, protein-protein interactions occurring typically between the effector domain and other cell-specific nuclear proteins are thought to be responsible for differential in vivo DNA binding of TFs. For instance KRAB-mediated gene silencing requires binding to the corepressor KAP-1. The KRAB:KAP-1 interaction requires the RING-B box-coiled coil (RBCC) domain (Peng H. et al). Therefore, also protein-protein interactions participate in generating different DNA-binding specificities. Another factor that determines in vivo TF binding is the local chromatin environment (Arvey et al., 2012). In addition, natural TFs them self belong to a cell-specific transcriptome map (regulators of regulators), therefore they are finely tuned by other cell-specific TF sets which control their activation or repression eventually resulting in cell-specific function.

Therefore in summary both natural transcription factors and artificial DBDs domains coupled to effector domains have both a DBD and effectors domains which attracts by protein-protein interactions a number of other proteins which can ultimately result in either transcriptional repression or transcriptional activation.

On the contrary, artificial isolated DBDs are external to the topology of the regulatory network and are transcriptionally independent from the endogenous cell-specific regulatory code (whole cell-specific transcriptome map). Therefore, artificial DNA-binding domains are suited to generate potent means to efficaciously and safely modulate transcription, then leading to generate therapeutics.

The present invention will be illustrated by means of non-limiting examples in reference to the following figures.

BRIEF DESCRIPTION OF THE FIGURES

FIG. 1. A—Schematic representation of the ZF6 transcriptional repressor (ZF6-KRAB; Mussolino et al 2011 (EMBO Mol Med. 2011 March; 3(3):118-28) and the novel ZF6-DBD. B—DNA sequence on the Human promoter proximal region, in capitals the DNA bases binding sites for both ZF6-KRAB and ZF6-DBD. C— Western Blot analysis following transfection on HEK293 cells, using anti HA epitope antibody, showing the different molecular weight of ZF6-KRAB (34 KDa) compared to ZF6-DBD (22 KDa). Total protein quantity was normalized with anti tubulin antibody.

FIG. 2.A [eyes before injection of eGFP (baseline, P30) vs eyes injected with eGFP (P50)]; FIG. 2.B [eyes before injection of ZF6-KRAB (baseline, P30) vs eyes injected with ZF6-KRAB (P50)]; FIG. 2.B [eyes before injection of ZF6-DBD (baseline, P30) vs eyes injected with ZF6-DBD (P50)].

FIG. 4. A Histogram from quantitative RT-PCR analysis of hRHO and Gnat1 mRNA levels in transduced retinas, with ZF6-DBD (17 eyes with rhodopsin down-regulation on 21 eyes analyzed) and ZF6-KRAB (10 eyes with rhodopsin down-regulation on 11 eyes analyzed) The values were normalized with murine GAPDH and Act β transcript levels, $*p<0.01$; $p<0.001$, $*p<0.0001$ as statistically significance differences between ZF6-DBD injected eyes vs eGFP injected eyes (t-test). (B) Average expression levels of the AAV8 vector transgenes upon subretinal injections of 1×10E9 vector particles of AAV8-CMV-EGFP, AAV8-CMV-ZF6-DBD and AAV8-CMV-ZF6-KRAB (C) Western blot analysis on RHO in retinal samples treated with AAV8-CMV-EGFP, AAV8-CMV-ZF6-DBD and AAV8-CMV-ZF6-KRAB (D) Immunofluorescence analysis of P347S mice injected with AAV8-CMV-ZF6-DBD. (E) HA stained retina shows nuclear localization of the HA tag and lack of its presence in AAV8-CMV-EGFP control. (F-H) human-specific 3A6 antibodies does not label wild type retinas (F), is virtually absent in AAV8-CMV-ZF6-DBD treated eye (G) and label AAV8-CMV-EGFP treated control retinas (H).

FIG. 6. Electrophysiological responses of retina recorded by ERG analysis of P347S mice injected at P4, P14 and P30 P30 subretinally with AAV8-CMV-ZF6-DBD or AAV8-CMV-EGFP (1×10E9 vg) and analyzed at P30 or P50 (P30 injected cohort). A Representative wave form of eyes treated with ZF6-DBD (P4, P14, P30) and eGFP treated eyes (P30) at different luminance. B Representative wave form of eyes treated with ZF6-DBD (black line) and eGFP treated eyes (grey line) at different time point of injection; P4 top panel, P14 middle panel and P30 bottom panel. C Mean delta ERG response between ZF6-DBD injected eyes vs contralateral eyes injected with eGFP at different time point.

FIG. 9. A. Expression analysis of endogenous transcription factors (CRX and NRL) compared to ZF6-DBD delivered by AAV's in pig's retinas. B. Expression levels (in FPKM) of known Master Transcription Factors in the retina.

We used the upstream region of the rhodopsin promoter (3000 bp up) as a negative control, in this case there are not differences between treated and untreated region. *pValue<0.05

Figure 11:
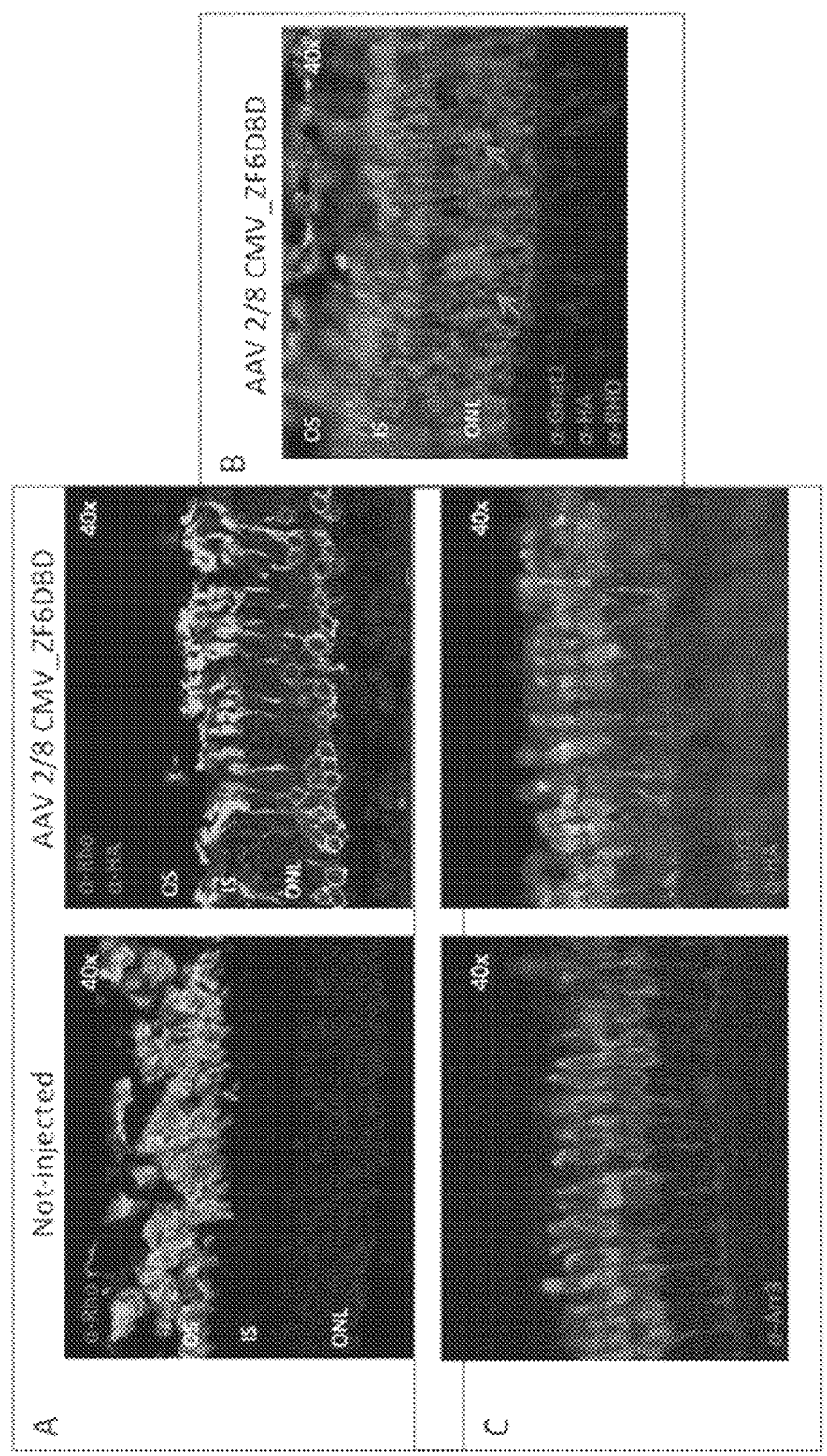

FIG. 11. Morphological characterization of pigs retina injected with AAV8-CMV-ZF6-DBD A. Coimmunolabeling analysis of pigs retinae for rhodopsin 1D4 and HA-tag, that identified the ZF6-DBD protein, injected ZF6-DBD. B. Triple immunofluorescence analysis using rhodopsin 1D4, HA-tag and GNAT1 of ZF6-DBD injected retina. C. Immunofluorescence analysis using cone arrestin antibody (Arr3; indicating the integrity of the cones. Magnification: 40×; OS, outer segments; IS, inner segments; ONL, outer nuclear layer.

Figure 12:
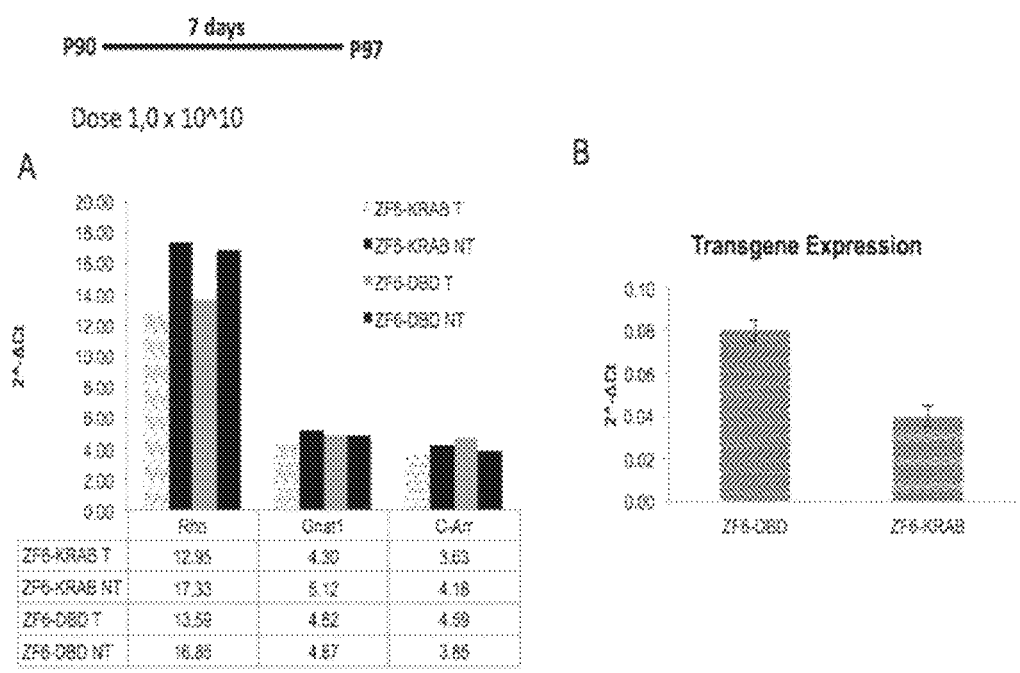

FIG. 12. A) AAV8-CMV-ZF6-DBD and AAV8-CMV-ZF6-KRAB delivery to P90 pigs retinas at a vector dose of 1×10E10 vg, resulted in highly significant endogenous porcine Rhodopsin transcript repression at P97 compared to controls (ZF-KRAB not transduced area (NT) and ZF-DBD non transduced area (NT). B) Transgene expression levels (RT-PCR) obtained from harvested retinas.

Figure 13:
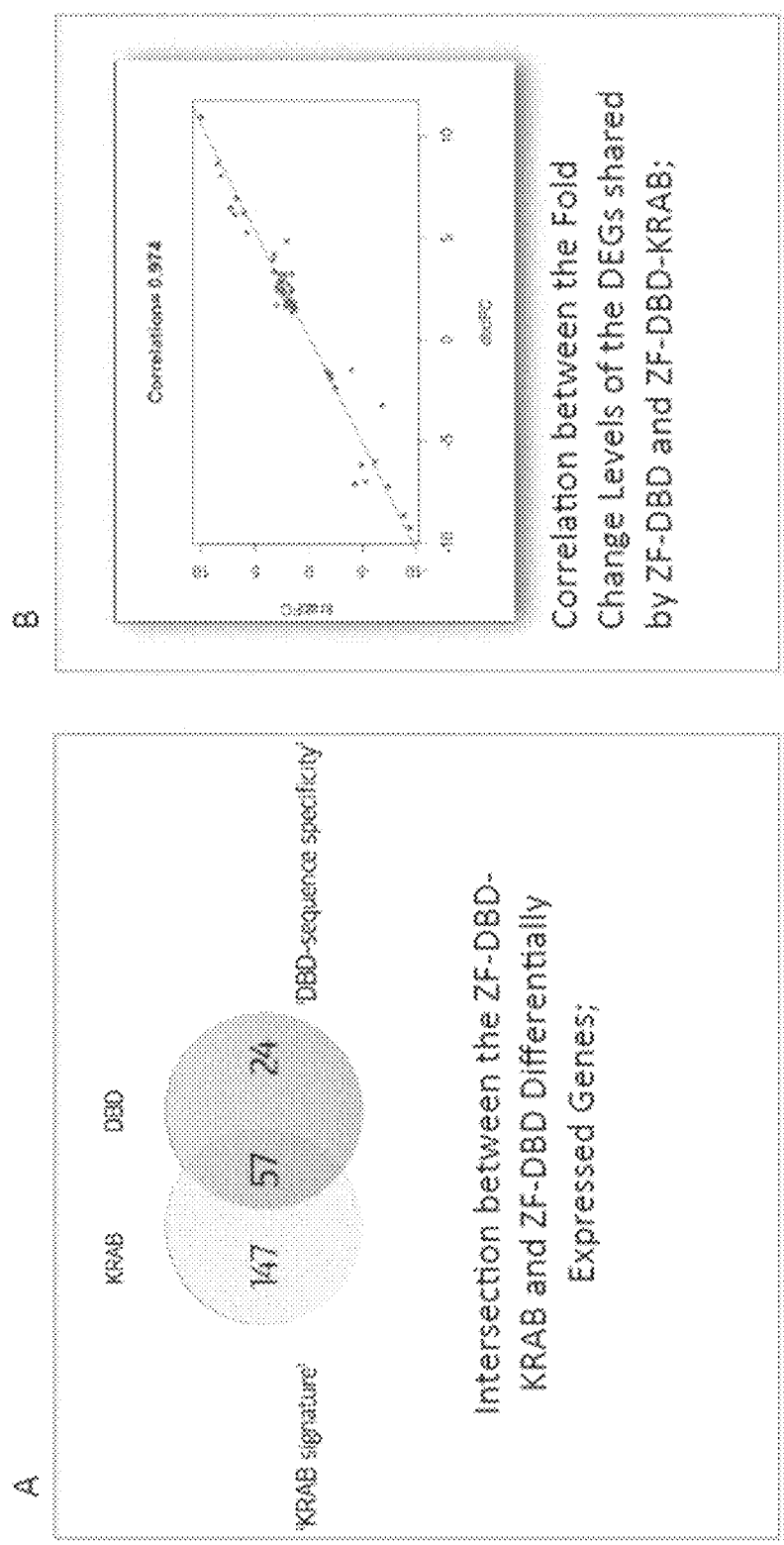

FIG. 13. A. Intersection between the ZF6-KRAB and ZF-DBD Differentially Expressed Genes; B. Correlation between the Fold Change Levels of the DEGs shared by ZF-DBD and ZF-DBD-KRAB; Differentially expressed genes (FDR<0.05) shown as a Vann diagram and Correlation level between the fold changes levels of the differentially expressed genes in common between DBD-KRAB and DBD treatments, showing that the intersection between ZF6-KRAB and ZF6-DBD (57 DEGs) are functionally correlated and therefore likely binding the same genome targets.

Figure 14:
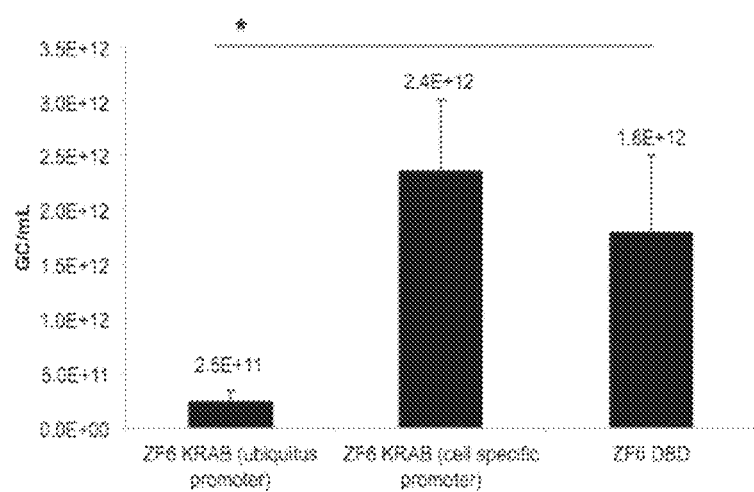

FIG. 14. Vector particles assessed by qPCR following AAV8 vector production. N=4 AAV8-CMV-ZF6-KRAB, n=2 AAV8-RHOK-ZF6-KRAB, n=2 AAV8-CMV-ZF6-DBD. *p<0.01 significant statistical differences between ZF6-DBD vs ZF6-KRAB (ubiquitous promoter).

Figure 15:
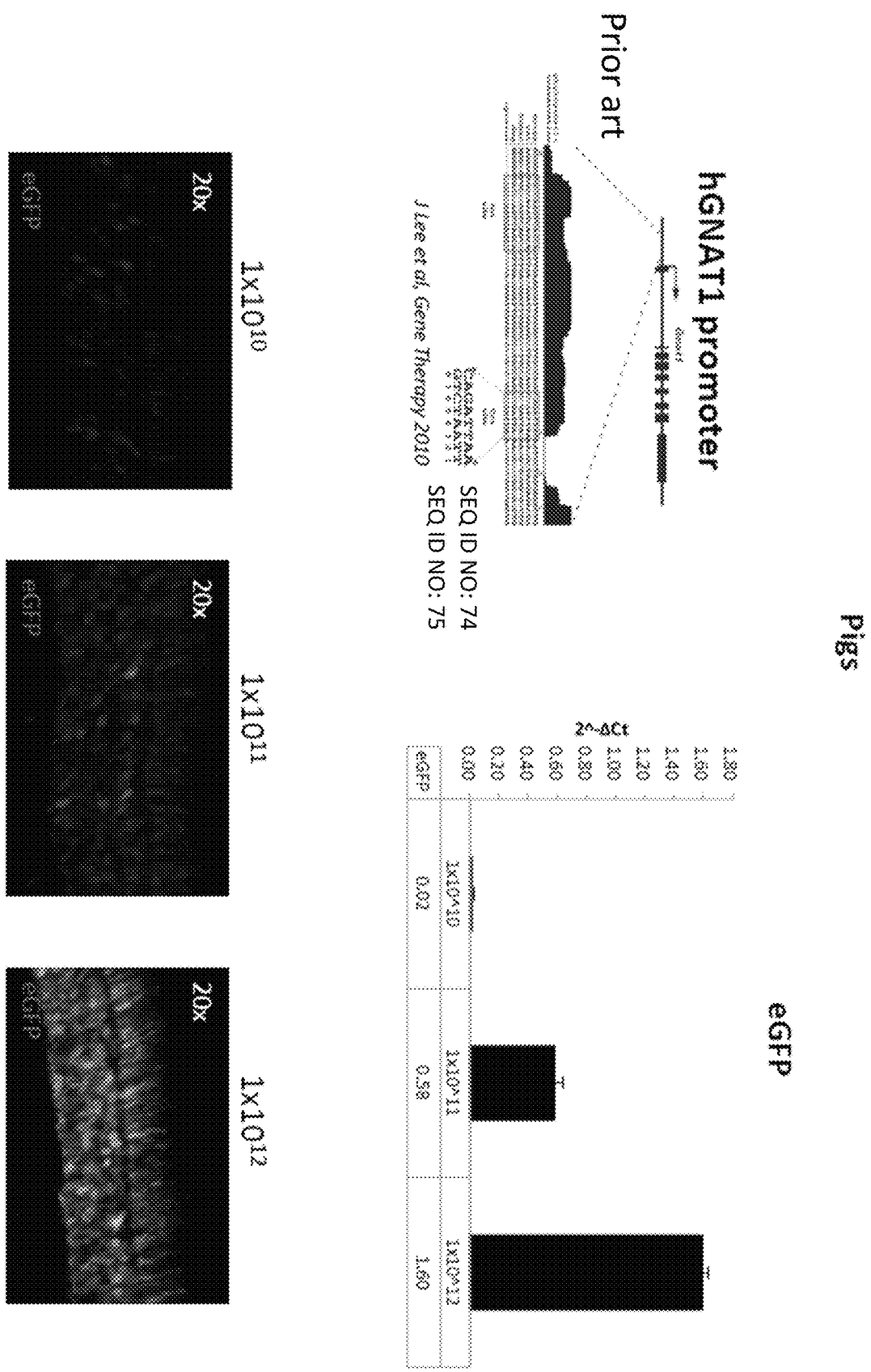

FIG. 15. Assessment in porcine adult retinae of human GNAT1 promoter strength for RHO replacement step of the silencing replacement strategy. Upper left panel: picture representing the GNAT1 promoter locus including a mutation in the CRX TF binding site, which enables enhancement of gene expression (J. Lee et al, Gene Therapy 2010). Upper right panel: levels of transgene transcript (EGFP) after delivery in the subretinal spaces of increasing AAV8 vector doses containing the GNAT1 elements (AAV8hGNAT1-EGFP: 1×10e10; 1×10e11; 1×10e12 vg). Lower panels: representative pictures of histological analysis of the retina treated at different vector doses (1×10e10; 1×10e11; 1×10e12 vg).

FIG. 16. Silencing and replacement experiment in pigs A. Expression levels of endogenous retina's genes of Pigs injected with AAV8-CMV-ZF6-DBD (dose: $1\times10^{11}$) and AAV8-hGNAT1-hRHO (dose $1\times10^{12}$) sacrificed 15 days after injection. B. Expression levels of ZF6-DBD in injected eyes.

Figure 17:
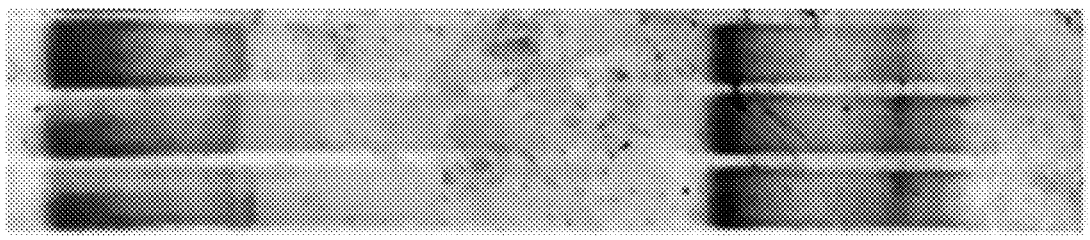

FIG. 17. Identification of the minimal core sequence recognized by ZF6-DBD. Gel mobility shift analysis of ZF6-DBD DNA binding to the hRho proximal promoter region (hRho 43 bp) including ZF6-DBDCis-seq (A). The sequence of the hRho 43 bp wild type, hRho 43 bp mut F and hRho 43 bp mut L oligonucleotides are indicated (B); the core sequence is underlined, and the bases that have been mutated are indicated in green (B).

Figure 18:
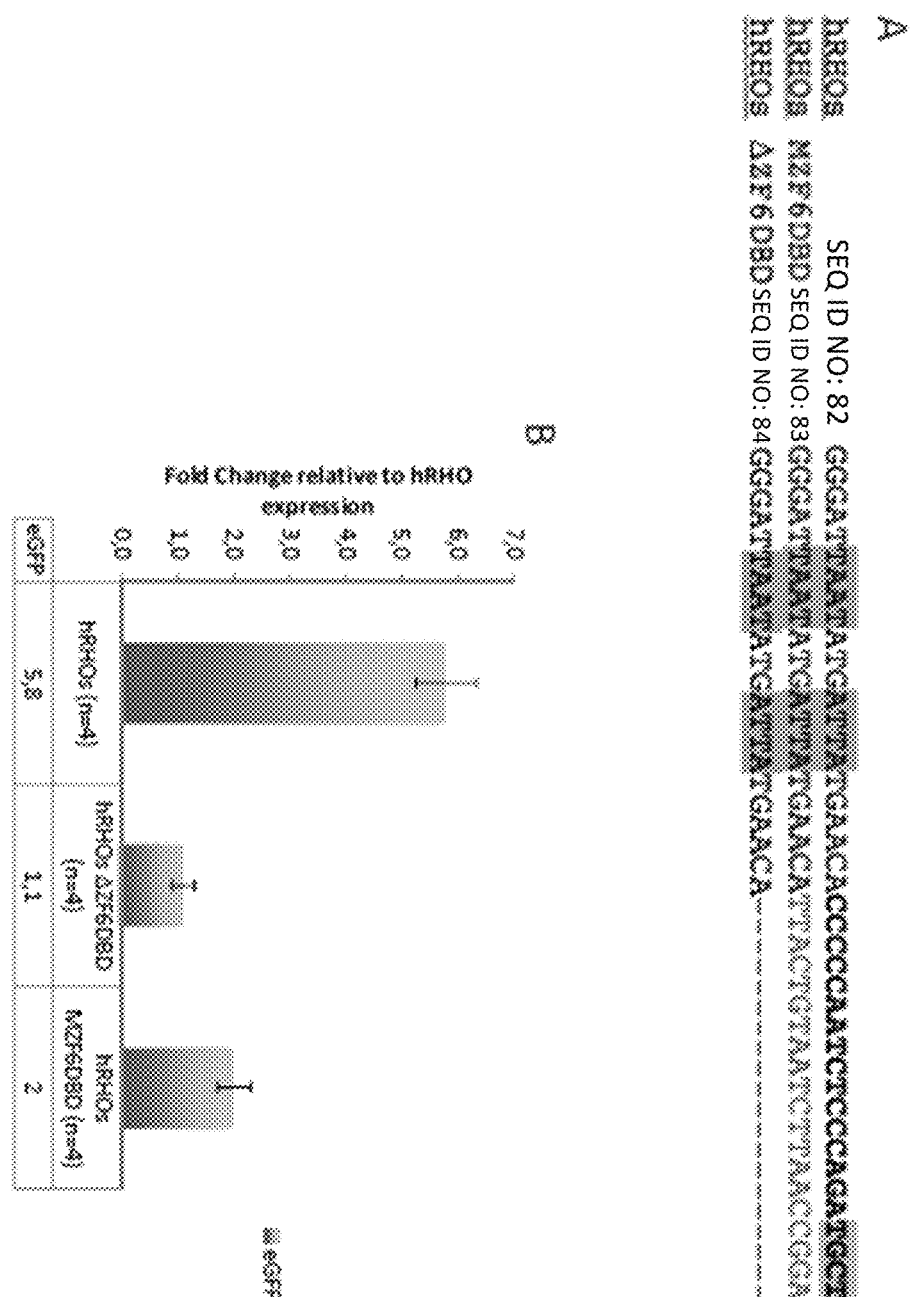

FIG. 18. A. Sequences of human rhodopsin proximal promoter: wild type, ZF6-DBDCis-seq mutated (MZF6-DBD) and ZF6-DBDCis-seq deleted (ΔZF6-DBD) respectively (in bold ZF6-DBDCis-seq,) B. Expression levels of eGFP evaluated by fold change analysis relative to expression of reporter vector (hRHO).

FIG. 19. Assessment of cis-regulatory (ZF6 DNA-binding motif) significance in vivo by AAV8 vector (1×10E9 vg) retinal delivery of a reporter (EGFP) expression cassette lacking the ZF6 target DNA motif (GGGGGT-TAGagGGTCTACGA SEQ ID No. 22; ΔZF6; AAV8-hRHO-ΔZF6-5'UTR-EGFP). A eGFP expression levels of AAV8-hRHO-5'UTR-EGFP and AAV8-hRHO-ΔZF6-5'UTR-EGFP in injected eyes by qRT-PCR using primers on polyA (bGH, bovine growth hormone polyA). ***p<0.0001 significance statistical differences between RHO-5'UTR-eGFP injected eyes vs hRHO-ΔZF6-5'UTR-EGFP. B eGFP expression levels of AAV8-hRHO-5'UTR-EGFP and AAV8-hRHO-ΔZF6-5'UTR-EGFP in injected eyes by histological analysis.

Figure 20:
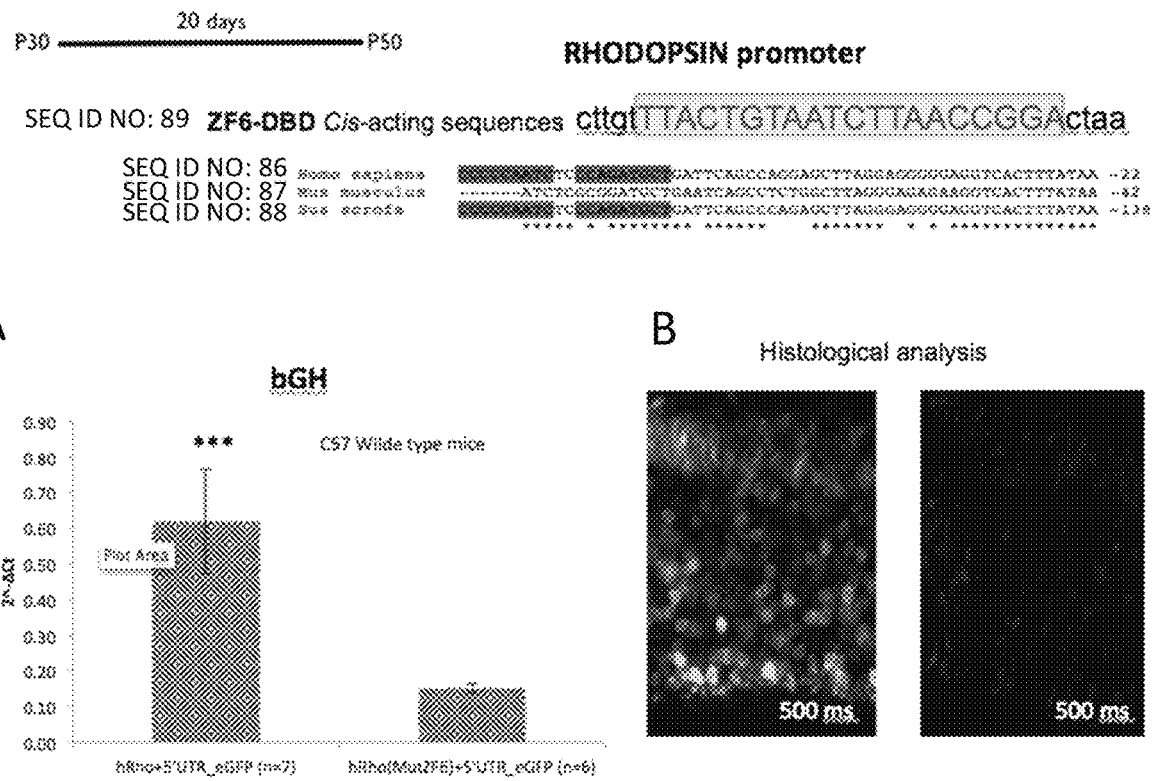

FIG. 20. Assessment of cis-regulatory (ZF6 DNA-binding motif) significance in vivo by AAV8 vector (1×10E9 vg) retinal delivery of a reporter (EGFP) expression cassette lacking the ZF6 target DNA motif (TTACTGTAATCT-TAACCGGA [SEQ ID No. 29]; MutZF6; AAV8-hRHO-MutZF6-5'UTR-EGFP). A eGFP expression levels of AAV8-hRHO-5'UTR-EGFP and AAV8-hRHO-ΔZF6-5'UTR-EGFP in injected eyes by qRT-PCR using primers on polyA (bGH, bovine growth hormone polyA). ***p<0.0001 significance statistical differences between RHO-5'UTR-eGFP injected eyes vs hRHO-MutZF6-5'UTR-EGFP. B eGFP expression levels of AAV8-hRHO-5'UTR-EGFP and AAV8-hRHO-MutZF6-5'UTR-EGFP in injected eyes by histological analysis.

Figure 21:
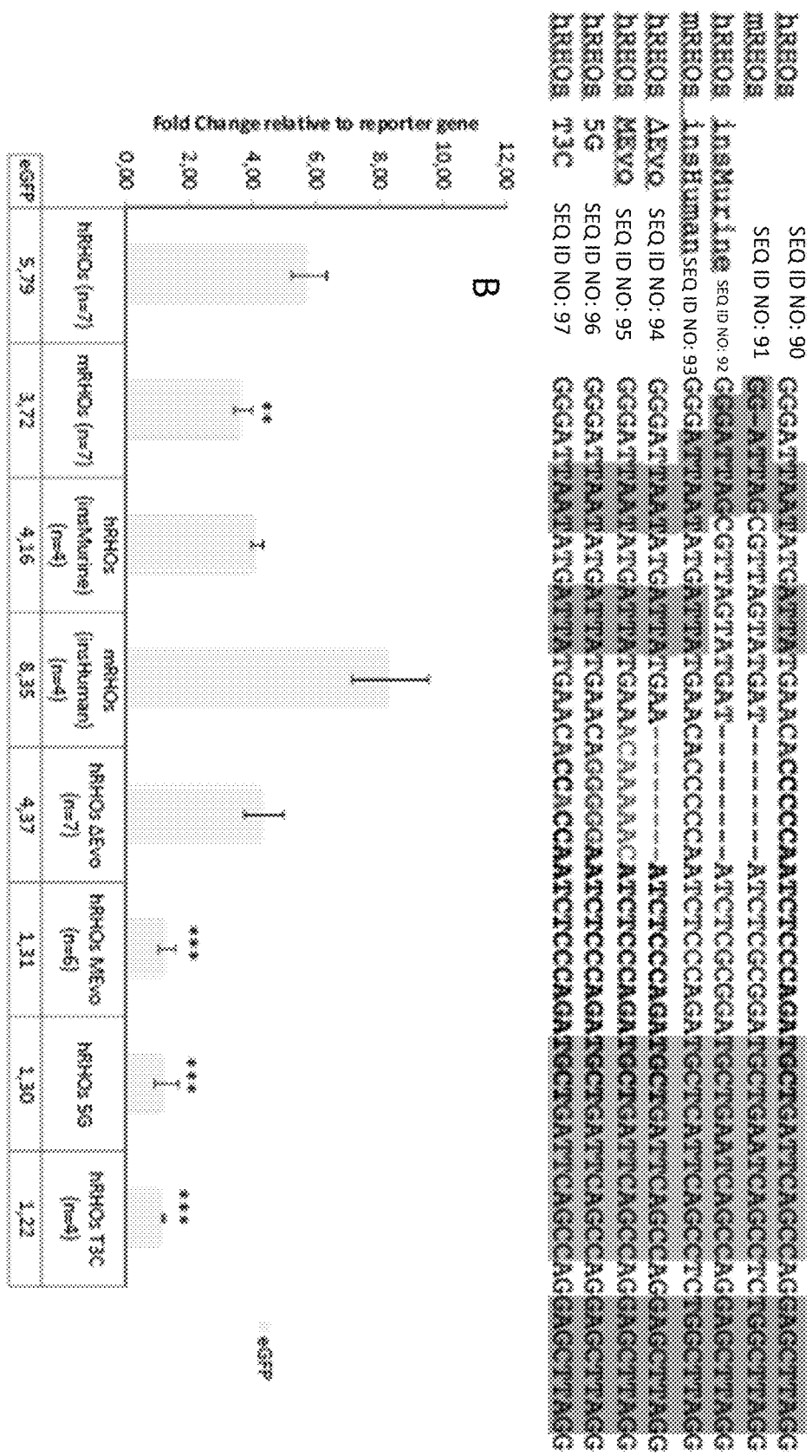

FIG. 21. A. Sequences of rhodopsin proximal promoter: hRHOs, mRHOs, hRHOs insMurine, mRHO insHuman, hRHOs ΔEvo, hRHOs Mevo, hRHOs 5G and hRHOs T3C. (in bold ZF6-DBDCis-seq). B. Expression levels of eGFP evaluated by fold change analysis relative to expression of reporter vector (hRHO). pvalue<0.01; *pvalue<0.001

Figure 22:
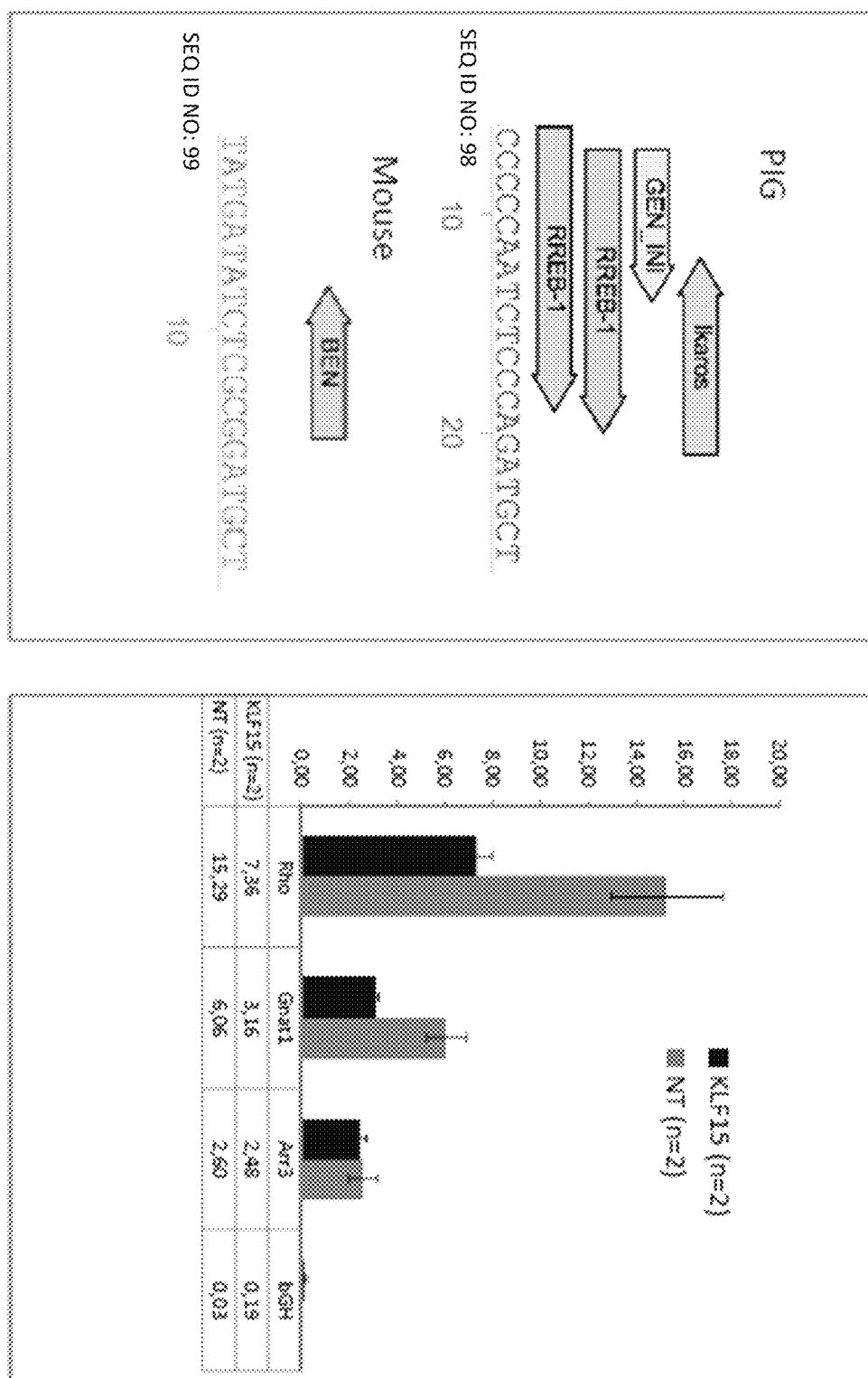

FIG. 22 A. Transfac analysis of the 25 bp containing the ZF6-DBDCis-seq, 100 bp upstream the TSS. This site is reported in literature to cointain the binding sites for klf15 (pig sequence). B. Expression levels of endogenous retina's genes of Pigs injected with AAV8-CMV-hKLF15 (dose: $2\times10^{10}$) sacrificed 15 days after injection. (NT, not transduced area;)

Figure 23:
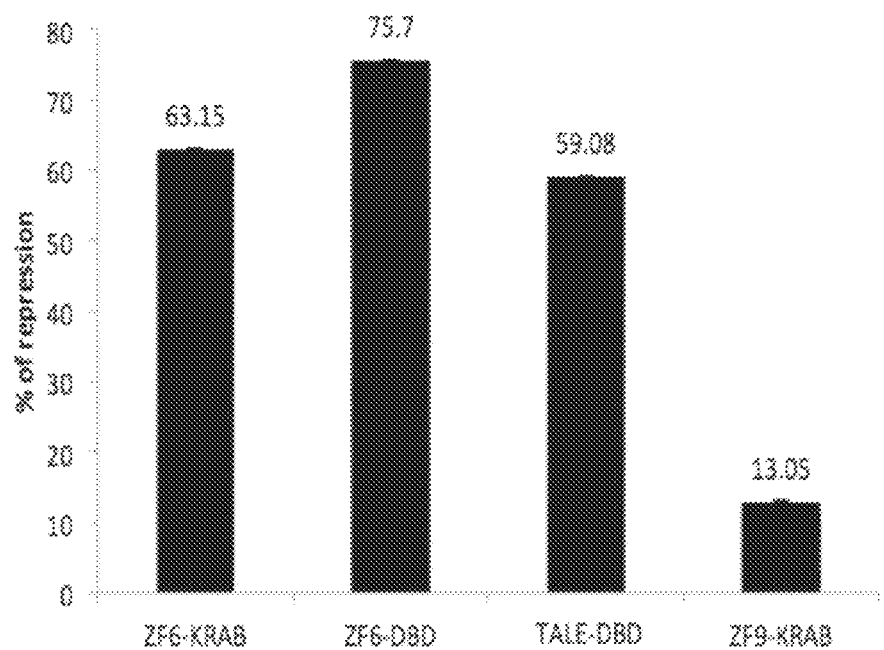

FIG. 23. Histogram showing the extent of repression relative to CRX transactivation of the luciferase activity mediated by ZF6-KRAB, ZF6-DBD, TALE-DBD and a control ZF9-KRAB. ZF6-KRAB, ZF6-DBD and TALE-DBD significantly repress the luciferase activity induced by CRX.

Figure 25:
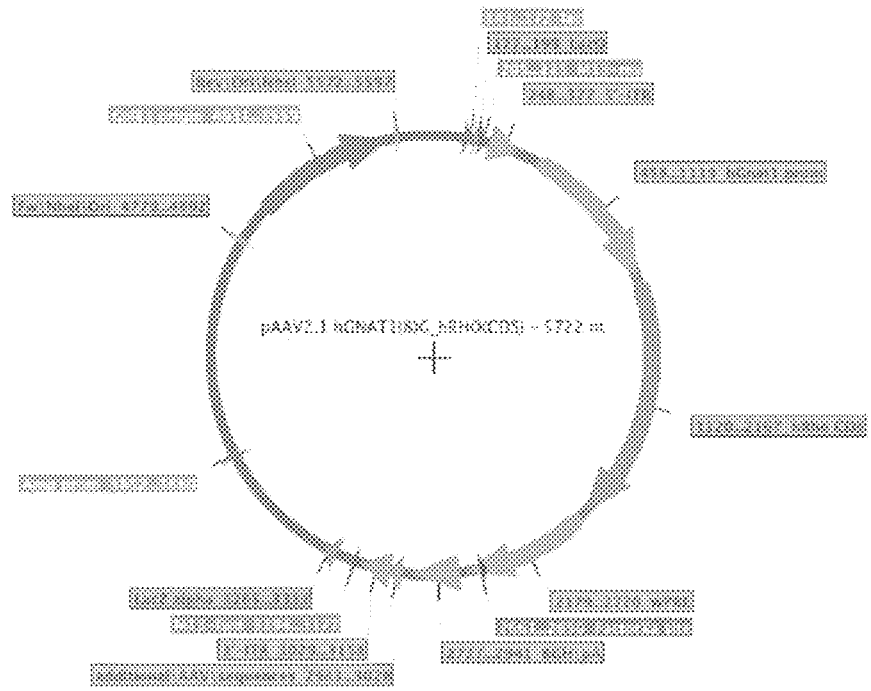

FIG. 24. pAAV2.1-CMVZF6-DBD. Features:
5'-ITR: [248: 377-CW]
3'-ITR: [2692: 2821-CW]
additional\AAV\sequences: [2646: 2691-CW]
CMV\promotor: [458: 1040-CW]
SV40\misc\intron\(Promega): [1078: 1210-CW]
WPRE: [1847: 2383-CW]
BGH\pA: [2390: 2604-CW]
ITR_RT_fw: [292: 309-CW]
ITR_RT_rev: [352: 372-CW]
ITR_RT_rev: [2697: 2717-CW]
ITR_RT_fw: [2760: 2777-CW]
AmpR: [3585: 4445-CW]
ZF6\DBD: [: 1227: 1829-CW]
ITR: Inverted Terminal Repeat
CMV: Cytomegalovirus
BGH: bovine growth hormone polyA
AmpR: Ampicillin Resistance
WPRE: woodchuck hepatitis posttranscriptional regulatory element FIG. 25. pAAV2.1-hGNAT1-h RHO. Features:
5'-ITR: [248: 377-CW]
3'-ITR: [3029: 3158-CW]
additional\AAV\sequences: [2983: 3028-CW]
WPRE: [2179: 2720-CW]
BGH\pA: [2727: 2941-CW]
Rev\Ori\Nhel: [5572: 5597-CW]
Fw\Nhel\Ori: [4779: 4802-CW]
M13-fwd: [3194: 3177-CCW]
M13-rev: [205: 225-CW]
ColE1 origin: [4931: 5559-CW]
LacZ alpha: [3265: 3333-CW]
LacO: [177: 199-CW]
Amp prom: [3852: 3880-CW]
lac: [143: 172-CW]
FactorXa site: [2661: 2650-CCW]
hGnatl prom: [458: 1119-CW]
hRho CDS: [1120: 2167-CW]

Figure 26:
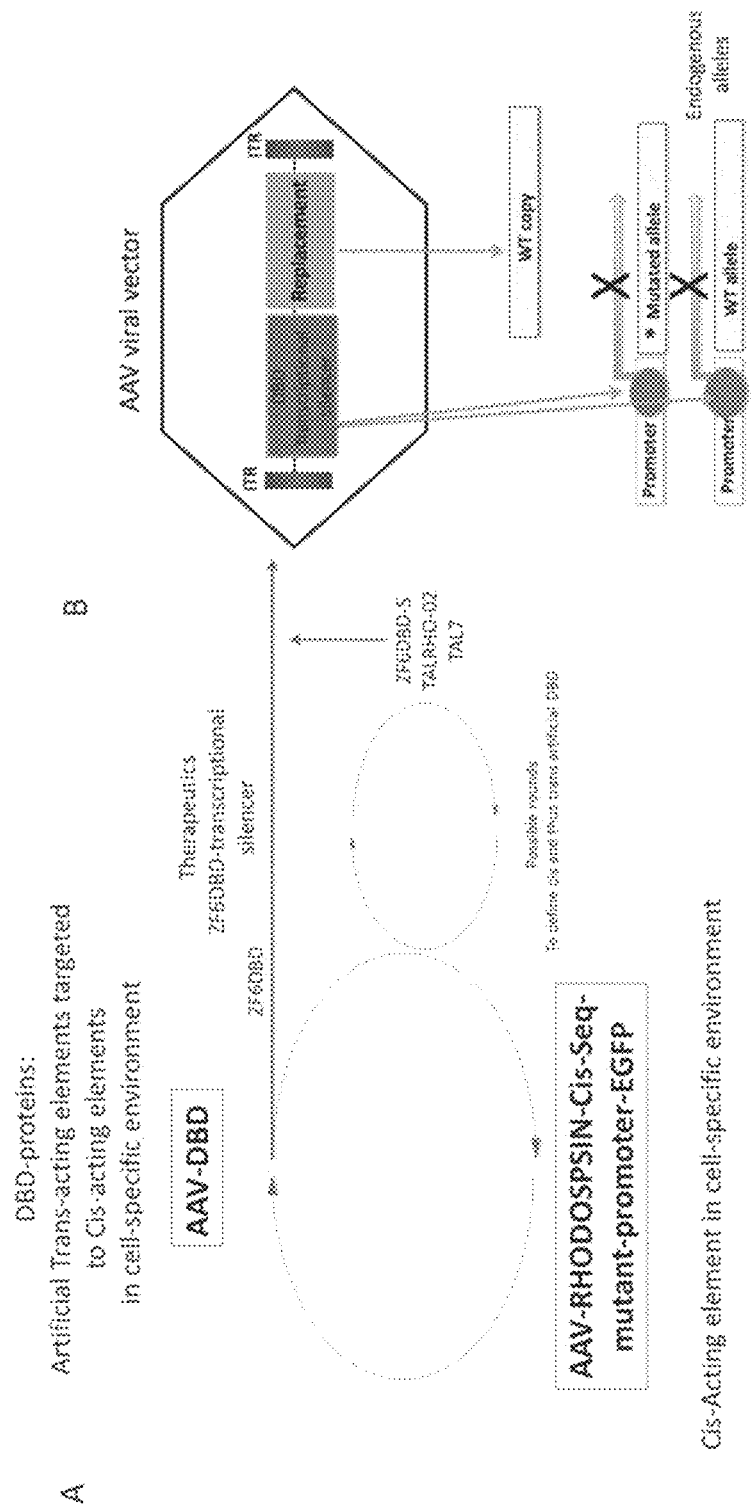

FIG. 26. Overall method to generate DNA-binding protein targeted to CIS-acting elements to modulate transcription. A—Taking advantage of the gene transfer efficacy of AAV vectors to photoreceptors it is possible to study the activity of CIS-acting elements within the appropriate cell-specific environment (AAV-Cis-acting elements-REPORTER, i.e. AAV-RHO-promoter-mutant-EG FP delivered in vivo to photoreceptors). Once identified the sensitive Cis-acting elements it is possible to generate a DNA-binding protein targeted to this sequence (AAV-ZF6-DBD for instance) to mimic the Cis-acting effect. ZF6DBD-5 TALRHO-02 and TAL7 DBD domains generated after isolation of Cis-acting properties within RHO promoter. B—After the generation of a RHO silencer as thereof reported, it is possible to generate a AAV vector containing it and couple this to a replacement construct (i.e. RHODOPSIN) to generate a Silencing (ZF6-DBD) and Replacement (RHODOPSIN) strategy.

Figure 27:
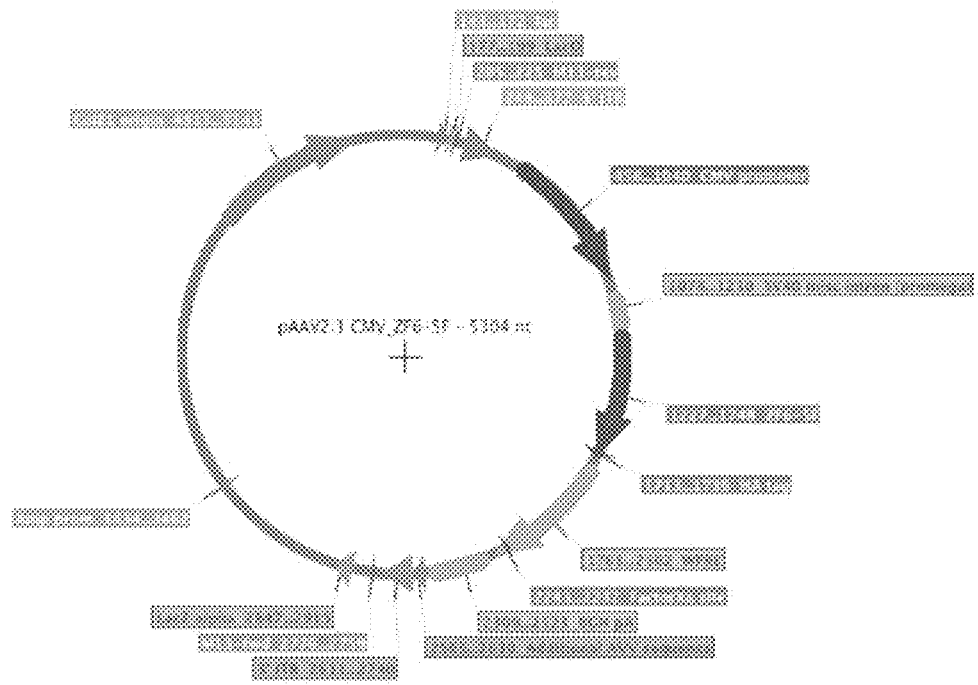

FIG. 27. pAAV2.1-CMV-ZF6-5F. Features:
5' ITR: [248: 377-CW]
CMV promoter: [458: 1040-CW]
SV40 misc intron (promega): [1078: 1210-CW]
BGH pA: [2309: 2523-CW]
Additional AW sequence: [2565: 2610-CW]
3' ITR: [2611: 2740-CW]
WPRE: [1761: 2302-CW]
M13-fwd: [2776: 2759-CCW]
M13-rev: [205: 225-CW]
ColE1 origin: [4513: 5141-CW]
LacZ alpha: [2847: 2915-CW]
LacO: [177: 199-CW]
Amp prom: [3434: 3462-CW]
lac: [143: 172-CW]
HA tag: [1713: 1739-CW]
FactorXa site: [2243: 2232-CCW]
ZF6-5F (also called ZF6-5): [1227: 1748-CW]

Figure 28:
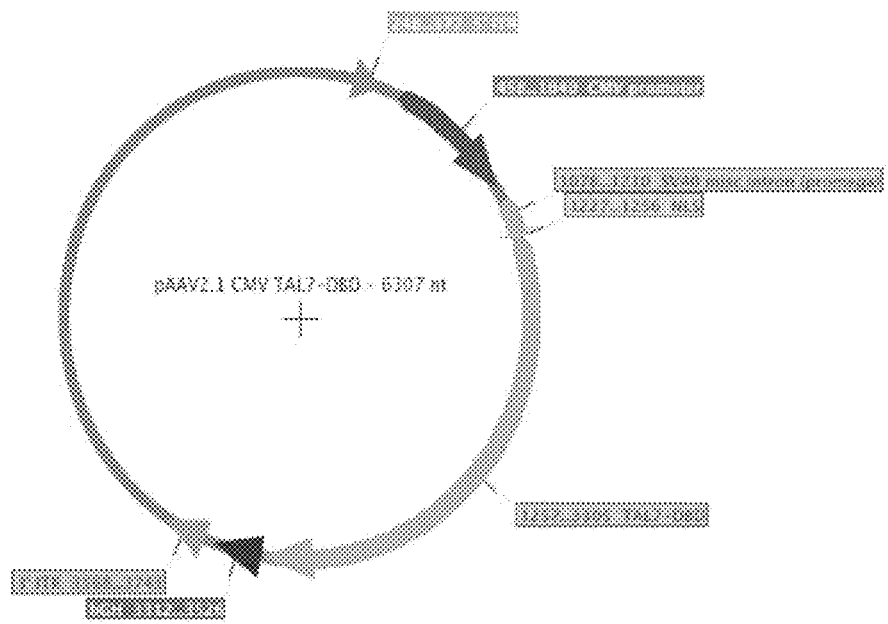

FIG. 28. pAAV2.1-CMV-TAL7-DBD. Features:
Features:
5' ITR: [248: 377-CW]
CMV promoter: [458: 1040-CW]
SV40 misc intron (promega): [1078: 1210-CW]
NLS: [1227: 1256-CW]
TAL7-DBD: [1257: 3305-CW]
bGH: [3312: 3526-CW]
3' ITR: [3568: 3743-CW]

Figure 29:
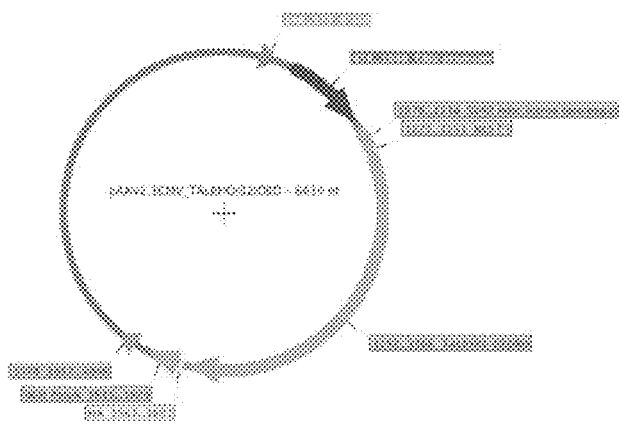

FIG. 29. pAAV2.1-CMV-TALRHO(02)DBD. Features:
5' ITR: [248: 377-CW]
CMV promoter: [458: 1040-CW]
SV40 misc intron (promega): [1078: 1210-CW]
NLS [*]: [1227: 1251-CW]
TALRHO(02)DBD: [1252: 3566-CW]
HA: [3567: 3602-CW]
3'ITR: [3917: 4046-CW]
bGH PolyA: [3615: 3829-CW]

Figure 30:
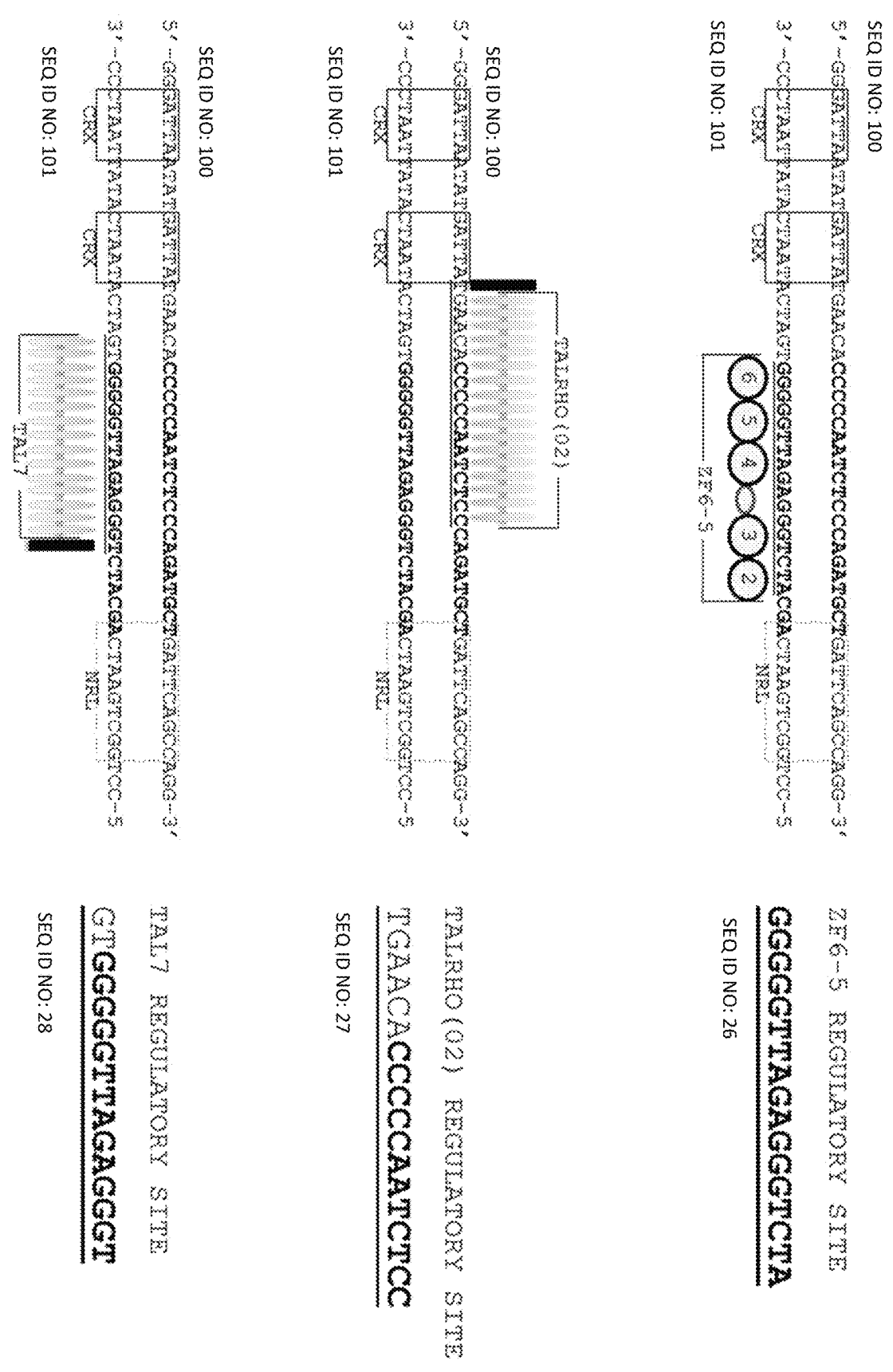

FIG. 30. Schematic representation of binding of ZF6-5F, TAL7-DBD and TALRHO(02)DBD with human and porcine rhodopsin promoter. Shifting the target site of DBD domains (Zinc Finger-based and TALE technologies) based on the ZF6-DBDCis-seq elements results, see FIG. 21. Considering the sensitivity of the CCCCCA [SEQ ID No. 30] sequence within the genomic ZF6-DBDCis-seq, artificial DNA binding proteins were either partially fragmented, ZF6-5F corresponding to the same amino acids composition of ZF6-DBD but lacking the last Finger (Finger 6, FIG. 7) or targeting a 5" upstream sequence centering the CCCCCA [SEQ ID NO. 30] sequence. In the case of TALRHO(02) (17 modules) 6 bases upstream on the + strand. In the case of TAL7 (15 modules) 2 bases upstream on the—strand. The target sequences are underlined, in bold the ZF6-DBDCis-seq. Boxes CRX binding sites, dotted box NRL binding site.

Figure 31:
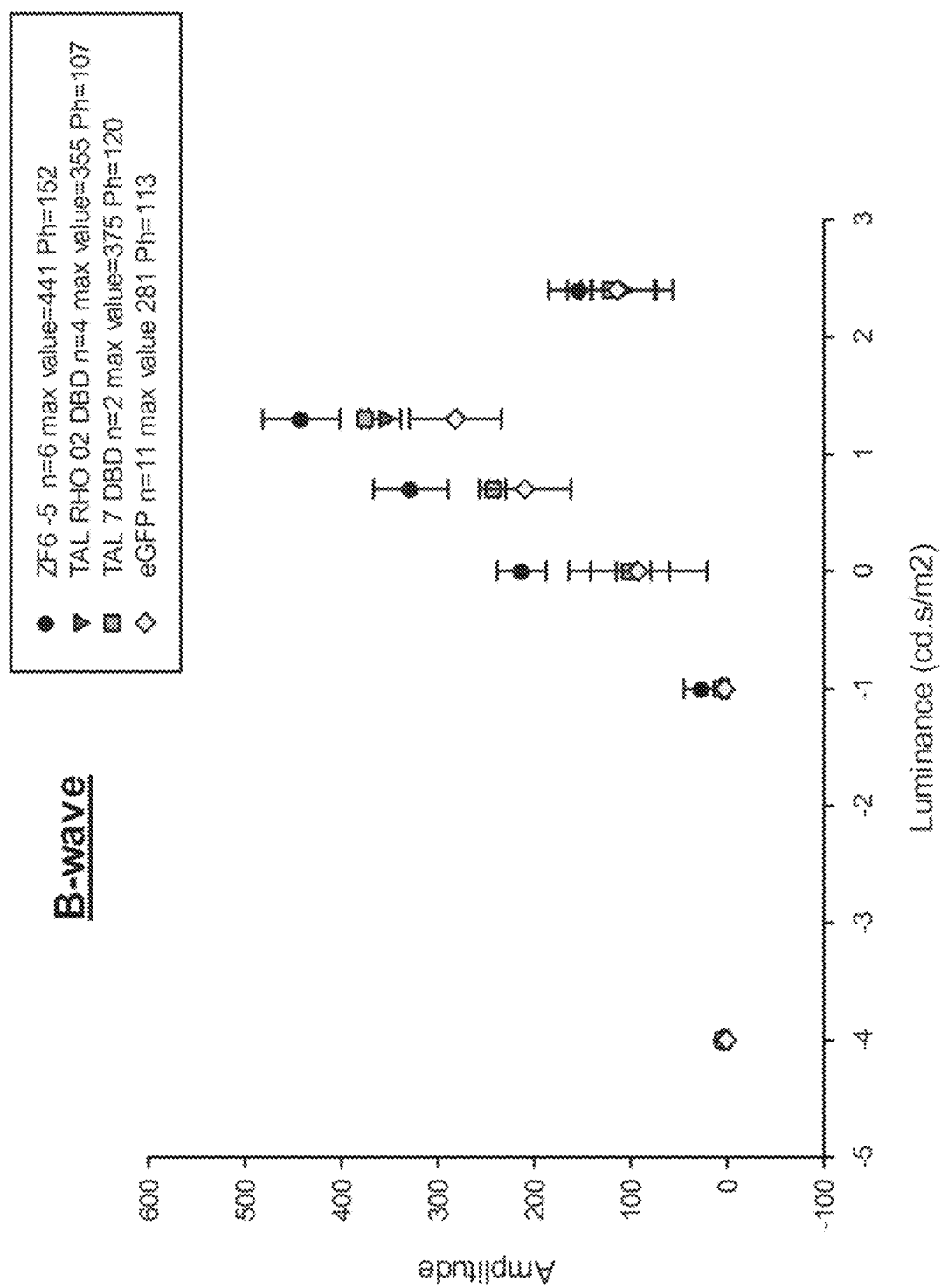

FIG. 31. Electrophysiological responses of retina recorded by ERG analysis, on P347S mice injected subretinally with AAV8-CMV-ZF6-5F or AAV8-CMV-TALRHO (02)DBD or AAV8-CMV-TAL7-DBD (1×10E9 vg) at P15. The amplitudes represent retinal responses evoked by increasing light intensities under scotopic (dim light) and photopic (bright light) conditions. B-wave amplitudes 15 days after vector delivery (P30 mice), the electrophysiologic responses of the retina were preserved in ZF6-5F, TALRHO (02) and TAL7 treated eyes compared to control contralateral EGFP injected eye.

Sequences
Nucleotide sequence of human rhodopsin promoter and its 5'UTR
(SEQ ID No. 1)
Cagatcttcccacctagccacctggcaaactgctccttctctcaaaggcccaaacatggcctcccagactgcaac ccccaggcagtcaggccctgtctccacaacctcacagccaccctggacggaatctgcttcttcccacatttgagtc -continued

```
ctcctcagcccctgagctcctctgggcagggctgtttctttccatctttgtattcccaggggcctgcaaataaatg tttaatgaacgaacaagagagtgaattccaattccatgcaacaaggattgggctcctgggccctaggctatgtgtc tggcaccagaaacggaagctgcaggttgcagcccctgccctcatggagctcctcctgtcagaggagtgtggggact ggatgactccagaggtaacttgtgggggaacgaacaggtaaggggctgtgtgacgagatgagagactgggagaata aaccagaaagtctctagctgtccagaggacatagcacagaggcccatggtccctatttcaaacccaggccaccaga ctgagctgggacccttgggacagacaagtcatgcagaagttaggggaccttctcctcccttttcctggatcctgagt acctctcctccctgacctcaggcttcctcctagtgtcaccttggcccctcttagaagccaattaggccctcagttt ctgcagcgggattaatatgattatgaacaccccaatctcccagatgctgattcagccaggagcttaggaggggg aggtcactttataagggtctggggggtcagaacccagagtcatccagctggagccctgagtggctgagctcaggc cttcgcagcattcttgggtgggagcagccacgggtcagccacaagggccacagcc
```

Nucleotide sequence of ZF6-DBD
(SEQ ID No. 2)

```
atgatcgatctggaacctggcgaaaaaccgtataagtgcccagaatgcggcaagtcttttttcccagtctggccacc tgacggaacatcagcgcactcacaccggcgagaaaccatataaatgtccggagtgcggcaagagctttagccagaa tagcacccctgaccgaacatcagcgtacgcacacgggtgaaaagccatataaatgccctgagtgcggcaaatcctt agcacctctggccatctggtccgtcaccagcgcacccaccagaataagaagggcggttctggtgacggtaaaaaga aacagcacgcctgtccagagtgtggcaaatctttttcccgtgaagacaacctgcacactccagcgcactcatac tggcgagaaaccttacaagtgtccggaatgtggtaagagcttctccacttccggccatctggttcgtcaccagcgc acgcacaccggcgaaaaaccatacaagtgcccggaatgcggcaaatcattctcccgtagcgacaaactggttcgtc accaacgtacgcataccggtaaaaagacttcctctagatacccgtacgacgttccagactatgcatcttga
```

Protein Sequence of ZF6-DBD
(SEQ ID No. 3)

MIDLEPGEKPYKCPECGKSFSQSGHLTEHQRTHTGEKPYKCPECGKSFSQNSTLTEHQRTHTGEKPYKCPECGKSF

STSGHLVRHQRTHQNKKGGSGDGKKKQHACPECGKSFSREDNLHTHQRTHTGEKPYKCPECGKSFSTSGHLVRHQR

THTGEKPYKCPECGKSFSRSDKLVRHQRTHTGKKTSSRYPYDVPDYAS*

Nucleotide sequence of ZF2
(SEQ ID No. 4)

```
atgatcgatctggaacctggcgaaaaaccgtataagtgcccagaatgcggcaagtcttttttccacctctggcaatc tggtgcgccatcagcgcactcacaccggcgagaaaccatataaatgtccggagtgcggcaagagctttagcactag cggcgagctggtccgtcatcagcgtacgcacacgggtgaaaagccatataaatgccctgagtgcggcaaatccttt agcacctctggtaacctggtacgtcaccagcgcacccacacgggccgttcttctgtagagtctgcgtgcgtcacct ctgtactggttgccctcctgccggctacctctgcaccgactcaggtgagcggtgaaaagccatacaaatgtccaga gtgtggcaaatctttttcccagtctggcaacctgactgaacaccagcgcactcatactggcgagaaaccttacaag tgtccggaatgtggtaagagcttctcctccaaaaagcatctggctgagcaccagcgcacgcacaccggcgaaaaac catacaagtgcccggaatgcggcaaatcattcagctccaaaaaggctctgactgagcaccaacgtacgcataccgg taaaaagacttcctctagaccgaaaaagaaacgcaaagtttacccatacgacgtacctgattatgcaagctga
```

Protein sequence of ZF2
(SEQ ID No. 5)

MIDLEPGEKPYKCPECGKSFSTSGNLVRHQRTHTGEKPYKCPECGKSFSTSGELVRHQRTHTGEKPYKCPECGKSF

STSGNLVRHQRTHTGRSSVESACVTSVLVALLPATSAPTQVSGEKPYKCPECGKSFSQSGNLTEHQRTHTGEKPYK

CPECGKSFSSKKHLAEHQRTHTGEKPYKCPECGKSFSSKKALTEHQRTHTGKKTSSRPKKKRKVYPYDVPDYAS*

Nucleotide sequence of TAL01

(SEQ ID No. 6)

atgtacccatacgatgtcccagactacgcgaatttaatgtcgcggacccggctcccttcccacccgcacccagcc cagcgttttcggccgactcgttctcagacctgcttaggcagttcgacccctcactgtttaacacatcgttgttcga ctcccttcctccgtttggggcgcaccatacggaggcggccaccggggagtgggatgaggtgcagtcgggattgaga gctgcggatgcaccaccccaaccatgcgggtggccgtcaccgctgcccgaccgccgagggcgaagcccgcaccaa ggcggagggcagcgcaaccgtccgacgcaagccccgcagcgcaagtagatttgagaactttgggatattcacagca gcagcaggaaaagatcaagcccaaagtgaggtcgacagtcgcgcagcatcacgaagcgctggtgggtcatgggttt acacatgcccacatcgtagccttgtcgcagcaccctgcagcccttggcacggtcgccgtcaagtaccaggacatga ttgcggcgttgccggaagccacacatgaggcgatcgtcggtgtggggaaacagtggagcggagcccgagcgcttga ggccctgttgacggtcgcgggagagctgagagggcctcccctcagctggacacgggccagttgctgaagatcgcg aagcggggaggagtcacggcggtcgaggcggtgcacgcgtggcgcaatgcgctcacgggagcacccctcaacctga ccccagagcaggtcgtggcaattgcgagccatgacggggaaagcaggcactcgaaaccgtccagaggttgctgcc tgtgctgtgccaagcgcacggacttacgccagagcaggtcgtggcaattgcgagcaacatcggggaaagcaggca ctcgaaaccgtccagaggttgctgcctgtgctgtgccaagcgcacggactaaccccagagcaggtcgtggcaattg cgagcaacaacggggaaagcaggcactcgaaaccgtccagaggttgctgcctgtgctgtgccaagcgcacgggtt gaccccagagcaggtcgtggcaattgcgagccatgacggggaaagcaggcactcgaaaccgtccagaggttgctg cctgtgctgtgccaagcgcacggcctgaccccagagcaggtcgtggcaattgcgagcaacatcggggaaagcagg cactcgaaaccgtccagaggttgctgcctgtgctgtgccaagcgcacggactgacaccagagcaggtcgtggcaat tgcgagcaacggaggggaaagcaggcactcgaaaccgtccagaggttgctgcctgtgctgtgccaagcgcacgga cttacacccgaacaagtcgtggcaattgcgagccatgacggggaaagcaggcactcgaaaccgtccagaggttgc tgcctgtgctgtgccaagcgcacggacttacgccagagcaggtcgtggcaattgcgagcaacggaggggaaagca ggcactcgaaaccgtccagaggttgctgcctgtgctgtgccaagcgcacggactaaccccagagcaggtcgtggca attgcgagcaacaacggggaaagcaggcactcgaaaccgtccagaggttgctgcctgtgctgtgccaagcgcacg ggttgaccccagagcaggtcgtggcaattgcgagcaacaacggggaaagcaggcactcgaaaccgtccagaggtt gctgcctgtgctgtgccaagcgcacggcctgaccccagagcaggtcgtggcaattgcgagcaacaacggggaaag caggcactcgaaaccgtccagaggttgctgcctgtgctgtgccaagcgcacggactgacaccagagcaggtcgtgg caattgcgagcaacatcggggaaagcaggcactcgaaaccgtccagaggttgctgcctgtgctgtgccaagcgca cggcctcaccccagagcaggtcgtggcaattgcgagcaacaacggggaaagcaggcactcgaaaccgtccagagg ttgctgcctgtgctgtgccaagcgcacggacttacgccagagcaggtcgtggcaattgcgagcaacatcggggaa agcaggcactcgaaaccgtccagaggttgctgcctgtgctgtgccaagcgcacggactaaccccagagcaggtcgt ggcaattgcgagcaacggaggggaaagcaggcactcgaaaccgtccagaggttgctgcctgtgctgtgccaagcg cacgggttgaccccagagcaggtcgtggcaattgcgagcaacggaggggaaagcaggcactcgaaaccgtccaga ggttgctgcctgtgctgtgccaagcgcacggactcacgcctgagcaggtagtggctattgcatccaataacggggg cagacccgcactggagtcaatcgtggcccagctttcgaggccggaccccgcgctggccgcactcactaatgatcat cttgtagcgctggcctgcctcggcggacgacccgccttggatgcggtgaagaaggggctcccgcacgcgcctgcat tgattaagcggaccaacagaaggattcccgagaggacatcacatcgagtggcagatcacgcgcaagtggtccgcgt gctcggattcttccagtgtcactccaccccgcacaagcgttcgatgacgccatgactcaatttggtatgtcgaga cacggactgctgcagctcttcgtagagtcggtgtcacagaactcgaggcccgctcgggcacactgcctcccgcct cccagcggtgggacaggattctccaagcgagcggtatgaaacgcgcgaagccttcacctacgtcaactcagacacc

```
tgaccaggcgagccttcatgcgttcgcagactcgctggagagggatttggacgcgccctcgcccatgcatgaaggg gaccaaactcgcgcgtcagctagccccaagaagaagagaaaggtggaggccagctga
```

Protein Sequence of TAL01

(SEQ ID No. 7)

```
MYPYDVPDYANLMSRTRLPSPPAPSPAFSADSFSDLLRQFDPSLFNTSLFDSLPPFGAHHTEAATGEWDEVQSGLR

AADAPPPTMRVAVTAARPPRAKPAPRRRAAQPSDASPAAQVDLRTLGYSQQQQEKIKPKVRSTVAQHHEALVGHGF

THAHIVALSQHPAALGTVAVKYQDMIAALPEATHEAIVGVGKQWSGARALEALLTVAGELRGPPLQLDTGQLLKIA

KRGGVTAVEAVHAWRNALTGAPLNLTPEQVVAIASHDGGKQALETVQRLLPVLCQAHGLTPEQVVAIASNIGGKQA

LETVQRLLPVLCQAHGLTPEQVVAIASNNGGKQALETVQRLLPVLCQAHGLTPEQVVAIASHDGGKQALETVQRLL

PVLCQAHGLTPEQVVAIASNIGGKQALETVQRLLPVLCQAHGLTPEQVVAIASNGGGKQALETVQRLLPVLCQAHG

LTPEQVVAIASHDGGKQALETVQRLLPVLCQAHGLTPEQVVAIASNGGGKQALETVQRLLPVLCQAHGLTPEQVVA

IASNNGGKQALETVQRLLPVLCQAHGLTPEQVVAIASNNGGKQALETVQRLLPVLCQAHGLTPEQVVAIASNNGGK

QALETVQRLLPVLCQAHGLTPEQVVAIASNIGGKQALETVQRLLPVLCQAHGLTPEQVVAIASNNGGKQALETVQR

LLPVLCQAHGLTPEQVVAIASNIGGKQALETVQRLLPVLCQAHGLTPEQVVAIASNGGGKQALETVQRLLPVLCQA

HGLTPEQVVAIASNGGGKQALETVQRLLPVLCQAHGLTPEQVVAIASNNGGRPALESIVAQLSRPDPALAALTNDH

LVALACLGGRPALDAVKKGLPHAPALIKRTNRRIPERTSHRVADHAQVVRVLGFFQCHSHPAQAFDDAMTQFGMSR

HGLLQLFRRVGVTELEARSGTLPPASQRWDRILQASGMKRAKPSPTSTQTPDQASLHAFADSLERDLDAPSPMHEG

DQTRASASPKKKRKVEAS*
```

Nucleotide sequence of TAL02 (on reverse strand of human Rhodopsin promoter)

(SEQ ID No. 8)

```
atgtacccatacgatgtcccagactacgcgaatttaaaccccaagaagaagcggaaggtgcacgggaattctgcga gcgcgccgccgccgcgcggcgcagccgagcgatgcgagcccggcggcgcaggtggatctgcgcaccctgggcta tagccagcagcagcaggaaaaaattaaaccgaaagtgcgcagcaccgtggcgcagcatcatgaagcgctggtgggc catggctttacccatgcgcatattgtggcgctgagccagcatccggcggcgctgggcaccgtggcggtgaaatatc aggatatgattgcggcgctgccggaagcgacccatgaagcgattgtgggcgtgggcaaacagtggagcggcgcgcg cgcgctggaagcgctgctgaccgtggcgggcgaactgcgcggcccgccgctgcagctggataccggccagctgctg aaaattgcgaaacgcggcggcgtgaccgcggtggaagcggtgcatgcgtggcgcaacgcgctgaccggcgcgccgc tgaacctgaccccgcagcaggtggtggcgattgcgagccatgatggcggcaaacaggcgctggaaaccgtgcagcg cctgctgccggtgctgtgccaggcgcatggcctgaccccggaacaggtggtggcgattgcgagcaacggcggcggc aaacaggcgctggaaaccgtgcagcgcctgctgccggtgctgtgccaggcgcatggcctgaccccggaacaggtgg tggcgattgcgagcaacaacggcggcaaacaggcgctggaaaccgtgcagcgcctgctgccggtgctgtgccaggc gcatggcctgaccccggaacaggtggtggcgattgcgagcaacaacggcggcaaacaggcgctggaaaccgtgcag cgcctgctgccggtgctgtgccaggcgcatggcctgaccccggaacaggtggtggcgattgcgagcaacaacggcg gcaaacaggcgctggaaaccgtgcagcgcctgctgccggtgctgtgccaggcgcatggcctgaccccggaacaggt ggtggcgattgcgagcaacattggcggcaaacaggcgctggaaaccgtgcagcgcctgctgccggtgctgtgccag gcgcatggcctgaccccgcagcaggtggtggcgattgcgagcaacaacggcggcaaacaggcgctggaaaccgtgc aggcgctgctgccggtgctgtgccaggcgcatggcctgaccccggaacaggtggtggcgattgcgagcaacattgg cggcaaacaggcgctggaaaccgtgcaggcgctgctgccggtgctgtgccaggcgcatggcctgaccccggaacag gtggtggcgattgcgagcaacggcggcggcaaacaggcgctggaaaccgtgcagcgcctgctgccggtgctgtgcc aggcgcatggcctgaccccgcagcaggtggtggcgattgcgagcaacggcggcggcaaacaggcgctggaaaccgt gcagcgcctgctgccggtgctgtgccaggcgcatggcctgaccccgcagcaggtggtggcgattgcgagcaacaac ggcggcaaacaggcgctggaaaccgtgcagcgcctgctgccggtgctgtgccaggcgcatggcctgaccccggaac
``` aggtggtggcgattgcgagcaacaacggcggcaaacaggcgctggaaaccgtgcagcgcctgctgccggtgctgtg ccaggcgcatggcctgaccccggaacaggtggtggcgattgcgagcaacaacggcggcaaacaggcgctggaaacc gtgcagcgcctgctgccggtgctgtgccaggcgcatggcctgaccccggaacaggtggtggcgattgcgagcaaca acggcggcaaacaggcgctggaaaccgtgcagcgcctgctgccggtgctgtgccaggcgcatggcctgaccccgca gcaggtggtggcgattgcgagcaacaacggcggccgcccggcgctggaaagcattgtggcgcagctgagccgcccg gatccggcgctggcggcgctgaccggcagcTGA Protein Sequence of TAL02

(SEQ ID No. 9)

MYPYDVPDYANLNPKKKRKVHGNSASAPRRRAAQPSDASPAAQVDLRTLGYSQQQQEKIKPKVRSTVAQHHEALVG

HGFTHAHIVALSQHPAALGTVAVKYQDMIAALPEATHEAIVGVGKQWSGARALEALLTVAGELRGPPLQLDTGQLL

KIAKRGGVTAVEAVHAWRNALTGAPLNLTPQQVVAIASHDGGKQALETVQRLLPVLCQAHGLTPEQVVAIASNGGG

KQALETVQRLLPVLCQAHGLTPEVVAIASNNGGKQALETVQRLLPVLCQAHGLTPEQVVAIASNNGGKQALETVQ

RLLPVLCQAHGLTPEQVVAIASNNGGKQALETVQRLLPVLCQAHGLTPEQVVAIASNIGGKQALETVQRLLPVLCQ

AHGLTPQQVVAIASNNGGKQALETVQALLPVLCQAHGLTPEQVVAIASNIGGKQALETVQALLPVLCQAHGLTPEQ

VVAIASNGGGKQALETVQRLLPVLCQAHGLTPQQVVAIASNGGGKQALETVQRLLPVLCQAHGLTPQQVVAIASNN

GGKQALETVQRLLPVLCQAHGLTPEQVVAIASNNGGKQALETVQRLLPVLCQAHGLTPEQVVAIASNNGGKQALET

VQRLLPVLCQAHGLTPEQVVAIASNNGGKQALETVQRLLPVLCQAHGLTPQQVVAIASNNGGRPALESIVAQLSRP

DPALAALTGS* pAAV2.1 CMV_ZF6-DBD (SEQ ID No. 10)

agcgcccaatacgcaaaccgcctctccccgcgcgttggccgattcattaatgcagctggcacgacaggtttcccga ctggaaagcgggcagtgagcgcaacgcaattaatgtgagttagctcactcattaggcaccccaggctttacacttt atgcttccggctcgtatgttgtgtggaattgtgagcggataacaatttcacacaggaaacagctatgaccatgatt acgccagatttaattaaggCTGCGCGCTCGCTCGCTCACTGAGGCCGCCCGGGCAAAGCCCGGGCGTCGGGCGACC TTTGGTCGCCCGGCCTCAGTGAGCGAGCGAGCGCGCAGAGAGGGAGTGGCCAACTCCATCACTAGGGGTTCCTtgt agttaatgattaacccgccatgctacttatctacgtagccatgctctaggaagatcggaattcgcccttaagctag c*tagttattaatagtaatcaattacggggtcattagttcatagcccatatatggagttccgcgttacataacttac*

*ggtaaatggcccgcctggctgaccgcccaacgacccccgcccattgacgtcaataatgacgtatgttcccatagta*

*acgccaatagggactttccattgacgtcaatgggtggagtatttacggtaaactgcccacttggcagtacatcaag*

*tgtatcatatgccaagtacgccccctattgacgtcaatgacggtaaatggcccgcctggcattatgcccagtacat*

*gaccttatgggactttcctacttggcagtacatctacgtattagtcatcgctattaccatggtgatgcggttttgg*

*cagtacatcaatgggcgtggatagcggtttgactcacggggatttccaagtctccaccccattgacgtcaatggga*

*gtttgttttggcaccaaaatcaacgggactttccaaaatgtcgtaacaactccgccccattgacgcaaatgggcgg*

*taggcgtgtacggtgggaggtctatataagcagagctggtttagtgaaccgt*cagatcctgcagaagttggtcgtg aggcactgggcaggt*aagtatcaaggttacaagacaggtttaaggagaccaatagaaactgggcttgtcgagacag*

*agaagactcttgcgtttctgataggcacctattggtcttactgacatccactttgcctttctctccacagg*tgtcc aggcggccgcatgatcgatctggaacctggcgaaaaaccgtataagtgcccagaatgcggcaagtcttttttcccag tctggccacctgacggaacatcagcgcactcacaccggcgagaaaccatataaatgtccggagtgcggcaagagct ttagccagaatagcaccctgaccgaacatcagcgtacgcacacgggtgaaaagccatataaatgccctgagtgcgg caaatcctttagcacctctggccatctggtccgtcaccagcgcacccaccagaataagaagggcggttctggtgac ggtaaaaagaaacagcacgcctgtccagagtgtggcaaatctttttcccgtgaagacaacctgcacactcaccagc -continued gcactcatactggcgagaaaccttacaagtgtccggaatgtggtaagagcttctccacttccggccatctggttcg tcaccagcgcacgcacaccggcgaaaaaccatacaagtgcccggaatgcggcaaatcattctcccgtagcgacaaa ctggttcgtcaccaacgtacgcataccggtaaaaagacttcctctagatacccgtacgacgttccagactatgcat cttgaaagcttggatccaatcaACCTCTGGATTACAAAATTTGTGAAAGATTGACTGGTATTCTTAACTATGTTGC

TCCTTTTACGCTATGTGGATACGCTGCTTTAATGCCTTTGTATCATGCTATTGCTTCCCGTATGGCTTTCATTTTC

TCCTCCTTGTATAAATCCTGGTTGCTGTCTCTTTATGAGGAGTTGTGGCCCGTTGTCAGGCAACGTGGCGTGGTGT

GCACTGTGTTTGCTGACGCAACCCCCACTGGTTGGGGCATTGCCACCACCTGTCAGCTCCTTTCCGGGACTTTCGC

TTTCCCCCTCCCTATTGCCACGGCGGAACTCATCGCCGCCTGCCTTGCCCGCTGCTGGACAGGGGCTCGGCTGTTG

GGCACTGACAATTCCGTGGTGTTGTCGGGGAAGCTGACGTCCTTTCCATGGCTGCTCGCCTGTGTTGCCACCTGGA

TTCTGCGCGGGACGTCCTTCTGCTACGTCCCTTCGGCCCTCAATCCAGCGGACCTTCCTTCCCGCGGCCTGCTGCC

GGCTCTGCGGCCTCTTCCGCGTCTTCGagatctGCCTCGACTGTGCCTTCTAGTTGCCAGCCATCTGTTGTTTGCC

CCTCCCCCGTGCCTTCTTGACCCTGGAAGGTGCCACTCCCACTGTCCTTTCCTAATAAAATGAGGAAATTGCATC

GCATTGTCTGAGTAGGTGTCATTCTATTCTGGGGGGTGGGGTGGGGCAGGACAGCAAGGGGGAGGATTGGGAAGAC

AATAGCAGGCATGCTGGGGActcgagttaagggcgaattcccgattaggatcttcctagagCATGGCTACGTAGAT

AAGTAGCATGGCGGTTAATCATTAACTACAAGGAACCCCTAGTGATGGAGTTGGCCACTCCCTCTCTGCGCGCTC

GCTCGCTCACTGAGGCCGGGCGACCAAAGGTCGCCCGACGCCCGGGCTTTGCCCGGGCGGCCTCAGTGAGCGAGCG

AGCGCGCAGccttaattaacctaattcactggccgtcgttttacaacgtcgtgactgggaaaaccctggcgttacc caacttaatcgccttgcagcacatccccctttcgccagctggcgtaatagcgaagaggcccgcaccgatcgccctt cccaacagttgcgcagcctgaatggcgaatgggacgcgccctgtagcggcgcattaagcgcggcgggtgtggtggt tacgcgcagcgtgaccgctacacttgccagcgccctagcgcccgctcctttcgctttcttcccttcctttctcgcc acgttcgccggctttccccgtcaagctctaaatcgggggctccctttagggttccgatttagtgctttacggcacc tcgaccccaaaaaacttgattagggtgatggttcacgtagtgggccatcgccccgatagacggttttcgccctt gacgctggagttcacgttcctcaatagtggactcttgttccaaactggaacaacactcaaccctatctcggtctat tcttttgatttataagggattttccgatttcggcctattggttaaaaaatgagctgatttaacaaaaatttaacg cgaattttaacaaaatattaacgtttataatttcaggtggcatctttcggggaaatgtgcgcggaacccctatttg tttattttctaaatacattcaaatatgtatccgctcatgagacaataaccctgataaatgcttcaataatattga aaaaggaagagtATGAGTATTCAACATTTCCGTGTCGCCCTTATTCCCTTTTTTGCGGCATTTTGCCTTCCTGTTT

TTGCTCACCCAGAAACGCTGGTGAAAGTAAAAGATGCTGAAGATCAGTTGGGTGCACGAGTGGGTTACATCGAACT

GGATCTCAATAGTGGTAAGATCCTTGAGAGTTTTCGCCCCGAAGAACGTTTTCCAATGATGAGCACTTTTAAAGTT

CTGCTATGTGGCGCGGTATTATCCCGTATTGACGCCGGGCAAGAGCAACTCGGTCGCCGCATACACTATTCTCAGA

ATGACTTGGTTGAGTACTCACCAGTCACAGAAAAGCATCTTACGGATGGCATGACAGTAAGAGAATTATGCAGTGC

TGCCATAACCATGAGTGATAACACTGCGGCCAACTTACTTCTGACAACGATCGGAGGACCGAAGGAGCTAACCGCT

TTTTTGCACAACATGGGGGATCATGTAACTCGCCTTGATCGTTGGGAACCGGAGCTGAATGAAGCCATACCAAACG

ACGAGCGTGACACCACGATGCCTGTAGTAATGGTAACAACGTTGCGCAAACTATTAACTGGCGAACTACTTACTCT

AGCTTCCCGGCAACAATTAATAGACTGGATGGAGGCGGATAAAGTTGCAGGACCACTTCTGCGCTCGGCCCTTCCG

GCTGGCTGGTTTATTGCTGATAAATCTGGAGCCGGTGAGCGTGGGTCTCGCGGTATCATTGCAGCACTGGGGCCAG

ATGGTAAGCCCTCCCGTATCGTAGTTATCTACACGACGGGGAGTCAGGCAACTATGGATGAACGAAATAGACAGAT

CGCTGAGATAGGTGCCTCACTGATTAAGCATTGGTAActgtcagaccaagtttactcatatatactttagattgat ttaaaacttcatttttaatttaaaaggatctaggtgaagatcctttttgataatctcatgaccaaaatcccttaac gtgagttttcgttccactgagcgtcagaccccgtagaaaagatcaaaggatcttcttgagatcctttttttctgcg

```
cgtaatctgctgcttgcaaacaaaaaaaccaccgctaccagcggtggtttgtttgccggatcaagagctaccaact cttttccgaaggtaactggcttcagcagagcgcagataccaaatactgtccttctagtgtagccgtagttaggcc accacttcaagaactctgtagcaccgcctacatacctcgctctgctaatcctgttaccagtggctgctgccagtgg cgataagtcgtgtcttaccgggttggactcaagacgatagttaccggataaggcgcagcggtcgggctgaacgggg ggttcgtgcacacagcccagcttggagcgaacgacctacaccgaactgagatacctacagcgtgagctatgagaaa gcgccacgcttcccgaagggagaaaggcggacaggtatccggtaagcggcagggtcggaacaggagagcgcacgag ggagcttccaggggggaaacgcctggtatctttatagtcctgtcgggtttcgccacctctgacttgagcgtcgattt ttgtgatgctcgtcaggggggcggagcctatggaaaaacgccagcaacgcggcctttttacggttcctggccttt gctgcggttttgctcacatgttctttcctgcgttatcccctgattctgtggataaccgtattaccgcctttgagtg agctgataccgctcgccgcagccgaacgaccgagcgcagcgagtcagtgagcgaggaagcggaag
```

Features:
5'-ITR                               : [248:377 - CW] (AAA)
CMV\promotor                         : [458:1040 - CW] (aaa)
SV40\misc\intron\(Promega)           : [1078:1210 - CW] (aaa)
ZF6-DBD                              : [1227:1829 - CW] (aaa)
WPRE                                 : [1847:2383 - CW] (AAA)
BGH\pA                               : [2390:2604 - CW] (AAA)
additional\AAV\sequences             : [2646:2691 - CW] (AGC)
3'-ITR                               : [2692:2821 - CW] (AAA)
AmpR                                 : [3585:4445 - CW] (AAG)

Nucleotide sequence of the human transducin 1 (GNAT1) promoter (SEQ ID No. 11)

```
Tccctgcaggtcataaaatcccagtccagagtcaccagcccttcttaaccacttcctactgtgtgacccttcagc ctttacttcctcatcagtaaaatgaggctgatgatatgggcatccatactccagggccagtgtgagcttacaacaa gataaggagtggtgctgagcctggtgccgggcaggcagcaggcatgtttctcccaattatgccctctcactgccag ccccacctccattgtcctcaccccagggctcaaggttctgccttccccttttctcagccctgaccctactgaacat gtctccccactcccaggcagtgccagggcctctcctggagggttgcggggacagaaggacagccggagtgcagagt cagcggttgagggattggggctatgccagcTAatCCgaagggttgggggggctgagctggattcacctgtccttgt ctctgattggctcttggacacccctagccccccaaatcccactaagcagcccaccagggattgcacaggtccgtag agagccagttgattgcaggtcctcctggggccagaagggtgcctggaggccaggttctggggatcccctccatcc agaagaaccacctgctcactctgtcccttcgcctgctgctgggaccgcggccgc
```

Nucleotide sequence of ZF6-5F (also called ZF6-5)

(SEQ ID No. 12)

```
atgatcgatctggagccaggtgaaaagccttataagtgccctgaatgcgggaaatcattcagccagaactccacac ttaccgagcaccagagaacccatactggggagaaaccctataagtgcccagaatgtgggaagtctttctctaccag cggacacttggtcaggcaccagagaacgcaccagaacaagaaaggaggttctggtgatggcaagaagaagcagcat gcttgtcccgaatgcggcaagtcctttagcagggaggacaatctgcacactcaccaacgcacacatactggcgaga agccgtacaagtgtcccgaatgtggcaaaagtttctccacaagtggacatctcgttcgtcaccagcgaacccacac cggagagaaaccctacaaatgcccagagtgtgggaaatccttttcacggagcgacaaactggtgagacatcaacgc actcatacaggcaagaaaacgagctcacggtaccccttacgatgtgcctgactatgccagttaataa
```

Protein sequence of ZF6-5F (also called ZF6-5)

(SEQ ID No. 13)

MIDLEPGEKPYKCPECGKSFSQNSTLTEHQRTHTGEKPYKCPECGKSFSTSGHLVRHQRTHQNKKGGSGDGKKKQH

ACPECGKSFSREDNLHTHQRTHTGEKPYKCPECGKSFSTSGHLVRHQRTHTGEKPYKCPECGKSFSRSDKLVRHQR

THTGKKTSSRYPYDVPDYAS

-continued

Nucleotide sequence of TAL7-DBD
(SEQ ID No. 14)

gcaagtgccccaagaaggcgggccgcccagccttctgacgctagccccgctgcccaggtggatctgcgaacgctgg gttattctcagcagcagcaagagaagattaagcctaaggtccggagtactgtggcacagcaccatgaggctctggt cgggcacggcttcacgcacgcacacatcgttgcactctcccagcaccctgccgcgctgggcacagtggcagtgaag taccaagatatgattgcggcacttcccgaagctactcacgaggccatcgtcggcgttgggaagcagtggtcaggcg ctagggcaccggaggcaccgctgactgtggccggggagcttcgcggaccccccctgcagCtggacacaggccagct gctgaagatagcaaaacgaggaggcgtcacagctgtagaggccgtgcatgcgtggcgcaatgcccttaccggggcc cctctgaatctgaccccgcagcaagtggtagccattgcgtctaacaacggagggaaacaggcactcgagacagttc aacggctgctccccgtgctttgccaggcgcacggactgaccccagaacaagtggtggcgatcgcctcaaataacgg cggcaaacaggctcttgaaaccgtgcagagactgctgccagtactgtgccaggctcatggcctgaccccagagcag gttgtggccatcgcttcaaacaatggcggtaaacaggcgctcgagactgtccagaggctgttgcctgtgctctgcc aagctcatggcctgacgccgaacaggtggttgccatcgctagcaacatcggcggcaagcaagctctcgagacagt gcaacggctgctgcccgtactctgccaggcacatgggctgactcccgagcaagtggttgctattgcatctaacaac ggcggaaagcaggcgctggagactgtccagcgtttgcttcctgttttgtgtcaggctcacggcttgacgcccgaac aggtagtggccatagcctccaacatcggaggaaaacaggcacttgaaacagtccagaggcttctccccgtcctgtg ccaagcccatggcctcactccacagcaagtagtggctattgcatccaatggaggcgggaaacaagccttggaaacc gtccaggccctgctgcctgtcctgtgccaggcacacgggctgacacctgaacaggtggtcgcaattgccagtaatg gtggcgggaagcaagccctggagactgttcaggctttgctgcccgttctgtgtcaagcacacggtctgactccaga acaggttgtggctatcgcctccaataatggtggcaaacaggctctcgaaacagtgcagaggctgctgcccgtgctg tgtcaagcccatggcctgaccccacagcaggtcgtggccattgcctctaataatggaggtaaacaggccctggaga cagtccagagattgcttccagttctgtgtcaggcccacgggctgaccctcaacaggtcgtcgccatcgcctcaaa caacggtggcaagcaggcactcgagactgtgcagcggctcttgcctgtgctgtgtcaagcccatggactgaccccg gaacaggtggttgccattgccagcaacaacggtgggaaacaggctttggaaaccgtgcaacgcctgctgccggttc tgtgccaggctcacgggcttacccggaacaggtggtagctatcgctagcaataatggagggaagcaggccctgga aacagtgcagagactgctccccgtcctctgccaggcacacggactcaccccggagcaagtggtcgccatagcctcc aacggtggagggaagcaggcactggagacagtgcagagacttctcccagtgctctgtcaggctcatgggctcaccc ctcaacaggtagtagccatagctagtaacaatggaggtcgtccagcattggagagcatcgtggcgcagctgagccg cccagacccagcgcttgccgccttgaccggaagctatccctacgacgtgcctgattacgcttaataaaagctt Protein sequence of TAL7-DBD
(SEQ ID No. 15)

MPKKKRKVTSASAPRRRAAQPSDASPAAQVDLRTLGYSQQQQEKIKPKVRSTVAQHHEALVGHGFTHAHIVALSQH

PAALGTVAVKYQDMIAALPEATHEAIVGVGKQWSGARALEALLTVAGELRGPPLQLDTGQLLKIAKRGGVTAVEAV

HAWRNALTGAPLNLTPQQVVAIASNNGGKQALETVQRLLPVLCQAHGLTPEQVVAIASNNGGKQALETVQRLLPVL

CQAHGLTPEQVVAIASNNGGKQALETVQRLLPVLCQAHGLTPEQVVAIASNIGGKQALETVQRLLPVLCQAHGLTP

EQVVAIASNNGGKQALETVQRLLPVLCQAHGLTPEQVVAIASNIGGKQALETVQRLLPVLCQAHGLTPQQVVAIAS

NGGGKQALETVQALLPVLCQAHGLTPEQVVAIASNNGGKQALETVQALLPVLCQAHGLTPEQVVAIASNNGGKQAL

ETVQRLLPVLCQAHGLTPQQVVAIASNNGGKQALETVQRLLPVLCQAHGLTPQQVVAIASNNGGKQALETVQRLLP

VLCQAHGLTPEQVVAIASNNGGKQALETVQRLLPVLCQAHGLTPEQVVAIASNNGGKQALETVQRLLPVLCQAHGL

TPEQVVAIASNGGGKQALETVQRLLPVLCQAHGLTPQQVVAIASNNGGRPALESIVAQLSRPDPALAALTGSYPYD

VPDYA-

-continued

Nucleotide sequence of TALRHO(02)DBD (SEQ ID No. 16)

ctagcgcccccagaagaagggccgctcagccttccgatgcctctcctgccgcccaggtggacctgagaaccctggg ctacagccagcagcagcaggaaaagatcaagcccaaagtgcggagcaccgtggcccagcaccacgaagccctcgtg ggccacggctttacccacgctcacatcgtggccctgagccagcatcctgccgctctgggaaccgtggccgtgaagt accaggacatgatcgccgccctgcccgaggccacacacgaggctatcgtgggcgtgggcaagcagtggtccggcgc tagagcactcgaggccttgctgacagtggccggcgagctgagaggccctccactgcagctggacaccggccagctg ctgaagatcgccaagcggggaggcgtgacagccgtggaagccgtgcacgcttggcggaatgccctgacaggcgctc ccctgaaccctacgccgcagcaggtggtggccatcgccagccacgatggcggcaagcaggcgctggagacggtgca gcggctgcttccggtgctgtgccaggcccatggcctgaccccggagcaggtggtggccatcgccagcaatattggt ggcaagcaggcgctggagacggtgcagcggattgttgccggtgctgtgccaggcccatggcctgaccccggagcagg tggtggccatcgccagccacgacggtggcaagcaggcgctggagactgtccagcggctgttgccggtgctgtgcca ggcccatggcctgaccccggagcaggtggtggccatcgccagcaatggcggtggcaagcaggcgcttgagacggtg cagcggctgttgccggtgctgtgccaggcccatggcctgaccccggagcaggtggtggccatcgccagcaatggcg gtggcaagcaggctctggagacggtgcagcggctgttgccggtgctgtgccaggcccatggcctgaccccggagca ggtggtggccatcgccagcaatggcggggggcaagcaggcgctggagacggtgcagcggctgttgccggtgctgtgc caggcccatggcctgaccccgcagcaggtggtggccatcgccagcaatattggcggcaagcaggcgctggagacgg tgcaggcgctgttgccggtgctgtgccaggcccatggcctgaccccggagcaggtggtggccatcgcaagcaatgg cggtggcaagcaggcgctggagacggtgcaggcgctgttgccggtgctgtgccaggcccatggcctgaccccggag caggtggtggcaatcgccagcaatattggtggcaagcaggcgctggagacggtgcagcggctgttgccggtgctgt gccaggcccatggcctgaccccgcaacaggtggtagccatcgccagcaatattggtggcaagcaggcgctggagac ggtgcagcggctgttgccggtgctgtgccaggcccatggcctgacacccagcaggtggtagcgatcgccagcaat aagggtggcaagcaggcgctggagacggtgcagcggctgcttccggtgctgtgccaggcccatggcctgaccccgg agcaggtggtggccatcgccagcaataagggtggcaagcaggcgctggagacggtgcagcgattgttgccggtgct gtgccaggcccatggcctgaccccggagcaggtggtggccatcgccagcaataagggtggcaagcaggcgctggag actgtccagcggctgttgccggtgctgtgccaggcccatggcctgaccccggagcaggtggtggccatcgccagca atggcggtggcaagcaggcgcttgagacggtgcagcggctgttgccggtgctgtgccaggcccatggcctgacccc gcagcaggtggtggccatcgccagccacgacggtggcaagcaggctctggagacggtgcagcggctgttgccggtg ctgtgccaggcccatggcctgaccccggagcaggtggtggccatcgccagcaatggcggggggcaagcaggcgctgg agacggtgcagcggctgttgccggtgctgtgccaggcccatggcctgaccccgcagcaggtggtggccatcgccag caataagggcggcaagcaggcgctggagacggtgcaggcgctgttgccggtgctgtgccaggcccatggcctgaca ccccagcaggtcgtggccattgccagcaacaagggaggcagacccgccctggaatctattgtggcccagctgagca gacccgacccagctctggccgccctgacaggatcc Protein sequence of TALRHO02DBD (SEQ ID No. 17)

MPKKKRKVTSAPRRRAAQPSDASPAAQVDLRTLGYSQQQQEKIKPKVRSTVAQHHEALVGHGFTHAHIVALSQHPA

ALGTVAVKYQDMIAALPEATHEAIVGVGKQWSGARALEALLTVAGELRGPPLQLDTGQLLKIAKRGGVTAEAVHA

WRNALTGAPLNLTPQQVVAIASHDGGKQALETVQRLLPVLCQAHGLTPEQVVAIASNIGGKQALETVQRLLPVLCQ

AHGLTPEQVVAIASHDGGKQALETVQRLLPVLCQAHGLTPEQVVAIASNGGGKQALETVQRLLPVLCQAHGLTPEQ

VVAIASNGGGKQALETVQRLLPVLCQAHGLTPEQVVAIASNGGGKQALETVQRLLPVLCQAHGLTPQQVVAIASNI

GGKQALETVQALLPVLCQAHGLTPEQVVAIASNGGGKQALETVQALLPVLCQAHGLTPEQVVAIASNIGGKQALET

VQRLLPVLCQAHGLTPQQVVAIASNIGGKQALETVQRLLPVLCQAHGLTPQQVVAIASNKGGKQALETVQRLLPVL

-continued

CQAHGLTPEQVVAIASNKGGKQALETVQRLLPVLCQAHGLTPEQVVAIASNKGGKQALETVQRLLPVLCQAHGLTP

EQVVAIASNGGGKQALETVQRLLPVLCQAHGLTPQQVVAIASHDGGKQALETVQRLLPVLCQAHGLTPEQVVAIAS

NGGGKQALETVQRLLPVLCQAHGLTPQQVVAIASNKGGKQALETVQALLPVLCQAHGLTPQQVVAIASNKGGRPAL

ESIVAQLSRPDPALAALTGSYPYDVPDYAS-

```
pAAV2.1 hGNAT1-hRHO
Features:
5'-ITR                   : [248:377   - CW]  (AAA)
3'-ITR                   : [3029:3158 - CW]  (AAA)
additional\AAV\sequences : [2983:3028 - CW]  (AGC)
WPRE                     : [2179:2720 - CW]  (AAA)
BGH\pA                   : [2727:2941 - CW]  (AAA)
Rev\Ori\NheI             : [5572:5597 - CW]  (AAA)
Fw\NheI\Ori              : [4779:4802 - CW]  (AAA)
M13-fwd                  : [3194:3177 - CCW] (AGC)

M13-rev                  : [205:225   - CW]  (AGC)

ColE1 origin             : [4931:5559 - CW]  (aaa)
LacZ alpha               : [3265:3333 - CW]  (AAA)
LacO                     : [177:199   - CW]  (AAA)
Amp prom                 : [3852:3880 - CW]  (AAG)
lac                      : [143:172   - CW]  (AAA)
hGnat1 prom              : [458:1119  - CW]  (aaa)
hRho CDS                 : [1120:2167 - CW]  (aaa)
```

(SEQ ID No. 18)

agcgcccaatacgcaaaccgcctctccccgcgcgttggccgattcattaatgcagctggcacgacaggtttcccga ctggaaagcgggcagtgagcgcaacgcaattaatgtgagttagctcactcattaggcaccccaggcTTTACACTTT

ATGCTTCCGGCTCGTATGTTgtgtGGAATTGTGAGCGGATAACAATTtcaca*CAGGAAACAGCTATGACCATG*att acgccagatttaattaaggCTGCGCGCTCGCTCGCTCACTGAGGCCGCCCGGGCAAAGCCCGGGCGTCGGGCGACC TTTGGTCGCCCGGCCTCAGTGAGCGAGCGAGCGCGCAGAGAGGGAGTGGCCAACTCCATCACTAGGGGTTCCTtgt agttaatgattaacccgccatgctacttatctacgtagccatgctctaggaagatcggaattcgcccttaagctag c*tccctgcaggtcataaaatcccagtccagagtcaccagcccttcttaaccacttcctactgtgtgacccttcag*

*cctttacttcctcatcagtaaaatgaggctgatgatatgggcatccatactccagggccagtgtgagcttacaaca*

*agataaggagtggtgctgagcctggtgccgggcaggcagcaggcatgtttctcccaattatgccctctcactgcca*

*gccccacctccattgtcctcaccccagggctcaaggttctgccttccccttttctcagccctgaccctactgaaca*

*tgtctcccactccaggcagtgccagggcctctcctggagggttgcggggacagaaggacagccggagtgcagag*

*tcagcggttgagggattggggctatgccagctaatccgaagggttgggggggctgagctggattcacctgtccttg*

*tctctgattggctcttggacaccctagcccccaaatcccactaagcagccccaccaggattgcacaggtccgta*

*gagagccagttgattgcaggtcctcctggggccagaagggtgcctgggaggccaggttctggggatcccctccatc*

*cagaagaaccacctgctcactctgtcccttcgcctgctgctgggaccgcggccgc*atgaatggcacagaaggccct aacttctacgtgcccttctccaatgcgacgggtgtggtacgcagcccttcgagtacccacagtactacctggctg agccatggcagttctccatgctggccgcctacatgtttctgctgatcgtgctgggcttcccccatcaacttcctcac gctctacgtcaccgtccagcacaagaagctgcgcacgcctctcaactacatcctgctcaacctagccgtggctgac ctcttcatggtcctaggtggcttcaccagcacccttacacctctctgcatggatacttcgtcttcgggcccacag gatgcaatttggagggcttctttgccacccctgggcggtgaaattgccctgtggtccttggtggtcctggccatcga gcggtacgtggtggtgtgtaagcccatgagcaacttccgcttcggggagaaccatgccatcatgggcgttgccttc acctgggtcatggcgctggcctgcgccgcaccccactcgccggctggtccaggtacatccccgagggcctgcagt gctcgtgtgaatcgactactacacgctcaagccggaggtcaacaacgagtcttttgtcatctacatgttcgtggt ccacttcaccatccccatgattatcatcttttttctgctatgggcagctcgtcttcaccgtcaaggaggccgctgcc cagcagcaggagtcagccaccacacagaaggcagagaaggaggtcacccgcatggtcatcatcatggtcatcgctt tcctgatctgctgggtgccctacgccagcgtggcattctacatcttcacccaccagggctccaacttcggtcccat cttcatgaccatcccagcgttctttgccaagagcgccgccatctacaaccctgtcatctatatcatgatgaacaag cagttccggaactgcatgctcaccaccatctgctgcggcaagaacccactgggtgacgatgaggcctctgctaccg tgtccaagacggagacgagccaggtggccccggcctaaaagcttggatcc<u>AATCAACCTCTGGATTACAAAATTTG</u>

<u>TGAAAGATTGACTGGTATTCTTAACTATGTTGCTCCTTTTACGCTATGTGGATACGCTGCTTTAATGCCTTTGTAT</u>

<u>CATGCTATTGCTTCCCGTATGGCTTTCATTTTCTCCTCCTTGTATAAATCCTGGTTGCTGTCTCTTTATGAGGAGT</u>

<u>TGTGGCCCGTTGTCAGGCAACGTGGCGTGGTGTGCACTGTGTTTGCTGACGCAACCCCCACTGGTTGGGGCATTGC</u>

<u>CACCACCTGTCAGCTCCTTTCCGGGACTTTCGCTTTCCCCCTCCCTATTGCCACGGCGGAACTCATCGCCGCCTGC</u>

<u>CTTGCCCGCTGCTGGACAGGGGCTCGGCTGTTGGGCACTGACAATTCCGTGGTGTTGTCGGGGAAGCTGACGTCCT</u>

<u>TTCCATGGCTGCTCGCCTGTGTTGCCACCTGGATTCTGCGCGGGACGTCCTTCTGCTACGTCCCTTCGGCCCTCAA</u>

<u>TCCAGCGGACCTTCCTTCCCGCGGCCTGCTGCCGGCTCTGCGGCCTCTTCCGCGTCTTCG</u>agatct<u>GCCTCGACTG</u>

<u>TGCCTTCTAGTTGCCAGCCATCTGTTGTTTGCCCCTCCCCCGTGCCTTCCTTGACCCTGGAAGG</u>t<u>GCCACTCCCAC</u>

<u>TGTCCTTTCCTAATAAAATGAGGAAATTGCATCGCATTGTCTGAGTAGGTGTCATTCTATTCTGGGGGGTGGGGTG</u>

<u>GGGCAGGACAGCAAGGGGGAGGATTGGGAAGACAATAGCAGGCATGCTGGGGA</u>ctcgagttaagggcgaattcccg attaggatcttcctagag*CATGGCTACGTAGATAAGTAGCATGGCGGGTTAATCATTAACTACA*AGGAACCCCTAG

TGATGGAGTTGGCCACTCCCTCTCTGCGCGCTCGCTCGCTCACTGAGGCCGGGCGACCAAAGGTCGCCCGACGCCC

GGGCTTTGCCCGGGCGGCCTCAGTGAGCGAGCGAGCGCGCAGccttaattaacctaattc*ACTGGCCGTCGTTTTA*

*CA*acgtcgtgactgggaaaaccctggcgttacccaacttaatcgccttgcagcacatccccctttcgccagcTGGC

GTAATAGCGAAGAGGCCCGCACCGATCGCCCTTCCCAACAGTTGCGCAGCCTGAATGGCGAATGGgacgcgccctg tagcggcgcattaagcgcggcgggtgtggtggttacgcgcagcgtgaccgctacacttgccagcgccctagcgccc gctcctttcgctttcttcccttcctttctcgccacgttcgccggctttccccgtcaagctctaaatcggggggctcc ctttagggttccgatttagtgctttacggcacctcgaccccaaaaaacttgattagggtgatggttcacgtagtgg gccatcgccccgatagacggtttttcgccctttgacgctggagttcacgttcctcaatagtggactcttgttccaa actggaacaacactcaaccctatctcggtctattcttttgatttataagggattttccgatttcggcctattggt taaaaaatgagctgatttaacaaaaatttaacgcgaattttaacaaaatattaacgtttataatttcaggtggcat ctttcggggaaatgtgcgcggaacccctatttgtttatttttctaaataca*TTCAAATATGTATCCGCTCATGAGA*

*CAAT*aaccctgataaatgcttcaataatattgaaaaaggaagagtatgagtattcaacatttccgtgtcgcccttta ttcccttttttgcggcattttgccttcctgttttttgctcacccagaaacgctggtgaaagtaaaagatgctgaaga tcagttgggtgcacgagtgggttacatcgaactggatctcaatagtggtaagatccttgagagttttcgccccgaa gaacgttttccaatgatgagcacttttaaagttctgctatgtggcgcggtattatcccgtattgacgccgggcaag agcaactcggtcgccgcatacactattctcagaatgacttggttgagtactcaccagtcacagaaaagcatcttac ggatggcatgacagtaagagaattatgcagtgctgccataaccatgagtgataacactgcggccaacttacttctg acaacgatcggaggaccgaaggagctaaccgcttttttgcacaacatgggggatcatgtaactcgccttgatcgtt gggaaccggagctgaatgaagccataccaaacgacgagcgtgacaccacgatgcctgtagtaatggtaacaacgtt gcgcaaactattaactggcgaactacttactctagcttcccggcaacaattaatagactggatggaggcggataaa gttgcaggaccacttctgcgctcggcccttccggctggctggtttattgctgataaatctggagccggtgagcgtg ggtctcgcggtatcattgcagcactggggccagatggtaagccctcccgtatcgtagttatctacacgacggggag tcaggcaactatggatgaacgaaatagacagatcgctgagataggtgcctcactgattaagcattgGTAACTGTCA

GACCAAGTTTACtcatatatactttagattgatttaaaacttcatttttaatttaaaaggatctaggtgaagatcc ttttttgataatctcatgaccaaaatcccttaacgtgagttttcgttccactgagcgtcagaccccg*tagaaaagat*

*caaaggatcttcttgagatcctttttttctgcgcgtaatctgctgcttgcaaacaaaaaaaccaccgctaccagcg*

*gtggtttgtttgccggatcaagagctaccaactctttttccgaaggtaactggcttcagcagagcgcagataccaa*

*atactgtccttctagtgtagccgtagttaggccaccacttcaagaactctgtagcaccgcctacatacctcgctct*

*gctaatcctgttaccagtggctgctgccagtggcgataagtcgtgtcttaccgggttggactcaagacgatagtta*

*ccggataaggcgcagcggtcgggctgaacggggggttcgtgcacacagcccagcttggagcgaacgacctacaccg*

*aactgagatacctacagcgtgagctatgagaaagcgccacgcttcccgaagggagaaaggcggacaggtatccggt*

*aagcggcagggtcggaacaggagagcgcacgagggagcttccagggggaaacgcctggtatctttatagtcctgtc*

*gggtttcgccacctctgacttgagcgtcgatttttgtgatgctcgtcaggggggcggagcctatggaaaaacgcca*

*gcaacgcggcc*ttttttacggttcCTGGCCTTTTGCTGCGGTTTTGCTCAcatgttctttcctgcgttatcccctga ttctgtggataaccgtattaccgcctttgagtgagctgataccgctcgccgcagccgaacgaccgagcgcagcgag tcagtgagcgaggaagcggaag pAAV2.1-CMV-ZF6-5F
Features:
```
5'ITR                         : [248:377   - CW]  (AAA)
CMV promoter                  : [458:1040  - CW]  (aaa)
SV40 misc intron (promega)    : [1078:1210 - CW]  (aaa)
BGH pA                        : [2309:2523 - CW]  (AAA)
Additional AVV sequence       : [2565:2610 - CW]  (AGC)
3'ITR                         : [2611:2740 - CW]  (AAA)
WPRE                          : [1761:2302 - CW]  (AAA)
M13-fwd                       : [2776:2759 - CCW] (AGC)

M13-rev                       : [205:225   - CW]  (AGC)

ColE1 origin                  : [4513:5141 - CW]  (aaa)
LacZ alpha                    : [2847:2915 - CW]  (AAA)
LacO                          : [177:199   - CW]  (AAA)
Amp prom                      : [3434:3462 - CW]  (AAG)
lac                           : [143:172   - CW]  (AAA)
HA tag                        : [1713:1739 - CW]  (aaa)

FactorXa site                 : [2243:2232 - CCW] (aaa)

ZF6-5F                        : [1227:1748 - CW]  (aaa)
```

(SEQ ID No. 19)
agcgcccaatacgcaaaccgcctctccccgcgcgttggccgattcattaatgcagctggcacgacaggtttcccga ctggaaagcgggcagtgagcgcaacgcaattaatgtgagttagctcactcattaggcaccccaggTTTACACTTT

ATGCTTCCGGCTCGTATGTTgtgtGGAATTGTGAGCGGATAACAATTtcaca*CAGGAAACAGCTATGACCATG*att acgccagatttaattaaggCTGCGCGCTCGCTCGCTCACTGAGGCCGCCCGGGCAAAGCCCGGGCGTCGGGCGACC TTTGGTCGCCCGGCCTCAGTGAGCGAGCGAGCGCGCAGAGAGGGAGTGGCCAACTCCATCACTAGGGGTTCCTtgt agttaatgattaacccgccatgctacttatctacgtagccatgctctaggaagatcggaattcgcccttaagctag c*tagttattaatagtaatcaattacggggtcattagttcatagcccatatatggagttccgcgttacataactac*

*ggtaaatggcccgcctggctgaccgcccaacgacccccgcccattgacgtcaataatgacgtatgttcccatagta*

*acgccaatagggactttccattgacgtcaatgggtggagtatttacggtaaactgcccacttggcagtacatcaag*

*tgtatcatatgccaagtacgccccctattgacgtcaatgacggtaaatggcccgcctggcattatgcccagtacat*

*gaccttatgggactttcctacttggcagtacatctacgtattagtcatcgctattaccatggtgatgcggttttgg*

*cagtacatcaatgggcgtggatagcggtttgactcacggggatttccaagtctccaccccattgacgtcaatggga*

*gtttgttttggcaccaaaatcaacgggactttccaaaatgtcgtaacaactccgccccattgacgcaaatgggcgg*

*taggcgtgtacggtgggaggtctatataagcagagctggtttagtgaaccgt*cagatcctgcagaagttggtcgtg aggcactgggcag*gtaagtatcaaggttacaagacaggtttaaggagaccaatagaaactgggcttgtcgagacag* agaagactcttgcgtttctgataggcacctattggtcttactgacatccactttgcctttctctccacaggtgtcc aggcggccgcatgatcgatctggagccaggtgaaaagccttataagtgcccgaatgcgggaaatcattcagccag aactccacacttaccgagcaccagagaacccatactggggagaaaccctataagtgcccagaatgtgggaagtctt tctctaccagcggacacttggtcaggcaccagagaacgcaccagaacaagaaaggaggttctggtgatggcaagaa gaagcagcatgcttgtcccgaatgcggcaagtcctttagcagggaggacaatctgcacactcaccaacgcacacat actggcgagaagccgtacaagtgtcccgaatgtggcaaaagtttctccacaagtggacatctcgttcgtcaccagc gaacccacaccggagagaaaccctacaaatgcccagagtgtgggaaatccttttcacggagcgacaaactggtgag acatcaacgcactcatacaggcaagaaaacgagctcacgg_taccct tacgatgtgcctgactatgcc_agttaataa aagcttggatcc<ins>AATCAACCTCTGGATTACAAAATTTGTGAAAGATTGACTGGTATTCTTAACTATGTTGCTCCTT</ins>

<ins>TTACGCTATGTGGATACGCTGCTTTAATGCCTTTGTATCATGCTATTGCTTCCCGTATGGCTTTCATTTTCTCCTC</ins>

<ins>CTTGTATAAATCCTGGTTGCTGTCTCTTTATGAGGAGTTGTGGCCCGTTGTCAGGCAACGTGGCGTGGTGTGCACT</ins>

<ins>GTGTTTGCTGACGCAACCCCCACTGGTTGGGGCATTGCCACCACCTGTCAGCTCCTTTCCGGGACTTTCGCTTTCC</ins>

<ins>CCCTCCCTATTGCCACGGCGGAACTCATCGCCGCCTGCCTTGCCCGCTGCTGGACAGGGGCTCGGCTGTTGGGCAC</ins>

<ins>TGACAATTCCGTGGTGTTGTCGGGGAAGCTGACGTCCTTTCCATGGCTGCTCGCCTGTGTTGCCACCTGGATTCTG</ins>

<ins>CGCGGGACGTCCTTCTGCTACGTCCCT</ins>_tcggccctcaat_<ins>CCAGCGGACCTTCCTTCCCGCGGCCTGCTGCCGGCTC</ins>

<ins>TGCGGCCTCTTCCGCGTCTTCG</ins>agatct<ins>GCCTCGACTGTGCCTTCTAGTTGCCAGCCATCTGTTGTTTGCCCCTCC</ins>

<ins>CCCGTGCCTTCCTTGACCCTGGAAGGTGCCACTCCCACTGTCCTTTCCTAATAAAATGAGGAAATTGCATCGCATT</ins>

<ins>GTCTGAGTAGGTGTCATTCTATTCTGGGGGGTGGGGTGGGGCAGGACAGCAAGGGGGAGGATTGGGAAGACAATAG</ins>

<ins>CAGGCATGCTGGGGA</ins>ctcgagttaagggcgaattcccgattaggatcttcctagag_CATGGCTACGTAGATAAGTA_

_GCATGGCGGGTTAATCATTAACTACA_AGGAACCCCTAGTGATGGAGTTGGCCACTCCCTCTCTGCGCGCTCGCTCG

CTCACTGAGGCCGGGCGACCAAAGGTCGCCCGACGCCCGGGCTTTGCCCGGGCGGCCTCAGTGAGCGAGCGAGCGC

GCAGccttaattaacctaattc_ACTGGCCGTCGTTTTACA_acgtcgtgactgggaaaaccctggcgttacccaact taatcgccttgcagcacatccccctttcgccagcTGGCGTAATAGCGAAGAGGCCCGCACCGATCGCCCTTCCCAA

CAGTTGCGCAGCCTGAATGGCGAATGGgacgcgccctgtagcggcgcattaagcgcggcgggtgtggtggttacgc gcagcgtgaccgctacacttgccagcgccctagcgcccgctcctttcgctttcttcccttcctttctcgccacgtt cgccggctttccccgtcaagctctaaatcgggggctccctttagggttccgatttagtgctttacggcacctcgac cccaaaaaacttgattagggtgatggttcacgtagtgggccatcgccccgatagacggtttttcgccctttgacgc tggagttcacgttcctcaatagtggactcttgttccaaactggaacaacactcaaccctatctcggtctattcttt tgatttataagggattttccgatttcggcctattggttaaaaaatgagctgatttaacaaaaatttaacgcgaat tttaacaaaatattaacgtttataatttcaggtggcatctttcggggaaatgtgcgcggaacccctatttgtttat ttttctaaataca_TTCAAATATGTATCCGCTCATGAGACAAT_aaccctgataaatgcttcaataatattgaaaaag gaagagtatgagtattcaacatttccgtgtcgcccttattcccttttttgcggcattttgccttcctgtttttgct cacccagaaacgctggtgaaagtaaaagatgctgaagatcagttgggtgcacgagtgggttacatcgaactggatc tcaatagtggtaagatccttgagagttttcgccccgaagaacgttttccaatgatgagcacttttaaagttctgct atgtggcgcggtattatcccgtattgacgccgggcaagagcaactcggtcgccgcatacactattctcagaatgac ttggttgagtactcaccagtcacagaaaagcatcttacggatggcatgacagtaagagaattatgcagtgctgcca taaccatgagtgataacactgcggccaacttacttctgacaacgatcggaggaccgaaggagctaaccgcttttttt gcacaacatgggggatcatgtaactcgccttgatcgttgggaaccggagctgaatgaagccataccaaacgacgag cgtgacaccacgatgcctgtagtaatggtaacaacgttgcgcaaactattaactggcgaactacttactctagctt -continued

```
cccggcaacaattaatagactggatggaggcggataaagttgcaggaccacttctgcgctcggcccttccggctgg ctggtttattgctgataaatctggagccggtgagcgtgggtctcgcggtatcattgcagcactggggccagatggt aagccctcccgtatcgtagttatctacacgacggggagtcaggcaactatggatgaacgaaatagacagatcgctg agataggtgcctcactgattaagcattggtaactgtcagaccaagtttactcatatactttagattgatttaaa acttcatttttaatttaaaaggatctaggtgaagatcctttttgataatctcatgaccaaaatcccttaacgtgag ttttcgttccactgagcgtcagaccccg𝑡𝑎𝑔𝑎𝑎𝑎𝑎𝑔𝑎𝑡𝑐𝑎𝑎𝑎𝑔𝑔𝑎𝑡𝑐𝑡𝑡𝑐𝑡𝑡𝑔𝑎𝑔𝑎𝑡𝑐𝑐𝑡𝑡𝑡𝑡𝑡𝑡𝑐𝑡𝑔𝑐𝑔𝑐𝑔𝑡𝑎𝑎

𝑡𝑐𝑡𝑔𝑐𝑡𝑔𝑐𝑡𝑡𝑔𝑐𝑎𝑎𝑎𝑐𝑎𝑎𝑎𝑎𝑎𝑎𝑎𝑐𝑐𝑎𝑐𝑐𝑔𝑐𝑡𝑎𝑐𝑐𝑎𝑔𝑐𝑔𝑔𝑡𝑔𝑔𝑡𝑡𝑡𝑔𝑡𝑡𝑡𝑔𝑐𝑐𝑔𝑔𝑎𝑡𝑐𝑎𝑎𝑔𝑎𝑔𝑐𝑡𝑎𝑐𝑐𝑎𝑎𝑐𝑡𝑐𝑡𝑡𝑡𝑡

𝑡𝑐𝑐𝑔𝑎𝑎𝑔𝑔𝑡𝑎𝑎𝑐𝑡𝑔𝑔𝑐𝑡𝑡𝑐𝑎𝑔𝑐𝑎𝑔𝑎𝑔𝑐𝑔𝑐𝑎𝑔𝑎𝑡𝑎𝑐𝑐𝑎𝑎𝑎𝑡𝑎𝑐𝑡𝑔𝑡𝑐𝑐𝑡𝑡𝑐𝑡𝑎𝑔𝑡𝑔𝑡𝑎𝑔𝑐𝑐𝑔𝑡𝑎𝑔𝑡𝑡𝑎𝑔𝑔𝑐𝑐𝑎𝑐𝑐𝑎𝑐

𝑡𝑡𝑐𝑎𝑎𝑔𝑎𝑎𝑐𝑡𝑐𝑡𝑔𝑡𝑎𝑔𝑐𝑎𝑐𝑐𝑔𝑐𝑐𝑡𝑎𝑐𝑎𝑡𝑎𝑐𝑐𝑡𝑐𝑔𝑐𝑡𝑐𝑡𝑔𝑐𝑡𝑎𝑎𝑡𝑐𝑐𝑡𝑔𝑡𝑡𝑎𝑐𝑐𝑎𝑔𝑡𝑔𝑔𝑐𝑡𝑔𝑐𝑡𝑔𝑐𝑐𝑎𝑔𝑡𝑔𝑔𝑐𝑔𝑎𝑡𝑎

𝑎𝑔𝑡𝑐𝑔𝑡𝑔𝑡𝑐𝑡𝑡𝑎𝑐𝑐𝑔𝑔𝑔𝑡𝑡𝑔𝑔𝑎𝑐𝑡𝑐𝑎𝑎𝑔𝑎𝑐𝑔𝑎𝑡𝑎𝑔𝑡𝑡𝑎𝑐𝑐𝑔𝑔𝑎𝑡𝑎𝑎𝑔𝑔𝑐𝑔𝑐𝑎𝑔𝑐𝑔𝑔𝑡𝑐𝑔𝑔𝑔𝑐𝑡𝑔𝑎𝑎𝑐𝑔𝑔𝑔𝑔𝑔𝑔𝑡𝑡𝑐

𝑔𝑡𝑔𝑐𝑎𝑐𝑎𝑐𝑎𝑔𝑐𝑐𝑐𝑎𝑔𝑐𝑡𝑡𝑔𝑔𝑎𝑔𝑐𝑔𝑎𝑎𝑐𝑔𝑎𝑐𝑐𝑡𝑎𝑐𝑎𝑐𝑐𝑔𝑎𝑎𝑐𝑡𝑔𝑎𝑔𝑎𝑡𝑎𝑐𝑐𝑡𝑎𝑐𝑎𝑔𝑐𝑔𝑡𝑔𝑎𝑔𝑐𝑡𝑎𝑡𝑔𝑎𝑔𝑎𝑎𝑎𝑔𝑐𝑔𝑐𝑐

𝑎𝑐𝑔𝑐𝑡𝑡𝑐𝑐𝑐𝑔𝑎𝑎𝑔𝑔𝑔𝑎𝑔𝑎𝑎𝑎𝑔𝑔𝑐𝑔𝑔𝑎𝑐𝑎𝑔𝑔𝑡𝑎𝑡𝑐𝑐𝑔𝑔𝑡𝑎𝑎𝑔𝑐𝑔𝑔𝑐𝑎𝑔𝑔𝑔𝑡𝑐𝑔𝑔𝑎𝑎𝑐𝑎𝑔𝑔𝑎𝑔𝑎𝑔𝑐𝑔𝑐𝑎𝑐𝑔𝑎𝑔𝑔𝑔𝑎𝑔𝑐

𝑡𝑡𝑐𝑐𝑎𝑔𝑔𝑔𝑔𝑔𝑎𝑎𝑎𝑐𝑔𝑐𝑐𝑡𝑔𝑔𝑡𝑎𝑡𝑐𝑡𝑡𝑡𝑎𝑡𝑎𝑔𝑡𝑐𝑐𝑡𝑔𝑡𝑐𝑔𝑔𝑔𝑡𝑡𝑡𝑐𝑔𝑐𝑐𝑎𝑐𝑐𝑡𝑐𝑡𝑔𝑎𝑐𝑡𝑡𝑔𝑎𝑔𝑐𝑔𝑡𝑐𝑔𝑎𝑡𝑡𝑡𝑡𝑡𝑔𝑡𝑔

𝑎𝑡𝑔𝑐𝑡𝑐𝑔𝑡𝑐𝑎𝑔𝑔𝑔𝑔𝑔𝑐𝑔𝑔𝑎𝑔𝑐𝑐𝑡𝑎𝑡𝑔𝑔𝑎𝑎𝑎𝑎𝑎𝑐𝑔𝑐𝑐𝑎𝑔𝑐𝑎𝑎𝑐𝑔𝑐𝑔𝑔𝑐𝑐ttttttacggttcctggccttttgctgc ggttttgctcacatgttctttcctgcgttatcccctgattctgtggataaccgtattaccgcctttgagtgagctg ataccgctcgccgcagccgaacgaccgagcgcagcgagtcagtgagcgaggaagcggaag pAAV2.1-CMV-TALRHO(02)DBD
Features:
5' ITR                          : [248:377 - CW] (AAA)
CMV promoter                    : [458:1040 - CW] (aaa)

SV40 misc intron (promega)      : [1078:1210 - CW] (aaa)
NLS [*]                         : [1227:1251 - CW] (AAA)
TALRHO-02DBD                    : [1252:3566 - CW] (aaa)
HA                              : [3567:3602 - CW] (AAA)
3'ITR                           : [3917:4046 - CW] (AAA)
bGH PolyA                       : [3615:3829 - CW] (AAA)
```

(SEQ ID No. 20)

```
agcgcccaatacgcaaaccgcctctccccgcgcgttggccgattcattaatgcagctggcacgacaggtttcccga ctggaaagcgggcagtgagcgcaacgcaattaatgtgagttagctcactcattaggcaccccaggctttacacttt atgcttccggctcgtatgttgtgtggaattgtgagcggataacaatttcacacaggaaacagctatgaccatgatt acgccagatttaattaaggCTGCGCGCTCGCTCGCTCACTGAGGCCGCCCGGGCAAAGCCCGGGCGTCGGGCGACC TTTGGTCGCCCGGCCTCAGTGAGCGAGCGAGCGCGCAGAGAGGGAGTGGCCAACTCCATCACTAGGGGTTCCTtgt agttaatgattaacccgccatgctacttatctacgtagccatgctctaggaagatcggaattcgcccttaagctag

𝑐𝑡𝑎𝑔𝑡𝑡𝑎𝑡𝑡𝑎𝑎𝑡𝑎𝑔𝑡𝑎𝑎𝑡𝑐𝑎𝑎𝑡𝑡𝑎𝑐𝑔𝑔𝑔𝑔𝑡𝑐𝑎𝑡𝑡𝑎𝑔𝑡𝑡𝑐𝑎𝑡𝑎𝑔𝑐𝑐𝑐𝑎𝑡𝑎𝑡𝑎𝑡𝑔𝑔𝑎𝑔𝑡𝑡𝑐𝑐𝑔𝑐𝑔𝑡𝑡𝑎𝑐𝑎𝑡𝑎𝑎𝑐𝑡𝑡𝑎𝑐

𝑔𝑔𝑡𝑎𝑎𝑎𝑡𝑔𝑔𝑐𝑐𝑐𝑔𝑐𝑐𝑡𝑔𝑔𝑐𝑡𝑔𝑎𝑐𝑐𝑔𝑐𝑐𝑐𝑎𝑎𝑐𝑔𝑎𝑐𝑐𝑐𝑐𝑐𝑔𝑐𝑐𝑐𝑎𝑡𝑡𝑔𝑎𝑐𝑔𝑡𝑐𝑎𝑎𝑡𝑎𝑎𝑡𝑔𝑎𝑐𝑔𝑡𝑎𝑡𝑔𝑡𝑡𝑐𝑐𝑐𝑎𝑡𝑎𝑔𝑡𝑎

𝑎𝑐𝑔𝑐𝑐𝑎𝑎𝑡𝑎𝑔𝑔𝑔𝑎𝑐𝑡𝑡𝑡𝑐𝑐𝑎𝑡𝑡𝑔𝑎𝑐𝑔𝑡𝑐𝑎𝑎𝑡𝑔𝑔𝑔𝑡𝑔𝑔𝑎𝑔𝑡𝑎𝑡𝑡𝑡𝑎𝑐𝑔𝑔𝑡𝑎𝑎𝑎𝑐𝑡𝑔𝑐𝑐𝑐𝑎𝑐𝑡𝑡𝑔𝑔𝑐𝑎𝑔𝑡𝑎𝑐𝑎𝑡𝑐𝑎𝑎𝑔

𝑡𝑔𝑡𝑎𝑡𝑐𝑎𝑡𝑎𝑡𝑔𝑐𝑐𝑎𝑎𝑔𝑡𝑎𝑐𝑔𝑐𝑐𝑐𝑐𝑐𝑡𝑎𝑡𝑡𝑔𝑎𝑐𝑔𝑡𝑐𝑎𝑎𝑡𝑔𝑎𝑐𝑔𝑔𝑡𝑎𝑎𝑎𝑡𝑔𝑔𝑐𝑐𝑐𝑔𝑐𝑐𝑡𝑔𝑔𝑐𝑎𝑡𝑡𝑎𝑡𝑔𝑐𝑐𝑐𝑎𝑔𝑡𝑎𝑐𝑎𝑡

𝑔𝑎𝑐𝑐𝑡𝑡𝑎𝑡𝑔𝑔𝑔𝑎𝑐𝑡𝑡𝑡𝑐𝑐𝑡𝑎𝑐𝑡𝑡𝑔𝑔𝑐𝑎𝑔𝑡𝑎𝑐𝑎𝑡𝑐𝑡𝑎𝑐𝑔𝑡𝑎𝑡𝑡𝑎𝑔𝑡𝑐𝑎𝑡𝑐𝑔𝑐𝑡𝑎𝑡𝑡𝑎𝑐𝑐𝑎𝑡𝑔𝑔𝑡𝑔𝑎𝑡𝑔𝑐𝑔𝑔𝑡𝑡𝑡𝑡𝑔𝑔

𝑐𝑎𝑔𝑡𝑎𝑐𝑎𝑡𝑐𝑎𝑎𝑡𝑔𝑔𝑔𝑐𝑔𝑡𝑔𝑔𝑎𝑡𝑎𝑔𝑐𝑔𝑔𝑡𝑡𝑡𝑔𝑎𝑐𝑡𝑐𝑎𝑐𝑔𝑔𝑔𝑔𝑎𝑡𝑡𝑡𝑐𝑐𝑎𝑎𝑔𝑡𝑐𝑡𝑐𝑐𝑎𝑐𝑐𝑐𝑐𝑎𝑡𝑡𝑔𝑎𝑐𝑔𝑡𝑐𝑎𝑎𝑡𝑔𝑔𝑔𝑎

𝑔𝑡𝑡𝑡𝑔𝑡𝑡𝑡𝑡𝑔𝑔𝑐𝑎𝑐𝑐𝑎𝑎𝑎𝑎𝑡𝑐𝑎𝑎𝑐𝑔𝑔𝑔𝑎𝑐𝑡𝑡𝑡𝑐𝑐𝑎𝑎𝑎𝑎𝑡𝑔𝑡𝑐𝑔𝑡𝑎𝑎𝑐𝑎𝑎𝑐𝑡𝑐𝑐𝑔𝑐𝑐𝑐𝑐𝑎𝑡𝑡𝑔𝑎𝑐𝑔𝑐𝑎𝑎𝑎𝑡𝑔𝑔𝑔𝑐𝑔𝑔

𝑡𝑎𝑔𝑔𝑐𝑔𝑡𝑔𝑡𝑎𝑐𝑔𝑔𝑡𝑔𝑔𝑔𝑎𝑔𝑔𝑡𝑐𝑡𝑎𝑡𝑎𝑡𝑎𝑎𝑔𝑐𝑎𝑔𝑎𝑔𝑐𝑡𝑔𝑔𝑡𝑡𝑡𝑎𝑔𝑡𝑔𝑎𝑎𝑐𝑐𝑔𝑡cagatcctgcagaagttggtcgtg
``` aggcactgggcaggtaagtatcaaggttacaagacaggtttaaggagaccaatagaaactgggcttgtcgagacag agaagactcttgcgtttctgataggcacctattggtcttactgacatccactttgcctttctctccacaggtgtcc aggcggccgcATGCCGAAGAAGAAGCGTAAAGTCActagcgccccagaagaaggccgctcagccttccgatgcc tctcctgccgccaggtggacctgagaaccctgggctacagccagcagcagcaggaaaagatcaagcccaaagtgc ggagcaccgtggcccagcaccacgaagccctcgtgggccacggctttacccacgctcacatcgtggccctgagcca gcatcctgccgctctgggaaccgtggccgtgaagtaccaggacatgatcgccgccctgcccgaggccacacacgag gctatcgtgggcgtgggcaagcagtggtccggcgctagagcactcgaggccttgctgacagtggccggcgagctga gaggccctccactgcagctggacaccggccagctgctgaagatcgccaagcggggaggcgtgacagccgtggaagc cgtgcacgcttggcggaatgccctgacaggcgctcccctgaaccttacgccgcagcaggtggtggccatcgccagc cacgatggcggcaagcaggcgctggagacggtgcagcggctgcttccggtgctgtgccaggcccatggcctgaccc cggagcaggtggtggccatcgccagcaatattggtggcaagcaggcgctggagacggtgcagcgattgttgccggt gctgtgccaggcccatggcctgaccccggagcaggtggtggccatcgccagccacgacggtggcaagcaggcgctg gagactgtccagcggctgttgccggtgctgtgccaggcccatggcctgaccccggagcaggtggtggccatcgcca gcaatggcggtggcaagcaggcgcttgagacggtgcagcggctgttgccggtgctgtgccaggcccatggcctgac cccggagcaggtggtggccatcgccagcaatggcggtggcaagcaggctctggagacggtgcagcggctgttgccg gtgctgtgccaggcccatggcctgaccccggagcaggtggtggccatcgccagcaatggcggggcaagcaggcgc tggagacggtgcagcggctgttgccggtgctgtgccaggcccatggcctgaccccgcagcaggtggtggccatcgc cagcaatattggcggcaagcaggcgctggagacggtgcaggcgctgttgccggtgctgtgccaggcccatggcctg accccggagcaggtggtggccatcgccaagcaatggcggtggcaagcaggcgctggagacggtgcaggcgctgttgc cggtgctgtgccaggcccatggcctgaccccggagcaggtggtggcaatcgccagcaatattggtggcaagcaggc gctggagacggtgcagcggctgttgccggtgctgtgccaggcccatggcctgaccccgcaacaggtggtagccatc gccagcaatattggtggcaagcaggcgctggagacggtgcagcggctgttgccggtgctgtgccaggcccatggcc tgacaccccagcaggtggtagcgatcgccagcaataagggtggcaagcaggcgctggagacggtgcagcggctgct tccggtgctgtgccaggcccatggcctgaccccggagcaggtggtggccatcgccagcaataagggtggcaagcag gcgctggagacggtgcagcgattgttgccggtgctgtgccaggcccatggcctgaccccggagcaggtggtggcca tcgccagcaataagggtggcaagcaggcgctggagactgtccagcggctgttgccggtgctgtgccaggcccatgg cctgaccccggagcaggtggtggccatcgccagcaatggcggtggcaagcaggcgcttgagacggtgcagcggctg ttgccggtgctgtgccaggcccatggcctgaccccgcagcaggtggtggccatcgccagccacgacggtggcaagc aggctctggagacggtgcagcggctgttgccggtgctgtgccaggcccatggcctgaccccggagcaggtggtggc catcgccagcaatggcggggcaagcaggcgctggagacggtgcagcggctgttgccggtgctgtgccaggcccat ggcctgaccccgcagcaggtggtggccatcgccagcaataagggcggcaagcaggcgctggagacggtgcaggcgc tgttgccggtgctgtgccaggcccatggcctgacaccccagcaggtcgtggccattgccagcaacaagggaggcag acccgccctggaatctattgtggcccagctgagcagacccgacccagctctggccgccctgacaggatccTACCCG

TACGACGTTCCAGACTATGCATCTTAATAAaagcttagatctGCCTCGACTGTGCCTTCTAGTTGCCAGCCATCTG

TTGTTTGCCCCTCCCCCGTGCCTTCCTTGACCCTGGAAGGTGCCACTCCCACTGTCCTTTCCTAATAAAATGAGGA

AATTGCATCGCATTGTCTGAGTAGGTGTCATTCTATTCTGGGGGGTGGGGTGGGGCAGGACAGCAAGGGGGAGGAT

TGGGAAGACAATAGCAGGCATGCTGGGGActcgagttaagggcgaattcccgattaggatcttcctagagcatggc tacgtagataagtagcatggcgggttaatcattaactacaAGGAACCCCTAGTGATGGAGTTGGCCACTCCCTCTC

TGCGCGCTCGCTCGCTCACTGAGGCCGGGCGACCAAAGGTCGCCCGACGCCCGGGCTTTGCCCGGGCGGCCTCAGT

GAGCGAGCGAGCGCGCAGccttaattaacctaattcactggccgtcgttttacaacgtcgtgactgggaaaaccct

-continued

```
ggcgttacccaacttaatcgccttgcagcacatccccctttcgccagctggcgtaatagcgaagaggcccgcaccg
atcgcccttcccaacagttgcgcagcctgaatggcgaatgggacgcgccctgtagcggcgcattaagcgcggcggg
tgtggtggttacgcgcagcgtgaccgctacacttgccagcgccctagcgcccgctcctttcgctttcttcccttcc
tttctcgccacgttcgccggctttccccgtcaagctctaaatcggggctccctttagggttccgatttagtgctt
tacggcacctcgaccccaaaaaacttgattagggtgatggttcacgtagtgggccatcgccccgatagacggtttt
tcgccctctgacgcggagttcacgttcctcaatagtggactctcgttccaaactggaacaacactcaaccctatc
tcggtctattcttttgatttataagggattttccgatttcggcctattggttaaaaaatgagctgatttaacaaa
aatttaacgcgaattttaacaaaatattaacgtttataatttcaggtggcatctttcggggaaatgtgcgcggaac
ccctatttgtttatttttctaaatacattcaaatatgtatccgctcatgagacaataaccctgataaatgcttcaa
taatattgaaaaaggaagagtatgagtattcaacatttccgtgtcgcccttattccctttttgcggcattttgcc
ttcctgttttgctcacccagaaacgctggtgaaagtaaaagatgctgaagatcagttgggtgcacgagtgggtta
catcgaactggatctcaatagtggtaagatccttgagagttttcgccccgaagaacgttttccaatgatgagcact
tttaaagttctgctatgtggcgcggtattatcccgtattgacgccgggcaagagcaactcggtcgccgcatacact
attctcagaatgacttggttgagtactcaccagtcacagaaaagcatcttacggatggcatgacagtaagagaatt
atgcagtgctgccataaccatgagtgataacactgcggccaacttacttctgacaacgatcggaggaccgaaggag
ctaaccgcttttttgcacaacatgggggatcatgtaactcgccttgatcgttgggaaccggagctgaatgaagcca
taccaaacgacgagcgtgacaccacgatgcctgtagtaatggtaacaacgttgcgcaaactattaactggcgaact
acttactctagcttcccggcaacaattaatagactggatggaggcggataaagttgcaggaccacttctgcgctcg
gcccttccggctggctggtttattgctgataaatctggagccggtgagcgtgggtctcgcggtatcattgcagcac
tggggccagatggtaagccctcccgtatcgtagttatctacacgacggggagtcaggcaactatggatgaacgaaa
tagacagatcgctgagataggtgcctcactgattaagcattggtaactgtcagaccaagtttactcatatatactt
tagattgatttaaaacttcatttttaatttaaaaggatctaggtgaagatcctttttgataatctcatgaccaaaa
tcccttaacgtgagttttcgttccactgagcgtcagaccccgtagaaaagatcaaaggatcttcttgagatccttt
ttttctgcgcgtaatctgctgcttgcaaacaaaaaaaccaccgctaccagcggtggtttgtttgccggatcaagag
ctaccaactctttttccgaaggtaactggcttcagcagagcgcagataccaaatactgtccttctagtgtagccgt
agttaggccaccacttcaagaactctgtagcaccgcctacatacctcgctctgctaatcctgttaccagtggctgc
tgccagtggcgataagtcgtgtcttaccgggttggactcaagacgatagttaccggataaggcgcagcggtcgggc
tgaacggggggttcgtgcacacagcccagcttggagcgaacgacctacaccgaactgagatacctacagcgtgagc
tatgagaaagcgccacgcttcccgaagggagaaaggcggacaggtatccggtaagcggcagggtcggaacaggaga
gcgcacgagggagcttccagggggaaacgcctggtatctttatagtcctgtcgggtttcgccacctctgacttgag
cgtcgatttttgtgatgctcgtcaggggggcggagcctatggaaaaacgccagcaacgcggcctttttacggttcc
tggccttttgctgcggttttgctcacatgttctttcctgcgttatcccctgattctgtggataaccgtattaccgc
ctttgagtgagctgataccgctcgccgcagccgaacgaccgagcgcagcgagtcagtgagcgaggaagcggaag
```

```
pAAV2.1-CMV-TAL7-DBD
Features:
5' ITR                        : [248:377 - CW] (AAA)
CMV promoter                  : [458:1040 - CW] (aaa)
SV40 misc intron (promega)    : [1078:1210 - CW] (aaa)
NLS                           : [1227:1256 - CW] (AAA)
TAL7-DBD                      : [1257:3305 - CW] (aaa)

bGH                           : [3312:3526 - CW] (AAA)
3' ITR                        : [3568:3743 - CW] (AAA)
```

(SEQ ID No. 21)

agcgcccaatacgcaaaccgcctctccccgcgcgttggccgattcattaatgcagctggcacgacaggtttcccga ctggaaagcgggcagtgagcgcaacgcaattaatgtgagttagctcactcattaggcaccccaggctttacacttt atgcttccggctcgtatgttgtgtggaattgtgagcggataacaatttcacacaggaaacagctatgaccatgatt acgccagatttaattaaggCTGCGCGCTCGCTCGCTCACTGAGGCCGCCCGGGCAAAGCCCGGGCGTCGGGCGACC TTTGGTCGCCCGGCCTCAGTGAGCGAGCGAGCGCGCAGAGAGGGAGTGGCCAACTCCATCACTAGGGGTTCCTtgt agttaatgattaacccgccatgctacttatctacgtagccatgctctaggaagatcggaattcgcccttaagctag c<u>tagttattaatagtaatcaattacggggtcattagttcatagcccatatatggagttccgcgttacataacttac</u>

<u>ggtaaatggcccgcctggctgaccgcccaacgacccccgccattgacgtcaataatgacgtatgttcccatagta</u>

<u>acgccaatagggactttccattgacgtcaatgggtggagtatttacggtaaactgcccacttggcagtacatcaag</u>

<u>tgtatcatatgccaagtacgccccctattgacgtcaatgacggtaaatggcccgcctggcattatgcccagtacat</u>

<u>gaccttatgggactttcctacttggcagtacatctacgtattagtcatcgctattaccatggtgatgcggttttgg</u>

<u>cagtacatcaatgggcgtggatagcggtttgactcacggggatttccaagtctccaccccattgacgtcaatggga</u>

<u>gtttgttttggcaccaaaatcaacgggactttccaaaatgtcgtaacaactccgccccattgacgcaaatggcgg</u>

<u>taggcgtgtacggtgggaggtctatataagcagagctggtttagtgaaccgt</u>cagatcctgcagaagttggtcgtg aggcactgggcag<u>gtaagtatcaaggttacaagacaggtttaaggagaccaatagaaactgggcttgtcgagacag</u>

<u>agaagactcttgcgtttctgataggcacctattggtcttactgacatccactttgcctttctctccacag</u>gtgtcc aggcggccgcATGCCGAAGAAGAAGCGTAAAGTGACTAGTgcaagtgccccaagaaggcgggccgcccagccttct gacgctagccccgctgcccaggtggatctgcgaacgctgggttattctcagcagcagcaagagaagattaagccta aggtccggagtactgtggcacagcaccatgaggctctggtcgggcacggcttcacgcacgcacacatcgttgcact ctcccagcaccctgccgcgctgggcacagtggcagtgaagtaccaagatatgattgcggcacttcccgaagctact cacgaggccatcgtcggcgttgggaagcagtggtcaggcgctagggcactggaggcactgctgactgtggccgggg agcttcgcggaccccccctgcagttggacacaggccagctgctgaagatagcaaaacgaggaggcgtcacagctgt agaggccgtgcatgcgtggcgcaatgcccttaccggggcccctctgaatctgaccccgcagcaagtggtagccatt gcgtctaacaacggagggaaacaggcactcgagacagttcaacggctgctccccgtgctttgccaggcgcacggac tgaccccagaacaagtggtggcgatcgcctcaaataacggcggcaaacaggctcttgaaaccgtgcagagactgct gccagtactgtgccaggctcatggcctgacccagagcaggttgtggccatcgcttcaaacaatggcggtaaacag gcgctcgagactgtccagaggctgttgcctgtgctctgccaagctcatggcctgacgcccgaacaggtggttgcca tcgctagcaacatcggcggcaagcaagctctcgagacagtgcaacggctgctgccccgtactctgccaggcacatgg gctgactcccgagcaagtggttgctattgcatctaacaacggcggaaagcaggcgctggagactgtccagcgtttg cttcctgttttgtgtcaggctcacggcttgacgcccgaacaggtagtggccatagcctccaacatcggaggaaaac aggcacttgaaacagtccagaggcttctccccgtcctgtgccaagcccatggcctcactccacagcaagtagtggc tattgcatccaatggaggcgggaaacaagccttggaaaccgtccaggccctgctgcctgtcctgtgccaggcacac

*gggctgacacctgaacaggtggtcgcaattgccagtaatggtggcgggaagcaagccctggagactgttcaggctt*

*tgctgcccgttctgtgtcaagcacacggtctgactccagaacaggttgtggctatcgcctccaataatggtggcaa*

*acaggctctcgaaacagtgcagaggctgctgcccgtgctgtgtcaagcccatggcctgaccccacagcaggtcgtg*

*gccattgcctctaataatggaggtaaacaggccctggagacagtccagagattgcttccagttctgtgtcaggccc*

*acgggctgacccctcaacaggtcgtcgccatcgcctcaaacaacggtggcaagcaggcactcgagactgtgcagcg*

*gctcttgcctgtgctgtgtcaagcccatggactgaccccggaacaggtggttgccattgccagcaacaacggtggg*

*aaacaggctttggaaaccgtgcaacgcctgctgccggttctgtgccaggctcacgggcttaccccggaacaggtgg*

*tagctatcgctagcaataatggagggaagcaggccctggaaacagtgcagagactgctcccgtcctctgccaggc*

*acacggactcaccccggagcaagtggtcgccatagcctccaacggtggagggaagcaggcactggagacagtgcag*

*agacttctcccagtgctctgtcaggctcatgggctcacccctcaacaggtagtagccatagctagtaacaatggag*

*gtcgtccagcattggagagcatcgtggcgcagctgagccgcccagacccagcgcttgccgccttgaccggaagcta*

*tccctacgacgtgcctgattacgcttaataaaagct*tagatctGCCTCGACTGTGCCTTCTAGTTGCCAGCCATCT

GTTGTTTGCCCCTCCCCCGTGCCTTCCTTGACCCTGGAAGGTGCCACTCCCACTGTCCTTTCCTAATAAAATGAGG

AAATTGCATCGCATTGTCTGAGTAGGTGTCATTCTATTCTGGGGGGTGGGGTGGGCAGGACAGCAAGGGGGAGGA

TTGGGAAGACAATAGCAGGCATGCTGGGGActcgagttaagggcgaattcccgattaggatcttcctagagCATGG

CTACGTAGATAAGTAGCATGGCGGGTTAATCATTAACTACAAGGAACCCCTAGTGATGGAGTTGGCCACTCCCTCT

CTGCGCGCTCGCTCGCTCACTGAGGCCGGGCGACCAAAGGTCGCCCGACGCCCGGGCTTTGCCCGGGCGGCCTCAG

TGAGCGAGCGAGCGCGCAGccttaattaacctaattcactggccgtcgttttacaacgtcgtgactgggaaaaccc tggcgttacccaacttaatcgccttgcagcacatccccctttcgccagctggcgtaatagcgaagaggcccgcacc gatcgcccttcccaacagttgcgcagcctgaatggcgaatgggacgcgccctgtagcggcgcattaagcgcggcgg gtgtggtggttacgcgcagcgtgaccgctacacttgccagcgccctagcgcccgctcctttcgctttcttcccttc ctttctcgccacgttcgccggctttccccgtcaagctctaaatcgggggctccctttagggttccgatttagtgct ttacggcacctcgaccccaaaaaacttgattagggtgatggttcacgtagtgggccatcgccccgatagacggttt ttcgccctttgacgctggagttcacgttcctcaatagtggactcttgttccaaactggaacaacactcaaccctat ctcggtctattcttttgatttataaggattttttccgatttcggcctattggttaaaaaatgagctgatttaacaa aaatttaacgcgaattttaacaaaatattaacgtttataatttcaggtggcatctttcggggaaatgtgcgcggaa cccctatttgtttatttttctaaatacattcaaatatgtatccgctcatgagacaataaccctgataaatgcttca ataatattgaaaaaggaagagtatgagtattcaacatttccgtgtcgcccttattcccttttttgcggcatttttgc cttcctgtttttgctcacccagaaacgctggtgaaagtaaaagatgctgaagatcagttgggtgcacgagtgggtt acatcgaactggatctcaatagtggtaagatccttgagagttttcgccccgaagaacgttttccaatgatgagcac ttttaaagttctgctatgtggcgcggtattatcccgtattgacgccgggcaagagcaactcggtcgccgcatacac tattctcagaatgacttggttgagtactcaccagtcacagaaaagcatcttacggatggcatgacagtaagagaat tatgcagtgctgccataaccatgagtgataacactgcggccaacttacttctgacaacgatcggaggaccgaagga gctaaccgcttttttgcacaacatgggggatcatgtaactcgccttgatcgttgggaaccggagctgaatgaagcc ataccaaacgacgagcgtgacaccacgatgcctgtagtaatggtaacaacgttgcgcaaactattaactggcgaac

```
tacttactctagcttcccggcaacaattaatagactggatggaggcggataaagttgcaggaccacttctgcgctc ggcccttccggctggctggtttattgctgataaatctggagccggtgagcgtgggtctcgcggtatcattgcagca ctggggccagatggtaagccctcccgtatcgtagttatctacacgacggggagtcaggcaactatggatgaacgaa atagacagatcgctgagataggtgcctcactgattaagcattggtaactgtcagaccaagtttactcatatatact ttagattgatttaaaacttcattttttaatttaaaaggatctaggtgaagatccttttttgataatctcatgaccaaa atcccttaacgtgagttttcgttccactgagcgtcagaccccgtagaaaagatcaaaggatcttcttgagatccctt ttttctgcgcgtaatctgctgcttgcaaacaaaaaaaccaccgctaccagcggtggtttgtttgccggatcaaga gctaccaactctttttccgaaggtaactggcttcagcagagcgcagataccaaatactgtccttctagtgtagccg tagttaggccaccacttcaagaactctgtagcaccgcctacatacctcgctctgctaatcctgttaccagtggctg ctgccagtggcgataagtcgtgtcttaccgggttggactcaagacgatagttaccggataaggcgcagcggtcggg ctgaacggggggttcgtgcacacagcccagcttggagcgaacgacctacaccgaactgagatacctacagcgtgag ctatgagaaagcgccacgcttcccgaagggagaaaggcggacaggtatccggtaagcggcagggtcggaacaggag agcgcacgagggagcttccaggggggaaacgcctggtatctttatagtcctgtcgggtttcgccacctctgacttga gcgtcgattttttgtgatgctcgtcaggggggcggagcctatggaaaaacgccagcaacgcggcctttttacggttc ctggccttttgctgcggttttgctcacatgttctttcctgcgttatcccctgattctgtggataaccgtattaccg cctttgagtgagctgataccgctcgccgcagccgaacgaccgagcgcagcgagtcagtgagcgaggaagcggaag
```

RT-PCR Studies

RNAs from tissues were isolated using RNEASY® Mini Kit (Qiagen) RNA isolation kit, according to the manufacturer protocol. cDNA was amplified from 1000 μg isolated RNA using QUANTITECT® Reverse Transcription Kit (Qiagen), as indicated in the manufacturer instructions. Transcript levels of transcripts were measured by real-time PCR using the LIGHTCYCLER® (Roche) and the following primers:

hRho_forward
[SEQ ID No. 31]
5'...CCATCCCAGCGTTCTTTGCC...3'
and hRho_reverse
[SEQ ID No. 32]
5'..GGCCTCATCGTCACCCAGTGGG...3';

mRho_forward
[SEQ ID No. 33]
5'...CTCTGCCAGCTTTCTTTGCT...3'
and mRho_reverse
[SEQ ID No. 34]
5'...GGCGTCGTCATCTCCCAGTGGA...3';

Gnat1_Forward
[SEQ ID No. 35]
5'...GACCGAGCCTCAGAATACCA...3'
and

Gnat1_reverse
[SEQ ID No. 36]
5'...GGAGAATTGAGTCTCGATAATACC...3'.

The levels of transgene were evaluated using the following primers:

bGH_Forward
[SEQ ID No. 37]
5'...TCTAGTTGCCAGCCATCTGTTGT...3'
and bGH_reverse
[SEQ ID No. 38]
5'...GGGAGTGGCACCTTCC...3'.

The PCRs with cDNA were carried out in a total volume of 20 μl, using 10 μl LIGHTCYCLER® 480 SYBR Green I Master Mix (Roche) and 400 nM primers under the following conditions: pre-Incubation, 50° C. for 5 min, cycling: 45 cycles of 95° C. for 10 s, 60° C. for 20 s and 72° C. for 20 s. All of the reactions were standardized against murine GAPDH and Act 3 using the following primers:

mGAPDH_forward
[SEQ ID No. 39]
5'...GTCGGTGTGAACGGATTTG...3' mGAPDH_reverse
[SEQ ID No. 40]
5'...CAATGAAGGGGTCGTTGATG...3';

Act_Forward
[SEQ ID No. 41]
5'...CAAGATCATTGCTCCTCCTGA...3'
and

Act_reverse
[SEQ ID No. 42]
5' CATCGTACTCCTGCTTGCTGA...3'

Each sample was analysed in duplicate in two-independent experiments.

Immunostaining Anti-HA Antibody

Frozen retinal sections were washed once with PBS and then fixed for 10 min in 4% PFA. Sections were immersed in a retrieval solution (0.01 M sodium citrate buffer, pH 6.0) and boiled three times in a microwave. After the Blocking solution (10% FBS, 10% NGS, 1% BSA) was added for 1 hour. The primary antibody mouse anti-HA (1:300, Covance) was in a Blocking solution and incubated overnight at 4° C. The secondary antibody (ALEXA FLUOR® 594,anti-mouse 1:1000, Molecular Probes, Invitrogen, Carlsbad, Calif.) has been incubated for 1 hour. A VECTASHIELD® (Vector Lab Inc., Peterborough, UK) antifade mounting medium with DAPI was used to visualize nuclei. Sections were photographed using either a ZEISS 700 Confocal Microscope (CARL ZEISS, Oberkochen, Germany) laser scanning confocal microscope or a LEICA Fluorescence Microscope System (Leica Microsystems GmbH, Wetzlar, Germany).

h-Rhodopsin 3A6 Antibody

Frozen retinal sections were washed once with PBS. Sections were then permeabilized for 1 hour in PBS containing 0.2% TRITON® X-100. Blocking solution containing 10% normal goat serum (Sigma-Aldrich, St. Louis, Mo.) was applied for 1 hour. Primary antibodies were diluted in Blocking solution and incubated overnight at 4° C. mouse anti-hRhodopsin 3A6(1:5 kindly provided by Robert S. Molday, University of British Columbia, Canada). The secondary antibody (ALEXA FLUOR® 594, anti-mouse 1:1000, Molecular Probes, Invitrogen, Carlsbad, Calif.) was incubated for 1 hour. VECTASHIELD® (Vector Lab Inc., Peterborough, UK) was used to visualize nuclei. Sections were photographed using a LEICA Fluorescence Microscope System (LEICA Microsystems GmbH, Wetzlar, Germany).

AAV Vector Preparations

AAV vectors were produced by the TIGEM AAV Vector Core, by triple transfection of HEK293 cells followed by two rounds of CsCl2 purification [Auricchio A, Hildinger M, O'Connor E, Gao G P, Wilson J M (2001) Isolation of highly infectious and pure adeno-associated virus type 2 vectors with a single-step gravity-flow column. Hum Gene Ther 12: 71-76.]. For each viral preparation, physical titers [genome copies (GC)/ml1 were determined by averaging the titer achieved by dot-blot analysis [Doria M, Ferrara A, Auricchio A (2013) AAV2/8 vectors purified from culture medium with a simple and rapid protocol transduce murine liver, muscle, and retina efficiently. Hum Gene Ther Methods] and by PCR quantification using TAQMAN® (Applied Biosystems, Carlsbad, Calif., USA) nuclease OCR assay. The pAAV2.1-CMV-ZF6-DBD and pAAV2.1-hGNAT1-hRHO used for vector preparation are represented respectively in FIGS. 24 and 25. The pAAV2.1-CMV-ZF6-5F, pAAV2.1-CMV-TAL7-DDB and pAAV2.1-CMV-TALRHOO2DBD used for vector preparation are represented respectively in FIGS. 27, 28 and 29. pAAV2.1-CMV was used for all vector preparation (FIG. 26).

Cis-Sequences Mutagenesis

The pAAV8-hRHO-ΔZF6-5'UTR-EGFP was generated via pAAV2.1 hRhoPromoter_eGFP plasmid mutagenesis by QuikChange II XL Site-Directed Mutagenesis Kit (Agilent Technologies) as indicated in the manufacturer instructions using the following primers:
Mut_forward 5' . . . attaatatgattatgaacagattcagccagg agctta . . . 3' [SEQ ID No. 43] and
Mut_Reverse 5' . . . taagctcctggctgaatctgttcataatcat attaat . . . 3' [SEQ ID No. 44].

The pAAV8-hRHO-MutZF6-5'UTR-EGFP was generated via pAAV2.1 hRhoPromoter_eGFP plasmid mutagenesis by QuikChange II XL Site-Directed Mutagenesis Kit (Agilent Technologies) as indicated in the manufacturer instructions using the following primers:
Mut_forward 5' . . . attaatatgattatgaacaTTACTGTAATCT-TAACCGGAgattcagccaggagctta . . . 3' [SEQ ID No. 45] and Mut_Reverse 5' . . . taagctcctggctgaatcTCCGGTTAA-GATTACAGTAAtgttcataatcatattaat . . . 3' [SEQ ID No. 46].

Electrophysiological Testing

The method is as described in Surace E M, Domenici L, Cortese K, Cotugno G, Di Vicino U, et al. (2005) Amelioration of both functional and morphological abnormalities in the retina of a mouse model of ocular albinism following AAV-mediated gene transfer. Mol Ther 12: 652-658).

Mice were dark reared for three hours and anesthetized. Flash electroretinograms (ERGs) were evoked by 10-ms light flashes generated through a Ganzfeld stimulator (CSO, Costruzione Strumenti Oftalmici, Florence, Italy) and registered as previously described. ERGs and b-wave thresholds were assessed using the following protocol. Eyes were stimulated with light flashes increasing from −5.2 to +1.3 log $cd*s/m^2$ (which correspond to $1\times10^{-5.2}$ to 20.0 $cd*s/m^2$) in scotopic conditions. The log unit interval between stimuli was 0.3 log from −5.4 to 0.0 log $cd*s/m^2$, and 0.6 log from 0.0 to +1.3 log $cd*s/m^2$. For ERG analysis in scotopic conditions the responses evoked by 11 stimuli (from −4 to +1.3 log $cd*s/m^2$) with an interval of 0.6 log unit were considered. To minimize the noise, three ERG responses were averaged at each 0.6 log unit stimulus from −4 to 0.0 log $cd*s/m^2$ while one ERG response was considered for higher (0.0−+1.3 log $cd*s/m^2$) stimuli. The time interval between stimuli was 10 seconds from −5.4 to 0.7 log $cd*s/m^2$, 30 sec from 0.7 to +1 log $cd*s/m^2$, or 120 seconds from +1 to +1.3 log $cd*s/m^2$. a- and b-waves amplitudes recorded in scotopic conditions were plotted as a function of increasing light intensity (from −4 to +1.3 log $cd*s/m^2$, FIGS. 1, S1 and S2). The photopic ERG was recorded after the scotopic session by stimulating the eye with ten 10 ms flashes of 20.0 $cd*s/m^2$ over a constant background illumination of 50 $cd/m^2$.

Vector Administration and Animal Model

P347S+/+ animals (Li T, Snyder W K, Olsson J E, Dryja T P (1996) Transgenic mice carrying the dominant rhodopsin mutation P347S: evidence for defective vectorial transport of rhodopsin to the outer segments. Proc Natl Acad Sci USA 93: 14176-14181) for breeding were kindly provided by Dr. G. Jane Farrar (Smurfit Institute of Genetics, Trinity College Dublin, Dublin, Ireland) and were bred in the animal facility of the Biotechnology Centre of the Cardarelli Hospital (Naples, Italy) with C57BL/6 mice (Charles Rivers Laboratories, Calco, Italy), to obtain the P347S+/− mice.

Mice

Mice were anesthetized with an intraperitoneal injection of 2 mL/100 g body weight of avertin [1.25% w/v of 2,2,2-tribromoethanol and 2.5% v/v of 2-methyl-2-butanol (Sigma-Aldrich, Milan, Italy)], then AAV vectors were delivered subretinally via a trans-scleral transchoroidal approach as described by Liang et al. [Liang F Q, Anand V, Maguire A M, Bennett J (2000) Intraocular delivery of recombinant virus. In: Rakoczy P E editor. Vision Research Protocols. Totowa: Humana Press Inc. 125-139.].

Pigs

Eleven-week-old Large White (LW) female piglets were utilized. Pigs were fasted overnight leaving water ad libitum. The anesthetic and surgical procedures for pigs were previously described [Mussolino C, della Corte M, Rossi S, Viola F, Di Vicino U, et al. (2011) AAV-mediated photoreceptor transduction of the pig cone-enriched retina. Gene Ther 18: 637-645].

AAV vectors were inoculated subretinally in the avascular nasal area of the posterior pole between the two main vascular arches, as performed in Mussolino et al [Mussolino C, della Corte M, Rossi S, Viola F, Di Vicino U, et al. (2011) AAV-mediated photoreceptor transduction of the pig cone-enriched retina. Gene Ther 18: 637-645]. This retinal region is crossed by a streak-like region that extends from the nasal to the temporal edge parallel to the horizontal meridian, where cone density is high, reaching 20000 to 35000 cone cells mm$^2$. Each viral vector was injected in a total volume of 100 µl, resulting in the formation of a subretinal bleb with a typical 'dome-shaped' retinal detachment, with a size corresponding to 5 optical discs.

Western Blot Analyses

Western blot analysis was performed on retinas, which were harvested. Samples were lysed in hypotonic buffer (10 mM Tris-HCl [pH 7.5], 10 mM NaCl, 1.5 mM MgCl2, 1% CHAPS, 1 mM PMSF, and protease inhibitors) and 20 µg of these lysates were separated by 12% SDS-PAGE. After the blots were obtained, specific proteins were labeled with anti-1D4 antibody anti-Rhodopsin-1D4 (1:500; Abcam, Cambridge, Mass.) and anti-β-tubulin (1:1000; Sigma-Aldrich, Milan, Italy) antibodies.

Cloning and Purification of the Proteins:

DNA fragments encoding the sequence of the engineered transcription factors ZF6-KRAB and ZF6-DBD to be expressed as maltose-binding protein (MBP) fusion were generated by PCR using the plasmids pAAV2.1 CMV ZF6-KRAB and pAAV2.1 CMV ZF6-DBD as a DNA template. The following oligonucleotides were used as primers: primer 1, 5'-GAATTCCATATGGAATTCCCCATG-GATGC-3' [SEQ ID No. 47] and primer 2, 5'-CGG-GATCCCTATCTAGAAGTCTTTTTACCGGTATG-3' [SEQ ID No. 48] for ZF6-KRAB and primer 3, 5'-GGAAT-TCCATATGCTGGAACCTGGCGAAAAACCG [SEQ ID No. 49] and primer 4 5'-CGGGATCCC-TATCTAGAAGTCTTTTTACCGGTATG-3' [SEQ ID No. 50] for ZF6-DBD. Both the PCR products were digested with the restriction enzymes NdeI and BamH1 and cloned into NdeI BamH1-digested pMal C5G (New England Biolabs) bacterial expression vector. The human Klf15 and human NR2E3 coding regions were PCR amplified from the human retina cDNA. The following oligonucleotides were synthetized on the basis of the published sequences (GeneBank accession number NM_014079.3 and NM_014249.3 respectively): primer 5, 5'-GGAATTCCATATG GAGACCAGACCAACAGCTC-3' [SEQ ID No. 51] and primer 6, 5'-CGGAATTCCTAGTTTTTGAACATATCAC-3' [SEQ ID No. 52] for hNR2e3; primer 7, 5'-GGAATTC-CATATGGTGGACCACTTACTTCCAG-3' [SEQ ID No. 53] and primer 8, 5'-CGGGATCC TCAGTTCACG-GAGCGCACGGAG-3' [SEQ ID No. 54] for hKlf15. The hKlf15 PCR product was digested with the restriction enzymes NdeI and BamH1 and cloned into NdeI BamH1-digested pMal C5G and the Nr2e3 PCR product was digested with the restriction enzymes NdeI and EcoRI and cloned into NdeI EcoRI-digested pMal C5G (New England Biolabs). All the plasmids obtained were sequenced to confirm that there were no mutations in the coding sequences. The fusion proteins were expressed in the *Escherichia coli* BL21DE3 host strain. The transformed cells were grown in rich medium plus 0.2% glucose (according to protocol from New England Biolabs) at 37° C. until the absorbance at 600 nm was 0.6-0.8, at which time the medium was supplemented with 200 µM ZnSO4, and protein expression was induced with 0.3 mM isopropyl 1-thio-β-D-galactopyranoside and was allowed to proceed for 2 h. The cells were then harvested, resuspended in 1×PBS (pH 7.4) (25), 1 mM phenylmethylsulfonyl fluoride, 1 µM leupeptin, 1 µM aprotinin, and 10 µg/ml lysozyme, sonicated, and centrifuged for 30 min at 27,500 relative centrifugal force. The supernatant was then loaded on amylose resin (New England Biolabs) according to the manufacturer's protocol. Following washes with 1×PBS, purified fractions were eluted in maltose elution buffer (10 mM maltose, 100 mM Tris (pH 8.0), and 100 mM NaCl).

Gel Mobility Shift Analysis:

Unless otherwise specified, 5 pmol of each of the purified proteins were incubated for 15 min on ice with 5 pmol of the specified labeled duplex oligonucleotide in the presence of 25 mM Hepes (pH 7.9), 50 mM KCl, 6.25 mM MgCl2, 1% Nonidet P-40 and 5% glycerol. After incubation, the mixture was loaded on a 5% polyacrylamide gel (29:1 acrylamide/bisacrylamide ratio) and run in 0.5×TBE at 4° C. (200 V for 2 h, 15 min). The gels were than stained with SYBR Green (Invitrogen) and acquired with Typhoon Trio++ scanner (GE Healthcare). Protein concentration was determined by a modified version of the Bradford procedure (Bio-Rad protein assay). In the case of the NR2E3 protein, an apparent higher protein concentration (20, 50 and 100 pmol) was required likely because not all the protein sample was correctly folded (see FIG. S1). The apparent affinity binding assay were measured by a gel mobility shift assay by performing a titration of the proteins with the hRho 65 bp and hRho 43 bp oligonucleotides. The fraction of protein—bound DNA was plotted against the protein concentration in the reaction mixture. All numerical values were obtained by computer quantification of the image using a Amersham Biosciences Typhoon Trio++ apparatus.

ChIP

For ChIP experiments, both ZF6-KRAB transduced and un-transduced region of the same retina were dissected from the eye.

ChIP was performed as follow: Retina was homogenized mechanically and cross linked using 1% formaldehyde in PBS at room temperature for 10 minutes, then quenched by adding glycine at final concentration 125 mM and incubated at room temperature for 5 minutes. Retina was washed three times in cold PBS 1× then cells were lysed in cell lysis buffer (Pipes 5 mM pH 8.0, Igepal 0.5%, Kcl 85 mM) for 15 min. Nuclei were lysed in nuclei lysis buffer (Tris HCl pH8.0 50 mM, EDTA 10 mM, SDS 0.8%) for 30 min.

Chromatin was shared using Covaris s220. The shared chromatin was immunoprecipitated over night with anti HA ChIP grade (abcam, ab 9110). The immunoprecipitated chromatin was incubated 3 hours with magnetic protein A/G beads (Invitrogen . . . ). Beads were than washed with wash buffers and DNA eluted in elution buffer (Tris HCl pH 8 50 mM, EDTA 1 mM, SDS 1%). Then real time was performed using primers on rhodopsin TSS and Rp130 TSS.

Triple-Immunostaining for Anti-HA, Anti-GNAT1, and Anti-Rhodopsin Antibody.

Frozen retinal sections were washed once with PBS and then fixed for 10 min in 4% PFA. Sections were immersed in a retrieval solution (0.01 M sodium citrate buffer, pH 6.0) and boiled three times in a microwave. After the Blocking solution (10% FBS, 10% NGS, 1% BSA) was added for 1 hour. The two primary antibody mouse anti-HA (1:300, Covance) and rabbit Gα T1 (Santacruz Biotechnology), were diluted in a Blocking solution and incubated overnight at 4° C. The secondary antibodies (Alexa Fluor® 594,anti-mouse 1:800, Molecular Probes, and Alexa Fluor® 488,anti-rabbit 1:500, Molecular Probes, Invitrogen, Carlsbad, Calif.) have been incubated for 1 hour, followed by three rinses with PBS. After the slides were incubated in blocking solution (10% NGS) for 1 hour and then incubated O.N with primary antibody mouse-1D4 (1:500, Abcam). The secondary antibodies (Alexa Fluor® 405,anti-mouse 1:200, Molecular Probes, Invitrogen) VECTASHIELD® (Vector Lab Inc., Peterborough, UK) was used to visualize nuclei. Sections were photographed using a LEICA Fluorescence Microscope System (LEICA Microsystems GmbH, Wetzlar, Germany).

RNASEQ

Samples were aligned to the Sus crofa genome (ensemble 10.2) and counts were estimated with RSEM. Normalization and differential expression analysis were performed with egdeR bioconductor package. We removed from the dataset genes with a count average of less than 3. The Filtering and Normalization processes retained 15508 genes out of the 22863 of the starting condition.

Hypergeometric Test

We used again the GO categories extracted from the dataset and calculated the probability of finding enriched a particular GO category in the extraction of the differentially expressed genes, 204 and 81 respectively, and then the 57 genes of the intersection, from the 15508 genes composing the total background.

Gene Set Enrichment Analysis GSEA

Genes in the experiment were ranked by their Fold Change value to get a gene list comprising the total 15508 genes of the filtered experiment. From that dataset we extracted 10734 Gene Ontology Categories (biomaRt package) and we filtered out those which had less than 10 genes, obtaining 1426 GO categories that we used as gene sets.

We performed a Gene Set Enrichment analysis procedure (Source code was downloaded from the BroadInstitute-link) 1426 times obtaining 1426 Enrichment Scores and the associated Pvalue.

Results and Discussion

DNA-Binding Specificities of Artificial Zinc-Finger-Based Protein: Generation and Characterization of ZF6-DBD To repress transcriptionally the human RHODOPSIN locus in Mussolino et al. 2011 (EMBO Mol Med. 2011 March; 3(3):118-28) a ZF6-KRAB construct was generated. This construct contains a DNA-binding domain generated by the sequential assembling of artificial Zinc finger based platform to target the human RHODOPSIN proximal region of the human RHO proximal promoter, the human-derived Krüppel-associated box (KRAB) repression domain at N-terminus of the protein, a Nuclear Localization Signal (NLS) and a HA tag.

The authors removed from the construct the KRAB domain (FIG. 1). The resulting construct ZF6-DBD encodes for a protein that possesses exclusively the DNA-binding domain, thus with in principle a significant reduced functional content and no repression ability and smaller in molecular weight than the ZF6-KRAB counterpart (FIG. 1C). Besides the local properties at the locus of the ZF6-DBD, the KRAB domain confer major functional genomic and epigenomic consequences on transcription output. Indeed, KRAB-ZFPs (Krüppel-associated box domain-zinc finger proteins) are vertebrate-restricted transcriptional repressors encoded in the hundreds by the mouse and human genomes. They act via an essential cofactor, KAP1, which recruits effectors responsible for the formation of facultative heterochromatin. The KRAB/KAP1 can mediate long-range transcriptional repression through heterochromatin spreading, and this process is at times countered by endogenous influences. Thus, in principle the lack of the KRAB domain should not produce distinct biological outcomes upon delivery to the retina.

Figure 2:
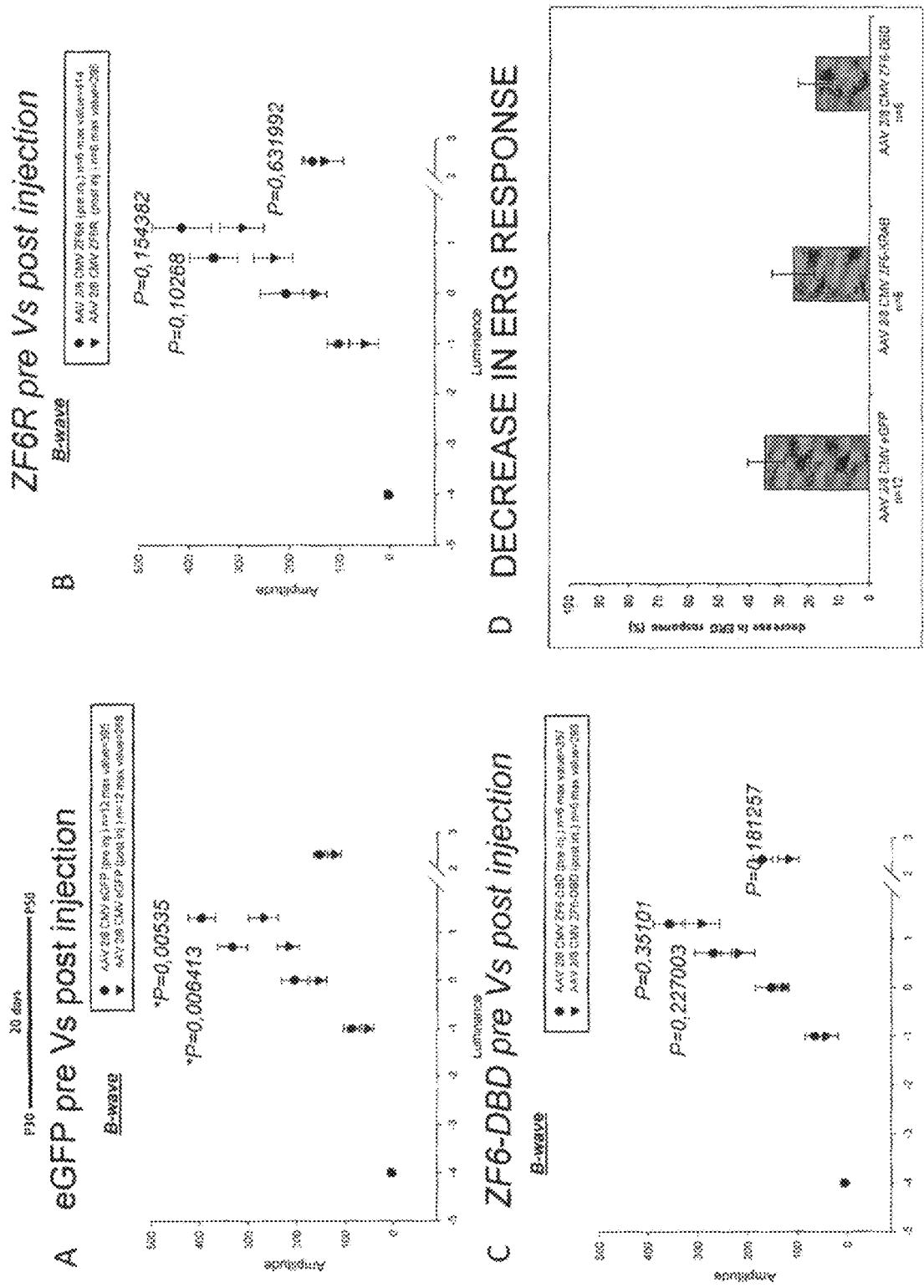
FIG. 2. Electrophysiological responses of retina recorded by ERG analysis, on P347S mice injected subretinally with AAV8-CMV-ZF6-DBD or AAV8-CMV-ZF6-KRAB or AAV8-CMV-EGFP (1×10E9 vg) at P30. A-C, The amplitudes represent retinal responses evoked by increasing light intensities under scotopic (dim light) and photopic (bright light) conditions. B-wave amplitudes before treatment (base-line: P30; black circles,) and after treatment (P50; triangles). Twenty days after vector delivery, the electrophysiologic responses of the retina were preserved in ZF6-DBD and ZF6-KRAB treated eyes compared to control contralateral EGFP injected eyes. D diagram representing the conservation of the functional retinal responses in both ZF6-DBD and ZF6-KRAB retinas compared to controls, however the ZF6-DBD outperformed ZF6-KRAB level of retinal function preservation. $*p<0.01$; $p<0.001$, $*p<0.0001$ as statistically significance differences (t-test) Statistical value.
Figure 3:
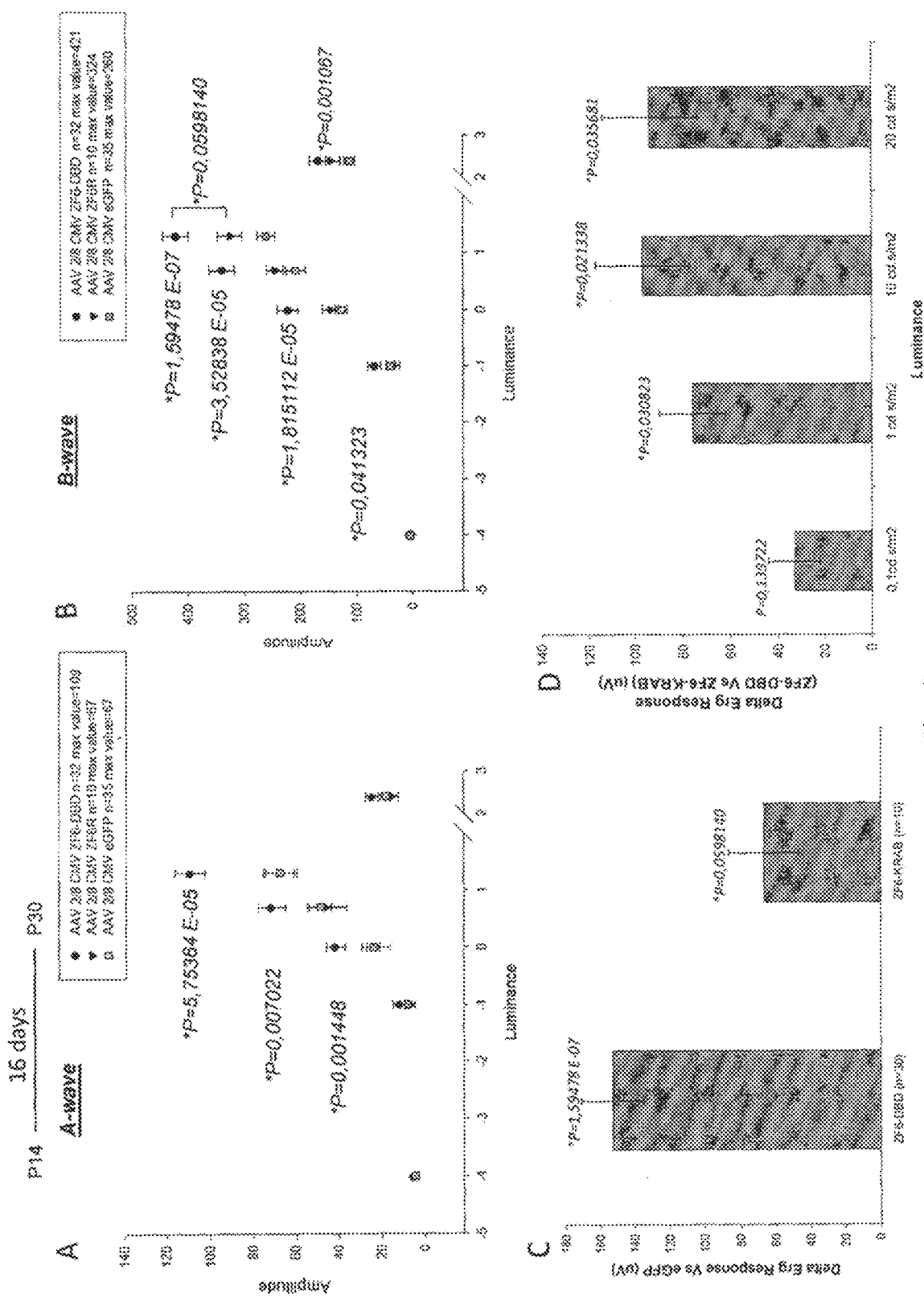
FIG. 3. Comparison of electrophysiological responses of retina recorded by ERG analysis, on P347S mice injected subretinally with AAV8-CMV-ZF6-DBD or AAV8-CMV-ZF6-KRAB or AAV8-CMV-EGFP (1×10E9 vg) at P14 and sacrificed at P30. A-B, The amplitudes represent retinal a- and b-waves responses evoked by increasing light intensities under scotopic (dim light) and photopic (bright light) conditions. Statistically significance differences in panel A between EGFP control eyes and ZF6-DBD injected eyes; in panel B between eGFP control eyes and ZF6-DBD injected eyes and between ZF6-DBD and ZF6-KRAB (square bracket). C, Fourteen days after vector delivery, the electrophysiologic responses of the retina were preserved much more significantly in ZF6-DBD than in ZF6-KRAB treated eyes; statistically significance difference between ZF6-DBD and ZF6-KRAB injected eyes vs eGFP injected eyes. D, diagram representing the direct comparison of conservation of retinal ERG responses relative to ZF6-DBD and ZF6-KRAB; statistically significance difference between ZF6-DBD injected eyes (n=32) vs ZF6-KRAB injected eyes (n=10). $*p<0.01$; $p<0.001$, $*p<0.0001$ as statistically significance differences (t-test).

To evaluate the in vivo functional activity of the ZF6-DBD, the authors generated an Adeno-associated virus (AAV) vector serotype 8 containing the ZF6-DBD under the transcriptional control of the ubiquitous Cytomegalovirus promoter fragment (CMV). In order to directly compare the activity of the ZF6-DBD to that of ZF6-KRAB previously described, the authors delivered both vectors (AAV8-CMV-ZF6-KRAB and the novel AAV8-CMV-ZF6-DBD) independently to the retina of the P347S mouse model of adRP. Before vector administration, at day 30 (P30), the authors measured the base-line retinal functional responses by electroretinogram responses (ERG; EMBO Mol Med. 2011 March; 3(3):118-28). Twenty days after delivery (P50, subretinal injection of a vector dose of 2.5×10e8 vector particles of AAV8-CMV-EGFP, AAV8-CMV-ZF6-DBD and AAV8-CMV-ZF6-KRAB, respectively) the retinal ERG responses were re-measured to assess retinal disease progression. As shown in FIG. 2, the most significant decrease of ERG responses were observed in the EGFP control eyes followed by the ZF6-KRAB and ZF6-DBD, respectively (FIG. 2, FIG. 2D). In particular, remarkably highly significant differences were observed between the ZF6-KRAB and ZF6-DBD ERG responses. ZF6-DBD treated eye show conserved responses compared to base-line measurements whereas a decrease of ERG responses was observed in the ZF6-KRAB, consistently with equivalent data in Mussolino et al 2011 (EMBO Mol Med. 2011 March; 3(3):118-28). To deepen the characterization of the therapeutic activity and the molecular mechanisms of the ZF6-DBD, the authors selected an earlier time point of subretinal AAV8-CMV-ZF6-DBD vector delivery in P347S mice, i.e. P14. At this stage the retina is fully differentiated and the P347S pathology is not yet evident. The authors injected a large series of mice (n=32) to generate a number of independent observations and ERG measurements. As shown in FIG. 3 the eyes treated with AAV8-CMV-ZF6-DBD demonstrate robust and consistent recovery of the ERG a-wave and b-wave responses along a wide range of luminance in both scotopic and photopic conditions when compared to EGFP treated eyes. In addition, when ZF6-DBD treated eyes were compared to AAV8-CMV-ZF6-KRAB treated eyes a statistically significant higher responses were observed in AAV8-CMV-ZF6-DBD treated eyes (FIG. 3C). Indeed, the direct comparison of ERG responses between ZF6-DBD and ZF6-KRAB before and after treatment show a statistical significant decrease of progression of P347S retinal responses loss in ZF6-DBD treated eyes (FIG. 3D). These data strongly indicate that the delivery of AAV8-CMV-ZF6-DBD to P347S retina result in a significant higher functional and therapeutic value than AAV8-CMV-ZF6-KRAB.

To investigate the transcriptional molecular consequences of AAV8-CMV-ZF6-DBD vector treatment in distinct cohorts of P347S animals, the authors collected the retinas and determined the expression levels of photoreceptor-specific transcripts. As shown in FIG. 4, subretinal administration of AAV8-CMV-ZF6-DBD result in a significant and specific downregulation of the Human RHO transcript levels and unaltered levels of GNA1 photoreceptor specific gene (FIG. 4 A). In addition, the authors calculate the average expression levels of the AAV8 vector transgenes upon subretinal injections of 1×10E9 vector particles of AAV8-CMV-EGFP, AAV8-CMV-ZF6-DBD and AAV8-

CMV-ZF6-KRAB (FIG. 4B) and found no statistically significant differences. To determine at protein levels the impact of the treatment the authors performed a western blot analysis on RHO in retinal samples treated with AAV8-CMV-EGFP, AAV8-CMV-ZF6-DBD and AAV8-CMV-ZF6-KRAB. As shown (FIG. 4C) a reduction of RHO protein was observed in both ZF6-DBD and ZF6-KRAB treated retinas compered to EGFP control retinas. Furthermore, an apparent higher reduction of RHO protein quantity was observed in ZF6-DBD relative to ZF6-KRAB treated retinas by immunofluorescence analysis (FIG. 4F-H). This result was also confirmed qualitatively in histological section (FIG. 4). Indeed, the use of an antibody that can discriminate between human and non-human RHO protein was used on P347S retinas and show lack of staining in human rhodopsin protein in ZF6-DBD treated retinas compared to EGFP control in which a positive staining is apparent in the degenerating photoreceptor outer segments. To further characterize the P347S phenotype the authors performed immunohistological studies. FIG. 4D depicts the nuclear localization of the ZF6-DBD 20 days after AAV8 subretinal gene transfer in P347S mice at P30. Anti-HA tag staining showed high transduction efficiency of photoreceptor cells and a nuclear localization. Besides lack of HA staining, the EGFP control retina show significant reduction of photoreceptor nuclei. These data suggest that AAV8 delivery of ZF6-DBD results in efficient and appropriate nuclear localization, leading to a partial preservation of retinal structure.

Figure 5:
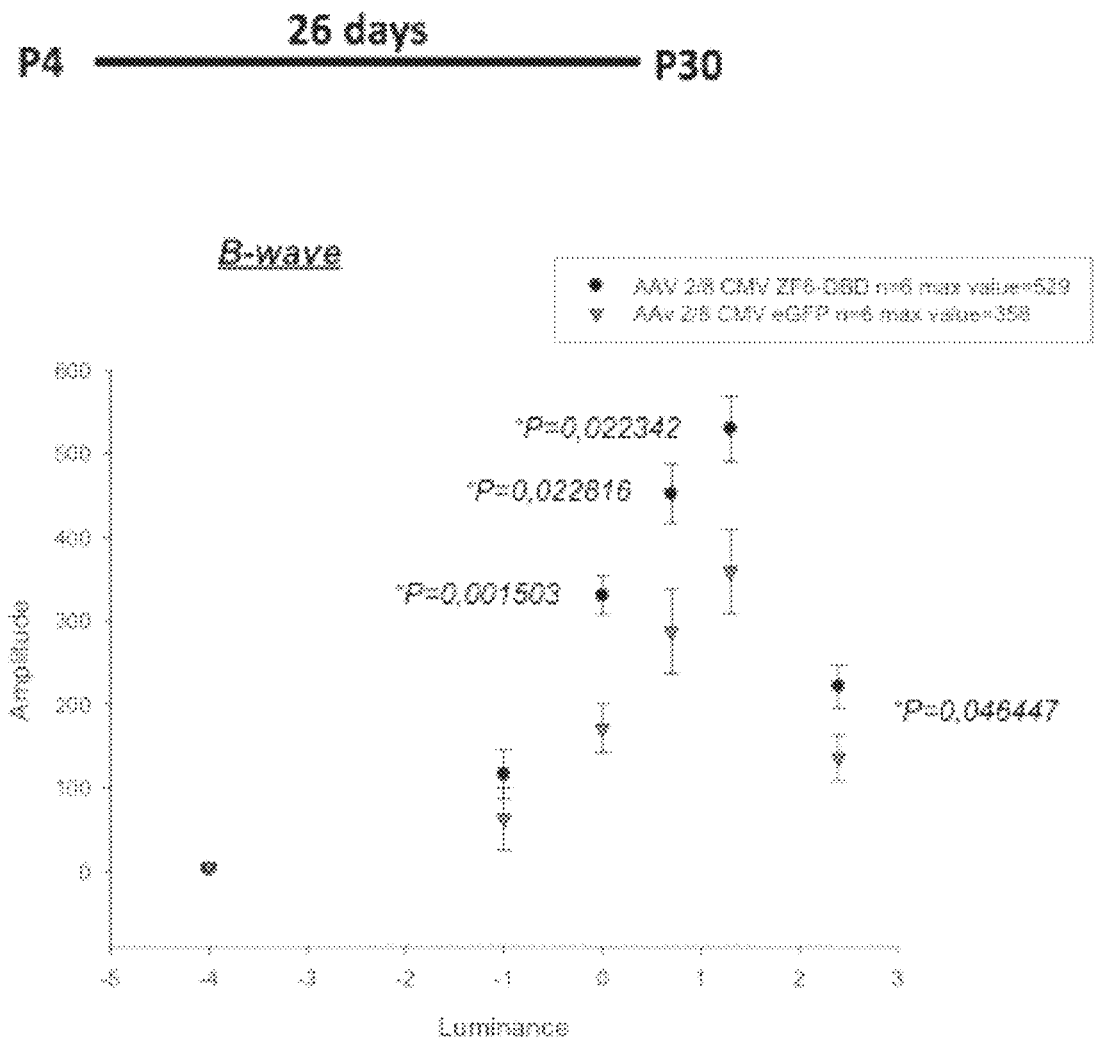
FIG. 5. Electrophysiological responses of retina recorded by ERG analysis, on P347S mice injected at P4 subretinally with AAV8-CMV-ZF6-DBD or AAV8-CMV-EGFP (1×10E9 vg) and analyzed at P30 between ZF6-DBD injected eyes vs eGFP injected eyes $*p<0.01$; $**p<0.001$, as statistically significance differences (t-test).

The regulatory DNA elements and epigenetics landscapes are dynamically activated during cell-fate transitions, lineage relationships, and dysfunction. Therefore, the accessibility of DNA-binding protein to DNA dynamically changes synchronously. In essence, one may assume that a DNA-binding protein may encounter a completely different genomic landscape depending on the developmental and metabolic status of the target cell. In this perspective the authors decided to test during active photoreceptor differentiation state, whether ZF6-DBD impact on retinal differentiation and whether a functional recovery of P347S retinal function may be, consistently with previous results, observable. The authors injected P347S mice at P4 subretinally with the AAV8-CMV-ZF6-DBD. At P4 retinal neuroblasts are in part still dividing whereas those that exit cell cycle are in active differentiation state. As shown in FIG. 5, 26 days after treatment (P30), the authors observed an higher retinal functional recovery as compared to both P14 and P30 treated eyes (FIG. 6). These data indicate that retinal development do not influence the safety and efficacy of ZF6-DBD.

FIG. 6 shows the major increase of therapeutic outcome when the AAV8-CMV-ZF6-DBD are performed at early time point.

One of the main hurdle to assess DNA binding specificities of a DNA-binding protein designated for a targeted genomic landscape, such as the human RHO promoter region of humans diseased photoreceptors, is the availability of other similar genomic context for testing. In particular the P347S mouse model possesses, besides the P347S mutated human rhodopsin gene, only 3.4 kb of the human RHO promoter, i.e. a limited portion of the RHO promoter and obviously no portions surrounding human rhodopsin gene, thus limiting the human genomic specificities of the somatic (photoreceptors) genomic cell-specific landscape (Li T, Snyder W K, Olsson J E, Dryja T P (1996) Transgenic mice carrying the dominant rhodopsin mutation P347S: evidence for defective vectorial transport of rhodopsin to the outer segments. Proc Natl Acad Sci USA 93: 14176-14181). In fact, both the random integration and the copy number variation of the P347S mutated human rhodopsin gene may impact a faithful resembling of the human RHO photoreceptor locus in rods.

Figure 7:
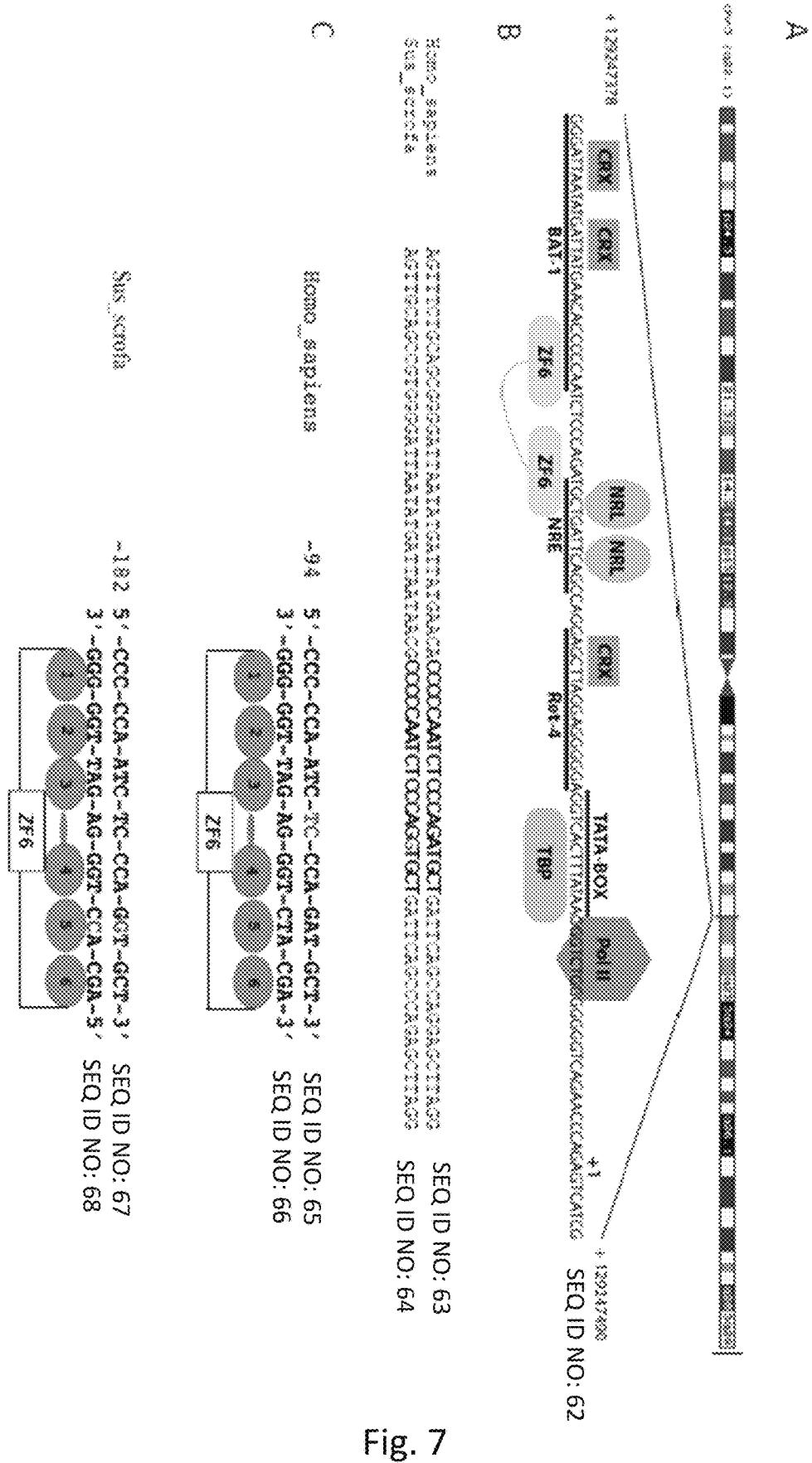
FIG. 7. A. Chromosome localization of proximal rhodopsin promoter. Schematic representation of the rhodopsin proximal promoter, indicating the transcription start site and the location of cis-regulatory elements and their cognate binding proteins. B. Alignment of human and porcine proximal promoter; Bold ZF6-DBDCis-seq; the mismatch between human and porcine ZF6-DBDCis-seq. C. Schematic representation of binding of the ZF6-DBD with human and porcine rhodopsin promoter.
Figure 8:
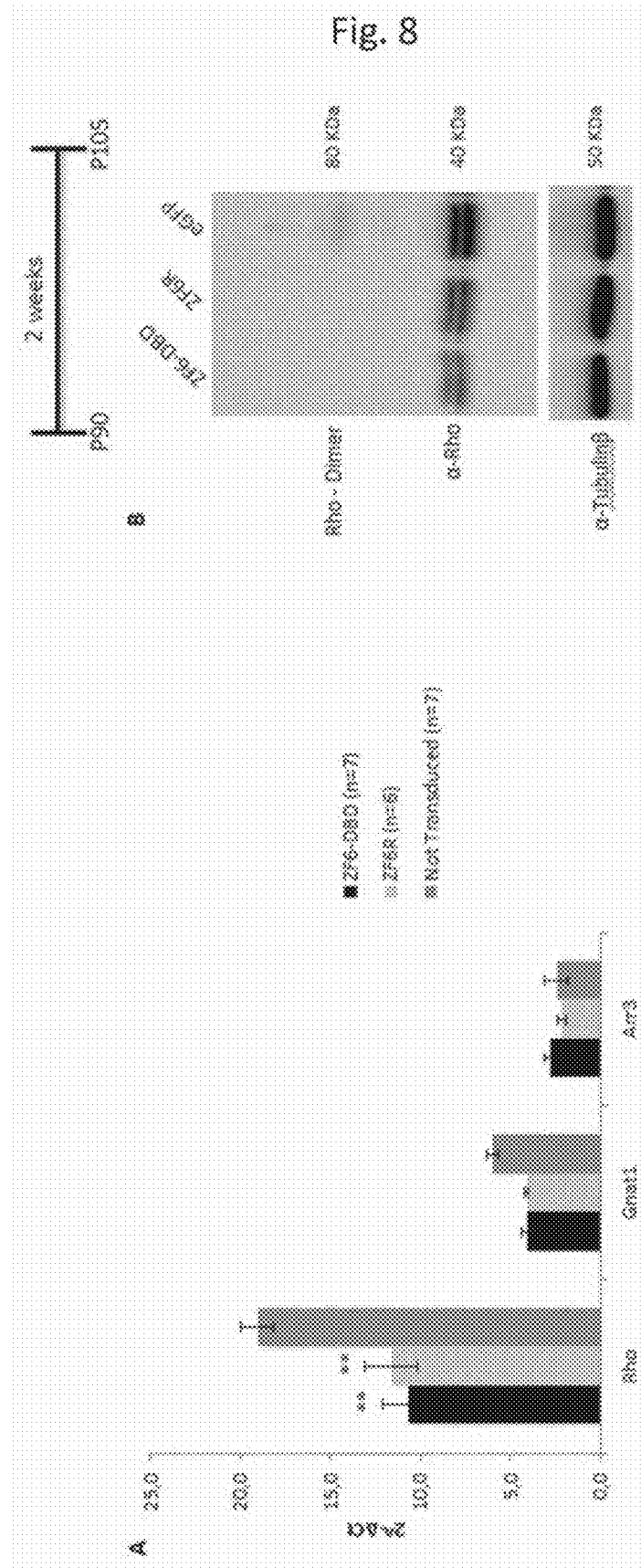
FIG. 8. Treatment of wild type pig's retinae with AAV8-CMV-ZF6-DBD or AAV8-CMV-ZF6-KRAB at P90 and sacrificed after 15 days (vector dose 2×10e10 vg). A Levels of retina's transcripts evaluated by qReal Time PCR. The ZF6-DBD reduced the endogenous rhodopsin expression compared with eGFP treated eyes, whereas the other genes of the retina are unaltered; **pvalue<0.01 B Western Blot analysis of lysate of pigs retinas using an α-RHO (1D4); α-Tubulin antibody was used for normalization.

Based on sequence identity between the human and the porcine ZF6-DBD target site (FIG. 7) the authors decided to assess the functional ability of the construct in the porcine retina. Authors subretinally injected a low dose (1×10e10) of AAV8-CMV-ZF6-DBD in a physiological intact genomic landscape of the porcine retina (adult female P90) whose RHO proximal promoter genomic region contains the ZF6 binding sequence with the exception of 1 mismatch (FIG. 7). To assess "pure" transcriptional effects and not possible secondary degeneration owed to rhodopsin knock-down, an early sacrifice was performed. Fifteen days after vector administration both qRT-PCR and Western Blot blot analysis on the transduced portion of the retina (EGFP positive) demonstrate 45% repression of rhodopsin transcript and robust reduction of Rho protein levels, respectively (FIG. 8). Remarkably, the ratio between levels of relative expression of ZF6-DBD and the resulting levels of repression is of a 3 logs unit.

Figure 10:
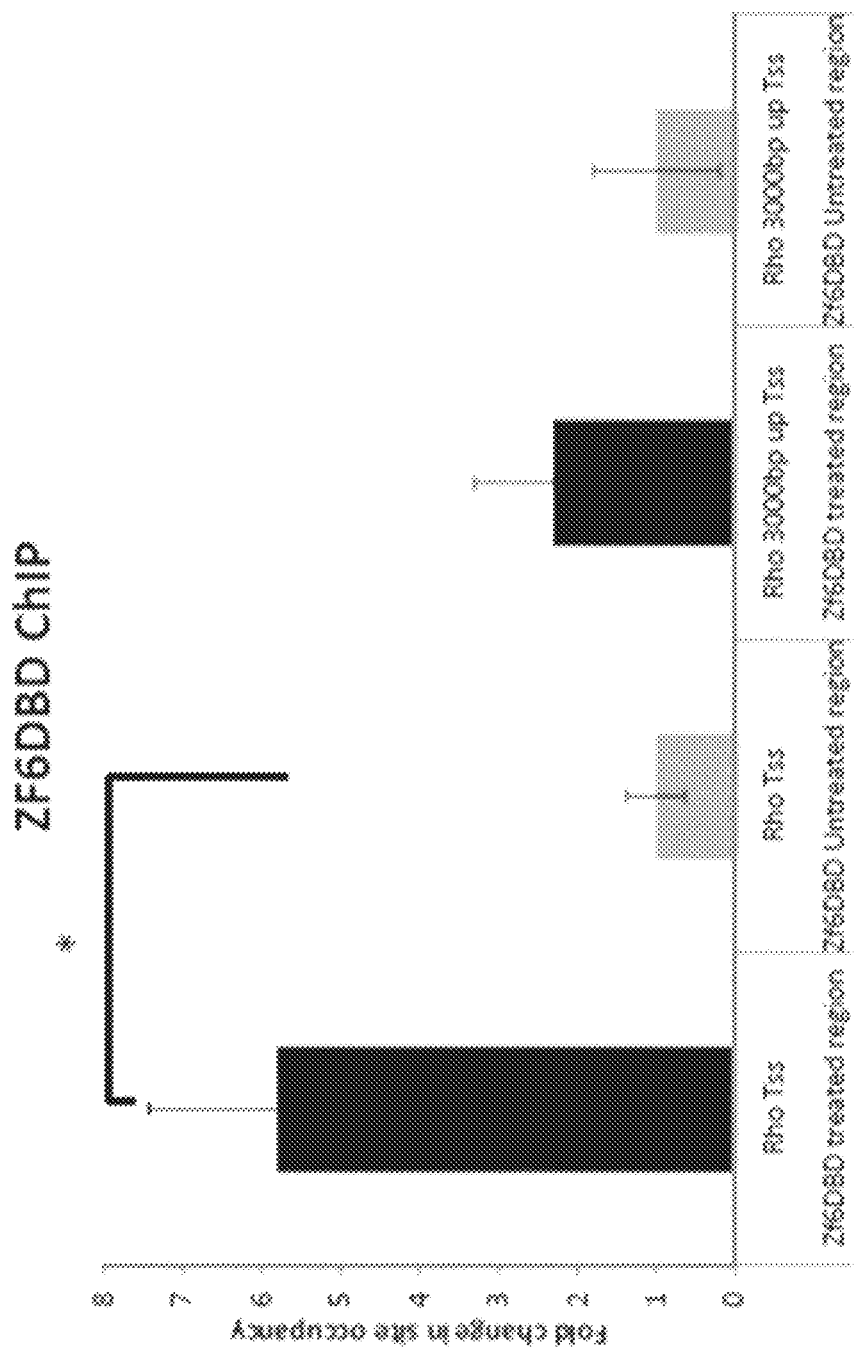
FIG. 10. Binding of ZF6-DBD (Zf6DBD) on rhodopsin promoter. ChIP analysis in *Sus scrofa* retina using antibody against HA. We compared the physical binding of ZF6-DBD on rhodopsin transcription starting site (Tss) in ZF6-DBD treated versus untreated portions of the retina. We observed a specific and statistically significant enrichment in the treated region comparing with the level of binding in untreated region.

Retinal transduction efficiency quantified as AAV8-CMV-ZF6-DBD transgene transcript levels (qRT-PCR) resulted in an on average of 148 fold to 32 lower than NRL and CRX, two endogenous rod-specific transcription factors used as reference (FIG. 9). Chromatin immunoprecipitation experiments (ChiP) on AAV vector transduced retina showed proper occupancy of the ZF6-DBD on the genomic target (FIG. 10). Co-immunoistochemical staining of retinas ZF6-DBD AAV-transduced with anti-HA tag antibody shows a strong nuclear localization. Co-immunostaining with a rod-specific marker (GNAT) shows that expression of ZF6-DBD inversely correlates with rhodopsin protein expression levels. In particular in the most intensively HA-stained rods rhodopsin is virtually absent. In addition, the outer segments of ZF6-DBD transduced rods appear completely collapsed, consistently with the fact that rod outer segments is composed quantitatively for 90% of rhodopsin which confers to the outer segment structural properties (as observed in rho knock out mice). Despite the absence of rhodopsin the number of rows of photoreceptor nuclei appear conserved (FIG. 11). Furthermore, the missexpression of ZF6-DBD in cones does not affect their morphological appearance, as also shown by the levels of cone specific transcript Arrestin 3 (FIG. 8). To assess an earlier time points the authors measured photoreceptor transcripts levels 7 days post injection, as shown (FIG. 12) the result were similar to that obtained at 15 days post-injection.

To evaluate the impact of the vector dose on the functionality of ZF6-DBD, the authors injected a series of porcine retinas with a double of the dose previously used, i.e. a vector dose of 2×10e10 vg. As shown in FIG. 12B, the higher dose of both AAV8-CMV-ZF6-DBD or AAV8-CMV-EGFP are mirrored in the transgene transcript levels assessed. However, the Rhodopsin transcript levels values were similar to that obtained with 1×10e10 vg.

Comparison Between ZF6KRAB and ZF6-DBD by RNA-Seq to Evaluate Off-Targets.

To gain insights in the interference pattern induced by our Artificial Transcription Factor, authors performed a whole transcriptome sequencing [RNA-Seq] (Mortazavi A, Williams B A, McCue K, Schaeffer L, Wold B. Nat Methods. 2008 July; 5(7):621-8). RNA-seq enables the detection of RNA-transcripts and levels resulting from the transcriptional machinery activity. Thus, RNA-seq measures the final output of target and off targets activity of DNA-binding protein. Differentially from ChIP-seq analysis, in which a whole genome map of a given DBD is provided, RNA-seq enables the detection of relevant functional activity (transcripts) deriving from binding in functional relevant genome sites (transcriptionally sensitive). The authors processed 11 retinae from pigs injected with ZF6-KRAB or ZF6-DBD at should not be construed as limiting the scope of the invention. The disclosures of all patent and scientific literature cited herein are expressly incorporated in their entirety by reference. 3 months and sacrificed after 8 or 15 days post injection. The dataset consisted of 3 ZF6-KRAB treated and 3 ZF6-DBD treated retinae plus 5 Controls (non transduced areas of the same retinae as internal controls, Table 2).

TABLE 2

Retinae used in the whole transcriptome sequencing [RNA-Seq]

| Description | # Reads | % of raw clusters per lane | % Perfect Index Reads | % One Mismatch Reads (Index) | % of >= Q30 Bases (PF) | Mean Quality Score (PF) |
|---|---|---|---|---|---|---|
| Control | 55.622.772,000 | 13.2 | 98.88 | 1.12 | 92.11 | 35.67 |
| Control | 55.969.232,000 | 16.63 | 99.1 | 0.9 | 94.36 | 36.42 |
| Control | 51.482.106,000 | 15.3 | 99.06 | 0.94 | 94.27 | 36.38 |
| Control | 45.364.948,000 | 13.48 | 99.26 | 0.74 | 94.48 | 36.48 |
| Control | 59.438.368,000 | 14.42 | 99.08 | 0.92 | 91.96 | 35.79 |
| DBD-treated | 45.584.960,000 | 10.82 | 98.22 | 1.78 | 92.48 | 35.82 |
| DBD-treated | 52.250.358,000 | 12.68 | 98.84 | 1.16 | 91.63 | 35.68 |
| DBD-treated | 67.242.006,000 | 16.32 | 99.38 | 0.62 | 92.1 | 35.83 |
| KRAB-treated | 127.962.394,000 | 30.38 | 98.84 | 1.16 | 92.47 | 35.84 |
| KRAB-treated | 65.608.020,000 | 19.49 | 98.95 | 1.05 | 94.09 | 36.31 |
| KRAB-treated | 50.299.864,000 | 14.95 | 99.37 | 0.63 | 94.46 | 36.46 |

The quality of the reads were assessed with the following Illumina index:
Raw clusters per lane. The number of clusters detected by the image analysis module.
% Perfect Index Reads. Percentage of index reads in this sample which perfectly matched thegiven index.
% One Mismatch Reads (Index). Percentage of index reads in this sample which had 1 mismatch to given index.
% of >= Q30. Bases Yield of bases with Q30 or higher from clusters passing filter divided by total yield of clusters passing filter.
Mean Quality Score (PF). The total sum of quality scores of clusters passing filter divided by total yield of clusters passing filter.

Authors filtered genes with average counts greater than or equal to 3, and selected those with an adjusted Pvalue of less than or equal to 0.05 to identify differential expressed genes (DEGs) in treated retinae, compared to controls. Surprisingly, authors found a lower number of disregulated genes induced by ZF6-DBD treatment compared to ZF-KRAB treatment and negligible levels of fluctuation of the genes from the treated sample compared to the wild type condition. We obtained, respectively, 81 DEGs in ZF6-DBD treated retinae (two of which include EGFP and ZF6-DBD) and 204 DEGs in ZF6-KRAB treated retinae (FIG. 13 and Tables 3 and 4).

TABLE 3A

ZF6-DBD differentially expressed genes (81, FDR < 0.05)

| logFC | logCPM | PValue | FDR | ensembl_gene_id | external_gene_id |
|---|---|---|---|---|---|
| 6.161438875 | −1.321679658 | 4.18E−09 | 2.03E−06 | eGFP | eGFP |
| 1.487261172 | 2.283931402 | 7.94E−05 | 0.017591012 | ENSSSCG00000000362 | RDH5 |
| 1.482647156 | 1.817939463 | 0.000120014 | 0.024755682 | ENSSSCG00000000371 | |
| 2.364830195 | 7.971622814 | 2.51E−11 | 1.72E−08 | ENSSSCG00000000660 | A2M |
| 1.643825956 | 4.355513069 | 4.21E−06 | 0.001242435 | ENSSSCG00000001427 | C4A |
| 1.583349095 | 4.333804953 | 9.16E−06 | 0.002463978 | ENSSSCG00000001544 | TEAD3 |
| 1.726632938 | 0.175566867 | 0.000163905 | 0.032053021 | ENSSSCG00000002800 | |
| 5.295063827 | −1.811005407 | 1.30E−05 | 0.003316718 | ENSSSCG00000002977 | AQN-3 |
| 1.384649577 | 3.478445175 | 0.000131777 | 0.026457357 | ENSSSCG00000003794 | RPE65 |
| 2.310104374 | −0.393948087 | 6.39E−06 | 0.001814431 | ENSSSCG00000004195 | ARG1 |
| 1.834158093 | 2.656659323 | 7.52E−07 | 0.000257385 | ENSSSCG00000006025 | PKHD1L1 |
| 4.18457531 | 4.770570467 | 3.67E−28 | 1.11E−24 | ENSSSCG00000006276 | CEBPD |
| 1.916837007 | 4.257050285 | 9.18E−08 | 3.55E−05 | ENSSSCG00000006780 | WNT2B |
| 6.230702371 | −1.31012621 | 1.26E−09 | 6.77E−07 | ENSSSCG00000008101 | |
| 1.743437437 | 4.759298225 | 9.56E−07 | 0.000320039 | ENSSSCG00000008203 | IGKC |
| 2.331043381 | 2.550751739 | 5.95E−10 | 3.32E−07 | ENSSSCG00000008995 | LRAT |
| 1.93058605 | −0.245200124 | 0.000226203 | 0.043115942 | ENSSSCG00000010474 | CYP26C1 |
| 1.606649504 | 1.818371052 | 2.96E−05 | 0.007312394 | ENSSSCG00000010529 | SFRP5 |
| 2.211790474 | 2.00049955 | 1.11E−08 | 5.04E−06 | ENSSSCG00000010613 | ITPRIP |
| 1.697535475 | 0.728072825 | 5.93E−05 | 0.013746241 | ENSSSCG00000010647 | ADRB1 |
| 2.253042038 | 0.761439468 | 8.93E−08 | 3.54E−05 | ENSSSCG00000010805 | |
| 2.454716019 | −0.912366572 | 4.57E−05 | 0.010741461 | ENSSSCG00000011148 | |
| 3.353107041 | −1.68318296 | 0.000253983 | 0.04721574 | ENSSSCG00000011153 | |
| 2.896043491 | −0.357884972 | 7.84E−08 | 3.19E−05 | ENSSSCG00000011579 | PPARG |
| 1.789015925 | 6.324065196 | 3.96E−07 | 0.000142141 | ENSSSCG00000011700 | CP |
| 2.495743157 | 3.868824302 | 6.93E−12 | 5.21E−09 | ENSSSCG00000011796 | CRYGS |
| 3.203364284 | −1.237480254 | 1.04E−05 | 0.002754767 | ENSSSCG00000012040 | OLIG1 |
| 2.106332374 | −0.928523554 | 0.000207676 | 0.04009205 | ENSSSCG00000016187 | |
| 1.354675874 | 10.17282403 | 0.000112212 | 0.023467997 | ENSSSCG00000017343 | GFAP |
| 2.726173516 | 2.905085892 | 3.80E−13 | 3.37E−10 | ENSSSCG00000017445 | KRT13 |
| 1.792487081 | 4.302359077 | 5.57E−07 | 0.000194981 | ENSSSCG00000017956 | CD68 |
| 4.840894235 | 2.334892081 | 1.09E−28 | 4.12E−25 | ENSSSCG00000020750 | |
| 2.744770611 | 3.961111153 | 7.09E−14 | 6.67E−11 | ENSSSCG00000021232 | SYNC |
| 3.261685338 | 0.185696149 | 6.73E−11 | 4.22E−08 | ENSSSCG00000023489 | CXCL9 |

TABLE 3A-continued

ZF6-DBD differentially expressed genes (81, FDR < 0.05)

| logFC | logCPM | PValue | FDR | ensembl_gene_id | external_gene_id |
|---|---|---|---|---|---|
| 9.146898753 | 1.125362761 | 6.08E−33 | 4.00E−29 | ENSSSCG00000023511 | |
| 2.807155473 | 3.351293821 | 4.28E−14 | 4.60E−11 | ENSSSCG00000023684 | |
| 2.465528094 | 6.065214845 | 4.49E−12 | 3.56E−09 | ENSSSCG00000023686 | TTR |
| 1.458243125 | 2.29726141 | 9.92E−05 | 0.021344169 | ENSSSCG00000024174 | TGIF1 |
| 2.243181843 | 2.199880858 | 3.76E−09 | 1.89E−06 | ENSSSCG00000024348 | |
| 3.068602752 | −0.624451392 | 1.07E−07 | 4.04E−05 | ENSSSCG00000024911 | |
| 2.452384041 | −0.287640749 | 1.39E−06 | 0.000444107 | ENSSSCG00000025300 | |
| 8.066972764 | 0.113415054 | 2.64E−22 | 3.98E−19 | ENSSSCG00000025378 | |
| 3.901609863 | −0.952775174 | 2.77E−08 | 1.16E−05 | ENSSSCG00000026645 | |
| 6.948122397 | 0.678811374 | 3.55E−26 | 7.63E−23 | ENSSSCG00000026986 | |
| 2.611916684 | −1.213146584 | 8.53E−05 | 0.018623654 | ENSSSCG00000027199 | |
| 3.230546458 | 2.305712341 | 3.18E−16 | 3.68E−13 | ENSSSCG00000027332 | IGKV-11 |
| 10.94582925 | 2.8177767 | 1.17E−53 | 1.77E−49 | ENSSSCG00000027582 | |
| 8.645978549 | 0.628323488 | 1.17E−27 | 2.93E−24 | ENSSSCG00000027868 | |
| 2.381559335 | −0.306330844 | 3.43E−06 | 0.001032648 | ENSSSCG00000028038 | |
| 1.954022522 | 0.758715053 | 6.20E−06 | 0.001796381 | ENSSSCG00000028112 | CLIC6 |
| 3.24013983 | 3.711384683 | 5.94E−18 | 7.45E−15 | ENSSSCG00000028233 | |
| 3.201851398 | −0.727843551 | 1.26E−07 | 4.63E−05 | ENSSSCG00000028525 | SAA4 |
| 1.909778622 | −0.064481227 | 7.72E−05 | 0.017348851 | ENSSSCG00000029057 | |
| 6.77493674 | −0.919742276 | 1.77E−12 | 1.48E−09 | ENSSSCG00000029210 | CLDN7 |
| 1.55267093 | 4.844054614 | 1.19E−05 | 0.00308997 | ENSSSCG00000030300 | MT2A |
| 2.029326209 | 0.305432221 | 8.23E−06 | 0.002293796 | ENSSSCG00000030447 | AKR1C3 |
| 2.615251213 | 0.175362169 | 2.77E−08 | 1.16E−05 | ENSSSCG00000030738 | IGKV-5 |
| 1.545630452 | 4.18656911 | 1.56E−05 | 0.003911372 | ENSSSCG00000030868 | IGLV-10 |
| 2.393496991 | 2.604144493 | 2.89E−10 | 1.67E−07 | ENSSSCG00000030893 | IGLV-3 |
| 6.487766272 | 1.60283372 | 7.97E−33 | 4.00E−29 | ZF6 | ZF6 |

TABLE 3B

Functional description of ZF6-DBD differentially expressed genes (81, FDR < 0.05)

| ensembl_gene_id | external_gene_id | description |
|---|---|---|
| eGFP | eGFP | eGFP |
| ENSSSCG00000000362 | RDH5 | retinol dehydrogenase 5 (11-cis/9-cis) [Source: HGNC Symbol; Acc: 9940] |
| ENSSSCG00000000371 | | Uncharacterized protein [Source: UniProtKB/TrEMBL; Acc: F1SPI9] |
| ENSSSCG00000000660 | A2M | alpha-2-macroglobulin [Source: HGNC Symbol; Acc: 7] |
| ENSSSCG00000001427 | C4A | Sus scrofa complement C4 (C4), mRNA. [Source: RefSeq mRNA; Acc: NM_001123089] |
| ENSSSCG00000001544 | TEAD3 | TEA domain family member 3 [Source: HGNC Symbol; Acc: 11716] |
| ENSSSCG00000002800 | | Uncharacterized protein [Source: UniProtKB/TrEMBL; Acc: F1RFT2] |
| ENSSSCG00000002977 | AQN-3 | Sus scrofa seminal plasma sperm motility inhibitor/spermadhesin AQN-3-like protein (SPMI), mRNA. [Source: RefSeq mRNA; Acc: NM_001031776] |
| ENSSSCG00000003794 | RPE65 | retinal pigment epithelium-specific protein 65 kDa [Source: HGNC Symbol; Acc: 10294] |
| ENSSSCG00000004195 | ARG1 | Arginase-1 [Source: UniProtKB/Swiss-Prot; Acc: Q95JC8] |
| ENSSSCG00000006025 | PKHD1L1 | polycystic kidney and hepatic disease 1 (autosomal recessive)-like 1 [Source: HGNC Symbol; Acc: 20313] |
| ENSSSCG00000006276 | CEBPD | CCAAT/enhancer binding protein (C/EBP), delta [Source: HGNC Symbol; Acc: 1835] |
| ENSSSCG00000006780 | WNT2B | wingless-type MMTV integration site family, member 2B [Source: HGNC Symbol; Acc: 12781] |
| ENSSSCG00000008101 | | Uncharacterized protein [Source: UniProtKB/TrEMBL; Acc: F1SUA0] |
| ENSSSCG00000008203 | IGKC | immunoglobulin kappa constant [Source: HGNC Symbol; Acc: 5716] |
| ENSSSCG00000008995 | LRAT | lecithin retinol acyltransferase (phosphatidylcholine-retinol O-acyltransferase) [Source: HGNC Symbol; Acc: 6685] |
| ENSSSCG00000010474 | CYP26C1 | cytochrome P450, family 26, subfamily C, polypeptide 1 [Source: HGNC Symbol; Acc: 20577] |
| ENSSSCG00000010529 | SFRP5 | secreted frizzled-related protein 5 [Source: HGNC Symbol; Acc: 10779] |
| ENSSSCG00000010613 | ITPRIP | inositol 1,4,5-trisphosphate receptor interacting protein [Source: HGNC Symbol; Acc: 29370] |
| ENSSSCG00000010647 | ADRB1 | beta-1 adrenergic receptor [Source: RefSeq peptide; Acc: NP_001116546] |
| ENSSSCG00000010805 | | Uncharacterized protein [Source: UniProtKB/TrEMBL; Acc: F1SAA5] |
| ENSSSCG00000011148 | | Uncharacterized protein [Source: UniProtKB/TrEMBL; Acc: F1RYV5] |
| ENSSSCG00000011153 | | Sus scrofa aldo-keto reductase family 1 member C2-like (LOC733635), mRNA. [Source: RefSeq mRNA; Acc: NM_001044570] |
| ENSSSCG00000011579 | PPARG | Sus scrofa peroxisome proliferator-activated receptor gamma (PPARG), mRNA. [Source: RefSeq mRNA; Acc: NM_214379] |

TABLE 3B-continued

Functional description of ZF6-DBD differentially expressed genes (81, FDR < 0.05)

| ensembl_gene_id | external_gene_id | description |
|---|---|---|
| ENSSSCG00000011700 | CP | ceruloplasmin (ferroxidase) [Source: HGNC Symbol; Acc: 2295] |
| ENSSSCG00000011796 | CRYGS | crystallin, gamma S [Source: HGNC Symbol; Acc: 2417] |
| ENSSSCG00000012040 | OLIG1 | oligodendrocyte transcription factor 1 [Source: HGNC Symbol; Acc: 16983] |
| ENSSSCG00000016187 | | Sus scrofa chromosome 2 open reading frame 62 (C15H2orf62), mRNA. [Source: RefSeq mRNA; Acc: NM_001190220] |
| ENSSSCG00000017343 | GFAP | Sus scrofa glial fibrillary acidic protein (GFAP), mRNA. [Source: RefSeq mRNA; Acc: NM_001244397] |
| ENSSSCG00000017445 | KRT13 | keratin 13 [Source: HGNC Symbol; Acc: 6415] |
| ENSSSCG00000017956 | CD68 | Uncharacterized protein [Source: UniProtKB/TrEMBL; Acc: F1ST28] |
| ENSSSCG00000020750 | | Uncharacterized protein [Source: UniProtKB/TrEMBL; Acc: I3L728] |
| ENSSSCG00000021232 | SYNC | syncoilin, intermediate filament protein [Source: HGNC Symbol; Acc: 28897] |
| ENSSSCG00000023489 | CXCL9 | Sus scrofa chemokine (C-X-C motif) ligand 9 (CXCL9), mRNA. [Source: RefSeq mRNA; Acc: NM_001114289] |
| ENSSSCG00000023511 | | Importin subunit alpha [Source: UniProtKB/TrEMBL; Acc: F1SV93] |
| ENSSSCG00000023684 | | Sus scrofa metallothionein 1A (MT1A), mRNA. [Source: RefSeq mRNA; Acc: NM_001001266] |
| ENSSSCG00000023686 | TTR | Sus scrofa transthyretin (TTR), mRNA. [Source: RefSeq mRNA; Acc: NM_214212] |
| ENSSSCG00000024174 | TGIF1 | TGFB-induced factor homeobox 1 [Source: HGNC Symbol; Acc: 11776] |
| ENSSSCG00000024348 | | Uncharacterized protein; Uncharacterized protein [Source: UniProtKB/TrEMBL; Acc: F1RVM0] |
| ENSSSCG00000024911 | | Metallothionein [Source: UniProtKB/TrEMBL; Acc: I3LP58] |
| ENSSSCG00000025300 | | Uncharacterized protein [Source: UniProtKB/TrEMBL; Acc: I3LHC3] |
| ENSSSCG00000025378 | | Uncharacterized protein [Source: UniProtKB/TrEMBL; Acc: F1S4G5] |
| ENSSSCG00000026645 | | Uncharacterized protein [Source: UniProtKB/TrEMBL; Acc: I3L970] |
| ENSSSCG00000026986 | | mitochondrial ribosomal protein S23 [Source: RefSeq peptide; Acc: NP_001230742] |
| ENSSSCG00000027199 | | Uncharacterized protein [Source: UniProtKB/TrEMBL; Acc: I3L9A9] |
| ENSSSCG00000027332 | IGKV-11 | |
| ENSSSCG00000027582 | | Uncharacterized protein [Source: UniProtKB/TrEMBL; Acc: F1SIH3] |
| ENSSSCG00000027868 | | Uncharacterized protein [Source: UniProtKB/TrEMBL; Acc: F1RLZ7] |
| ENSSSCG00000028038 | | Uncharacterized protein [Source: UniProtKB/TrEMBL; Acc: I3L695] |
| ENSSSCG00000028112 | CLIC6 | chloride intracellular channel 6 [Source: HGNC Symbol; Acc: 2065] |
| ENSSSCG00000028233 | | Uncharacterized protein [Source: UniProtKB/TrEMBL; Acc: F1SDH3] |
| ENSSSCG00000028525 | SAA4 | Sus scrofa serum amyloid A2 (LOC733603), mRNA. [Source: RefSeq mRNA; Acc: NM_001044552] |
| ENSSSCG00000029057 | | Uncharacterized protein [Source: UniProtKB/TrEMBL; Acc: I3LBK0] |
| ENSSSCG00000029210 | CLDN7 | Sus scrofa claudin 7 (CLDN7), mRNA. [Source: RefSeq mRNA; Acc: NM_001160076] |
| ENSSSCG00000030300 | MT2A | Metallothionein-2A [Source: UniProtKB/Swiss-Prot; Acc: P79379] |
| ENSSSCG00000030447 | AKR1C3 | Sus scrofa aldo-keto reductase family 1, member C1 (dihydrodiol dehydrogenase 1; 20-alpha (3-alpha)-hydroxysteroid dehydrogenase) (AKR1C1), mRNA. [Source: RefSeq mRNA; Acc: NM_001044618] |
| ENSSSCG00000030738 | IGKV-5 | |
| ENSSSCG00000030868 | IGLV-10 | Sus scrofa immunoglobulin lambda-like polypeptide 5 (LOC100152327), mRNA. [Source: RefSeq mRNA; Acc: NM_001243319] |
| ENSSSCG00000030893 | IGLV-3 | |
| ZF6 | ZF6 | ZF6 |

TABLE 4

ZF6-KRAB differentially expressed genes (204, FDR < 0.05)

| ensembl_gene_id | external_gene_id | logFC | logCPM | PValue | FDR |
|---|---|---|---|---|---|
| ZF6 | ZF6 | 7.278871303 | 2.413446532 | 3.28E−54 | 4.94E−50 |
| ENSSSCG00000027582 | | 9.966196799 | 1.859352668 | 2.28E−51 | 1.72E−47 |
| ENSSSCG00000021164 | | −9.421301813 | 1.829389425 | 1.38E−30 | 6.93E−27 |
| ENSSSCG00000027868 | | 8.488117179 | 0.55717728 | 7.85E−30 | 2.96E−26 |
| ENSSSCG00000008318 | VAX2 | −4.592008926 | 3.602797713 | 3.49E−28 | 1.04E−24 |
| ENSSSCG00000028996 | ALDH1A1 | 3.483184476 | 3.22934307 | 4.16E−28 | 1.04E−24 |
| ENSSSCG00000026986 | | 6.732615212 | 0.395768447 | 1.06E−27 | 2.28E−24 |
| ENSSSCG00000005385 | NOR-1 | −4.021873624 | 4.205792595 | 2.39E−26 | 4.49E−23 |
| ENSSSCG00000006276 | CEBPD | 3.223955907 | 3.967228489 | 4.87E−26 | 8.16E−23 |
| ENSSSCG00000025378 | | 8.144255564 | 0.263169934 | 1.02E−25 | 1.54E−22 |
| ENSSSCG00000028235 | | −4.906529139 | 2.454069444 | 1.21E−25 | 1.66E−22 |
| ENSSSCG00000023287 | | −8.822956672 | 1.315511692 | 8.12E−25 | 1.02E−21 |
| ENSSSCG00000005973 | | −8.422224465 | 0.869702364 | 1.77E−21 | 2.05E−18 |
| ENSSSCG00000023684 | | 2.778132732 | 3.384018554 | 1.36E−19 | 1.47E−16 |
| ENSSSCG00000000660 | A2M | 2.598474784 | 8.178849644 | 3.43E−19 | 3.45E−16 |
| ENSSSCG00000012441 | | 5.859096846 | −0.248802256 | 4.44E−19 | 4.17E−16 |

TABLE 4-continued

ZF6-KRAB differentially expressed genes (204, FDR < 0.05)

| ensembl_gene_id | external_gene_id | logFC | logCPM | PValue | FDR |
|---|---|---|---|---|---|
| ENSSSCG00000009867 | TBX5 | 2.722582775 | 3.277152929 | 5.48E-19 | 4.85E-16 |
| ENSSSCG00000010647 | ADRB1 | 2.961660472 | 1.669675424 | 1.23E-17 | 1.03E-14 |
| ENSSSCG00000028579 | | 5.132387018 | -0.329896827 | 6.44E-17 | 5.10E-14 |
| ENSSSCG00000011796 | CRYGS | 2.444168826 | 3.872635866 | 3.23E-16 | 2.43E-13 |
| ENSSSCG00000022626 | | -7.701933686 | 0.225138089 | 8.05E-16 | 5.77E-13 |
| ENSSSCG00000029135 | TNFRSF25 | 6.784172639 | -0.978780652 | 1.89E-14 | 1.30E-11 |
| ENSSSCG00000005580 | | -3.232678111 | 1.152547156 | 4.64E-14 | 3.04E-11 |
| ENSSSCG00000025618 | TAP | -7.401264148 | -0.055915235 | 9.95E-14 | 6.24E-11 |
| ENSSSCG00000001427 | C4A | 2.170535452 | 4.754134462 | 1.48E-13 | 8.90E-11 |
| ENSSSCG00000024842 | | -7.366719165 | -0.086540906 | 1.90E-13 | 1.10E-10 |
| eGFP | eGFP | 6.879599151 | -0.830177726 | 2.15E-13 | 1.20E-10 |
| ENSSSCG00000010613 | ITPRIP | 2.334986909 | 2.129686743 | 6.07E-13 | 3.26E-10 |
| ENSSSCG00000030825 | IGLV-9 | 2.205038931 | 2.493456626 | 2.72E-12 | 1.41E-09 |
| ENSSSCG00000011808 | SST | -2.45398974 | 3.207201493 | 3.24E-12 | 1.63E-09 |
| ENSSSCG00000006114 | CU207250.1 | -5.263297108 | -0.219630606 | 4.51E-12 | 2.19E-09 |
| ENSSSCG00000027332 | IGKV-11 | 2.242297263 | 1.597076937 | 4.32E-11 | 2.03E-08 |
| ENSSSCG00000014118 | | 2.100682625 | 2.399287953 | 4.92E-11 | 2.24E-08 |
| ENSSSCG00000030344 | CLDN19 | -2.128091826 | 5.422541347 | 6.72E-11 | 2.98E-08 |
| ENSSSCG00000023405 | | -4.256319433 | -0.049264717 | 7.11E-11 | 3.06E-08 |
| ENSSSCG00000021518 | | -6.847646235 | -0.534420885 | 1.84E-10 | 7.71E-08 |
| ENSSSCG00000028038 | | 2.803560602 | 0.035763608 | 2.80E-10 | 1.14E-07 |
| ENSSSCG00000017956 | CD68 | 1.81318436 | 4.351969763 | 6.74E-10 | 2.67E-07 |
| ENSSSCG00000005638 | LCN2 | 1.98192396 | 1.873024646 | 1.17E-09 | 4.53E-07 |
| ENSSSCG00000017445 | KRT13 | 1.898163514 | 2.367389814 | 1.28E-09 | 4.84E-07 |
| ENSSSCG00000013669 | PIN1 | -2.038042266 | 3.172198854 | 2.16E-09 | 7.94E-07 |
| ENSSSCG00000008101 | | 6.030278211 | -1.426659959 | 3.98E-09 | 1.43E-06 |
| ENSSSCG00000030009 | | 2.177491095 | 0.535024395 | 4.42E-09 | 1.55E-06 |
| ENSSSCG00000011106 | CREB | -1.87605221 | 5.315766307 | 6.10E-09 | 2.09E-06 |
| ENSSSCG00000015791 | | -6.532238692 | -0.774577709 | 8.36E-09 | 2.80E-06 |
| ENSSSCG00000006780 | WNT2B | 1.690202352 | 4.141918489 | 9.62E-09 | 3.15E-06 |
| ENSSSCG00000008311 | CYP26B1 | 1.881313879 | 1.56416778 | 1.39E-08 | 4.45E-06 |
| ENSSSCG00000028056 | | -6.485990517 | -0.822733143 | 1.49E-08 | 4.67E-06 |
| ENSSSCG00000006288 | SELP | 1.789553263 | 2.144819403 | 2.10E-08 | 6.46E-06 |
| ENSSSCG00000012584 | CAPN6 | 1.837714952 | 1.790378611 | 2.18E-08 | 6.57E-06 |
| ENSSSCG00000000893 | AMDHD1 | 1.778794681 | 1.949948478 | 2.86E-08 | 8.45E-06 |
| ENSSSCG00000017439 | KRT32 | 3.328917064 | -0.885115105 | 3.32E-08 | 9.62E-06 |
| ENSSSCG00000017343 | GFAP | 1.57700841 | 10.33435702 | 3.59E-08 | 1.02E-05 |
| ENSSSCG00000002702 | | -1.995809314 | 2.441457013 | 4.45E-08 | 1.24E-05 |
| ENSSSCG00000023686 | TTR | 1.568992576 | 5.463993077 | 5.63E-08 | 1.54E-05 |
| ENSSSCG00000015879 | DAPL1 | -1.876520953 | 2.486448545 | 7.91E-08 | 2.13E-05 |
| ENSSSCG00000016216 | | 1.623790563 | 2.583287658 | 1.11E-07 | 2.94E-05 |
| ENSSSCG00000030927 | IGKV-7 | 1.864125612 | 1.167586657 | 1.15E-07 | 2.98E-05 |
| ENSSSCG00000015476 | CHI3L1 | 1.704816958 | 1.860170428 | 1.25E-07 | 3.19E-05 |
| ENSSSCG00000002977 | AQN-3 | 5.75514981 | -1.56554597 | 1.56E-07 | 3.88E-05 |
| ENSSSCG00000027199 | | 3.008503143 | -0.913744531 | 1.57E-07 | 3.88E-05 |
| ENSSSCG00000014726 | HBE1 | 3.319650799 | -1.068390305 | 1.96E-07 | 4.75E-05 |
| ENSSSCG00000016859 | C7 | 2.585298944 | -0.582668229 | 2.01E-07 | 4.80E-05 |
| ENSSSCG00000003471 | EPHA2 | -1.654310889 | 5.545689573 | 2.18E-07 | 5.12E-05 |
| ENSSSCG00000012344 | TROP | -6.189962598 | -1.050550077 | 2.24E-07 | 5.18E-05 |
| ENSSSCG00000008664 | FAM84A | 1.51503585 | 4.28099978 | 2.31E-07 | 5.26E-05 |
| ENSSSCG00000010529 | SFRP5 | 1.65635865 | 1.889769252 | 2.85E-07 | 6.39E-05 |
| ENSSSCG00000014725 | HBB | 1.50380937 | 4.273198499 | 2.88E-07 | 6.39E-05 |
| ENSSSCG00000026526 | CATSPER4 | -1.715254319 | 3.059935797 | 3.42E-07 | 7.46E-05 |
| ENSSSCG00000025300 | | 2.325237299 | -0.201989204 | 3.51E-07 | 7.49E-05 |
| ENSSSCG00000028233 | | 1.583574525 | 2.548471964 | 3.53E-07 | 7.49E-05 |
| ENSSSCG00000031054 | IGLV-8 | 1.502354529 | 3.745540811 | 3.71E-07 | 7.77E-05 |
| ENSSSCG00000008314 | ATP6V1B1 | -2.802711683 | -0.090041988 | 4.29E-07 | 8.84E-05 |
| ENSSSCG00000001544 | TEAD3 | 1.478566173 | 4.300276435 | 4.51E-07 | 9.18E-05 |
| ENSSSCG00000020750 | | 2.057455347 | 0.13829939 | 5.02E-07 | 0.000100693 |
| ENSSSCG00000008203 | IGKC | 1.45884815 | 4.60744638 | 5.74E-07 | 0.000113804 |
| ENSSSCG00000010044 | IGLC | 1.427680446 | 6.221668726 | 7.03E-07 | 0.000137509 |
| ENSSSCG00000017988 | CCDC42 | -6.05087467 | -1.134401072 | 7.94E-07 | 0.000151653 |
| ENSSSCG00000030790 | TMP-CH242-74M17.6 | 1.434363459 | 4.90554081 | 7.96E-07 | 0.000151653 |
| ENSSSCG00000004666 | | 1.429918138 | 5.053265136 | 8.15E-07 | 0.000153438 |
| ENSSSCG00000012026 | | -1.563348806 | 5.521915562 | 8.55E-07 | 0.000158981 |
| ENSSSCG00000000368 | MMP19 | 1.538739124 | 2.402691957 | 8.98E-07 | 0.000163967 |
| ENSSSCG00000009361 | POSTN | -1.651323076 | 3.078247143 | 9.04E-07 | 0.000163967 |
| ENSSSCG00000001025 | DSP | -1.578978542 | 4.701438353 | 9.18E-07 | 0.000164532 |
| ENSSSCG00000026645 | | 3.342731042 | -1.285181501 | 1.12E-06 | 0.000198073 |
| ENSSSCG00000001463 | LMP2 | 1.631568363 | 1.464768231 | 1.30E-06 | 0.000222002 |
| ENSSSCG00000011014 | BAMBI | 1.399092473 | 5.437359075 | 1.29E-06 | 0.000222002 |
| ENSSSCG00000030300 | MT2A | 1.40614253 | 4.780105759 | 1.27E-06 | 0.000222002 |
| ENSSSCG00000028112 | CLIC6 | 1.788198678 | 0.685384933 | 1.50E-06 | 0.000254591 |
| ENSSSCG00000013909 | CRLF1 | -1.59558768 | 3.34754256 | 1.55E-06 | 0.000258658 |
| ENSSSCG00000007476 | KCNG1 | -2.018785429 | 0.861309241 | 1.76E-06 | 0.000290585 |

TABLE 4-continued

ZF6-KRAB differentially expressed genes (204, FDR < 0.05)

| ensembl_gene_id | external_gene_id | logFC | logCPM | PValue | FDR |
|---|---|---|---|---|---|
| ENSSSCG00000014117 | THBS4 | 1.652704034 | 1.328535904 | 1.81E−06 | 0.000296296 |
| ENSSSCG00000011579 | PPARG | 2.401952047 | −0.58397614 | 2.13E−06 | 0.000345026 |
| ENSSSCG00000011700 | CP | 1.360654082 | 6.077544507 | 2.29E−06 | 0.000367366 |
| ENSSSCG00000029057 | | 1.94464886 | −0.013698301 | 2.65E−06 | 0.000420124 |
| ENSSSCG00000021903 | | 1.387771198 | 3.544489252 | 3.30E−06 | 0.000518105 |
| ENSSSCG00000002405 | ISM2 | 2.722054775 | −0.934957401 | 3.48E−06 | 0.000540571 |
| ENSSSCG00000001849 | APN | 1.337786801 | 5.212659863 | 3.79E−06 | 0.000581635 |
| ENSSSCG00000002254 | NR2F2 | 1.336608682 | 4.757494906 | 4.34E−06 | 0.000653654 |
| ENSSSCG00000016034 | COL3A1 | 1.427097718 | 2.505396608 | 4.34E−06 | 0.000653654 |
| ENSSSCG00000030868 | IGLV-10 | 1.335802347 | 4.091296314 | 5.30E−06 | 0.000790079 |
| ENSSSCG00000011299 | CLEC3B | 1.330266254 | 4.088671808 | 6.24E−06 | 0.000920597 |
| ENSSSCG00000031039 | CH242-138G12.1 | 1.324506968 | 4.099240963 | 6.60E−06 | 0.000964785 |
| ENSSSCG00000005591 | GPR144 | −1.972315058 | 0.439273597 | 6.80E−06 | 0.000972395 |
| ENSSSCG00000010474 | CYP26C1 | 2.026835328 | −0.149447024 | 6.82E−06 | 0.000972395 |
| ENSSSCG00000027130 | TNFRSF12A | 1.506949411 | 1.493356909 | 6.85E−06 | 0.000972395 |
| ENSSSCG00000013586 | LRRC8E | −1.405155206 | 6.384255319 | 7.08E−06 | 0.000996884 |
| ENSSSCG00000015326 | COL1A2 | 1.335306634 | 3.180155195 | 9.01E−06 | 0.001256406 |
| ENSSSCG00000030493 | | −1.922546385 | 0.067845409 | 1.03E−05 | 0.001405464 |
| ENSSSCG00000030921 | APOA1 | 1.262954556 | 8.871636525 | 1.03E−05 | 0.001405464 |
| ENSSSCG00000023571 | SLC22A6 | 1.890532432 | −0.127955088 | 1.10E−05 | 0.001490728 |
| ENSSSCG00000011193 | | −1.731095609 | 0.92403661 | 1.12E−05 | 0.001504273 |
| ENSSSCG00000007687 | | 1.501232704 | 1.369094351 | 1.19E−05 | 0.001587449 |
| ENSSSCG00000001775 | KIAA1024 | −1.450049976 | 3.111445323 | 1.41E−05 | 0.001844456 |
| ENSSSCG00000031037 | IGLV-7 | 1.284074794 | 3.907251242 | 1.41E−05 | 0.001844456 |
| ENSSSCG00000007978 | HBA | 1.289660764 | 3.384246848 | 1.50E−05 | 0.001951528 |
| ENSSSCG00000010567 | | 2.563415593 | −1.030332238 | 1.54E−05 | 0.00198195 |
| ENSSSCG00000009535 | EFNB2 | 1.313346868 | 2.896821833 | 1.56E−05 | 0.001996794 |
| ENSSSCG00000003616 | FAM167B | 1.544905227 | 0.814294012 | 1.94E−05 | 0.002461052 |
| ENSSSCG00000015579 | PTGS2 | 1.408411371 | 1.529012479 | 2.05E−05 | 0.002576355 |
| ENSSSCG00000008205 | | 1.379378606 | 1.804099487 | 2.41E−05 | 0.002997975 |
| ENSSSCG00000004789 | THBS1 | 1.386127955 | 1.584300222 | 2.64E−05 | 0.00325634 |
| ENSSSCG00000017433 | KRT14 | 1.682438076 | 0.150290364 | 2.86E−05 | 0.003507267 |
| ENSSSCG00000007208 | TRIB3 | 1.573855551 | 0.572992142 | 3.22E−05 | 0.003910219 |
| ENSSSCG00000025199 | | −5.538872942 | −1.50336671 | 3.27E−05 | 0.003941846 |
| ENSSSCG00000015073 | TAGLN | 1.202913563 | 5.086931232 | 3.41E−05 | 0.00408057 |
| ENSSSCG00000029488 | ADAMTS1 | −1.28638316 | 5.80239426 | 3.82E−05 | 0.004525127 |
| ENSSSCG00000012871 | FGF19 | −1.549202144 | 1.622025872 | 3.96E−05 | 0.004663449 |
| ENSSSCG00000006238 | CYP7A1 | 1.445878111 | 0.979201435 | 4.07E−05 | 0.004752933 |
| ENSSSCG00000000371 | | 1.322655428 | 1.758632172 | 4.22E−05 | 0.004885597 |
| ENSSSCG00000016925 | PLK2 | 1.173624523 | 7.168363336 | 4.32E−05 | 0.004966309 |
| ENSSSCG00000003218 | | 1.185606835 | 5.081386288 | 4.40E−05 | 0.005017141 |
| ENSSSCG00000023435 | DBI | 1.154619081 | 7.170454577 | 5.72E−05 | 0.006472065 |
| ENSSSCG00000012448 | ITM2A | 1.165789128 | 5.248491196 | 5.77E−05 | 0.006487842 |
| ENSSSCG00000009304 | | −1.293307771 | 3.487022927 | 6.27E−05 | 0.006996706 |
| ENSSSCG00000026352 | | −1.231808722 | 10.19474378 | 6.66E−05 | 0.007361948 |
| ENSSSCG00000027743 | | −5.440155591 | −1.562592136 | 6.70E−05 | 0.007361948 |
| ENSSSCG00000005608 | ANGPTL2 | −1.281986455 | 3.951456839 | 6.93E−05 | 0.007560486 |
| ENSSSCG00000003920 | HPDL | 1.26216541 | 2.102692194 | 7.04E−05 | 0.007623102 |
| ENSSSCG00000027426 | BCL3 | 1.202113649 | 3.040207852 | 7.37E−05 | 0.0079292 |
| ENSSSCG00000016129 | GPR1 | 1.266453483 | 1.922670612 | 7.74E−05 | 0.008264422 |
| ENSSSCG00000004665 | | 1.154885363 | 4.321949725 | 7.86E−05 | 0.008279066 |
| ENSSSCG00000011153 | | 3.203544367 | −1.747204409 | 7.83E−05 | 0.008279066 |
| ENSSSCG00000017995 | USP43 | −1.381937633 | 1.96198567 | 9.03E−05 | 0.009444632 |
| ENSSSCG00000009285 | | 1.531834842 | 0.175962901 | 0.000105867 | 0.010994071 |
| ENSSSCG00000027157 | | 1.119639934 | 5.449380281 | 0.000108503 | 0.01190657 |
| ENSSSCG00000010447 | ACTA2 | 1.142592138 | 4.051922593 | 0.000109418 | 0.011208254 |
| ENSSSCG00000005981 | FBXO32 | −1.320353738 | 2.529565398 | 0.000110251 | 0.011217244 |
| ENSSSCG00000005465 | SUSD1 | 1.388192538 | 0.954004685 | 0.000114299 | 0.011551136 |
| ENSSSCG00000004937 | SLC24A1 | −1.180929024 | 8.321327013 | 0.000129694 | 0.013019562 |
| ENSSSCG00000000021 | | 1.298184515 | 1.347468778 | 0.000135707 | 0.013532972 |
| ENSSSCG00000025038 | KCNJ13 | 1.152327943 | 2.897875873 | 0.000143229 | 0.014189096 |
| ENSSSCG00000001765 | ADAMTS7 | 1.114024891 | 4.167902825 | 0.000149256 | 0.014689517 |
| ENSSSCG00000010475 | | 1.121780912 | 3.604898784 | 0.000161097 | 0.015751956 |
| ENSSSCG00000003666 | | 2.405544016 | −1.314582503 | 0.000169445 | 0.016461343 |
| ENSSSCG00000000362 | RDH5 | 1.181360924 | 2.137207703 | 0.000171911 | 0.016593803 |
| ENSSSCG00000000252 | KRT8 | 1.198124222 | 1.824455456 | 0.000193035 | 0.01851411 |
| ENSSSCG00000002471 | ISG12(A) | 1.066942412 | 7.321497721 | 0.000201211 | 0.019176197 |
| ENSSSCG00000010670 | | −3.037273164 | −1.087678902 | 0.000225687 | 0.021373576 |
| ENSSSCG00000030789 | IGLV-12 | 1.425595961 | 0.346574743 | 0.000228384 | 0.021493758 |
| ENSSSCG00000004822 | | −1.362860321 | 1.50229323 | 0.000235293 | 0.021671133 |
| ENSSSCG00000006958 | | −1.318173573 | 1.289064592 | 0.000235611 | 0.021671133 |
| ENSSSCG00000010966 | CCL19 | 1.241151729 | 1.385285141 | 0.000233994 | 0.021671133 |
| ENSSSCG00000023522 | TGM2 | 1.109360818 | 3.12698286 | 0.000236025 | 0.021671133 |
| ENSSSCG00000005844 | NRARP | −1.526644903 | 0.648314986 | 0.000251402 | 0.022943097 |
| ENSSSCG00000001454 | SLA-DRB2 | 1.117045267 | 2.703738492 | 0.000267252 | 0.024242677 |

TABLE 4-continued

ZF6-KRAB differentially expressed genes (204, FDR < 0.05)

| ensembl_gene_id | external_gene_id | logFC | logCPM | PValue | FDR |
|---|---|---|---|---|---|
| ENSSSCG00000029763 | IFI35 | 1.19684919 | 1.652633522 | 0.000271242 | 0.024457263 |
| ENSSSCG00000013243 | | 1.062345771 | 4.364649576 | 0.000283889 | 0.025445201 |
| ENSSSCG00000026706 | | 1.046555773 | 5.905478618 | 0.000286213 | 0.025501738 |
| ENSSSCG00000004869 | CNDP1 | −1.134057025 | 4.891103102 | 0.000298422 | 0.026433209 |
| ENSSSCG00000012676 | MBNL3 | 1.154626998 | 1.953463734 | 0.000307282 | 0.027058819 |
| ENSSSCG00000014167 | GLRX | 1.089333825 | 2.868159622 | 0.000315672 | 0.027635984 |
| ENSSSCG00000026893 | | 1.22446082 | 1.315176753 | 0.000336082 | 0.029252741 |
| ENSSSCG00000007336 | NNAT | −1.102116732 | 8.216715009 | 0.000338674 | 0.029308905 |
| ENSSSCG00000030165 | MAFF | −1.187786375 | 2.775823765 | 0.000346288 | 0.029796621 |
| ENSSSCG00000012121 | EGFL6 | 1.083823774 | 2.803072585 | 0.000378167 | 0.032354772 |
| ENSSSCG00000016040 | | 1.053773608 | 3.492067128 | 0.000412629 | 0.035008578 |
| ENSSSCG00000016664 | NPSR1 | 1.425076667 | 0.056848049 | 0.000413835 | 0.035008578 |
| ENSSSCG00000021968 | SLC19A3 | 1.099315302 | 2.41242279 | 0.000421772 | 0.035480722 |
| ENSSSCG00000028137 | SIK1 | −1.132681252 | 3.380470736 | 0.000426873 | 0.035513033 |
| ENSSSCG00000028672 | GCKR | 1.036972785 | 4.354127968 | 0.000426294 | 0.035513033 |
| ENSSSCG00000012103 | GPR143 | 1.025731322 | 4.651253506 | 0.000431649 | 0.035713027 |
| ENSSSCG00000029683 | | −1.229070097 | 2.147485422 | 0.000445438 | 0.036652525 |
| ENSSSCG00000021606 | | 1.093528059 | 2.398455314 | 0.000454606 | 0.037203597 |
| ENSSSCG00000003526 | | 1.018304228 | 4.69319723 | 0.000472743 | 0.03842756 |
| ENSSSCG00000014560 | COX8H | 1.318634843 | 0.509688816 | 0.00047977 | 0.03842756 |
| ENSSSCG00000020745 | SPOT14 | 1.531718199 | −0.242125742 | 0.000478155 | 0.03842756 |
| ENSSSCG00000024447 | SPOT14 | 1.531718199 | −0.242125742 | 0.000478155 | 0.03842756 |
| ENSSSCG00000006001 | ENPP2 | 1.018874139 | 4.537120636 | 0.000483508 | 0.038522032 |
| ENSSSCG00000028525 | SAA4 | 2.18131888 | −1.259707727 | 0.000506863 | 0.040170245 |
| ENSSSCG00000024246 | CNG-1 | −1.065834331 | 9.647922064 | 0.000512961 | 0.040440686 |
| ENSSSCG00000001767 | | 1.176262148 | 1.282847139 | 0.00053922 | 0.042289434 |
| ENSSSCG00000006955 | GSDMD | 1.034289145 | 3.238356598 | 0.000558101 | 0.043424041 |
| ENSSSCG00000027638 | BMP2 | 1.383108978 | 0.035105047 | 0.000559454 | 0.043424041 |
| ENSSSCG00000001457 | SLA-DQB*G07 | 1.015329325 | 3.937483052 | 0.000582769 | 0.044693398 |
| ENSSSCG00000002032 | SLC7A8 | 0.988280816 | 6.743107019 | 0.000587578 | 0.044693398 |
| ENSSSCG00000003525 | C1QC | 0.993522664 | 5.65355153 | 0.000580825 | 0.044693398 |
| ENSSSCG00000003711 | CABYR | −1.113450064 | 3.189409491 | 0.00058768 | 0.044693398 |
| ENSSSCG00000004195 | ARG1 | 1.682085908 | −0.664989022 | 0.000607538 | 0.045971423 |
| ENSSSCG00000009138 | CFI | 0.992699248 | 5.253517842 | 0.000610677 | 0.045977844 |
| ENSSSCG00000027962 | | −2.269835139 | −0.719602499 | 0.000616484 | 0.046184183 |
| ENSSSCG00000005307 | | −1.40341989 | 0.56130106 | 0.000646505 | 0.047991968 |
| ENSSSCG00000012040 | OLIG1 | 2.580788988 | −1.522162646 | 0.000650177 | 0.047991968 |
| ENSSSCG00000030984 | GYPC | 1.097196116 | 1.873148896 | 0.000649252 | 0.047991968 |

Authors found a high level of concordance between the two sets of differentially expressed genes, with high Correlation on their Fold Changes Values, indicating that the two artificial construct share the same biochemical properties and are able to bind the same genes given their engineered binding specificity.

To exclude that the number of the 57 target genes in common between the two experiments is by chance, authors calculated the hypergeometric probability, that tests the probability of obtaining a specific subset of genes out of a population whom the composition is known, obtaining a pvalue<4.711962e-93. This value corroborates the finding that the two experiments share a great part of the interfered genes.

As shown in table 3, interestingly in ZF6-DBD treated retinae 60 DEGs out of 81 were up regulated and 21 were down regulated. This set of DEGs is not expected enriched in any functional relation. To determine whether relation were present among the 81 DEGs authors performed an hypergeometric test. Authors found enrichment (FDR<0.05) in two unrelated categories (GO: 0005576, extracellular region; GO: 0010951, negative regulation of endopeptidase activity). The fragments per kilobase of exon per million fragments mapped FPKM which accounts expression levels demonstrate expression, which compared to endogenous transcription factors appears very low. This result underscore the potency of the ZF6-DBD function (FIG. 9). Indeed, the level of expression of ZF6-DBD strongly suggest its specificity and affinity, also suggesting that at least in part the ZF6-DBD does not compete with other endogenous TFs.

Notably the number of DEGs related to ZF6-DBD treatment (81) is consistently small if compared to those of a natural transcription factor such as the rod-specific transcription factor NRL (457). In addition ZF6-DBD silences RHO transcription with 148 folds less expression levels of NRL, measured with qRT-PCR.

The authors performed a Gene Set Enrichment Analysis (Gene Set enrichment analysis: A knowledge-based approach for interpreting genome-wide expression profiles: Subramanian et al. 2005) on the two sets of differentially expressed genes, to identify up or down—regulated processes in the two experiments. Authors observed that both the sets shared similar functions. Particularly in the context of the phototransduction, significative downregulation of these processes was found [GO:0042462, eye photoreceptor cell development; GO:0007602, phototransduction]. These data are consistent with the fact that RHO downregulation due to either ZF6-DBD or ZF6-KRAB activity results in secondary transcriptional changes (endogenous cell-specific regulatory code, i.e. whole cell-specific transcriptome map). Therefore, it is possible to infer that the primary physical targets of either ZF6-DBD or ZF6-KRAB (ZF6-DBD or ZF6-KRAB genome bound) are far less that those observed and that upon RHO downregulation a series of functionally related transcript are secondarily perturbed.

Therefore, ZF6-DBD is per se potent and mimics the intrinsic robustness of transcriptional signaling outperforming it, thanks to the fact that:

- Artificial DNA-binding domains are external to the topology of the regulatory network (interaction of the binding of the transcription factor to a specific DNA binding site near its target gene)
- Artificial DNA-binding domains are transcriptionally independent from the endogenous cell-specific regulatory code (whole cell-specific transcriptome map). Indeed, natural TFs themself belong to a cell-specific transcriptome map (regulators of regulators), therefore they are finely tuned by other cell-specific TF sets which control their transcriptional activation or repression eventually resulting in cell-specific function.
- Artificial DNA-binding domains are without protein-protein interaction domains As a further observation, the authors also hypothesize that the ZF6-DBD may have a safer profile than ZF6-KRAB during AAV vector production in which the plasmid containing the transgene (between the AAV-ITRs) is cotransfected with REP and CAP plasmids in HEK 293 cells (for methods see Auricchio et al, 2001). To be noted, during AAV vector production, if the transgene between the ITRs (i.e. ZF-KRAB or ZF-DBD) is under the control of an ubiquitous promoter like CMV, it is expressed in HEK 293 cells. The authors observed that, when the AAV8-CMV-ZF6-KRAB was produced, a very low vector yields was observed (FIG. 14). On the contrary, when ZF6-KRAB was under the control of a retinal specific promoter (RHOK) the titers of the vector was restore to normal yields (around $1 \times 10E12$). In the case of the ZF6-DBD production, the ubiquitous CMV promoter element and consequently ZF-DBD expression in production cells, had no negative effect and vector yields were within normal values (FIG. 10).

Replacement Strategy

For the second part of our therapeutic strategy for the treatment of autosomal dominant retinitis pigmentosa authors assessed the replacement of the ZF6 repressed alleles with wild type copy of human rhodopsin CDS. To set up the replacement conditions authors selected the human transducin 1 (GNAT1) promoter that is specific for rods (J Lee et al, Gene Therapy 2010) to deliver the transgene specifically in rods, and evaluated the dose of AAVs to have the best rods transduction. As the human rhodopsin promoter contains the binding site of ZF6, it cannot be used in the replacement strategy. Authors generated an AAV with eGFP reporter gene to evaluate the levels of transduction and to perform dose-response studies. Authors injected in pigs retinae three different doses of AAV8-hGNAT1-eGFP, $1 \times 1010$, $1 \times 1011$ and $1 \times 1012$. After 15 days we sacrificed the animals and we collected the retinae for the evaluation of the transcript levels and the localization of the eGFP in the retina. By qReal Time PCR we assessed the transcription levels of the eGFP and we observed an increase of the expression of the eGFP mRNA correlated with an increase of the dose used. When we evaluate the localization of the eGFP in retina we noticed that the expression is delimited only in rods. Based on these results, authors used a $1 \times 1012$ dose for the replacement. Therefore authors performed a silencing and replacement experiments in three months old pigs using two AAVs, an AAV8-CMV-ZF6-DBD, at a dose of $1 \times 1011$, for the repression of the endogenous porcine rhodopsin, and an AAV8-hGNAT1-hRHO at a dose of $1 \times 1012$. The expression levels of transcript, analysed 15 days post-injection, showed a repression of about the 55% of endogenous porcine rhodopsin and a replacement of repressed protein with human wild type CDS of about the 33% of total porcine rhodopsin. This data demonstrate that it is practicable to repress endogenous rhodopsin and replace it with an exogenous human rhodopsin. These are very promising results for the treatment of autosomal dominant retinitis pigmentosa caused by mutations in rhodopsin sequence in mutational independent manner (FIGS. 15 and 16). As shown, GNAT1 (rod-specific) and Arr3 (cone-specific) transcript levels are not affected by ZF6 miss-expression. This is also robustly confirmed by the RNA-seq data.

Contribution of Cis-Acting DNA Element (Cis-Regulatory Element, CRE) to Gene Expression.

Cis-regulatory potential of bound and not bound DNA genomic sequence motifs are determined by 1—chemical-physical properties of the DNA per se (the A, C, G, and T bases are chemical entities that, along with the inclusion of the backbone sugar and phosphate groups, create a three-dimensional double-stranded structure in which each base pair has a specific chemical and conformational signature) and by 2—epigenetics constrains, 3—complex of protein-protein interactions, 4—long distance physical connectivity (3D physical connectivity among distant genomic loci including distinct chromosomes) (Stamatoyannopoulos J A. Genome Res. 2012 September; 22(9):1602-11 and Rohs R, Jin X, West S M, Joshi R, Honig B, Mann R S. Annu Rev Biochem. 2010; 79:233-69). Indeed, most genomic DNA sequences defined by biochemical signatures lacked strong evolutionary conservation, and most highly conserved genomic DNA sequence elements escape annotation using biochemical and other functional assays. Moreover, nucleotide-level evolutionary conservation is by itself a poor predictor of functional regulatory variation and function (Maurano M T, Wang H, Kutyavin T, Stamatoyannopoulos J A. PLoS Genet. 2012; 8(3):e1002599).

Therefore, DNA sequence features or DNA information content is way more than a nucleotide sequence view as a one-dimensional string of letters based on an alphabet consisting of only four characters: A, C, G, and T, on the contrary a higher-order complexes between protein and genomic DNA exists (Stamatoyannopoulos J A. Genome Res. 2012 September; 22(9):1602-11 and Rohs R, Jin X, West S M, Joshi R, Honig B, Mann R S. Annu Rev Biochem. 2010; 79:233-69). A series of different methods have been employed to determine the DNA sequence features contained in genomic DNA (Genomic approaches towards finding cis-regulatory modules in animals. Hardison R C, Taylor J. Nat Rev Genet. 2012 Jun. 18; 13(7):469-83). Nevertheless, many of these methods rely on germ-line genomic engineering and thus lack one of the main feature urgently need in both basic science and medicine, the possibility to identify selective regulatory DNA active in space and time in a specific cell type in somatic cells over development, adult and aging, thus in each or in distinct categories of somatic cell types. Considering the poor prediction based on primary DNA sequence, a system to generate unbiased screening of possible regulatory DNA active in space and time in a somatic specific cell type is needed. The authors tested the hypothesis in which the above mentioned biochemical features of the ZF6-DBD may serve as a method to determine cis-regulatory elements in a specific cell type (photoreceptors) via AAV vector mediated gene transfer on somatic cells (photoreceptors).

Authors were able to demonstrate that a short sequence within ZF6-DBD target site (ZF6-DBDCis-seq), possesses base composition and length that is necessary to confer activity to RHO promoter. Such cognate 20 bp ZF6-DBD target site (is located on the human genomic promoter in position—94 from the transcription start site (FIG. 7).

In particular, authors showed that both an artificial DNA-binding protein covering the 20 bp of the human rhodopsin proximal promoter (ZF6-DBDCis-seq) and changing 5 bp contained within these sequence completely abolished RHO expression. Furthermore, authors were able to demonstrate that a single DNA base change can abolish RHO promoter driven expression. In addition; authors showed that this region is potentially controlled in non-rod specific cells via an endogenous transcriptional repressor KLF15 targeting the same genomic sequences of ZF6-DBD and that its missexpression in rods generates RHO transcriptional silencing.

Features of ZF6-DBDCis-Seq Genomic Element.

First authors investigated the DNA-protein interaction properties of the ZF6-DBDCis-seq. Gel mobility shift analysis demonstrated binding of ZF6-DBD on hRho proximal promoter region 43 bp oligonucleotide duplexes including the ZF6-DBD consensus sequence. Specificity was further supported by the ZF6-DBD binding when 18 bp ZF6-DBD core sequence was preserved and changed the 25 bp of the 43 bp oligonucleotide duplexes (hRho mut F and hRho mut L; FIG. 17)

Authors next investigated through complementation the genomic ZF6-DBDCis-seq. To isolate the features of ZF6-DBDCis-seq with high spatial resolution authors generate a short human RHO proximal promoter of 259 bp (164 bp from the TSS and the 95 bp of the 5' UTR; hRHOs). To determine the transcriptional output driven by hRHOs, authors generated an AAV-EGFP reporter construct (AAV8-hRHOs-EGFP) and injected it in adult WT C57BL6 mice and assess EGFP expression driven by hRHOs in vivo (Corbo Ref). Thus, in this experimental setting authors challenged this hRHOs promoter sequence against the entire nuclear proteome of mice photoreceptors. qRT-PCR analysis fifteen days after sub retinal delivery show that hRHOs reporter construct enable sustained EGFP expression in vivo (FIG. 18).

To determine cis-regulatory elements (regulatory DNA active in space and time) in a specific cell type (photoreceptors) via AAV vector mediated gene transfer on somatic cells (photoreceptors), the authors next generated constructs carrying deletion or mutagenesis of ZF6-DBDCis-seq. The authors generated 2 constructs: 1—with the complete deletion of the (GGGGGTTAGagGGTCTACGA [SEQ ID No. 22]; ΔZF6); 2—the mutagenized ZF6-DBD target (TTACTGTAATCTTAACCGGA [SEQ ID No. 29]; MutZF6) (FIGS. 19 and 20).

In order to test in vivo the functional consequences of the ΔZF6 and MutZF6 DNA changes in the proper cell type, the authors sought to investigate whether the use of AAV vector gene transfer to photoreceptors may represent a convenient method to carry out this assessment. The authors thus generated AAV8 vectors containing human RHO promoter (see methods) with its 5' UTR and with the ΔZF6 or MutZF6 embedded in their RHO promoter sequence to control EGFP expression (AAV8-hRHO-ΔZF6-5'UTR-EGFP and AAV8-hRHO-MutZF6-5'UTR-EGFP). After AAV vector production, wild type mice (P30) received or the AAV8-hRHO-ΔZF6-5'UTR-EGFP, or AAV8-hRHO-MutZF6-5'UTR-EGFP, or AAV8-hRHO-5'UTR-EGFP as positive control at a vector dose of 1×10e9 vg. As shown in FIGS. 11 and 12, after sacrifice (P50) both the RT-PCR and immunohistological studies showed that in both AAV8-hRHO-ΔZF6-5'UTR-EGFP, or AAV8-hRHO-MutZF6-5'UTR-EGFP injected eyes EGFP expression levels were highly significantly reduced compared to the promoter containing the complete RHO proximal promoter DNA sequence. This result suggests that the ZF6-DBD cis-acting element is necessary for the activity of hRHOs elements in photoreceptors. Additionally, the lack of conservation of the ZF6 target sequence in mice underscore the critical features and information content (including the architecture) contained in the regulatory DNA sequences which controls gene expression and the strength of the method of in vivo AAV vector delivery in the proper somatic cell target (i.e. photoreceptors) to unravel cis-regulatory elements function.

To narrow down the functional bases of activity of this ZF6-DBDCis-seq authors performed phylogeny sequence analysis. Unexpectedly the 5' of the ZF6-DBDCis-seq is not conserved in mouse Rho promoter sequence. Authors generated a murine version of the reporter construct; 243 bp (165 bp from the TSS and the 78 bp of the 5' UTR; mRHOs). Following 15 days after injection in adult WT C57BL6 mice the reporter activity was reduced (35%) compared to human counterpart. However, the activity was retained. Authors then wondered whether the TF binding sites architecture diverge between the two species. TF binding sites mapping, shows that NRL and CRX binding sites are flanking the ZF6-DBDCis-seq. Humans presents a further CRX binding site conserved in vertebrates that appears lacking in mouse. Thus, authors tested the hypothesis of whether the CRX and NRL binding sites together with the ZF6-DBDCis-seq generate a functional unit. Insertion of the murine "functional unit" (hRHOs InsMurine) in the human hRHOs remarkably mimics the transcriptional activity of the murine promoter fragment (FIG. 21). The reverse (mRHOs InsHuman), the human fragment In the murine RHO proximal promoter results in a slightly higher expression compared to hRHOs. These results support the model of a discrete functional unit present in both human and murine promoters. To further dissect the properties of this sequence authors tested whether the critical features of the 20 bp ZF6-DBDCis-seq were located in the CACCCCCA [SEQ ID No. 55] sequence not present in mouse sequence. Nucleotide change (hRHOs MEvo) completely abolishes activity, whereas deletion (hRHOs ΔEvo) of the same sequence surprisingly resulted in sustained activity. This result support that the ZF6-DBD DNA binding site on the genome is not an obvious endogenous TF binding site controlling, upon TF binding, transactivation of RHO-DOPSIN. The lack of a binding site coupled to preservation of activity and the shortness of the promoter used also rule out a "CTCF" looping mechanism. In addition, this result support that the sequence does not act as a TF binding site but that the nucleotide composition and the length may play an essential role in generating promoter function. Authors further test whether the nucleotide changes were sensitive to sequence composition replacing the CCCCC [SEQ ID No. 56] stretch with GGGGG [SEQ ID No. 57] (hRHOs 5G) but similar loss of activity was observed. To further determine the level of sensitivity of this sequence authors mutated only one base (CCACC [SEQ ID No. 58]; hRHOs T3C) and remarkably the activity of the promoter was extinguished (FIG. 21). These data support a model in which, the properties of this RHO regulatory genomic functional unit follows precise rules, the 20 bp-long genomic DNA linking the CRX and NRL DNA-binding sites (ZF6-DBDCis-seq) carries complex and specific features in length and nucleotide composition. This functional unit diverges in mouse, hoauthorsver it preserves the basic grammar governing the human counterpart. Indeed, this functional unit is reciprocally transportable in human and mouse RHO promoters (hRHOs InsMurine; mRHOs InsHuman) resulting in the same transcriptional output as it produces in the species it belongs to.

Based on the extraction of the RHO cis acting regulatory properties retrieved by the above experiments in photoreceptor specific context, the authors decided to use a trans DBD domain approach therein presented to mirror the Cis-acting effect generated by mutagenesis analysis (above). The authors generated a shorter version of ZF6-DBD, lacking the 6th finger, and thus restricting the target site of the DBD domain (FIG. 30). This artificial DBD domain called ZF6-5 or ZF6-5F (5 stands for 5 fingers) generates a more accurate targeting on the novel RHO cis-acting element identified, avoiding the potential interference of ZF6-DBD on the NRL site. This novel protein can generate an interference specifically centered to the RHO Cis-acting element CCCCCA [SEQ ID NO. 30]. To test the activity of ZF6-5 an AAV8 vector (AAV8-CMV-ZF6-5F) was injected in P347S mice at P15 and the functional outcome was assessed by ERG analysis at P30 (15 days after vector administration). As shown in FIG. 31, the activity of ZF6-5 generated a preservation of retinal function compared to controls (AAV8-EGFP). To further explore other potential trans DBD domains based on TAL technology and again more appropriately targeted to the RHO Cis-acting elements identified, the authors generated two TAL-based DNA binding domains as reported in FIG. 30. These two DBD domains, TALRHO (02) and TALI were then used to generate AAV8 vectors (AAV8-CMV-TALRHO(02)-DBD and AAV8-CMV-TALI-DBD) and tested in P347S mice; as above. Similarly to ZF6-5; both AAV8-CMV-TALRHO-(02)-DBD and AAV8-CMV-TALRHO-(02)-DBD generated a significant preservation of retinal function compared to EGFP injected controls. To further analyze the ZF6-DBDCis-seq authors scanned the 20 bp together with the corresponding murine sequence (TATGATATCTCGCGGATGCT, [SEQ ID No. 59]) by TRANSFAC analysis. As shown in FIG. 22 authors retrieved 3 matrixes for human and 1 distinct matrix for the mouse sequences. The matrix centered to the CCCCCA [SEQ ID NO. 30] sequence displays RREB-1 factor, which belong to the retinal specific KLF15 TF. KLF15 is a zinc-finger TF that showed in vitro binding to the CCCCCA [SEQ ID NO. 30] sequence. Based on the expression pattern KLF15, which is expressed in the retina with the exception of photoreceptors it was suggested that its function may rely on rhodopsin transcriptional expression blocking in non rods cells of the retina. Authors thought that if this is the case KLF15 missexpression to photoreceptor may result in RHO silencing. Authors generated an AAV8 vector carrying human KLF15 (AAV8-CMV-KLF15) and injected porcine retinae. Fifteen days after delivery AAV8-CMV-KLF15 transduction resulted in an impressive 50% repression of porcine rhodopsin and a similar relative repression of the rod-specific GNAT1 gene. These results suggest that another trans-acting element (endogenous TF) with known binding for the sequence CCCCCA [SEQ ID NO. 30] acts similarly to ZF6-DBD when missexpressed in rod cells.

These data strongly suggest that the cis-regulatory element targeted by the ZF6-DBD is a novel cis-regulatory element of human RHODOPSIN promoter critical for RHO-DOPSIN expression.

Therefore, ZF technology and AAV retinal gene transfer allowed determining the function of a regulatory DNA element in two reciprocal manners:

A) the design of ZF DBD without an effector domain, targeted to a DNA sequence can be used for the identification of novel cis-regulatory elements. In the case of ZF6-DBD the authors identified a previously unknown element. Moreover, considering the specific cell type in which a cis-regulatory element acts, the ability of AAV vector to express the ZF6-DBD constructs in space (in the authors' case, a—subretinal administration, b—of a vector with tropism for photoreceptors, and possibly with a photoreceptor-specific promoter) and in time (subretinal administration at different time-points) allow a tailored method to identify and to determine the properties of a cis-regulatory elements in time and space.

B) Many strategies can be employed to study genomic regulatory sequences (Genomic approaches towards finding cis-regulatory modules in animals. Hardison R C, Taylor J. Nat Rev Genet. 2012 Jun. 18; 13(7):469-83). However, the use of in vivo AAV vector mediated gene transfer is for the first time employed. The data the authors show describe a method to identify cis-regulatory elements activity with AAV vectors in somatic cells (FIGS. 14 and 19). A method in principle similar was described by White M A et al PNAS 2013 11952-11957, July 2013 (Massively parallel in vivo enhancer assay reveals that highly local features determine the cis-regulatory function of ChIP-seq peaks. White M A, Myers C A, Corbo J C, Cohen B A. Proc Natl Acad Sci USA. 2013 Jul. 16; 110(29):11952-7). Nevertheless, in that case retinal electroporation was used (instead of AAV8 vector).

Therefore authors propose a two-step method:

test in vivo (via AAV-vector delivery as shown by authors, or via high throughput electroporation as reported by White M A, Myers C A, Corbo J C, Cohen B A. Proc Natl Acad Sci USA. 2013 Jul. 16; 110(29):11952-7. Massively parallel in vivo enhancer assay reveals that highly local features determine the cis-regulatory function of ChIP-seq peaks.) a series of CIS-mutants (promoter, enhancers of a gene of interest) to identify the critical region controlling expression;

generate an artificial DNA-binding protein to mimic the CIS-effect that in principle can function either as an activator or a repressor.

Barrow et al PNAS 2012 test the hypothesis of using the Zinc finger technology for a known cis-regulatory element of the β-globin and used transgenesis method to proof that Zinc fingers without an effector domain can be used for study and modulating the function of a known cis-regulatory DNA elements but not a method to identify novel CREs. In addition, the transgenesis used by Barrow was employed with germ-line approach (random integration of the transgene with uncontrolled time and space expression and dosage) and not a germ-line targeted approach with the ZF-DBD under the control of an ubiquitous promoter. Therefore, that study suffers of the major limitation of lack of control of time and space, that are clearly critical to determine the function of cis-regulatory elements (regulatory DNA active in space and time) in a specific cell type. On the contrary, the method the authors used with somatic gene transfer mediated by AAV vectors allow to control dosage, cellular restriction (spatial resolution) and time (time of vector delivery; time resolution); this are crucial determinants for proper assessment of cis-regulatory elements (regulatory DNA active in space and time) in a specific cell type, in particular considering that current genomic studies are suggesting that the authors can legitimately consider "somatic cells composing the body are a genetic functional mosaicism".

In order to assess whether on the same ZF6 target DNA region another technology to generate DNA-binding domains can be applied, the authors used Transcription activator-like effector (TALE) technology (Breaking the code of DNA binding specificity of TAL-type III effectors. Boch J, Scholze H, Schornack S, Landgraf A, Hahn S, Kay S, Lahaye T, Nickstadt A, Bonas U. Science. 2009 Dec. 11; 326(5959):1509-12). Since this platform allows tailoring any DNA-binding protein starting with a T DNA base, the authors generated two constructs on the ZF6 target site as follow: TCAGCATCTGGGAGATTG [SEQ ID No. 24] and complementary sequence TCTGGGAGATTGGGGG [SEQ ID No. 60]. Transient transfection experiments on HEK293 cells show that the TALE-DBDs in vitro represses CRX mediated expression to a similar extent as ZF6-DBD and ZF6-KRAB (FIG. 23), suggesting that TALE technology can be an alternative to Zinc finger technology to employ the above described system.

The invention claimed is:

1. A nucleic acid molecule encoding a protein selected from the group consisting of: SEQ ID NO: 3, SEQ ID NO: 5, SEQ ID NO: 7, SEQ ID NO: 9, SEQ ID NO: 13, SEQ ID NO: 15, and SEQ ID NO: 17.

2. A vector comprising the nucleic acid molecule according to claim 1.

3. The vector according to claim 2, wherein said vector is a viral vector.

4. The vector according to claim 2, wherein said vector further comprises a human Rhodopsin coding sequence.

5. The vector according to claim 4, wherein said human Rhodopsin coding sequence is under the control of a retina specific promoter.

6. A host cell transformed by the vector as defined by claim 2, wherein the host cell is not a human organism.

7. A viral particle containing the vector as defined by claim 2.

8. A pharmaceutical composition comprising the nucleic acid according to claim 1.

9. A pharmaceutical composition comprising the vector according to claim 2, and a pharmaceutically acceptable excipient.

10. A pharmaceutical composition comprising the nucleic acid molecule according to claim 1, or comprising a vector, viral particle or host cell comprising said nucleic acid molecule, wherein said host cell is an isolated host cell.

11. The nucleic acid according to claim 1, that comprises a nucleic acid sequence selected from the group consisting of: SEQ ID NO: 2, SEQ ID NO: 4, SEQ ID NO: 6, SEQ ID NO: 8, SEQ ID NO: 12, SEQ ID NO: 14, and SEQ ID NO: 16.

12. The nucleic acid according to claim 1, that encodes a protein consisting of SEQ ID NO: 3.

13. The nucleic acid according to claim 1, that comprises SEQ ID NO: 2.

14. The vector according to claim 5, wherein the retina specific promoter is a rhodopsin kinase (RHOK) promoter, a transducin 1 (GNAT1) promoter, or a human transducin 1 (GNAT1) promoter.

15. The vector according to claim 4, wherein said human Rhodopsin coding sequence is under the control of a retina specific promoter, and wherein the nucleic acid molecule encodes a protein of SEQ ID NO: 3, and the nucleic acid molecule further encodes a nuclear localization sequence.

16. The vector according to claim 5, wherein the nucleic acid molecule encodes a protein of SEQ ID NO: 3 or SEQ ID NO: 13, and the nucleic acid molecule further encodes a nuclear localization sequence.

17. A method of treating an autosomal dominant retinitis pigmentosa caused by a mutation in a Rhodopsin gene in a subject, comprising,
    administering an effective amount of a composition comprising the vector according to claim 5 to a retina of the subject, wherein said vector is an adeno-associated viral (AAV) vector.

* * * * *